United States Patent
Or et al.

(10) Patent No.: US 7,419,962 B2
(45) Date of Patent: *Sep. 2, 2008

(54) 3,6-BICYCLOLIDES

(75) Inventors: Yat Sun Or, Watertown, MA (US); Datong Tang, Watertown, MA (US); Ying Sun, Waltham, MA (US); Yonghua Gai, North Grafton, MA (US); Guoyou Xu, Auburndale, MA (US); Zhe Wang, Hockessin, DE (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 106 days.

This patent is subject to a terminal disclaimer.

(21) Appl. No.: 11/295,736

(22) Filed: Dec. 6, 2005

(65) Prior Publication Data

US 2006/0142214 A1 Jun. 29, 2006

Related U.S. Application Data

(63) Continuation-in-part of application No. 11/008,581, filed on Dec. 7, 2004, now Pat. No. 7,229,972.

(51) Int. Cl.
*A61K 31/70* (2006.01)
*C07H 17/08* (2006.01)

(52) U.S. Cl. .................. 514/29; 536/7.2; 536/7.3; 536/7.4

(58) Field of Classification Search ............ None
See application file for complete search history.

(56) References Cited

U.S. PATENT DOCUMENTS

| | | | |
|---|---|---|---|
| 5,866,549 A | 2/1999 | Or et al. | |
| 6,075,011 A | 6/2000 | Or et al. | |
| 6,664,238 B1 * | 12/2003 | Su et al. | 514/29 |
| 6,734,292 B1 | 5/2004 | Omura et al. | |
| 6,794,377 B2 * | 9/2004 | Peukert et al. | 514/183 |
| 7,291,602 B2 * | 11/2007 | Tang et al. | 514/29 |

FOREIGN PATENT DOCUMENTS

| EP | 0 559 896 | 11/1991 |
|---|---|---|
| WO | WO 93/21200 | 10/1993 |
| WO | WO 97/10251 | 3/1997 |
| WO | WO 00/78773 | 12/2000 |
| WO | WO 03/095466 | 11/2003 |
| WO | WO 03/097659 | 11/2003 |

OTHER PUBLICATIONS

Zhenkun, Ma, et al., "Novel Erythromycin Derivatives With Aryl Groups Tethered to the C-6 Position are Potent Protein Synthesis Inhibitors and Active Against Multidrug-Resistant Respiratory Pathogens," *J. Med. Chem.*, 44:4137-4156 (2001).

* cited by examiner

*Primary Examiner*—Elli Peselev
(74) *Attorney, Agent, or Firm*—Carolyn S. Elmore; Darlene A. Vanstone; Elmore Patent Law Group

(57) ABSTRACT

The present invention discloses compounds of formula (I) or pharmaceutically acceptable salts, esters, or prodrugs thereof:

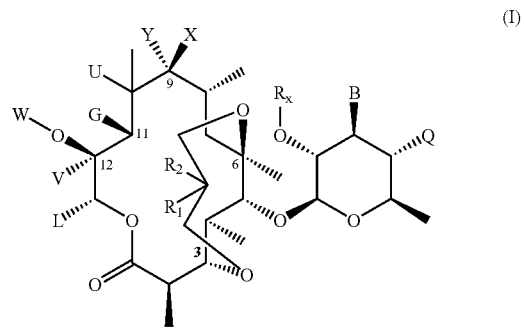

which exhibit antibacterial properties. The present invention further relates to pharmaceutical compositions comprising the aforementioned compounds for administration to a subject in need of antibiotic treatment. The invention also relates to methods of treating a bacterial infection in a subject by administering a pharmaceutical composition comprising the compounds of the present invention. The invention further includes process by which to make the compounds of the present invention.

47 Claims, No Drawings

3,6-BICYCLOLIDES

RELATED APPLICATION

This application is a continuation-in-part of U.S. application Ser. No. 11/008,581, filed Dec. 7, 2004 now U.S. Pat. No. 7,229,972. The entire teachings of the above application are incorporated herein by reference.

TECHNICAL FIELD

The present invention relates to novel semisynthetic macrolides having antibacterial activity that are useful in the treatment and prevention of bacterial infections. More particularly, the invention relates to 3,6-bicyclolide compounds, compositions containing such compounds and methods for using the same, as well as processes for making such compounds.

BACKGROUND OF THE INVENTION

The spectrum of activity of macrolides, including erythromycin, covers most relevant bacterial species responsible for upper and lower respiratory tract infections. 14-membered ring macrolides are well known for their overall efficacy, safety and lack of serious side effects. Erythromycin however is quickly degraded into inactive products in the acidic medium of the stomach resulting in low bioavailability and gastrointestinal side effects. Improvement of erythromycin pharmacokinetics has been achieved through the synthesis of more acid-stable derivatives, for example, roxithromycin, clarithromycin, and the 15-membered ring macrolide azithromycin. However, all these drugs, including 16-membered ring macrolides, present several drawbacks. They are inactive against $MLS_B$-resistant streptococci ($MLS_B$=Macrolides-Lincosamides-type B Streptogramines) and with the exception of azithromycin, weakly active against *Haemophilus influenzae*. Futhermore, the resistance of *Streptococcus pneumoniae* to erythromycin has increased significantly in recent years (5% to above 40%). There is a high percentage of cross-resistance to penicillin among these isolates, with a worldwide epidemic spread of 10-40% in some areas.

There is, therefore, a clear need for new macrolides that overcome the problem of pneumococcal resistance, have good pharmacokinetic properties and acid stability while continuing to be active against *H. influenzae*. These new macrolides will be ideal candidates for drug development in the first line therapy of upper respiratory tract infections ("URTI") and lower respiratory tract infections ("LRTI").

Kashimura et al. have disclosed 6-O-methylerythromycin derivatives having a tricyclic basic nuclear structure in European Application 559896, published Nov. 11, 1991. Also, Asaka et al. have disclosed 5-O-desoaminylerythronolide derivatives containing a tricyclic carbamate structure in PCT Application WO 93/21200, published Apr. 22, 1992.

Recently erythromycin derivatives containing a variety of substituents at the 6-O position have been disclosed in U.S. Pat. Nos. 5,866,549 and 6,075,011 as well as PCT Application WO 00/78773. Furthermore, Ma et al. have described erythromycin derivatives with aryl groups tethered to the C-6 position in *J. Med. Chem.*, 44, pp 4137-4156 (2001). PCT application WO 97/10251, published Mar. 20, 1997, discloses intermediates useful for preparation of 6-O-methyl 3-descladinose erythromycin derivatives. U.S. Pat. Nos. 5,866,549 and 6,075,011, and PCT application WO 00/78773, published Dec. 28, 2000, disclose certain 6-O-substituted erythromycin derivatives.

PCT Application WO 03/095466 A1, published Nov. 20, 2003 and PCT Application WO 03/097659 A1, published Nov. 27, 2003 disclose a series of bicyclic erythromycin derivatives.

SUMMARY OF THE INVENTION

The present invention provides a novel class of C3-C6 bridged erythromycin compounds that possess antibacterial activity.

The compounds of the present invention are represented by formula (I) as illustrated below:

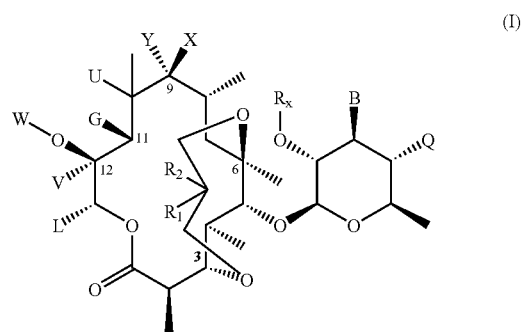

(I)

or the pharmaceutically acceptable salts, esters and prodrugs thereof, wherein $R_1$ is selected from the group consisting of:
  a) hydrogen; deuterium;
  b) methyl;
  c) allyl;
  d) —$CH_2OH$;
  e) aryl; substituted aryl;
  f) heteroaryl; substituted heteroaryl;
  g) —$C_1$-$C_6$ alkyl, —$C_2$-$C_6$ alkenyl, or —$C_2$-$C_6$ alkynyl containing 0, 1, 2, or 3 heteroatoms selected from O, S or N, optionally substituted with one or more substituents selected from halogen, aryl, substituted aryl, heteroaryl, or substituted heteroaryl;

$R_2$ is selected from the group consisting of:
  a) hydrogen;
  b) hydroxy;
  c) activated hydroxy;

when $R_1$ is H, $R_2$ is selected from the group consisting of:
  a) hydrogen;
  b) hydroxy;
  c) activated hydroxy;
  d) $N_3$;
  e) $NH_2$;
  f) CN;
  g) protected hydroxy;
  h) protected amino;
  i)-A-$R_3$, where A is O, S, S(O), $SO_2$, NH, $NCH_3$, NH(CO), NH(CO)NH or $NHSO_2$; and $R_3$ is independently selected from the group consisting of:
    (i) hydrogen;
    (ii) aryl; substituted aryl; heteroaryl; substituted heteroaryl;
    (iii) —$C_1$-$C_6$ alkyl, —$C_2$-$C_6$ alkenyl, or —$C_2$-$C_6$ alkynyl containing 0, 1, 2, or 3 heteroatoms selected from O, S or N, optionally substituted with one or more substituents selected from halogen, aryl, substituted aryl, heteroaryl, or substituted heteroaryl;

provided that when A=S(O) or $SO_2$, $R_3$ cannot be hydrogen;

(j)

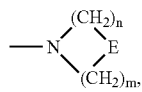

wherein E is absent, O, S, S(O), $S(O)_2$, $NR_3$, $N(CO)R_3$, $NSO_2R_3$, or $CHR_3$; n=1, 2, or 3; and m=2 or 3, where $R_3$ is as previously defined;

alternatively, $R_1$ and $R_2$ taken together with the carbon atom to which they are attached is:
  a) C=O;
  b) $C(OR_4)(OR_5)$, where $R_4$ and $R_5$ are selected from the group consisting of $C_1$-$C_{12}$ alkyl, aryl or substituted aryl; or taken together are —$(CH_2)_m$—, and where m is 2 or 3;
  c) $C(SR_4)(SR_5)$, where $R_4$ and $R_5$ are as previously defined above;
  d) C=$CHR_3$, where $R_3$ is as previously defined;
  e) C=CNH(amino protecting group)
  f) C=N-Z-$R_3$, where Z is absent, O, NH, NH(CO), NH(CO)NH or $NHSO_2$; and $R_3$ is as previously defined;

X and Y are:
  a) when one of X and Y is a hydrogen, the other is selected from:
    (i) hydrogen;
    (ii) deuterium;
    (iii) hydroxy;
    (iv) protected hydroxy;
    (v) amino;
    (vi) protected amino; and
    (vii)

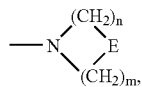

wherein E is absent, O, S, S(O), $S(O)_2$, $NR_3$, $N(CO)R_3$, $NSO_2R_3$, or $CHR_3$; n=1, 2, or 3; and m=2 or 3, where $R_3$ is as previously defined;

b) X, Y taken together with the carbon atom to which they are attached is:
  (i) C=O;
  (ii) C=N—$OR_6$, wherein $R_6$ is selected from the group consisting of:
    1. hydrogen;
    2. —$CH_2O(CH_2)_2OCH_3$;
    3. —$CH_2O(CH_2O)_nCH_3$, wherein n is as previously defined;
    4. —$C_1$-$C_{12}$ alkyl, containing 0, 1, 2, or 3 heteroatoms, optionally substituted with one or more substituents selected from the group consisting of halogen, aryl, substituted aryl, heteroaryl and substituted heteroaryl;
    5. $C_3$-$C_{12}$ cycloalkyl;
    6. C(O)—$C_1$-$C_{12}$ alkyl;
    7. C(O)—($C_3$-$C_{12}$ cycloalkyl);
    8. C(O)—$R_3$, wherein $R_3$ is as previously defined; and
    9. —$Si(R_a)(R_b)(R_c)$, wherein $R_a$, $R_b$ and $R_c$ are each independently selected from the group consisting of $C_1$-$C_{12}$ alkyl, aryl and substituted aryl;
  (iii) C=N—O—$C(R_7)(R_8)$—O—$R_9$, wherein $R_7$ and $R_8$ taken together with the carbon atom to which they are attached form a $C_3$ to $C_{12}$ cycloalkyl group or each independently is selected from the group consisting of: hydrogen and $C_1$-$C_{12}$ alkyl; and $R_9$ is selected from the group consisting of:
    1. —$C_1$-$C_{12}$ alkyl, optionally substituted with one or more substituents selected from the group consisting of halogen, aryl, substituted aryl, heteroaryl and substituted heteroaryl;
    2. —$C_3$-$C_{12}$ cycloalkyl; and
    3. —$Si(R_a)(R_b)(R_c)$, wherein $R_a$, $R_b$ and $R_c$ are as previously defined;

W is selected from the group consisting of:
  a) hydrogen;
  b) methyl;
  c) allyl;
  d) —$OCH_2SCH_3$ G is selected from the group consisting of:
  a) hydroxy;
  b) —O-aryl; —O-substituted aryl; —O-heteroaryl; —O-substituted heteroaryl;
  c) —$OC_1$-$C_6$ alkyl, —$OC_2$-$C_6$ alkenyl, or —$OC_2$-$C_6$ alkynyl containing 0, 1, 2, or 3 heteroatoms selected from O, S or N, optionally substituted with one or more substituents selected from halogen, aryl, substituted aryl, heteroaryl, or substituted heteroaryl;

U is hydrogen;

When U and G are taken together to form a bond, W is selected from the group consisting of:
  a) hydrogen;
  b) —C(O)LGp, where LGp is a leaving group, such as but not limited to, Cl, imidazole, triazole, cyano, p-nitrobenzene and the like;

Alternatively, structure

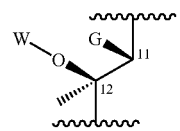

of formula (I) taken together is:
  a)
  b)

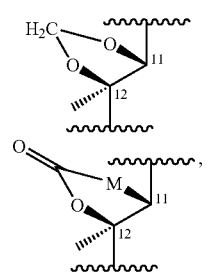

where M is O or N-J-$R_{20}$, and where J is absent, O, NH, NH(CO), or N=CH; and $R_{20}$ is selected from the group consisting of:
  i. hydrogen;
  ii. aryl; substituted aryl; heteroaryl; substituted heteroaryl;

iii. —$C_1$-$C_6$ alkyl, —$C_2$-$C_6$ alkenyl, or —$C_2$-$C_6$ alkynyl containing 0, 1, 2, or 3 heteroatoms selected from O, S or N, optionally substituted with one or more substituents selected from halogen, aryl, substituted aryl, heteroaryl, or substituted heteroaryl;

B is $NR_{30}R_{40}$; wherein $R_{30}$ and $R_{40}$ is independently selected from the group consisting of hydrogen, acyl, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, saturated or unsaturated heterocyclic group; or can be taken together with the nitrogen atom to which they are attached to form a substituted or unsubstituted heterocyclic or heteroaromatic ring; preferably B is $N(CH_3)_2$;

V is selected from the group consisting of hydrogen, azido, cyano, nitro, aldehyde, carboxylic acid, amide, a substituted or unsubstituted, saturated or unsaturated aliphatic group; preferably V is $CH_3$;

Q is selected from the group consisting of:
  (a) hydrogen;
  (b) protected hydroxy;
  (c) $OR_{21}$, where $R_{21}$ is selected from the group consisting of:
    (i) hydrogen;
    (ii) aryl; substituted aryl; heteroaryl; substituted heteroaryl;
    (iii) —$C_1$-$C_6$ alkyl, —$C_2$-$C_6$ alkenyl, or —$C_2$-$C_6$ alkynyl containing 0, 1, 2, or 3 heteroatoms selected from O, S or N, optionally substituted with one or more substituents selected from halogen, aryl, substituted aryl, heteroaryl, or substituted heteroaryl;
    (iv) —$C_3$-$C_{12}$ cycloalkyl containing 0, 1, 2, or 3 heteroatoms selected from O, S or N, optionally substituted with one or more substituents selected from halogen, aryl, substituted aryl, heteroaryl, or substituted heteroaryl;

L is selected from the group consisting of:
  (a) —$CH_2CH_3$;
  (b) —$CH(OH)CH_3$;
  (c) —$C_1$-$C_6$ alkyl, —$C_2$-$C_6$ alkenyl, or —$C_2$-$C_6$ alkynyl optionally substituted with one or more substituents selected from the group consisting of aryl, substituted aryl, heteroaryl, and substituted heteroaryl;

Rx is hydrogen, hydroxy protecting group or hydroxy prodrug group.

In another embodiment of the present invention there are disclosed pharmaceutical compositions comprising a therapeutically effective amount of a compound of the invention in combination with a pharmaceutically acceptable carrier or excipient. In yet another embodiment of the invention are methods of treating antibacterial infections in a subject in need of such treatment with said pharmaceutical compositions. Suitable carriers and formulations of the compounds of the present invention are disclosed.

DETAILED DESCRIPTION OF THE INVENTION

In a first embodiment of the compounds of the present invention are compounds represented by formula I as illustrated above, or a pharmaceutically acceptable salt, ester or prodrug thereof.

In a second embodiment of the compounds of the present invention are compounds represented by formula II as illustrated below, or a pharmaceutically acceptable salt, ester or prodrug thereof:

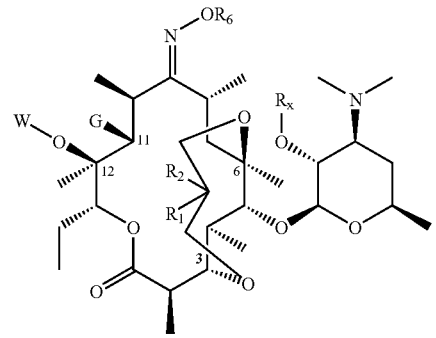

where W, $R_1$, $R_2$, $R_6$ and $R_x$ are as previously defined.

In a third embodiment of the compounds of the present invention are compounds represented by formula III as illustrated below, or a pharmaceutically acceptable salt, ester or prodrug thereof:

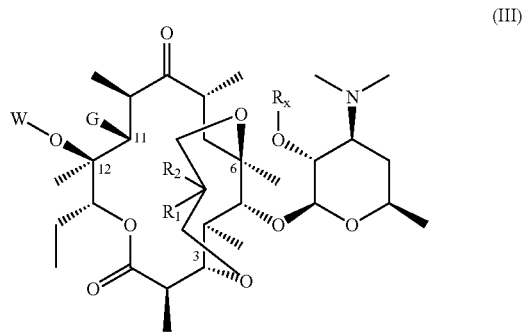

where W, $R_1$, $R_2$ and $R_x$ are as previously defined.

In a fourth embodiment of the compounds of the present invention are compounds represented by formula IV as illustrated below, or a pharmaceutically acceptable salt, ester or prodrug thereof:

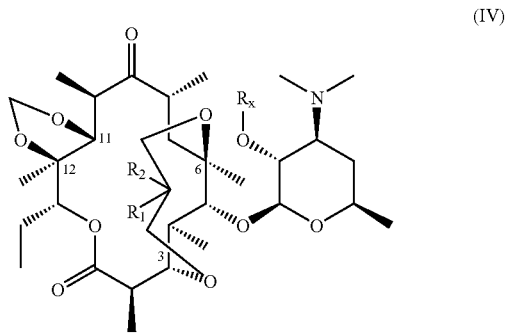

where $R_1$, $R_2$ and $R_x$ are as previously defined.

In a fifth embodiment of the compounds of the present invention are compounds represented by formula V as illustrated below, or a pharmaceutically acceptable salt, ester or prodrug thereof:

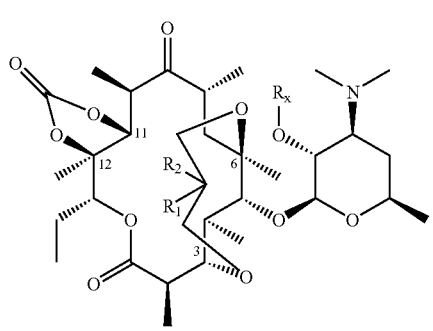

(V)

where $R_1$, $R_2$ and $R_x$ are as previously defined.

In a sixth embodiment of the compounds of the present invention are compounds represented by formula VI as illustrated below, or a pharmaceutically acceptable salt, ester or prodrug thereof:

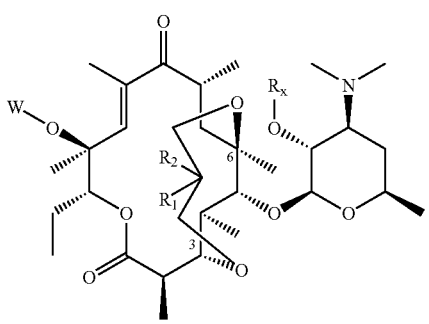

(VI)

where W, $R_1$, $R_2$ and $R_x$ are as previously defined.

In a seventh embodiment of the compounds of the present invention are compounds represented by formula VII as illustrated below, or a pharmaceutically acceptable salt, ester or prodrug thereof:

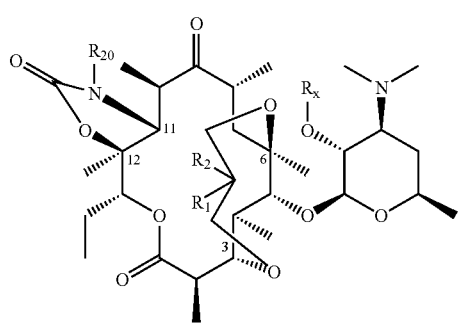

(VII)

where $R_1$, $R_2$, $R_{20}$ and $R_x$ are as previously defined.

In an eighth embodiment of the compounds of the present invention are compounds represented by formula VIII as illustrated below, or a pharmaceutically acceptable salt, ester or prodrug thereof:

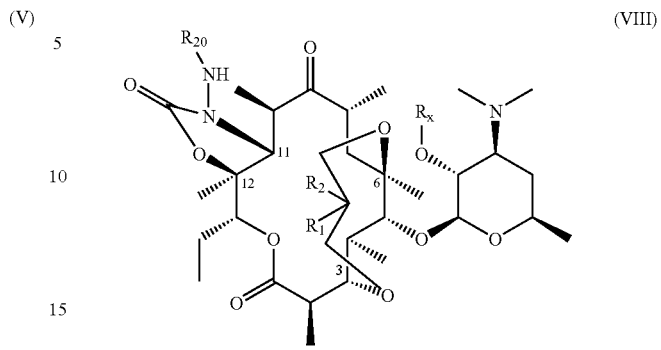

(VIII)

where $R_1$, $R_2$, $R_x$ and $R_{20}$ are as previously defined.

In a ninth embodiment of the compounds of the present invention are compounds represented by formula IX as illustrated below, or a pharmaceutically acceptable salt, ester or prodrug thereof:

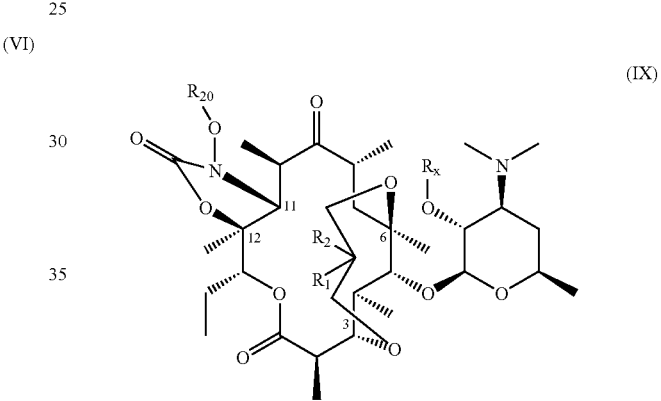

(IX)

where $R_1$, $R_2$, $R_x$ and $R_{20}$ are as previously defined.

In a tenth embodiment of the compounds of the present invention are compounds represented by formula X as illustrated below, or a pharmaceutically acceptable salt, ester or prodrug thereof:

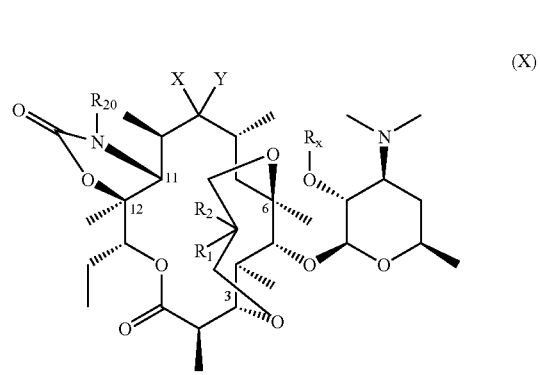

(X)

where $R_1$, $R_2$, X, Y, $R_{20}$ and $R_x$ are as previously defined.

Representative compounds according to the invention are those selected from the group consisting of:

Compounds (1)-(10) of the formula A:

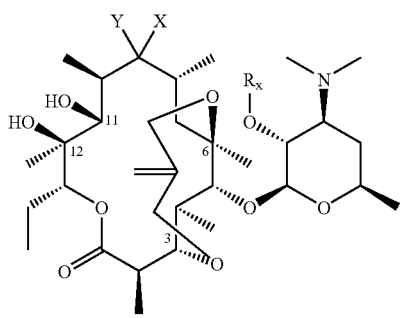

(A)

wherein X and Y taken together with the carbon to which they are attached (CXY) and Rx are delineated for each example in TABLE 1:

TABLE 1

| Compound | CXY | Rx |
|---|---|---|
| (1) | C=NOAc | Ac |
| (2) | C=NOBz | Bz |
| (3) | C=NOSiEt$_3$ | SiEt$_3$ |
| (4) | ![cyclohexyl oxime isopropyl ether] C=NO-C(cyclohexyl)-O-iPr | Ac |
| (5) | C=NO-C(Me)$_2$-O-iPr | Ac |
| (6) | C=NOH | H |
| (7) | C=NH | H |
| (8) | CH(NH$_2$) | H |

TABLE 1-continued

| Compound | CXY | Rx |
|---|---|---|
| (9) | C=O | H |
| (10) | C=O | Ac |
| (10a) | C=NAc | Ac |
| (10b) | C=NAc | H |

(11) Compound of formula V, wherein $R_1$ and $R_2$ taken together with the carbon atom to which they are attached are C=CH$_2$, and Rx=Ac.

(12) Compound of formula V, wherein $R_1$ and $R_2$ taken together with the carbon atom to which they are attached are C=CH$_2$, and Rx=H.

(13) Compound of formula VI, wherein $R_1$ and $R_2$ taken together with the carbon atom to which they are attached are C=CH$_2$, W=C(O)-(imidazol-1-yl) and Rx=H.

Further representative species of the present invention are:

Compounds (14)-(300) of the formula (VII):

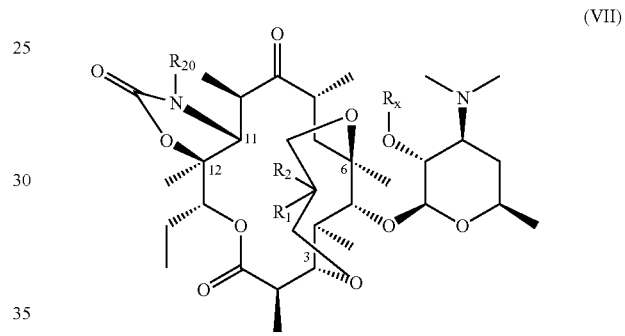

(VII)

wherein $R_1$ and $R_2$ taken together with the carbon to which they are attached (CR$_1$R$_2$), $R_{20}$ and Rx are delineated for each example in Table 2.

TABLE 2

| Compound | R$_{20}$ | CR$_1$R$_2$ | Rx |
|---|---|---|---|
| (14) | H | C=CH$_2$ | Ac |
| (15) | H | C=CH$_2$ | H |
| (16) | H | C=O | Ac |
| (17) | H | C=O | H |
| (18) | -(CH$_2$)$_4$-Ph | C=CH$_2$ | Ac |
| (19) | -(CH$_2$)$_4$-Ph | C=CH$_2$ | H |
| (20) | -(CH$_2$)$_3$-Ph | C=CH$_2$ | Ac |

TABLE 2-continued

| Compound | R$_{20}$ | CR$_1$R$_2$ | Rx |
|---|---|---|---|
| (21) | HN-CH$_2$CH$_2$-phenyl | C=CH$_2$ | H |
| (22) | HN-(CH$_2$)$_3$-phenyl | C=CH$_2$ | Ac |
| (23) | HN-CH$_2$CH$_2$-(1-naphthyl) | C=CH$_2$ | H |
| (24) | HN-CH$_2$CH$_2$-(2-naphthyl) | C=CH$_2$ | Ac |
| (25) | CH$_3$-N-CH$_2$CH$_2$-(2-naphthyl) | C=CH$_2$ | H |
| (26) | -(CH$_2$)$_4$-[1,2,3-triazol-1-yl]-4-(pyridin-3-yl) | C=CH$_2$ | Ac |
| (27) | -(CH$_2$)$_4$-[1,2,3-triazol-1-yl]-4-(pyridin-3-yl) | C=CH$_2$ | H |
| (28) | -(CH$_2$)$_4$-[tetrazol-2-yl]-5-(pyridin-3-yl) | C=CH$_2$ | Ac |
| (29) | -(CH$_2$)$_4$-[tetrazol-2-yl]-5-(pyridin-3-yl) | C=CH$_2$ | H |
| (30) | -(CH$_2$)$_4$-phenyl | C=O | Ac |

TABLE 2-continued
| Compound | R$_{20}$ | CR$_1$R$_2$ | Rx |
|---|---|---|---|
| (31) | 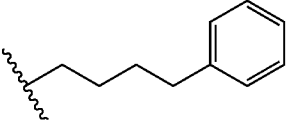 | C=O | H |
| (32) | 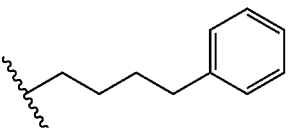 | CHCH$_3$ | H |
| (33) | 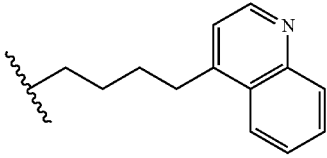 | C=CH$_2$ | Ac |
| (34) | 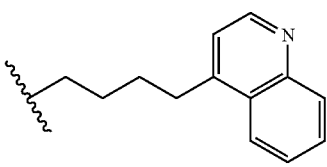 | C=CH$_2$ | H |
| (35) | H | C=NO[CH$_2$Ph] | Ac |
| (36) | H | C=NO[CH$_2$Ph] | H |
| (37) | H | C=NO[(CH$_2$)$_2$Ph] | Ac |
| (38) | H | C=NO[(CH$_2$)$_2$Ph] | H |
| (39) | H | C=NO[(CH$_2$)$_3$Ph] | Ac |
| (40) | H | C=NO[(CH$_2$)$_3$Ph] | H |
| (41) | H | C=NO[(CH$_2$)$_4$Ph] | Ac |
| (42) | H | C=NO[(CH$_2$)$_4$Ph] | H |
| (43) | H | C=NO[Ph] | Ac |
| (44) | H | C=NO[Ph] | H |
| (45) | H | C=NO[(CH$_2$)$_5$Ph] | Ac |
| (46) | H | C=NO[(CH$_2$)$_5$Ph] | H |
| (47) | H | 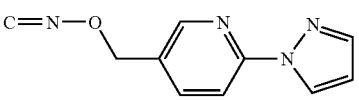 | Ac |
| (48) | H | 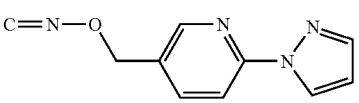 | H |
| (49) | H | 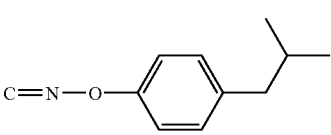 | Ac |
| (50) | H | 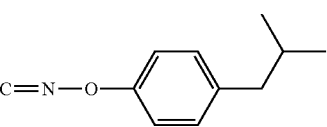 | H |
| (51) | H | 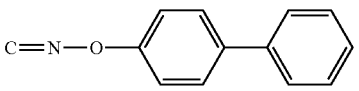 | Ac |
| (52) | H | 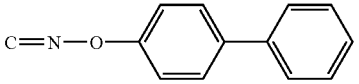 | H |

TABLE 2-continued

| Compound | $R_{20}$ | $CR_1R_2$ | Rx |
|---|---|---|---|
| (53) | H | C=N—O—(2-naphthyl) | Ac |
| (54) | H | C=N—O—(2-naphthyl) | H |
| (55) | H | C=N—O—(3-pyridyl) | Ac |
| (56) | H | C=N—O—(3-pyridyl) | H |
| (57) | H | C=NNH[Ph] | Ac |
| (58) | H | C=NNH[Ph] | H |
| (59) | H | C=CH[CH=CHPh] | Ac |
| (60) | H | CH(CH$_2$)$_3$Ph | H |
| (61) | H | CHCH$_3$ | H |
| (62) | H | CHOH | Ac |
| (63) | H | CHOH | H |
| (64) | H | C=N—O—(3-benzyloxyphenyl) | Ac |
| (65) | H | C=N—O—(3-benzyloxyphenyl) | H |
| (66) | H | C=N—O—(4-chlorophenyl) | Ac |
| (67) | H | C=N—O—(4-chlorophenyl) | H |
| (68) | H | C=N—O—(3-chlorophenyl) | Ac |
| (69) | H | C=N—O—(3-chlorophenyl) | H |
| (70) | H | C=N—O—(2-chlorophenyl) | Ac |

TABLE 2-continued
| Compound | R20 | CR1R2 | Rx |
|---|---|---|---|
| (71) | H | 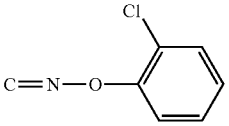 | H |
| (72) | H | 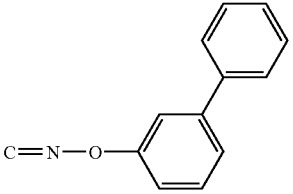 | Ac |
| (73) | H | 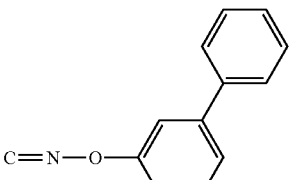 | H |
| (74) | H | 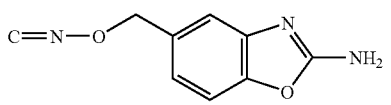 | Ac |
| (75) | H | 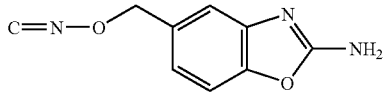 | H |
| (76) | H | 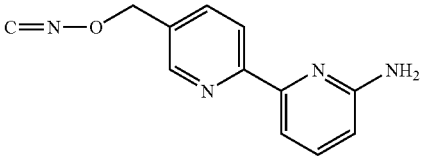 | Ac |
| (77) | H | 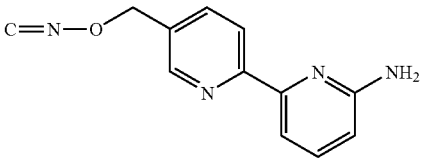 | H |
| (78) | 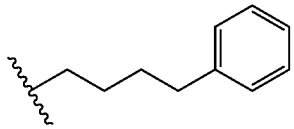 | C=NO[Ph] | Ac |
| (79) | 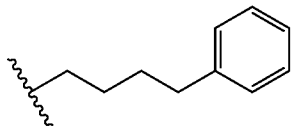 | C=NO[Ph] | H |
| (80) | 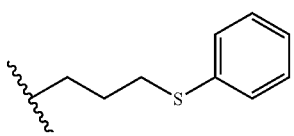 | C=CH2 | H |

TABLE 2-continued

| Compound | R$_{20}$ | CR$_1$R$_2$ | Rx |
| --- | --- | --- | --- |
| (81) | [3-(benzylthio)propyl group] | C=CH$_2$ | H |
| (82) | H | C=N—O—CH$_2$—C≡CH | Ac |
| (83) | H | C=N—O—CH$_2$—C≡CH | H |
| (84) | H | C=N—O—CH$_2$—(2-(thiazol-2-yl)phenyl) | Ac |
| (85) | H | C=N—O—CH$_2$—(2-(thiazol-2-yl)phenyl) | H |
| (86) | H | C=N—O—CH$_2$—(3-(thiazol-2-yl)phenyl) | Ac |
| (87) | H | C=N—O—CH$_2$—(3-(thiazol-2-yl)phenyl) | H |
| (88) | H | C=N—O—CH$_2$—(4-(thiazol-2-yl)phenyl) | Ac |
| (89) | H | C=N—O—CH$_2$—(4-(thiazol-2-yl)phenyl) | H |
| (90) | H | C=N—O—CH$_2$—(1H-benzotriazol-1-yl) | Ac |

TABLE 2-continued
| Compound | R20 | CR1R2 | Rx |
|---|---|---|---|
| (91) | H | 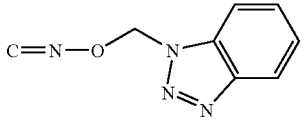 | H |
| (92) | H | 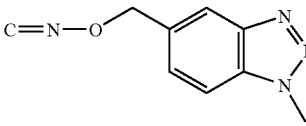 | Ac |
| (93) | H | 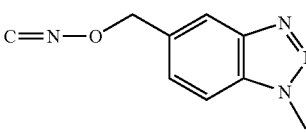 | H |
| (94) | H | 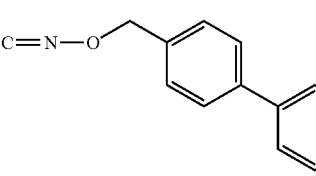 | Ac |
| (95) | H | 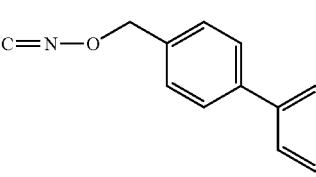 | H |
| (96) | H | 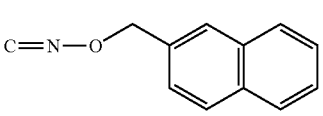 | Ac |
| (97) | H | 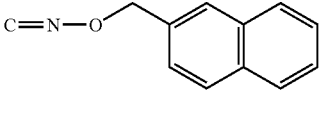 | H |
| (98) | H | 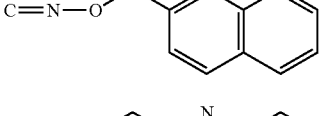 | Ac |
| (99) | H | 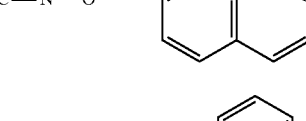 | H |
| (100) | H | 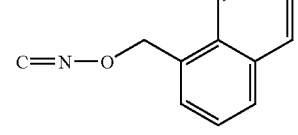 | Ac |
| (101) | H | 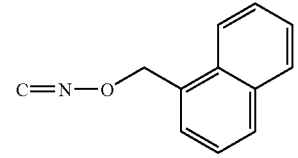 | H |

TABLE 2-continued
| Compound | $R_{20}$ | $CR_1R_2$ | Rx |
|---|---|---|---|
| (102) | H | 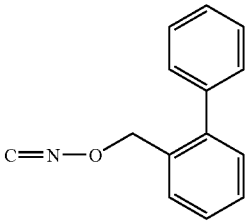 | Ac |
| (103) | H | 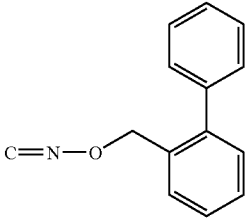 | H |
| (104) | H | 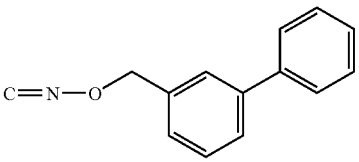 | Ac |
| (105) | H | 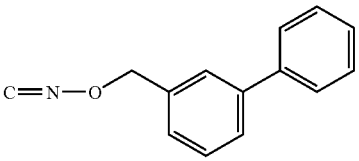 | H |
| (106) | H | 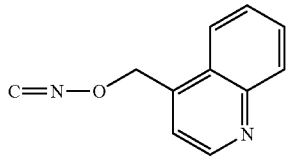 | Ac |
| (107) | H | 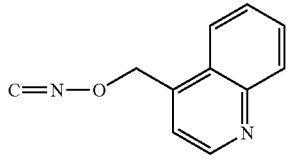 | H |
| (108) | H | 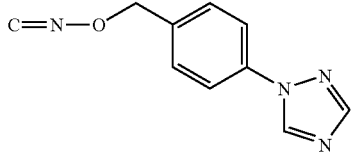 | Ac |
| (109) | H | 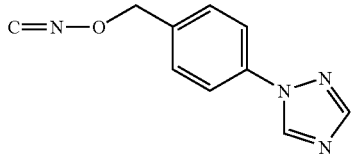 | H |

TABLE 2-continued

| Compound | R₂₀ | CR₁R₂ | Rx |
| --- | --- | --- | --- |
| (110) | H | C=N-O-CH₂-[1,3,4-oxadiazole]-(4-methylphenyl) | Ac |
| (111) | H | C=N-O-CH₂-[1,3,4-oxadiazole]-(4-methylphenyl) | H |
| (112) | H | C=N-O-CH₂-quinoxalinyl | Ac |
| (113) | H | C=N-O-CH₂-quinoxalinyl | H |
| (114) | H | C=N-O-CH₂-(3-(1H-pyrazol-1-yl)phenyl) | Ac |
| (115) | H | C=N-O-CH₂-(3-(1H-pyrazol-1-yl)phenyl) | H |
| (116) | H | C=N-O-CH₂-(3-(3-methyl-1H-pyrazol-1-yl)phenyl) | Ac |
| (117) | H | C=N-O-CH₂-(3-(3-methyl-1H-pyrazol-1-yl)phenyl) | H |
| (118) | H | phenyl-C≡C-CH₂- | Ac |
| (119) | H | phenyl-C≡C-CH₂- | H |

TABLE 2-continued
| Compound | $R_{20}$ | $CR_1R_2$ | Rx |
|---|---|---|---|
| (120) | H | 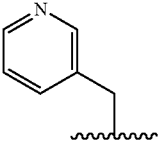 | Ac |
| (121) | H | 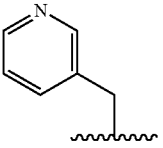 | H |
| (122) | H | 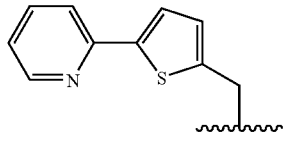 | Ac |
| (123) | H | 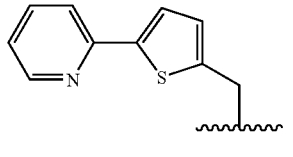 | H |
| (124) | H | 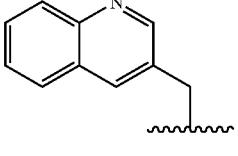 | Ac |
| (125) | H | 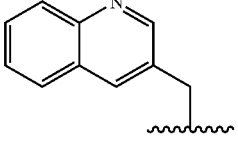 | H |
| (126) | H | 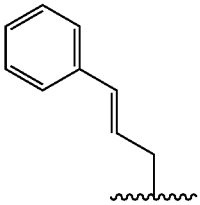 | Ac |
| (127) | H | 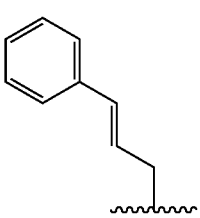 | H |
| (128) | H | 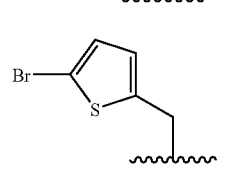 | Ac |

TABLE 2-continued
| Compound | R20 | CR1R2 | Rx |
|---|---|---|---|
| (129) | H | 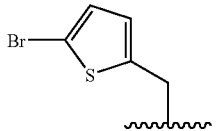 5-bromothien-2-ylmethyl | H |
| (130) | H | 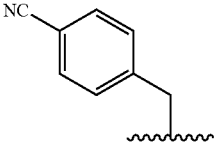 4-cyanobenzyl | Ac |
| (131) | H | 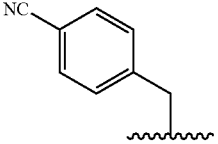 4-cyanobenzyl | H |
| (132) | H | 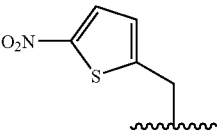 5-nitrothien-2-ylmethyl | Ac |
| (133) | H | 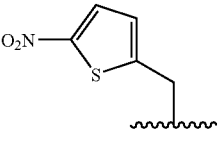 5-nitrothien-2-ylmethyl | H |
| (134) | H | C=N—OH | Ac |
| (135) | H | C=N—OH | H |
| (136) | H | 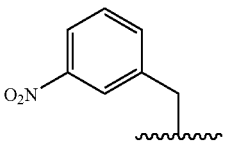 3-nitrobenzyl | Ac |
| (137) | H | 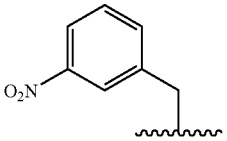 3-nitrobenzyl | H |
| (138) | H | 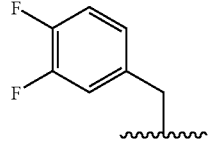 3,4-difluorobenzyl | Ac |
| (139) | H | 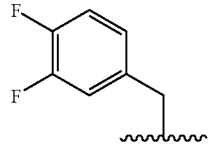 3,4-difluorobenzyl | H |
| (140) | H | 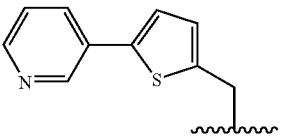 5-(pyridin-3-yl)thien-2-ylmethyl | Ac |

TABLE 2-continued
| Compound | R20 | CR1R2 | Rx |
|---|---|---|---|
| (141) | H | 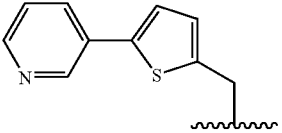 | H |
| (142) | H | 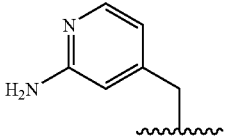 | Ac |
| (143) | H | 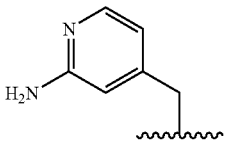 | H |
| (144) | H | 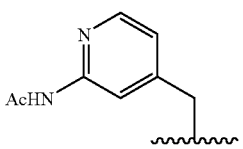 | Ac |
| (145) | H | 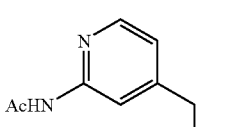 | H |
| (146) | H | 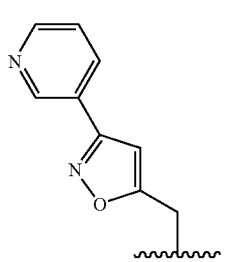 | Ac |
| (147) | H | 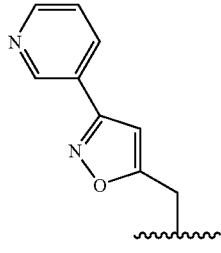 | H |
| (148) | H | 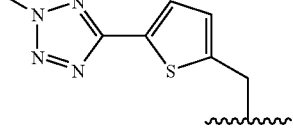 | Ac |

TABLE 2-continued

| Compound | R₂₀ | CR₁R₂ | Rx |
|---|---|---|---|
| (149) | H | 2-methyl-tetrazol-5-yl-thiophene-CH₂- | H |
| (150) | H | 4-(pyrazol-1-yl)phenyl-CH₂- | Ac |
| (151) | H | 4-(pyrazol-1-yl)phenyl-CH₂- | H |
| (152) | H | 4-(1,2,3-thiadiazol-4-yl)phenyl-CH₂- | Ac |
| (153) | H | 4-(1,2,3-thiadiazol-4-yl)phenyl-CH₂- | H |
| (154) | H | 4-(imidazol-1-yl)phenyl-CH₂- | Ac |
| (155) | H | 4-(imidazol-1-yl)phenyl-CH₂- | H |
| (156) | H | C≡N-O-CH₂-(1H-[1,2,3]triazolo[4,5-b]pyridin-7-yl) | Ac |

TABLE 2-continued

| Compound | R20 | CR1R2 | Rx |
|---|---|---|---|
| (157) | H | C=N-O-CH2-(triazolopyridine, 1H-[1,2,3]triazolo[4,5-b]pyridin-7-yl) | H |
| (158) | H | C=N-O-CH2-(2,2'-bipyridin-6-yl) | Ac |
| (159) | H | C=N-O-CH2-(2,2'-bipyridin-6-yl) | H |
| (160) | H | C=N-O-CH2-(6'-fluoro-2,3'-bipyridin-6-yl) | Ac |
| (161) | H | C=N-O-CH2-(6'-fluoro-2,3'-bipyridin-6-yl) | H |
| (162) | H | C=N-O-CH2-(6-(pyrimidin-5-yl)pyridin-2-yl) | Ac |
| (163) | H | C=N-O-CH2-(6-(pyrimidin-5-yl)pyridin-2-yl) | H |
| (164) | H | C=N-O-CH2-(2'-chloro-2,3'-bipyridin-6-yl) | Ac |
| (165) | H | C=N-O-CH2-(2'-chloro-2,3'-bipyridin-6-yl) | H |

TABLE 2-continued

| Compound | R20 | CR1R2 | Rx |
|---|---|---|---|
| (166) | H | [pyridine-fluoropyridine oxime methyl structure] | Ac |
| (167) | H | [pyridine-fluoropyridine oxime methyl structure] | H |
| (168) | H | [pyridine-pyrimidine oxime methyl structure] | Ac |
| (169) | H | [pyridine-pyrimidine oxime methyl structure] | H |
| (170) | H | [pyridine-pyridine oxime methyl structure] | Ac |
| (171) | H | [pyridine-pyridine oxime methyl structure] | H |
| (172) | H | [pyridine-bromopyrimidine oxime methyl structure] | Ac |
| (173) | H | [pyridine-bromopyrimidine oxime methyl structure] | H |
| (174) | H | [pyridine-pyrimidine oxime methyl structure] | Ac |

TABLE 2-continued

| Compound | $R_{20}$ | $CR_1R_2$ | Rx |
|---|---|---|---|
| (175) | H | C=N—O—CH₂-(pyridine)-(pyrimidine) | H |
| (176) | H | C=N—O—CH₂-(pyridine)-(pyridine-NH₂) | Ac |
| (177) | H | C=N—O—CH₂-(pyridine)-(pyridine-NH₂) | H |
| (178) | H | C=N—O—CH₂-(pyridine)-(pyridine-OH) | H |
| (179) | H | C=N—O—CH₂-(pyridine)-(pyrazine-NH₂) | Ac |
| (180) | H | C=N—O—CH₂-(pyridine)-(pyrazine-NH₂) | H |
| (181) | H | C=N—O—CH₂-(pyridine-CN) | Ac |
| (182) | H | C=N—O—CH₂-(pyridine-CN) | H |
| (183) | H | C=N—O—CH₂-(pyridine)-(pyridazine-Cl) | Ac |

TABLE 2-continued

| Compound | R20 | CR1R2 | Rx |
|---|---|---|---|
| (184) | H | [structure: C=N-O-CH2-pyridine-pyridazine-Cl] | H |
| (185) | H | [structure: C=N-O-CH2-pyridine-pyridazine] | H |
| (186) | H | [structure: C=N-O-CH2-phenyl-CN] | Ac |
| (187) | H | [structure: C=N-O-CH2-phenyl-CN] | H |
| (188) | H | [structure: C=N-O-CH2-thiophene-pyridine-NH2] | Ac |
| (189) | H | [structure: C=N-O-CH2-thiophene-pyridine-NH2] | H |
| (190) | H | [structure: C=N-O-CH2-pyridine-pyrazine-NH2] | Ac |
| (191) | H | [structure: C=N-O-CH2-pyridine-pyrazine-NH2] | H |
| (192) | H | [structure: C=N-O-CH2-pyridine-pyridine-NH2] | Ac |

TABLE 2-continued

| Compound | R20 | CR1R2 | Rx |
|---|---|---|---|
| (193) | H | C=N-O-CH2-(pyridine)-(pyridine)-NH2 | H |
| (194) | H | C=N-O-CH2-(pyridine)-(pyridine)(NH2) | Ac |
| (195) | H | C=N-O-CH2-(pyridine)-(pyridine)(NH2) | H |
| (196) | H | C=N-O-CH2-(pyridine)-(pyridine)-NH2 | Ac |
| (197) | H | C=N-O-CH2-(pyridine)-(pyridine)-NH2 | H |
| (198) | H | C=N-O-CH2-(pyridine)-(phenyl)-NH2 | Ac |
| (199) | H | C=N-O-CH2-(pyridine)-(phenyl)-NH2 | H |
| (200) | H | C=N-O-CH2-(pyridine)-NH2 | Ac |
| (201) | H | C=N-O-CH2-(pyridine)-NH2 | H |

TABLE 2-continued

| Compound | R₂₀ | CR₁R₂ | Rx |
| --- | --- | --- | --- |
| (202) | H | C=N—O—CH₂-(6-hydroxypyridin-2-yl) | H |
| (203) | H | C=N—O—CH₂-(6'-amino-[2,3'-bipyridin]-6-yl) | Ac |
| (204) | H | C=N—O—CH₂-(6'-amino-[2,3'-bipyridin]-6-yl) | H |
| (205) | H | C=N—O—CH₂-(pyridin-2-yl) | Ac |
| (206) | H | C=N—O—CH₂-(pyridin-2-yl) | H |
| (207) | H | C=N—O—CH(CH₃)-(pyridin-2-yl) | Ac |
| (208) | H | C=N—O—CH(CH₃)-(pyridin-2-yl) | H |
| (209) | H | C=N—O—CH₂-[3-(1H-tetrazol-5-yl)phenyl] | Ac |
| (210) | H | C=N—O—CH₂-[3-(1H-tetrazol-5-yl)phenyl] | H |
| (211) | CH₃ | C=CH₂ | Ac |
| (212) | CH₃ | C=CH₂ | H |
| (213) | CH₃ | C=O | Ac |
| (214) | CH₃ | C=O | H |

TABLE 2-continued

| Compound | R20 | CR1R2 | Rx |
|---|---|---|---|
| (215) | CH3 | C=N—O—CH2-pyrido[2,3-b]pyrazin-8-yl | Ac |
| (216) | CH3 | C=N—O—CH2-pyrido[2,3-b]pyrazin-8-yl | H |
| (217) | CH3 | C=N—O—CH2-(6'-amino-2,2'-bipyridin-6-yl) | Ac |
| (218) | CH3 | C=N—O—CH2-(6'-amino-2,2'-bipyridin-6-yl) | H |
| (219) | H | C=N—NH—C(O)—C6H5 | Ac |
| (220) | H | C=N—NH—C(O)—C6H5 | H |
| (221) | H | C=N—NH—C(O)-pyridin-2-yl | Ac |
| (222) | H | C=N—NH—C(O)-pyridin-2-yl | H |
| (223) | H | C=N—NH—S(O)2—C6H5 | Ac |

TABLE 2-continued
| Compound | R20 | CR1R2 | Rx |
|---|---|---|---|
| (224) | H | 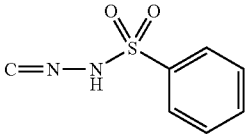 | H |
| (225) | H | 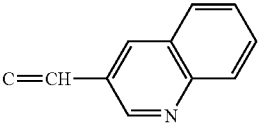 | Ac |
| (226) | H | 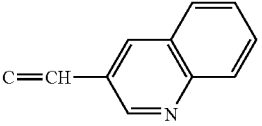 | H |
| (227) | H | 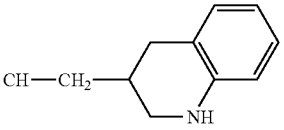 | H |
| (228) | H | 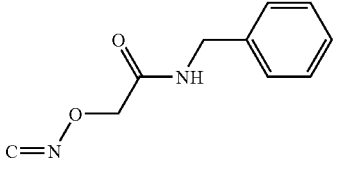 | Ac |
| (229) | H | 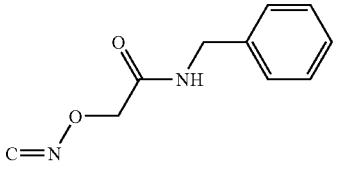 | H |
| (230) | H | 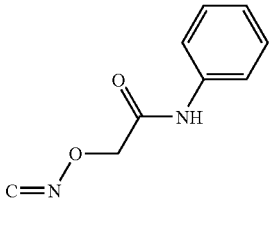 | Ac |
| (231) | H | 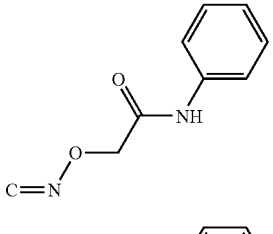 | H |
| (232) | H | 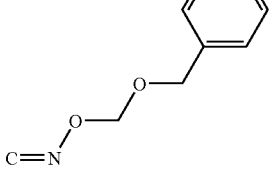 | Ac |

TABLE 2-continued

| Compound | R₂₀ | CR₁R₂ | Rx |
| --- | --- | --- | --- |
| (233) | H | C(=N-O-CH₂-O-CH₂-C₆H₅) | H |
| (234) | H | C(=N-O-[pyrrolidin-3-yl-N-(pyridin-2-yl)]) | Ac |
| (235) | H | C(=N-O-[pyrrolidin-3-yl-N-(pyridin-2-yl)]) | H |
| (236) | H | C(=N-O-CH₂CH₂-O-C₆H₅) | Ac |
| (237) | H | C(=N-O-CH₂CH₂-O-C₆H₅) | H |
| (238) | H | C(=N-O-CH₂CH₂-S-C₆H₅) | Ac |
| (239) | H | C(=N-O-CH₂CH₂-S-C₆H₅) | H |

TABLE 2-continued
| Compound | R20 | CR1R2 | Rx |
|---|---|---|---|
| (240) | H | 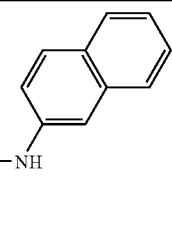 | Ac |
| (241) | H | 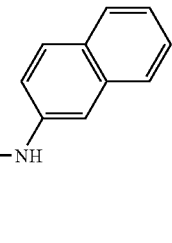 | H |
| (242) | H | 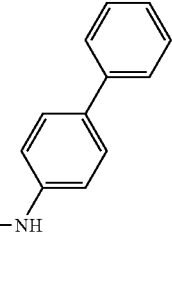 | Ac |
| (243) | H | 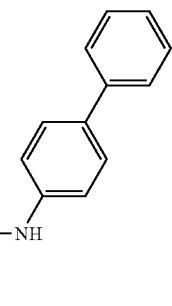 | H |
| (244) | H | 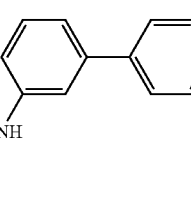 | Ac |
| (245) | H | 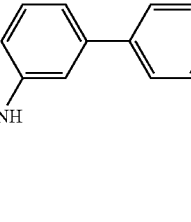 | H |

TABLE 2-continued

| Compound | $R_{20}$ | $CR_1R_2$ | Rx |
|---|---|---|---|
| (246) | H | 2-phenylphenyl-NH-C(O)-CH$_2$-O-N=C | Ac |
| (247) | H | 2-phenylphenyl-NH-C(O)-CH$_2$-O-N=C | H |
| (248) | H | naphthalen-1-yl-CH$_2$-NH-C(O)-CH$_2$-O-N=C | Ac |
| (249) | H | naphthalen-1-yl-CH$_2$-NH-C(O)-CH$_2$-O-N=C | H |
| (250) | H | quinolin-4-yl-CH$_2$-NH-C(O)-CH$_2$-O-N=C | Ac |
| (251) | H | quinolin-4-yl-CH$_2$-NH-C(O)-CH$_2$-O-N=C | H |

TABLE 2-continued

| Compound | R20 | CR1R2 | Rx |
|---|---|---|---|
| (252) | H | benzamide-N-CH2CH2-O-N=C | Ac |
| (253) | H | benzamide-N-CH2CH2-O-N=C | H |
| (254) | H | naphthalenesulfonamide-N-CH2CH2-O-N=C | Ac |
| (255) | H | naphthalenesulfonamide-N-CH2CH2-O-N=C | H |
| (256) | H | quinoline-4-carboxamide-N-CH2CH2-O-N=C | Ac |
| (257) | H | quinoline-4-carboxamide-N-CH2CH2-O-N=C | H |
| (258) | H | quinoxalin-2-yl-CH2-O-N=C | Ac |

TABLE 2-continued

| Compound | R20 | CR1R2 | Rx |
|---|---|---|---|
| (259) | H | quinoxalin-2-yl-CH=N-O-CH2 | H |
| (260) | H | quinazolin-4-yl-CH=N-O-CH2 | Ac |
| (261) | H | quinazolin-4-yl-CH=N-O-CH2 | H |
| (262) | H | 2,1,3-benzothiadiazol-4-yl-CH=N-O-CH2 | Ac |
| (263) | H | 2,1,3-benzothiadiazol-4-yl-CH=N-O-CH2 | H |
| (264) | H | pyrido[2,3-b]pyrazin-3-yl-CH=N-O-CH2 | Ac |
| (265) | H | pyrido[2,3-b]pyrazin-3-yl-CH=N-O-CH2 | H |
| (266) | H | cinnolin-4-yl-CH=N-O-CH2 | Ac |

TABLE 2-continued

| Compound | R20 | CR1R2 | Rx |
|---|---|---|---|
| (267) | H | [cinnoline-CH2-O-N=C] | H |
| (268) | H | [amino-pyrido-pyrazine-CH2-O-N=C] | Ac |
| (269) | H | [amino-pyrido-pyrazine-CH2-O-N=C] | H |
| (270) | H | [1,5-naphthyridine-CH2-O-N=C] | Ac |
| (271) | H | [1,5-naphthyridine-CH2-O-N=C] | H |
| (272) | H | [amino-1,5-naphthyridine-CH2-O-N=C] | Ac |
| (273) | H | [amino-1,5-naphthyridine-CH2-O-N=C] | H |
| (274) | H | [1,5-naphthyridine-CH2-O-N=C] | Ac |

TABLE 2-continued
| Compound | R20 | CR1R2 | Rx |
|---|---|---|---|
| (275) | H | 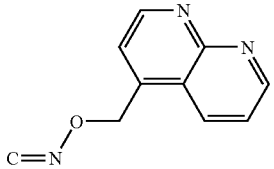 | H |
| (276) | H | 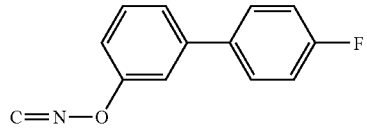 | H |
| (277) | H | 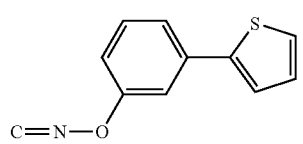 | Ac |
| (278) | H | 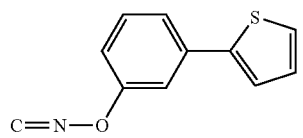 | H |
| (279) | H | 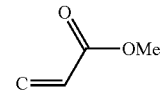 | Ac |
| (280) | H | 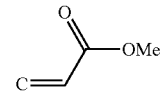 | H |
| (281) | H | 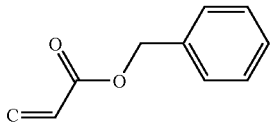 | Ac |
| (282) | H | 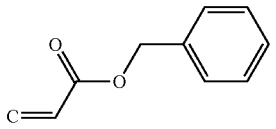 | H |
| (283) | H | 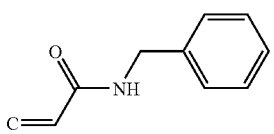 | Ac |
| (284) | H | 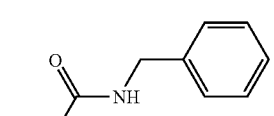 | H |
| (285) | H | 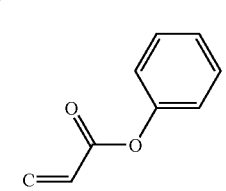 | Ac |

TABLE 2-continued

| Compound | $R_{20}$ | $CR_1R_2$ | Rx |
| --- | --- | --- | --- |
| (286) | H | phenyl acrylate (C=CH-C(=O)-O-Ph) | H |
| (287) | H | N-phenyl acrylamide (C=CH-C(=O)-NH-Ph) | Ac |
| (288) | H | N-phenyl acrylamide (C=CH-C(=O)-NH-Ph) | H |
| (289) | H | N-(naphthalen-1-yl) acrylamide | Ac |
| (290) | H | N-(naphthalen-1-yl) acrylamide | H |
| (291) | H | N-(naphthalen-2-yl) acrylamide | Ac |
| (292) | H | N-(naphthalen-2-yl) acrylamide | H |
| (293) | H | N-(quinolin-3-yl) acrylamide | Ac |

TABLE 2-continued

| Compound | R$_{20}$ | CR$_1$R$_2$ | Rx |
|---|---|---|---|
| (294) | H | quinolin-3-yl-NH-C(=O)-CH=CH- | H |
| (295) | H | quinolin-4-yl-O-CH$_2$-CH=CH- | Ac |
| (296) | H | quinolin-4-yl-O-CH$_2$-CH=CH- | H |
| (297) | H | phenyl-NH-CH$_2$-CH=CH- | Ac |
| (298) | H | phenyl-NH-CH$_2$-CH=CH- | H |
| (299) | H | quinolin-3-yl-NH-CH$_2$-CH=CH- | Ac |
| (300) | H | quinolin-3-yl-NH-CH$_2$-CH=CH- | H |

Further representative species of the present invention are:

Compounds (301)-(425) of the formula (VII):

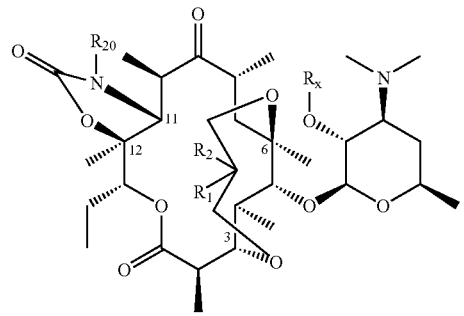

(VII)

wherein $R_1$, $R_2$, $R_{20}$ and Rx are delineated for each example in Table 3.

TABLE 3

| Compound | $R_{20}$ | $R_1$ | $R_2$ | Rx |
|---|---|---|---|---|
| (301) | H | cyclohexyl-C(=NO-iPr)- | OH | Ac |
| (302) | H | cyclohexyl-C(=NO-iPr)- | OH | H |
| (303) | H | (CH3)2C(=NO-iPr)- | H | Ac |
| (304) | H | (CH3)2C(=NO-iPr)- | H | H |
| (305) | H | -(CH2)4-Ph | H | Ac |
| (306) | H | -(CH2)4-Ph | H | H |
| (307) | H | -(CH2)4-Ph | H | Ac |
| (308) | H | -(CH2)4-Ph | H | H |

TABLE 3-continued

| Compound | $R_{20}$ | $R_1$ | $R_2$ | Rx |
|---|---|---|---|---|
| (309) | H | -(CH2)4-Ph | H | H |
| (310) | H | PhCH2CH2-NH- | H | Ac |
| (311) | H | PhCH2CH2-NH- | H | H |
| (312) | H | Ph(CH2)3-NH- | H | Ac |
| (313) | H | Ph(CH2)3-NH- | H | H |
| (314) | H | (1-naphthyl)-CH2CH2-NH- | H | Ac |
| (315) | H | (1-naphthyl)-CH2CH2-NH- | H | H |
| (316) | H | (2-naphthyl)-CH2CH2-NH- | H | Ac |
| (317) | H | (2-naphthyl)-CH2CH2-NH- | H | H |
| (318) | H | (2-naphthyl)-CH2CH2-N(CH3)- | H | H |

TABLE 3-continued

| Compound | R20 | R1 | R2 | Rx |
|---|---|---|---|---|
| (319) | H | [1-(pyridin-2-yl)-1H-1,2,3-triazol-4-yl]pentyl | H | Ac |
| (320) | H | [1-(pyridin-3-yl)-1H-1,2,3-triazol-4-yl]pentyl | H | H |
| (321) | H | [1-(pyridin-2-yl)-1H-1,2,3-triazol-4-yl]pentyl | H | Ac |
| (322) | H | [1-(pyridin-3-yl)-1H-1,2,3-triazol-4-yl]pentyl | H | H |
| (323) | H | OH (R−) | H | Ac |
| (324) | H | [2-(pyridin-3-yl)-2H-tetrazol-5-yl]pentyl | H | Ac |
| (325) | H | [2-(pyridin-3-yl)-2H-tetrazol-5-yl]pentyl | H | H |
| (326) | H | [2-(pyridin-3-yl)-2H-tetrazol-5-yl]pentyl | H | Ac |
| (327) | H | [2-(pyridin-3-yl)-2H-tetrazol-5-yl]pentyl | H | H |
| (328) | H | OSO2CH3 (S−) | H | Ac |
| (329) | H | N3 | H | Ac |
| (330) | H | N3 | H | H |
| (331) | H | NH2 | H | Ac |
| (332) | H | NH2 | H | H |
| (333) | H | 5-phenylpentyl | H | Ac |

TABLE 3-continued

| Compound | R20 | R1 | R2 | Rx |
|---|---|---|---|---|
| (334) | H | 5-phenylpentyl | H | H |
| (335) | H | 5-phenylpentyl | H | Ac |
| (336) | H | 4-phenylbutyl | H | H |
| (337) | H | 4-phenylbutyl | H | Ac |
| (338) | H | 5-phenylpentyl | H | H |
| (339) | H | 4-(quinolin-4-yl)butyl | H | Ac |
| (340) | H | 4-(quinolin-4-yl)butyl | H | H |
| (341) | H | 4-(quinolin-4-yl)butyl | H | Ac |
| (342) | H | 4-(quinolin-4-yl)butyl | H | H |
| (343) | H | C=N−O−CH2−[6-(1H-pyrazol-1-yl)pyridin-3-yl] | H | Ac |

TABLE 3-continued
| Compound | R20 | R1 | R2 | Rx |
|---|---|---|---|---|
| (344) | H |  | H | H |
| (345) | H |  | H | Ac |
| (346) | H |  | H | H |
| (347) | H |  | H | Ac |
| (348) | H |  | H | H |
| (349) | H |  | H | Ac |
| (350) | H |  | H | H |
| (351) | H |  | H | Ac |
| (352) | H |  | H | H |
| (353) | H |  | H | Ac |
| (354) | H |  | H | H |
| (355) | H |  | H | Ac |
| (356) | H |  | H | H |
TABLE 3-continued
| Compound | R20 | R1 | R2 | Rx |
|---|---|---|---|---|
| (357) | H |  | H | Ac |
| (358) | H |  | H | H |
| (359) | H |  | H | Ac |
| (360) | H |  | H | H |
| (361) | H |  | H | Ac |
| (362) | H |  | H | H |
| (363) | H |  | H | Ac |
| (364) | H |  | H | H |
| (365) | H |  | H | Ac |
| (366) | H |  | H | H |
| (367) | H |  | H | Ac |
| (368) | H |  | H | H |
| (369) | H |  | H | Ac |

TABLE 3-continued
| Compound | R20 | R1 | R2 | Rx |
|---|---|---|---|---|
| (370) | H | 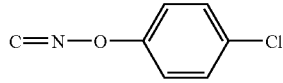 | H | H |
| (371) | H | 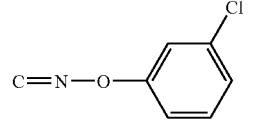 | H | Ac |
| (372) | H | 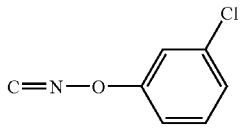 | H | H |
| (373) | H | 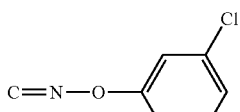 | H | Ac |
| (374) | H | 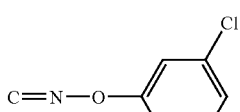 | H | H |
| (375) | H | 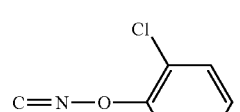 | H | Ac |
| (376) | H | 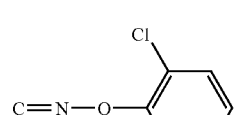 | H | H |
| (377) | H | 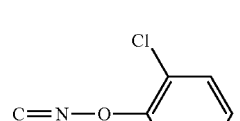 | H | Ac |
| (378) | H | 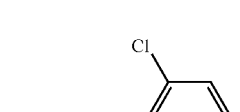 | H | H |
| (379) | H | 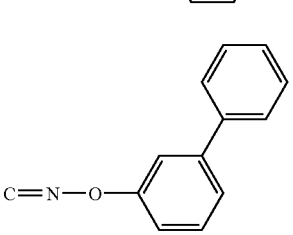 | H | Ac |
TABLE 3-continued
| Compound | R20 | R1 | R2 | Rx |
|---|---|---|---|---|
| (380) | H | 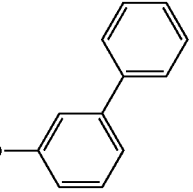 | H | Ac |
| (381) | H | 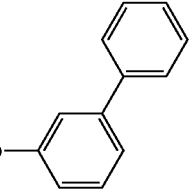 | H | H |
| (382) | H | 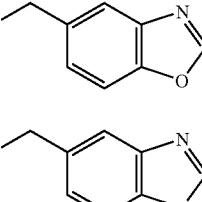 | H | Ac |
| (383) | H | 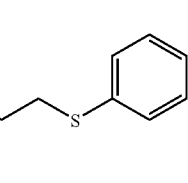 | H | H |
| (384) | H | 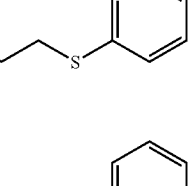 | H | Ac |
| (385) | H | 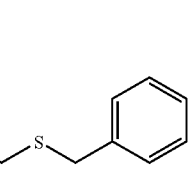 | H | H |
| (386) | H | 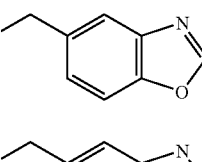 | H | Ac |
| (387) | H | 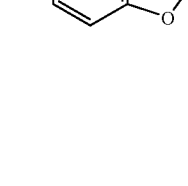 | H | H |
| (388) | H |  | H | Ac |
| (389) | H |  | H | H |

TABLE 3-continued
| Compound | R20 | R1 | R2 | Rx |
|---|---|---|---|---|
| (390) | H |  | H | Ac |
| (391) | H |  | H | H |
| (392) | H |  | H | Ac |
| (393) | H |  | H | H |
| (394) | H |  | H | Ac |
| (395) | H |  | H | H |
| (396) | H |  | H | Ac |
| (397) | H |  | H | H |
| (398) | H | 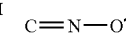 | H | Ac |
| (399) | H | 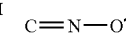 | H | H |
| (400) | H |  | H | Ac |
| (401) | H |  | H | H |
| (402) | H |  | H | H |
| (403) | H |  | H | Ac |
| (404) | H |  | H | H |
| (405) | H |  | H | Ac |
| (406) | H |  | H | H |
| (407) | H |  | H | Ac |
| (408) | H |  | H | H |
| (409) | H |  | H | Ac |

TABLE 3-continued

| Compound | R$_{20}$ | R$_1$ | R$_2$ | Rx |
|---|---|---|---|---|
| (410) | H | C=N—O—CH$_2$-(2-naphthyl) | H | H |
| (411) | H | C=N—O—CH$_2$-(2-quinolinyl) | H | Ac |
| (412) | H | C=N—O—CH$_2$-(2-quinolinyl) | H | H |
| (413) | H | C=N—O—CH$_2$-(1-naphthyl) | H | Ac |
| (414) | H | C=N—O—CH$_2$-(1-naphthyl) | H | H |
| (415) | H | C=N—O—CH$_2$-(2-biphenyl) | H | Ac |
| (416) | H | C=N—O—CH$_2$-(2-biphenyl) | H | H |
| (417) | H | C=N—O—CH$_2$-(3-biphenyl) | H | Ac |
| (418) | H | C=N—O—CH$_2$-(3-biphenyl) | H | H |
| (419) | H | C=N—O—CH$_2$-(4-quinolinyl) | H | Ac |
| (420) | H | C=N—O—CH$_2$-(4-quinolinyl) | H | H |
| (421) | H | C=N—O—CH$_2$-[4-(1,2,4-triazol-1-yl)phenyl] | H | Ac |
| (422) | H | C=N—O—CH$_2$-[4-(1,2,4-triazol-1-yl)phenyl] | H | H |
| (423) | H | C=N—O—CH$_2$-[5-(4-methylphenyl)-1,3,4-oxadiazol-2-yl] | H | H |
| (424) | H | C=N—O—CH$_2$-(6-quinoxalinyl) | H | H |
| (425) | H | C=N—O—CH$_2$-[3-(pyrazol-1-yl)phenyl] | H | H |

(426) Compound of formula VIII, wherein R$_1$ and R$_2$ taken together with the carbon atom to which they are attached are C=CH$_2$, R$_{20}$=H, and Rx=Ac.

(427) Compound of formula VIII, wherein R$_1$ and R$_2$ taken together with the carbon atom to which they are attached are C=CH$_2$, and R$_{20}$=Rx=H.

(428) Compound of formula VIII, wherein R$_1$ and R$_2$ taken together with the carbon atom to which they are attached are C=CH$_2$, R$_{20}$=(phenylpropyl), and Rx=Ac.

(429) Compound of formula IX, wherein $R_1$ and $R_2$ taken together with the carbon atom to which they are attached are C=$CH_2$, $R_{20}$=H, and Rx=Ac.

(430) Compound of formula IX, wherein $R_1$ and $R_2$ taken together with the carbon atom to which they are attached are C=$CH_2$, and $R_{20}$=Rx=H.

(431) Compound of formula IX, wherein $R_1$ and $R_2$ taken together with the carbon atom to which they are attached are C=$CH_2$, $R_{20}$=(phenylpropyl) and Rx=Ac.

(432) Compound of formula II, wherein $R_1$ and $R_2$ taken together with the carbon atom to which they are attached are C(OH)$CH_2$OH, W=$R_{20}$=H, and $R_6$=Rx=Bz.

(433) Compound of formula II, wherein $R_1$ and $R_2$ taken together with the carbon atom to which they are attached are C(OH)$CH_2$OH, and W=$R_{20}$=$R_6$=Rx=H.

(434) Compound of formula V, wherein $R_1$ and $R_2$ taken together with the carbon atom to which they are attached are C=O, and Rx=Ac.

(435) Compound of formula V, wherein $R_1$ and $R_2$ taken together with the carbon atom to which they are attached are C=O, and Rx=H.

(436) Compound of formula V, wherein $R_1$ and $R_2$ taken together with the carbon atom to which they are attached are C=NO[6'-amino-[2,2']bipyridinyl-4-ylmethyl], and Rx=Ac.

(437) Compound of formula V, wherein $R_1$ and $R_2$ taken together with the carbon atom to which they are attached are C=NO[6'-amino-[2,2']bipyridinyl-4-ylmethyl], and Rx=H.

(438) Compound of formula X, wherein $R_1$ and $R_2$ taken together with the carbon atom to which they are attached are C=$CH_2$, X and Y taken together with the carbon atom to which they are attached are C=NOH, $R_{20}$=H, and Rx=Ac.

(439) Compound of formula X, wherein $R_1$ and $R_2$ taken together with the carbon atom to which they are attached are C=$CH_2$, X and Y taken together with the carbon atom to which they are attached are C=NOH, and $R_{20}$=Rx=H.

(440) Compound of formula X, wherein $R_1$ and $R_2$ taken together with the carbon atom to which they are attached are C=$CH_2$, X and Y taken together with the carbon atom to which they are attached are C=$NOCH_3$, $R_{20}$=H, and Rx=Ac.

(441) Compound of formula X, wherein $R_1$ and $R_2$ taken together with the carbon atom to which they are attached are C=$CH_2$, X and Y taken together with the carbon atom to which they are attached are C=$NOCH_3$, and $R_{20}$=Rx=H.

(442) Compound of formula X, wherein $R_1$ and $R_2$ taken together with the carbon atom to which they are attached are C=$CH_2$, X and Y taken together with the carbon atom to which they are attached are C=$NOCH_2CH_3$, $R_{20}$=H, and Rx=Ac.

(443) Compound of formula X, wherein $R_1$ and $R_2$ taken together with the carbon atom to which they are attached are C=$CH_2$, X and Y taken together with the carbon atom to which they are attached are C=$NOCH_2CH_3$, and $R_{20}$=Rx=H.

(444) Compound of formula X, wherein $R_1$ and $R_2$ taken together with the carbon atom to which they are attached are C=NO[quinoxalin-6-ylmethyl], X and Y taken together with the carbon atom to which they are attached are C=NOH, and $R_{20}$=Rx=H.

Further representative species of the present invention are:

Compounds (445)-(606) of the formula B:

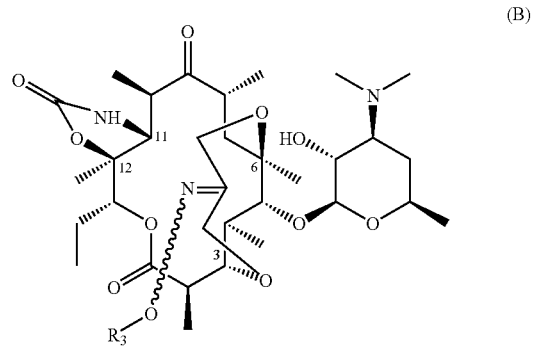

wherein $R_3$ is delineated for each example in Table 4.

TABLE 4

| Compound | $R_3$ |
|---|---|
| (445) | (3-(3-methylpyrazol-1-yl)phenyl)methyleneaminoxy group |
| (446) | 4-phenylbut-3-yn-1-yl |
| (447) | 2-(pyridin-3-yl)ethyl |
| (448) | 2-(5-(pyridin-2-yl)thiophen-2-yl)ethyl |
| (449) | quinolin-3-ylmethyl |
| (450) | 4-phenylbut-3-en-1-yl |

TABLE 4-continued
| Compound | R₃ |
|---|---|
| (451) | 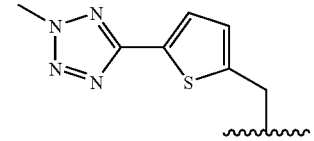 |
| (452) | 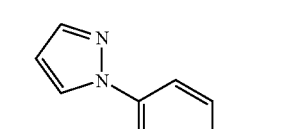 |
| (453) | 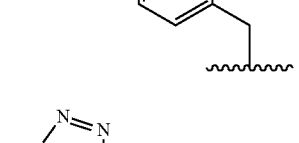 |
| (454) | 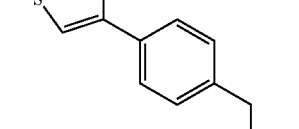 |
| (455) | 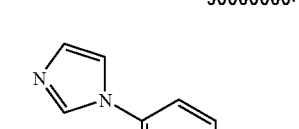 |
| (456) | 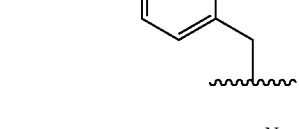 |
| (457) | 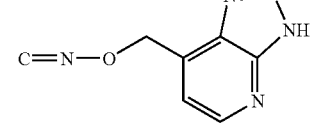 |
| (458) | 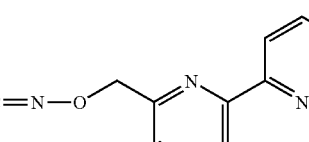 |
| (459) | 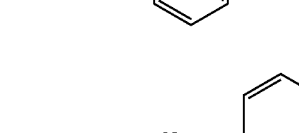 |
| (460) | 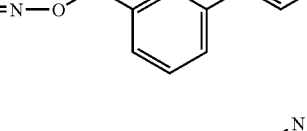 |
| (461) | 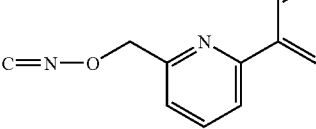 |
| (462) |  |
| (463) |  |
| (464) | |
| (465) | |
| (466) | |
| (467) | |

TABLE 4-continued

| Compound | R₃ |
|---|---|
| (468) | [pyridine-pyridine with Cl, CH₂-O-N=C] |
| (469) | [pyridine-pyridine with F, CH₂-O-N=C] |
| (470) | [pyridine-pyrazine, CH₂-O-N=C] |
| (471) | [pyridine-pyridine, CH₂-O-N=C] |
| (472) | [pyridine-pyrimidine with Br, CH₂-O-N=C] |
| (473) | [pyridine-pyrimidine, CH₂-O-N=C] |
| (474) | [pyridine-pyridine with NH₂, CH₂-O-N=C] |
| (475) | [pyridine-pyridine with OH, CH₂-O-N=C] |
| (476) | [pyridine-pyrazine with NH₂, CH₂-O-N=C] |

TABLE 4-continued

| Compound | R₃ |
|---|---|
| (477) | [pyridine with CN, CH₂-O-N=C] |
| (478) | [pyridine-pyridazine with Cl, CH₂-O-N=C] |
| (479) | [pyridine-pyridazine, CH₂-O-N=C] |
| (480) | [benzene with CN, CH₂-O-N=C] |
| (481) | [thiophene-pyridine with NH₂, CH₂-O-N=C] |
| (482) | [pyridine-pyrazine with NH₂, CH₂-O-N=C] |
| (483) | [pyridine-pyridine with NH₂, CH₂-O-N=C] |
| (484) | [pyridine-pyridine with NH₂, CH₂-O-N=C] |
| (485) | [pyridine-pyridazine with NH₂, CH₂-O-N=C] |

TABLE 4-continued
| Compound | R₃ |
|---|---|
| (486) |  |
| (487) |  |
| (488) |  |
| (489) | 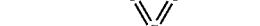 |
| (490) |  |
| (491) |  |
| (492) |  |
| (493) |  |
| (494) |  |
| (495) |  |
| (496) |  |
| (497) |  |
| (498) |  |
| (499) | |
| (500) | |
| (501) | |
| (502) | |
| (503) | |
| (504) | |

TABLE 4-continued

| Compound | R₃ |
|---|---|
| (505) | 2-(phenylthio)ethyl attached via O-N=C |
| (506) | N-(naphthalen-2-yl)-2-(oxyimino)acetamide derivative |
| (507) | N-(biphenyl-4-yl)-2-(oxyimino)acetamide derivative |
| (508) | N-(biphenyl-3-yl)-2-(oxyimino)acetamide derivative |
| (509) | N-(biphenyl-2-yl)-2-(oxyimino)acetamide derivative |
| (510) | N-(naphthalen-1-ylmethyl)-2-(oxyimino)acetamide derivative |
| (511) | N-(quinolin-4-ylmethyl)-2-(oxyimino)acetamide derivative |
| (512) | N-(2-(oxyimino)ethyl)benzamide derivative |
| (513) | N-(2-(oxyimino)ethyl)naphthalene-1-sulfonamide derivative |
| (514) | N-(2-(oxyimino)ethyl)quinoline-4-carboxamide derivative |
| (515) | quinoxalin-2-ylmethyl oxyimino derivative |
| (516) | quinazolin-4-ylmethyl oxyimino derivative |
| (517) | benzo[c][1,2,5]thiadiazol-4-ylmethyl oxyimino derivative |

TABLE 4-continued
| Compound | R₃ |
|---|---|
| (518) |  |
| (519) | 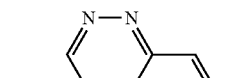 |
| (520) | 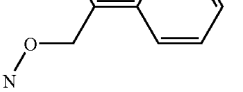 |
| (521) | 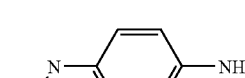 |
| (522) | 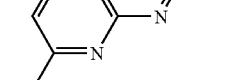 |
| (523) | 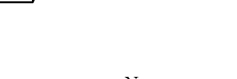 |
| (524) | 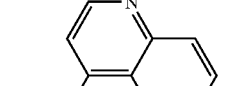 |
| (525) | 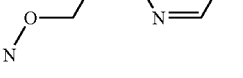 |
| (526) | 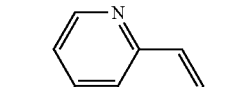 |
| (527) | |
| (528) | |
| (529) | |
| (530) | |
| (531) | |
| (532) | |
| (533) | |
| (534) | |
| (535) | |

TABLE 4-continued
| Compound | R₃ |
|---|---|
| (536) | 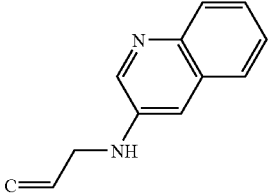 |
| (537) | 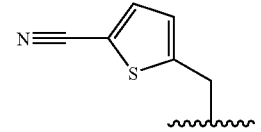 |
| (538) | 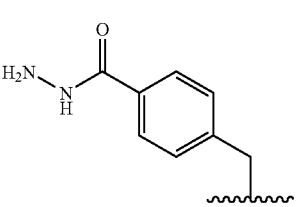 |
| (539) | 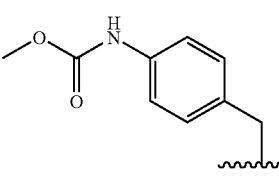 |
| (540) | 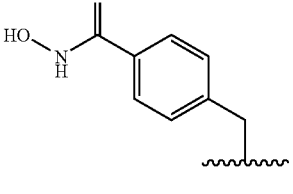 |
| (541) | 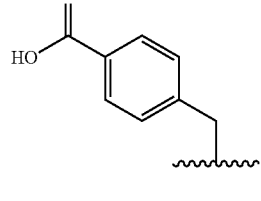 |
| (542) | 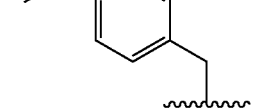 |
| (543) | 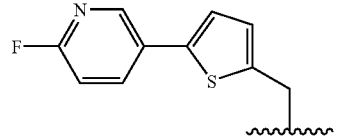 |
| (544) | 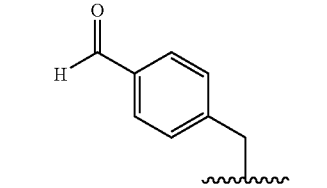 |
| (545) | 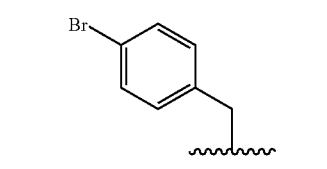 |
| (546) | 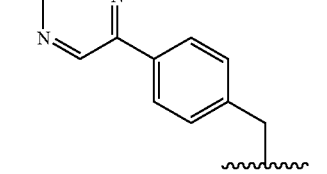 |
| (547) | 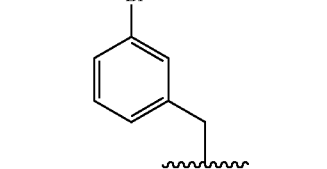 |
| (548) | 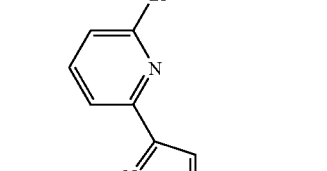 |
| (549) | 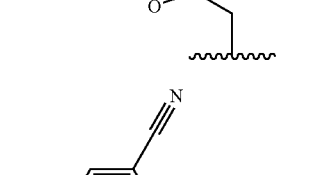 |

TABLE 4-continued
| Compound | R₃ |
|---|---|
| (550) | 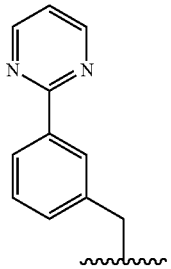 |
| (551) | 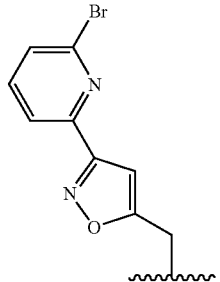 |
| (552) | 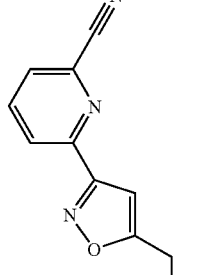 |
| (553) | 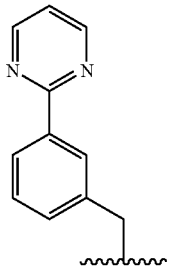 |
| (554) | 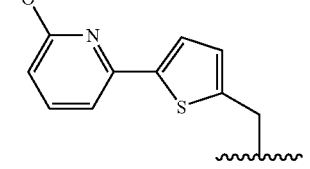 |
| (555) | 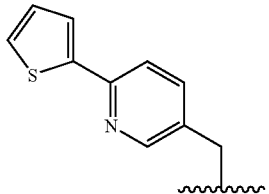 |
TABLE 4-continued
| Compound | R₃ |
|---|---|
| (556) | 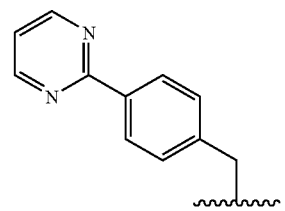 |
| (557) | 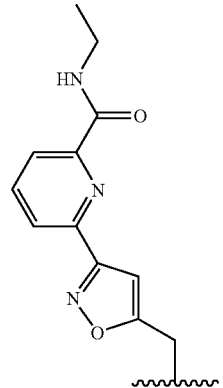 |
| (558) | 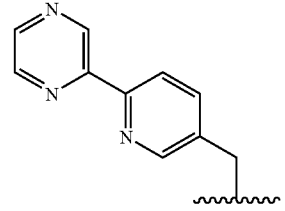 |
| (559) | 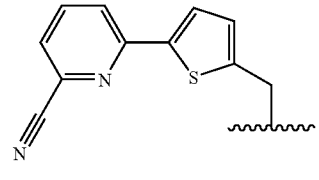 |
| (560) | 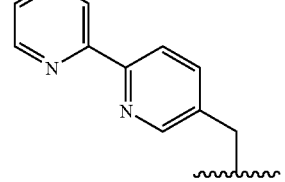 |
| (561) | 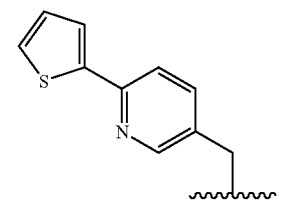 |

TABLE 4-continued
| Compound | R₃ |
|---|---|
| (562) | 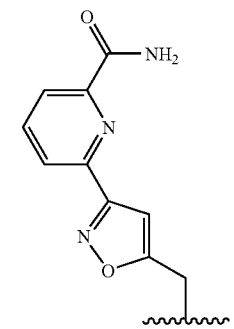 |
| (563) | 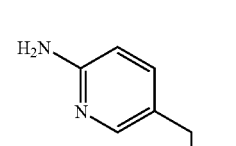 |
| (564) | 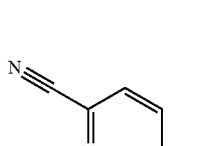 |
| (565) | 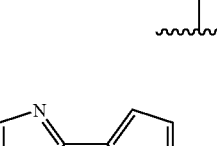 |
| (566) | 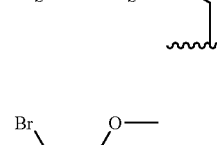 |
| (567) | 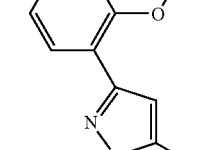 |
| (568) |  |
| (569) |  |
| (570) |  |
| (571) |  |
| (572) |  |
| (573) |  |

TABLE 4-continued
| Compound | R₃ |
|---|---|
| (574) | 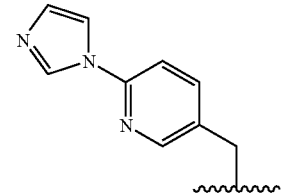 |
| (575) | 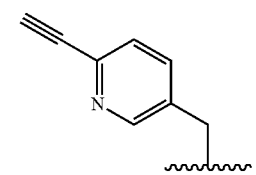 |
| (576) | 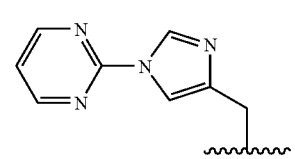 |
| (577) | 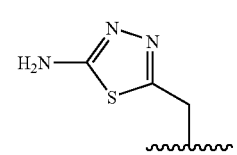 |
| (578) | 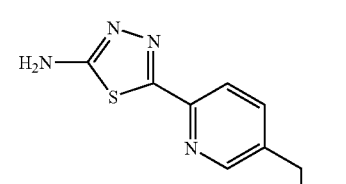 |
| (579) | 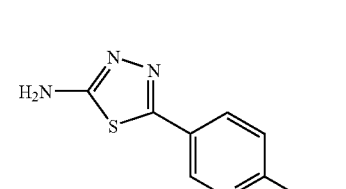 |
| (580) | 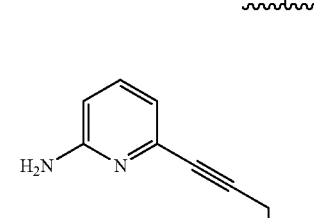 |
| (581) | 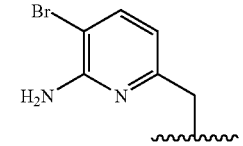 |
| (582) | 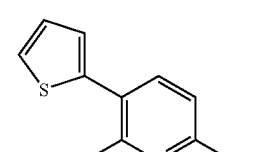 |
| (583) | 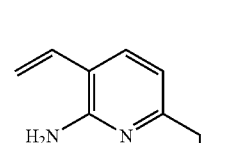 |
| (584) | 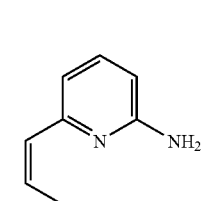 |
| (585) | 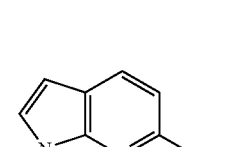 |
| (586) | 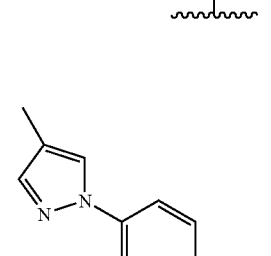 |
| (587) | 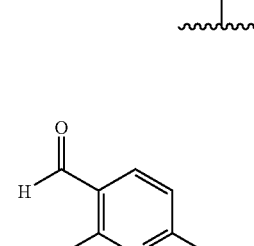 |

TABLE 4-continued

| Compound | R₃ |
|---|---|
| (588) | [triazolyl-pyridyl group] |
| (589) | [5-hydroxy-1,3,4-thiadiazolyl-pyridyl group] |
| (590) | [1,3,4-thiadiazolyl-pyridyl group] |
| (591) | [4-iodo-pyrazolyl-pyridyl group] |
| (592) | [3-methyl-pyrazolyl-pyridyl group] |
| (593) | [3-trifluoromethyl-pyrazolyl-pyridyl group] |
| (594) | [4-vinyl-pyrazolyl-pyridyl group] |

TABLE 4-continued

| Compound | R₃ |
|---|---|
| (595) | [4-cyano-pyrazolyl-pyridyl group] |
| (596) | [pyrazolyl-pyrimidinyl group] |
| (597) | [3-(dimethylaminomethyleneamino)-1,2,4-triazolyl-pyridyl group] |
| (598) | [5-bromothienyl-pyrazolyl-pyridyl group] |
| (599) | [thienyl-pyrazolyl-pyridyl group] |
| (600) | [2-amino-3-(pyrimidin-2-yl)pyridyl group] |
| (601) | [1H-indazol-6-yl group] |

TABLE 4-continued

| Compound | R₃ |
|---|---|
| (602) | [pyrazole-pyridine N-oxide-CH₂ structure] |
| (603) | [pyrazole-fluoropyridine-CH₂ structure] |
| (604) | [2-aminobenzothiazole-CH₂ structure] |
| (605) | [2-aminobenzimidazole-CH₂ structure] |
| (606) | [benzotriazole-CH₂ structure] |

A further embodiment of the present invention includes pharmaceutical compositions comprising any single compound delineated herein, or a pharmaceutically acceptable salt, ester, or prodrug thereof, with a pharmaceutically acceptable carrier or excipient.

Yet another embodiment of the present invention is a pharmaceutical composition comprising a combination of two or more compounds delineated herein, or a pharmaceutically acceptable salt, ester, or prodrug thereof, with a pharmaceutically acceptable carrier or excipient.

Yet a further embodiment of the present invention is a pharmaceutical composition comprising any single compound delineated herein in combination with one or more antibiotics known in the art, or a pharmaceutically acceptable salt, ester, or prodrug thereof, with a pharmaceutically acceptable carrier or excipient.

In addition, the present invention contemplates processes of making any compound delineated herein via any synthetic method delineated herein.

Definitions

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system having one or two aromatic rings including, but not limited to, phenyl, naphthyl, tetrahydronaphthyl, indanyl, idenyl and the like.

The term "heteroaryl," as used herein, refers to a mono- or polycyclic (e.g. bi-, or tri-cyclic or more) aromatic radical or ring having from five to ten ring atoms of which one or more ring atom is selected from, for example, S, O and N; zero, one or two ring atoms are additional heteroatoms independently selected from, for example, S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

In accordance with the invention, any of the aryls, substituted aryls, heteroaryls and substituted heteroaryls described herein, can be any aromatic group. Aromatic groups can be substituted or unsubstituted.

The terms "$C_1$-$C_6$ alkyl," or "$C_1$-$C_{12}$ alkyl," as used herein, refer to saturated, straight- or branched-chain hydrocarbon radicals containing between one and six, or one and twelve carbon atoms, respectively. Examples of $C_1$-$C_6$ alkyl radicals include, but are not limited to, methyl, ethyl, propyl, isopropyl, n-butyl, tert-butyl, neopentyl and n-hexyl radicals; and examples of $C_1$-$C_{12}$ alkyl radicals include, but are not limited to, ethyl, propyl, isopropyl, n-hexyl, octyl, decyl, dodecyl radicals.

The term "$C_2$-$C_6$ alkenyl," as used herein, denotes a monovalent group derived from a hydrocarbon moiety containing from two to six carbon atoms having at least one carbon-carbon double bond by the removal of a single hydrogen atom. Alkenyl groups include, but are not limited to, for example, ethenyl, propenyl, butenyl, 1-methyl-2-buten-1-yl, and the like.

The term "$C_2$-$C_6$ alkynyl," as used herein, denotes a monovalent group derived from a hydrocarbon moiety containing from two to six carbon atoms having at least one carbon-carbon triple bond by the removal of a single hydrogen atom. Representative alkenyl groups include, but are not limited to, for example, ethynyl, 1-propynyl, 1-butynyl, and the like.

The term "$C_3$-$C_{12}$-cycloalkyl," as used herein, denotes a monovalent group derived from a monocyclic or polycyclic saturated carbocyclic ring compound by the removal of a single hydrogen atom. Examples include, but not limited to, cyclopropyl, cyclobutyl, cyclopentyl, cyclohexyl, bicyclo [2.2.1]heptyl, and bicyclo[2.2.2]octyl.

It is understood that any alkyl, alkenyl, alkynyl and cycloalkyl moiety described herein can also be an aliphatic group, an alicyclic group or a heterocyclic group. An "aliphatic group" is non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted.

The term "alicyclic," as used herein, denotes a monovalent group derived from a monocyclic or bicyclic saturated carbocyclic ring compound by the removal of a single hydrogen atom. Examples include, but are not limited to, cyclopropyl, cyclobutyl, cyclopentyl, cyclohexyl, bicyclo[2.2.1]heptyl, and bicyclo[2.2.2]octyl. Such alicyclic groups may be further substituted.

The term "heterocyclic" as used herein, refers to a non-aromatic 5-, 6- or 7-membered ring or a bi- or tri-cyclic group fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, (iv) any of the above rings may be fused to a benzene ring, and (v) the remaining ring atoms are carbon atoms which may be optionally oxo-substituted. Representative heterocycloalkyl groups include, but are not limited to, [1,3] dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl. Such heterocyclic groups may be further substituted.

The terms "substituted aryl", "substituted heteroaryl," "substituted $C_1$-$C_6$ alkyl," or "substituted $C_1$-$C_{12}$ alkyl," "substituted $C_2$-$C_6$ alkenyl," "substituted $C_2$-$C_6$ alkynyl," "substituted $C_1$-$C_8$ alkylene," "substituted $C_2$-$C_8$ alkenylene," "substituted $C_2$-$C_8$ alkynylene," "substituted aliphatic," as used herein, refer to aryl, heteroaryl, $C_1$-$C_6$ alkyl, $C_1$-$C_{12}$ alkyl, $C_2$-$C_6$ alkenyl, $C_2$-$C_6$ alkynyl, $C_1$-$C_8$ alkylene, $C_2$-$C_8$ alkenylene, substituted $C_2$-$C_8$ alkynylene, aliphatic groups as previously defined, substituted by independent replacement of one, two, or three or more of the hydrogen atoms thereon with substituents including, but not limited to, —F, —Cl, —Br, —I, —OH, protected hydroxyl, —$NO_2$, —CN, —$C_1$-$C_{12}$-alkyl optionally substituted with, for example, halogen, $C_2$-$C_{12}$-alkenyl optionally substituted with, for example, halogen, —$C_2$-$C_{12}$-alkynyl optionally substituted with, for example, halogen, —$NH_2$, protected amino, —NH—$C_1$-$C_{12}$-alkyl, —NH—$C_2$-$C_{12}$-alkenyl, —NH—$C_2$-$C_{12}$-alkenyl, —NH—$C_3$-$C_{12}$-cycloalkyl, —NH-aryl, —NH-heteroaryl, —NH-heterocycloalkyl, -dialkylamino, -diarylamino, -diheteroarylaminq, —O—$C_1$-$C_{12}$-alkyl, —O—$C_2$-$C_{12}$-alkenyl, —O—$C_2$-$C_{12}$-alkenyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkenyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_{12}$-alkenyl, —CONH—$C_2$-$C_{12}$-alkenyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_{12}$-alkenyl, —$OCO_2$—$C_2$-$C_{12}$-alkenyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$, —OCONH—$C_1$-$C_{12}$-alkyl, —OCONH—$C_2$-$C_{12}$-alkenyl, —OCONH—$C_2$-$C_{12}$-alkenyl, —OCONH—$C_3$-$C_{12}$-cycloalkyl, —OCONH— aryl, —OCONH— heteroaryl, —OCONH-heterocycloalkyl, —NHC(O)—$C_1$-$C_{12}$-alkyl, —NHC(O)—$C_2$-$C_{12}$-alkenyl, —NHC(O)—$C_2$-$C_{12}$-alkenyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_{12}$-alkenyl, —$NHCO_2$—$C_2$-$C_{12}$-alkenyl, —$NHCO_2$—$C_3$-$C_{12}$-cycloalkyl, —$NHCO_2$—aryl, —$NHCO_2$— heteroaryl, —$NHCO_2$-heterocycloalkyl, —NHC(O)$NH_2$, —NHC(O)NH—$C_1$-$C_{12}$-alkyl, —NHC(O)NH—$C_2$-$C_{12}$-alkenyl, —NHC(O)NH—$C_2$-$C_{12}$-alkenyl, —NHC(O)NH—$C_3$-$C_{12}$-cycloalkyl, —NHC(O)NH-aryl, —NHC(O)NH-heteroaryl, —NHC(O)NH-heterocycloalkyl, —NHC(S)$NH_2$, —NHC(S)NH—$C_1$-$C_{12}$-alkyl, —NHC(S)NH—$C_2$-$C_{12}$-alkenyl, —NHC(S)NH—$C_2$-$C_{12}$-alkenyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)$NH_2$, —NHC(NH)NH—$C_1$-$C_{12}$-alkyl, —NHC(NH)NH—$C_2$-$C_{12}$-alkenyl, —NHC(NH)NH—$C_2$-$C_{12}$-alkenyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_{12}$-alkenyl, —NHC(NH)—$C_2$-$C_{12}$-alkenyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkenyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkenyl, —S(O)—$C_3$-$C_{12}$-cycloalkyl, —S(O)-aryl, —S(O)-heteroaryl, —S(O)-heterocycloalkyl —$SO_2NH_2$, —$SO_2$NH—$C_1$-$C_{12}$-alkyl, —$SO_2$NH—$C_2$-$C_{12}$-alkenyl, —$SO_2$NH—$C_2$-$C_{12}$-alkenyl, —$SO_2$NH—$C_3$-$C_{12}$-cycloalkyl, —$SO_2$NH—aryl, —$SO_2$NH— heteroaryl, —$SO_2$NH— heterocycloalkyl, —$NHSO_2$—$C_1$-$C_{12}$-alkyl, —$NHSO_2$—$C_2$-$C_{12}$-alkenyl, —$NHSO_2$—$C_2$-$C_{12}$-alkenyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_{12}$-alkenyl, —S—$C_2$-$C_{12}$-alkenyl, —S—$C_3$-$C_{12}$-cycloalkyl, —S-aryl, —S-heteroaryl, —S-heterocycloalkyl, or methylthiomethyl. It is understood that the aryls, heteroaryls, alkyls, and the like can be further substituted.

The term "halogen," as used herein, refers to an atom selected from fluorine, chlorine, bromine and iodine.

The term "hydroxy activating group", as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxy", as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the are described generally in T. H. Greene and P. G. M. Wuts, *Protective Groups in Organic Synthesis,* 3rd edition, John Wiley & Sons, New York (1999). Examples of hydroxylprotecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl(trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxylprotecting groups for the present invention are acetyl (Ac or —C(O) CH$_3$), benzoyl (Bz or —C(O)C$_6$H$_5$), and trimethylsilyl (TMS or —Si(CH$_3$)$_3$).

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group", as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally In Kenneth B. Sloan, *Prodrugs, Topical and Ocular Drug Delivery*, (Drugs and the Pharmaceutical Sciences; Volume 53), Marcel Dekker, Inc., New York (1992).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally In T. H. Greene and P. G. M. Wuts, *Protective Groups in Organic Synthesis,* 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "protected amino," as used herein, refers to an amino group protected with an amino protecting group as defined above.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, NY, 1986.

The term "protogenic organic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, NY, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described In R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject" as used herein refers to an animal. Preferably the animal is a mammal. More preferably the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of Formula I. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., *Journal of Drug Deliver Reviews,* 8:1-38(1992); Bundgaard, *J. of Pharmaceutical Sciences,* 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

This invention also encompasses pharmaceutical compositions containing, and methods of treating bacterial infections through administering, pharmaceutically acceptable prodrugs of compounds of the formula I. For example, compounds of formula I having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of formula I. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

As used herein, unless otherwise indicated, the term "bacterial infection(s)" or "protozoa infections"; includes, but is not limited to, bacterial infections and protozoa infections that occur in mammals, fish and birds as well as disorders related to bacterial infections and protozoa infections that may be treated or prevented by administering antibiotics such as the compounds of the present invention. Such bacterial infections and protozoa infections and disorders related to such infections include, but are not limited to, the following: pneumonia, otitis media, sinusitus, bronchitis, tonsillitis, cystic fibrosis and mastoiditis related to infection by *Streptococcus pneumoniae, Haemophilus influenzae, Moraxella catarrhalis, Staphylococcus aureus, Peptostreptococcus* spp, or *Pseudomonas* spp.; pharynigitis, rheumatic fever, and glomerulonephritis related to infection by *Streptococcus pyogenes,* Groups C and G streptococci, *Clostridium diptheriae,* or *Actinobacillus haemolyticum*; respiratory tract infections related to infection by *Mycoplasma pneumoniae, Legionella* pneumophila, Streptococcus pneumoniae, Haemophilus influenzae, or Chlamydia pneumoniae; uncomplicated skin and soft tissue infections, abscesses and osteomyelitis, and puerperal fever related to infection by Staphylococcus aureus, coagulase-positive staphylococci (i.e., S. epidermidis, S. hemolyticus, etc.), S. pyogenes, S. agalactiae, Streptococcal groups C-F (minute-colony streptococci), viridans streptococci, Corynebacterium spp., Clostridium spp., or Bartonella henselae; uncomplicated acute urinary tract infections related to infection by S. saprophyticus or Enterococcus spp.; urethritis and cervicitis; and sexually transmitted diseases related to infection by Chlamydia trachomatis, Haemophilus ducreyi, Treponema pallidum, Ureaplasma urealyticum, or Nesseria gonorrheae; toxin diseases related to infection by S. aureus (food poisoning and Toxic shock syndrome), or Groups A, S, and C streptococci; ulcers related to infection by Helicobacter pylori; systemic febrile syndromes related to infection by Borrelia recurrentis; Lyme disease related to infection by Borrelia burgdorferi; conjunctivitis, keratitis, and dacrocystitis related to infection by C. trachomatis, N. gonorrhoeae, S. aureus, S. pneumoniae, S. pyogenes, H. influenzae, or Listeria spp.; disseminated Mycobacterium avium complex (MAC) disease related to infection by Mycobacterium avium, or Mycobacterium intracellulare; gastroenteritis related to infection by Campylobacter jejuni; intestinal protozoa related to infection by Cryptosporidium spp. odontogenic infection related to infection by viridans streptococci; persistent cough related to infection by Bordetella pertussis; gas gangrene related to infection by Clostridium perfringens or Bacteroides spp.; Skin infection by S. aureus, Propionibacterium acne; atherosclerosis related to infection by Helicobacter pylori or Chlamydia pneumoniae; or the like.

Bacterial infections and protozoa infections and disorders related to such infections that may be treated or prevented in animals include, but are not limited to, the following: bovine respiratory disease related to infection by P. haemolytica., P. multocida, Mycoplasma bovis, or Bordetella spp.; cow enteric disease related to infection by E. coli or protozoa (i.e., coccidia, cryptosporidia, etc.), dairy cow mastitis related to infection by S. aureus, S. uberis, S. agalactiae, S. dysgalactiae, Klebsiella spp., Corynebacterium, or Enterococcus spp.; swine respiratory disease related to infection by A. pleuropneumoniae., P. multocida, or Mycoplasma spp.; swine enteric disease related to infection by E. coli, Lawsonia intracellularis, Salmonella spp., or Serpulina hyodyisinteriae; cow footrot related to infection by Fusobacterium spp.; cow metritis related to infection by E. coli; cow hairy warts related to Infection by Fusobacterium necrophorum or Bacteroides nodosus; cow pink-eye related to infection by Moraxella bovis, cow premature abortion related to infection by protozoa (i.e. neosporium); urinary tract infection in dogs and cats related to infection by E. coli; skin and soft tissue infections in dogs and cats related to infection by S. epidermidis, S. intermedius, coagulase neg. Staphylococcus or P. multocida; and dental or mouth infections in dogs and oats related to infection by Alcaligenes spp., Bacteroides spp., Clostridium spp., Enterobacter spp., Eubacterium spp., Peptostreptococcus spp., Porphfyromonas spp., Campylobacter spp., Actinomyces spp., Erysipelothrix spp., Rhodococcus spp., Trypanosoma spp., Plasmodium spp., Babesia spp., Toxoplasma spp., Pneumocystis spp., Leishmania spp., and Trichomonas spp. or Prevotella spp. Other bacterial infections and protozoa infections and disorders related to such infections that may be treated or prevented in accord with the method of the present invention are referred to in J. P. Sanford et al., "The Sanford Guide To Antimicrobial Therapy," 26th Edition, (Antimicrobial Therapy, Inc., 1996).

Antibacterial Activity

Susceptibility tests can be used to quantitatively measure the in vitro activity of an antimicrobial agent against a given bacterial isolate. Compounds are tested for in vitro antibacterial activity by a micro-dilution method. Minimal Inhibitory Concentration (MIC) is determined in 96 well microtiter plates utilizing the appropriate Mueller Hinton Broth medium (CAMHB) for the observed bacterial isolates. Antimicrobial agents are serially diluted (2-fold) in DMSO to produce a concentration range from about 64 µg/ml to about 0.03 µg/ml. The diluted compounds (2 µl/well) are then transferred into sterile, uninoculated CAMHB (0.2 mL) by use of a 96 fixed tip-pipetting station. The inoculum for each bacterial strain is standardized to $5 \times 10^5$ CFU/mL by optical comparison to a 0.5 McFarland turbidity standard. The plates are inoculated with 10 µl/well of adjusted bacterial inoculum. The 96 well plates are covered and incubated at 35+/−2° C. for 24 hours in ambient air environment. Following incubation, plate wells are visually examined by Optical Density measurement for the presence of growth (turbidity). The lowest concentration of an antimicrobial agent at which no visible growth occurs is defined as the MIC. The compounds of the invention generally demonstrated an MIC in the range from about 64 µg/ml to about 0.03 µg/ml.

All in vitro testing follows the guidelines described in the Approved Standards M7-A4 protocol, published by the National Committee for Clinical Laboratory Standards (NCCLS).

The invention further provides compositions and methods of treating patients suffering from an inflammatory condition comprising administering to a patient in need thereof, a therapeutically effective amount of at least one compound of Formulas I-IX, A or B. Specific examples of inflammatory conditions treatable according to the invention include, but are not limited to, scleritis; epi-scleritis; allergic conjunctivitis; pulmonary inflammatory diseases, particularly CF, asthma, chronic obstructive pulmonary disease (COPD), allergic bronchopulmonary aspergillosis (ABPA), and sarcoidosis; procto-sigmoiditis; allergic rhinitis; arthritis; tendonitis; apthous stomatitis; and inflammatory bowel disease.

The invention further provides compositions and methods for i) prophylactic treatment of those patients susceptible to the symptoms CF including pulmonary infection and inflammation associated with CF, ii) treatment at the initial onset of symptoms of pulmonary infection and inflammation associated with CF, and iii) treatment of ongoing or relapsing symptoms of infection and inflammation associated with CF. In accordance with the invention a compound according to any one of Formulas I-IX, A or B, is administered to a patient in need of treatment for CF, in amount sufficient to prevent, diminish or eradicate symptoms of CF including chronic pulmonary inflammation and infection.

Pharmaceutical Compositions.

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminun hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P, and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO 98/43,650 by Montgomery, all of which are incorporated herein by reference). A discussion of pulmonary delivery of antibiotics is also found in U.S. Pat. No. 6,014,969, incorporated herein by reference.

According to the methods of treatment of the present invention, bacterial infections, cystic fibrosis and inflammatory conditions are treated or prevented in a patient such as a human or another animal by administering to the patient a therapeutically effective amount of a compound of the invention, in such amounts and for such time as is necessary to achieve the desired result.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the formulae described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically exipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The pharmaceutical compositions of this invention can be administered orally to fish by blending said pharmaceutical compositions into fish feed or said pharmaceutical compositions may be dissolved in water in which infected fish are placed, a method commonly referred to as a medicated bath. The dosage for the treatment of fish differs depending upon the purpose of administration (prevention or cure of disease) and type of administration, size and extent of infection of the fish to be treated. Generally, a dosage of 5-1000 mg, preferably 20-100 mg, per kg of body weight of fish may be administered per day, either at one time or divided into several times. It will be recognized that the above-specified dosage is only a general range which may be reduced or increased depending upon the age, body weight, condition of disease, etc. of the fish.

Unless otherwise defined, all technical and scientific terms used herein are accorded the meaning commonly known to one of ordinary skill in the art. All publications, patents, published patent applications, and other references mentioned herein are hereby incorporated by reference in their entirety.

Abbreviations

Abbreviations which may be used in the descriptions of the scheme and the examples that follow are:

Ac for acetyl;
AIBN for azobisisobutyronitrile;
Bu$_3$SnH for tributyltin hydride;
CDI for carbonyldiimidazole;
dba for dibenzylidene acetone;

Ms for mesylate or O—SO$_2$—CF$_3$;
NaN(TMS)$_2$ for sodium bis(trimethylsilyl)amide;
NMMO for N-methylmorpholine N-oxide;
TEA for triethylamine;
THF for tetrahydrofuran;
TPP or PPh$_3$ for triphenylphosphine;
MOM for methoxymethyl;
Boc for t-butoxycarbonyl;
Bz for benzoyl;
Bn for benzyl;
Ph for phenyl;
POPd for dihydrogen dichlorobis(di-tert-butylphosphinito-□P)palladate(II);
TBS for tert-butyl dimethylsilyl; or
TMS for trimethylsilyl.

Synthetic Methods

The compounds and processes of the present invention will be better understood in connection with the following synthetic schemes that illustrate the methods by which the compounds of the invention may be prepared.

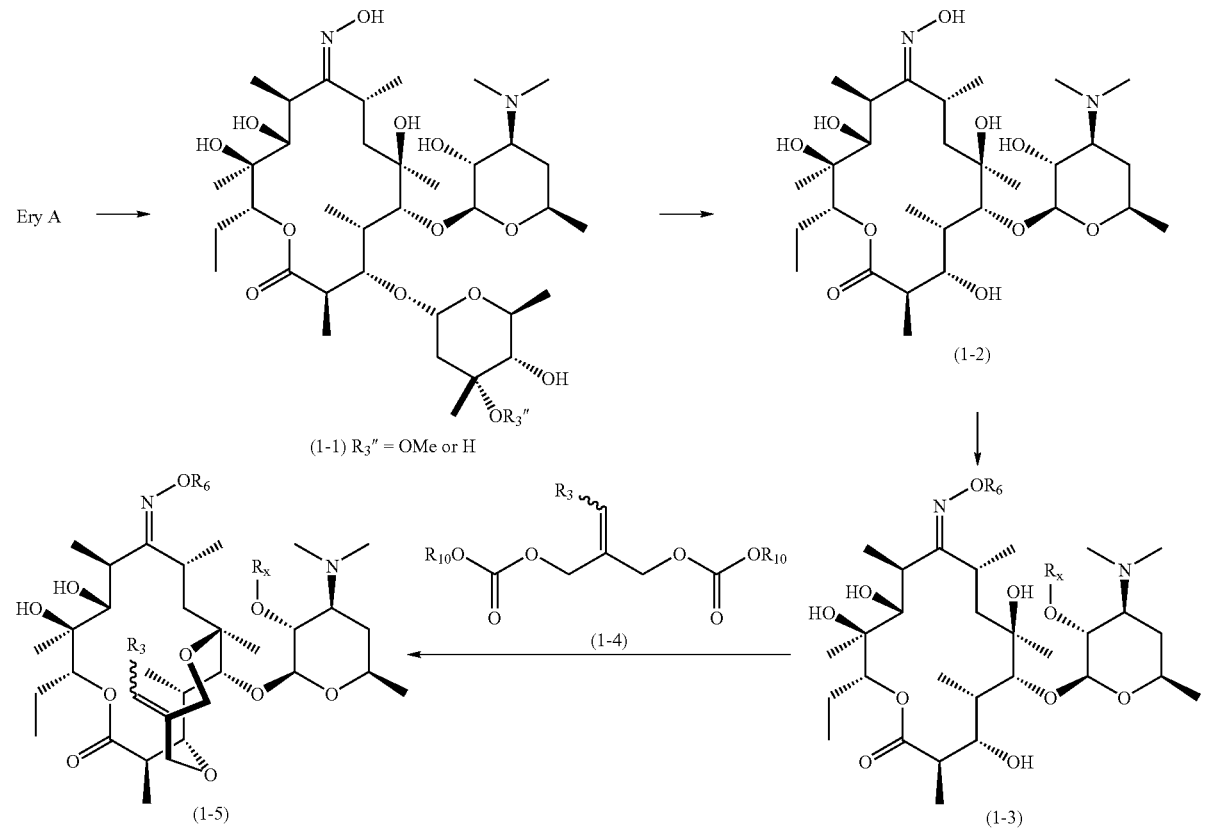

dppb for diphenylphosphino butane;
DBU for 1,8-diazabicyclo[5.4.0]undec-7-ene;
DEAD for diethylazodicarboxylate;
DMAP for dimethylaminopyridine;
DMF for dimethyl formamide;
DPPA for diphenylphosphoryl azide;
EtOAc for ethyl acetate;
MeOH for methanol;

A process of the invention, as illustrated in Scheme 1, involves preparing a compound of formula (1-5) by reacting a compound of formula (1-3) with a suitable alkylating agent.

In accordance with Scheme 1, the 9-keto group of erythromycins can be initially converted into an oxime by methods described in U.S. Pat. No. 4,990,602, followed by removal of the cladinose moiety of the macrolide of formula (1-1) either by mild acid hydrolysis or by enzymatic hydrolysis to afford compounds of formula (1-2). Representative acids include, but are not limited to, dilute hydrochloric acid, sulfueric acid, perchloric acid, chloroacetic acid, dichloroacetic acid or trifluoroacetic acid. Suitable solvents for the reaction include, but are not limited to, methanol, ethanol, isopropanol, butanol, water and mixtures there of. Reaction times are typically 0.5 to 24 hours. The reaction temperature is preferably 0-80° C.

The 2'-hydroxyl and the oxime groups are protected by reaction with suitable hydroxylprotecting reagents. Typical hydroxylprotecting reagents include, but are not limited to, acetylating agents, silylating agents, acid anhydrides, and the like. A more thorough discussion of solvents and conditions for protecting the hydroxyl group can be found in T. W. Greene and P. G. M. Wuts, *Protective Groups in Organic Synthesis*, $3^{rd}$ ed., John Wiley & Son, Inc, 1999. Acetylation of the hydroxyl group is typically accomplished by treating the compound (1-2) with an acetylating reagent such as acetic anhydride to give compound of formula (1-3).

The erythromycin derivative of formula (1-3) is then reacted with an alkylating agent of the formula:

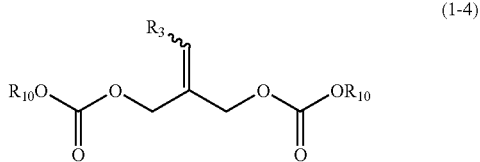

(1-4)

wherein $R_3$ is as previously defined and $R_{10}$ is $—C_1-C_{12}$ alkyl, $—C_1-C_{12}$ alkenyl, or $—C_1-C_{12}$ alkynyl optionally substituted with one or more substitutents selected from halogen, aryl, substituted aryl, heteroaryl, or substituted heteroaryl; $—C_3-C_{12}$ cycloalkyl.

Most palladium (0) catalysts are expected to work in this process. Some palladium (II) catalysts, such as palladium (II) acetate, which is converted into a palladium (0) species in-situ by the actions of a phosphine, will work as well. See, for example, Beller et al. *Angew. Chem. Int. Ed. Engl.,* 1995, 34 (17), 1848. The palladium catalyst can be selected from, but not limited to, palladium (II) acetate, tetrakis(triphenylphosphine)palladium (0), tris(dibenzylideneacetone)dipalladium, tetradibenzylideneacetone)dipalladium and the like. Palladium on carbon and palladium (II) halide catalysts are less preferred than other palladium catalysts for this process.

Suitable phosphines include, but are not limited to, triphenylphosphine, bis(diphenylphosphino)methane, bis(diphenylphosphino)ethane, bis(diphenylphosphino)propane, 1,4-bis(diphenylphosphino)butane, bis(diphenylphosphino)pentane, and tri-o-tolyl-phosphine, and the like. The reaction is carried out in an aprotic solvent, preferably at elevated temperature, preferably at or above 50° C. Suitable aprotic solvents include, but are not limited to, tetrahydrofuran, N,N-dimethylformamide, dimethyl sulfoxide, N-methyl-2-pyrrolidone, toluene, hexamethylphosphoric triamide, 1,2-dimethoxyethane, methyl-tert-butyl ether, heptane, acetonitrile, isopropyl acetate and ethyl acetate.

Generally, the alkylating agents have the formula (1-4) as previously described. The preferred alkylating agents are those wherein $R_{10}$ is tert-butyl, isopropyl or isobutyl. The alkylating reagents are prepared by reaction of a diol with a wide variety of compounds for incorporating the di-carbonate moiety. The compounds include, but are not limited to, tert-butyl chloroformate, di-tert-butyl dicarbonate, and 1-(tert-butoxycarbonyl)imidazole and the reaction is carried out in the presence of an organic or an inorganic base. The temperature of the reaction varies from about −30° C. to approximately 30° C.

An alternative method of converting the alcohol into the carbonate involves treating the alcohol with phosgene or triphosgene to prepare the chloroformate derivative of the diol. The di-chloroformate derivative is then converted into the di-carbonate by the methods described in Cotarca, L., Delogu, P., Nardelli, A., Sunijic, V, *Synthesis,* 1996, 553. The reaction can be carried out in a variety of organic solvents such as dichloromethane, toluene, diethyl ether, ethyl acetate and chloroform in the presence of a base. Examples of suitable bases include, but are not limited to, sodium hydroxide, potassium hydroxide, ammonium hydroxide, sodium carbonate, potassium carbonate, ammonium carbonate, DMAP, pyridine, triethylamine and the like. The temperature can vary from 0° C. to approximately 60° C. The reaction runs to completion in 3 to 5 hours.

Scheme 2

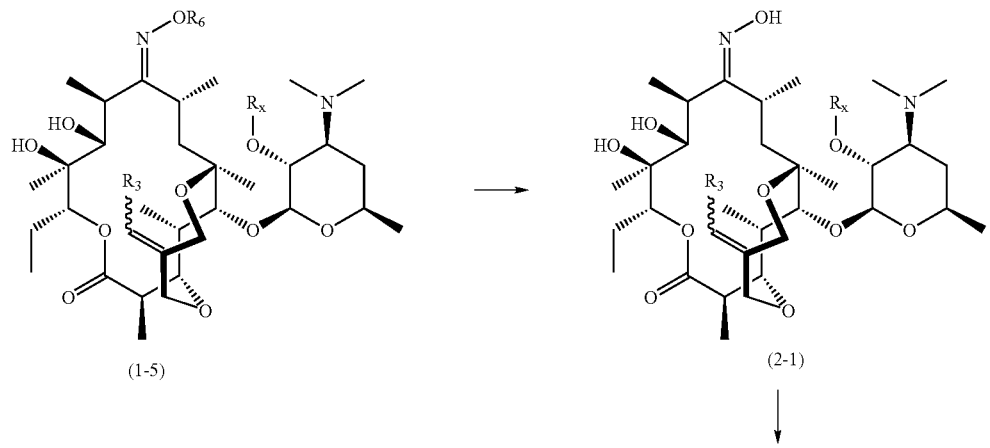

(1-5)    (2-1)

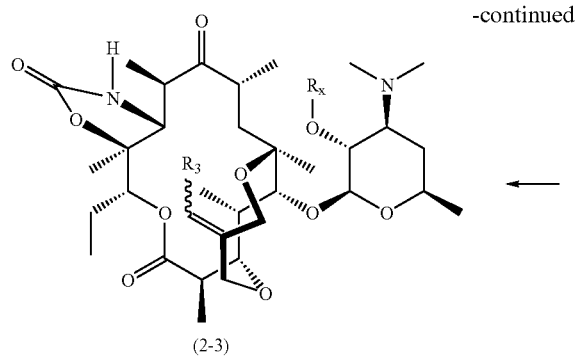
(2-3)

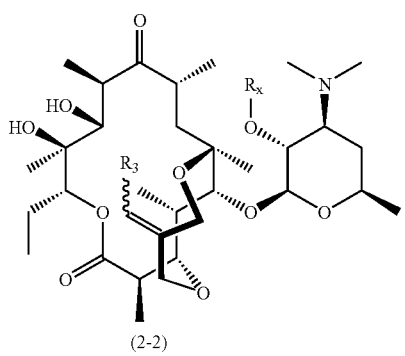
(2-2)

-continued

Scheme 2 outlined the synthesis of intermediate 2-3). Selective deprotection of the oxime is typically accomplished via alkaline hydrolysis in protic solvents. Representative alkali include lithium hydroxide, sodium hydroxide, potassium hydroxide, and the like. Solvents which are applicable include but are not limited to tetrahydrofuran, 1,4-dioxane, 1,2-dimethoxyethane, isopropanol, ethanol, butanol, water and mixtures thereof. The reaction temperature is preferably 0° to 35° C., and reaction time is preferably 0.5 to 24 hours.

In a like fashion, simultaneous deprotection of both the oxime and the 2' hydroxyl can be accomplished under a variey of conditions. Conditions for deprotection include, but are not limited to, treating with an alcoholic solvent at from room temperature to reflux, or treatment with a primary amine, such as butylamine. Alcoholic solvents preferred for the deprotection are methanol and ethanol. A more thorough discussion of the procedures, reagents and conditions for removing protecting groups is described in the literature, for example, by T. W. Greene and P. G. M. Wuts In "Protective Groups in Organic Synthesis" $3^{rd}$ ed., John Wiley & Son, Inc, 1999, referred to above herein.

Deoxygenation of compounds of formula (2-1) under reducing conditions gives the resulting imine followed by hydrolysis by aqueous alcohol at elevated temperature to give compounds of formula (2-2). Many reducing agents can be used to effect this transformation including, but not limited to: lithium aluminum hydride, titanium trichloride, sodium nitrite, sodium thiosulfate, sodium cyanoborohydride, borane, and various sulfides such as sodium hydrogen sulfide, sodium ethoxide. For a more detailed account of oxime reduction see J. March In "Advanced Organic Chemistry" $4^{th}$ ed., Wiley & Son, Inc, 1992, which is incorporated by reference herein.

A particularly useful method for the reduction of oximes to the corresponding imine uses a sulfite reducing agent, such as sodium nitrite, sodium hydrogensulfite or titanium trichloride under acidic conditions, typically in protic solvents. Representative acids include, but are not limited to, acetic acid, formic acid, dilute hydrochloric acid, dilute phosphoric acid, dilute sulfuric acid, and the like. Protic solvents include, but are not limited to, mixtures of water and methanol, ethanol, isopropanol, or butanol. The reaction is typically carried out at 25° to 110° C., preferably for between 1 and 10 hours.

Cyclic carbamates (2-3) can be prepared stepwise or via a one-pot procedure. Metallation and a subsequent reaction with CDI provide imidazolocarbonyl derivative, which is reacted with ammonia in a suitable solvent such as dimethylformamide, tetrahydrofuran, acetonitrile or the like at room temperature to slightly elevated temperature in the presence of base such as NaHMDS, NaH, or the like.

Scheme 3

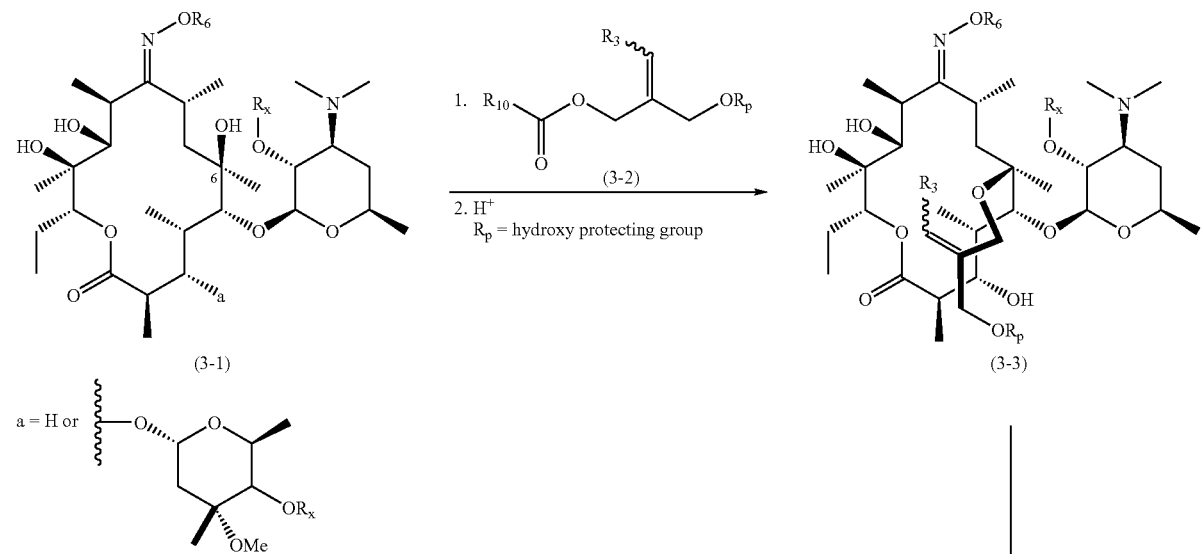

-continued

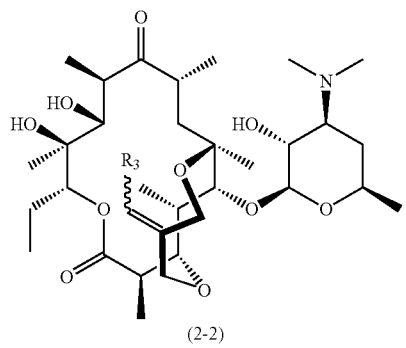

(2-2)

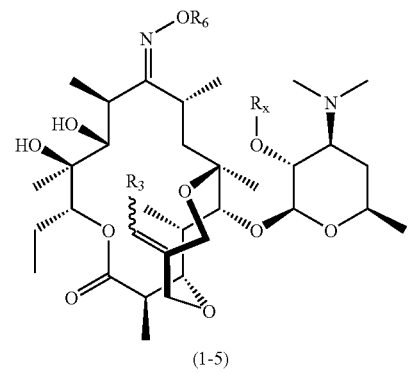

(1-5)

Alternatively, ketone (2-2) can also be prepared via a stepwise process as shown in Scheme 3. The initial step is the alkylation of the 6-hydroxy moiety of intermediate (3-1) with alkylating agents of formula (3-2), wherein $R_{10}$ are as previously defined and $R_p$ is hydroxylprotecting group, in the presence of Pd(0) as previously described in Scheme 1, followed by the removal of the cladinose moiety of formula (3-1) (if E is a cladinose) with either mild acid hydrolysis or by enzymatic hydrolysis to yield compounds of formula (3-3). Representative acids include dilute hydrochloric acid, sulfuric acid, perchloric acid, chloroacetic acid, dichloroacetic acid or trifluoroacetic acid. Suitable solvents for the reaction include methanol, ethanol, isopropanol, butanol, water and mixtures there of. Reaction times are typically 0.5 to 24 hours. The reaction temperature is preferably 0 to 80° C. Compounds of formula (3-3) can be converted to the cyclized products (1-5) via manipulation of $R_p$ to the $C(O)OR_{10}$, where $R_p$ and $R_{10}$ are as previously defined, subsequently by intramolecular cyclization in the presence of Pd(0) as previously described in Scheme 1. Finally, conversion of compounds of formula (1-5) to ketone (2-2) is as previously outlined in scheme 2.

Scheme 4

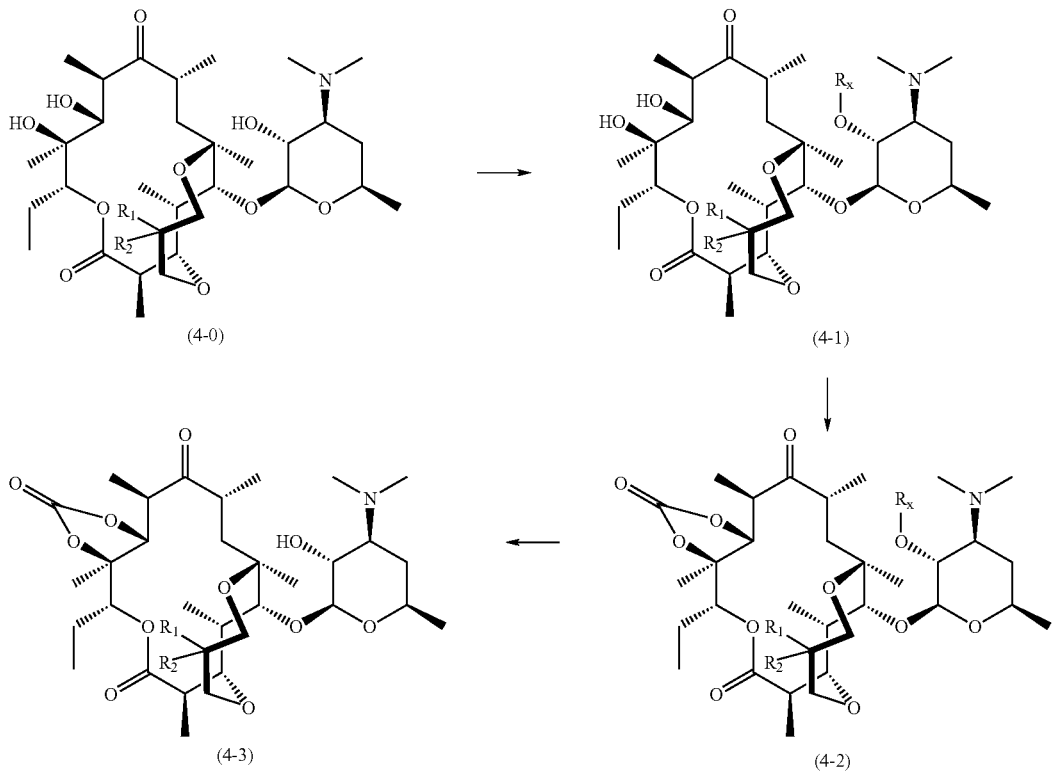

Scheme 4 gives an outline of the preparation of cyclic carbonates of formula (4-3). The 2' hydroxyl is protected with appropriate protecting groups, as previously describe in Scheme 1, leading to compounds of formula (4-1). The C11 and C12-OH can be cyclized under basic conditions with CDI or any phosgene equivalents to form derivative (4-2). Subsequently, the 2' hydroxylprotecting group is removed with the conditions described in Scheme 2, to furnish the desired cyclic carbonate (4-3) as a target compound.

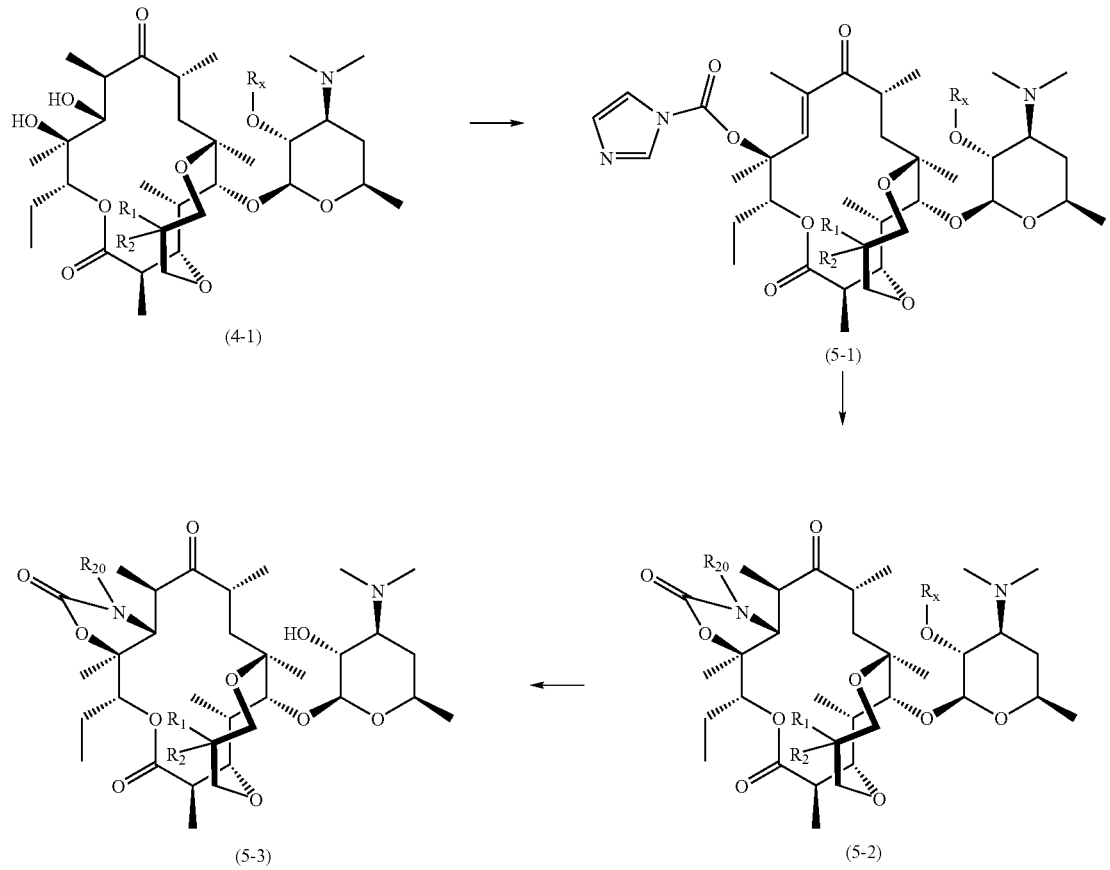

Scheme 5

A scheme for the preparation of C11-C12 cyclic carbamates of formula (5-3) is shown is Scheme 5. Metallation and a subsequent reaction with CDI provide imidazolocarbonyl derivative (5-1), which is reacted with ammonia or $R_{20}NH_2$, where $R_{20}$ is previously defined, in acetonitrile at elevated temperature. The product is the N-substituted oxazolidinone (5-2). The target compounds are available by removal of the 2'-hydroxylprotection group in the sugar moiety by conditions as previously described in Scheme 2.

Alternatively, compounds of formula (5-1) can be obtained via a stepwise by treating compounds of formula (4-1) with dioxolan-2-one and triethyl amine at elevated temperature, followed by activation of the C12-hydroxyl moiety with CDI or any phosgene equivalents.

Scheme 6

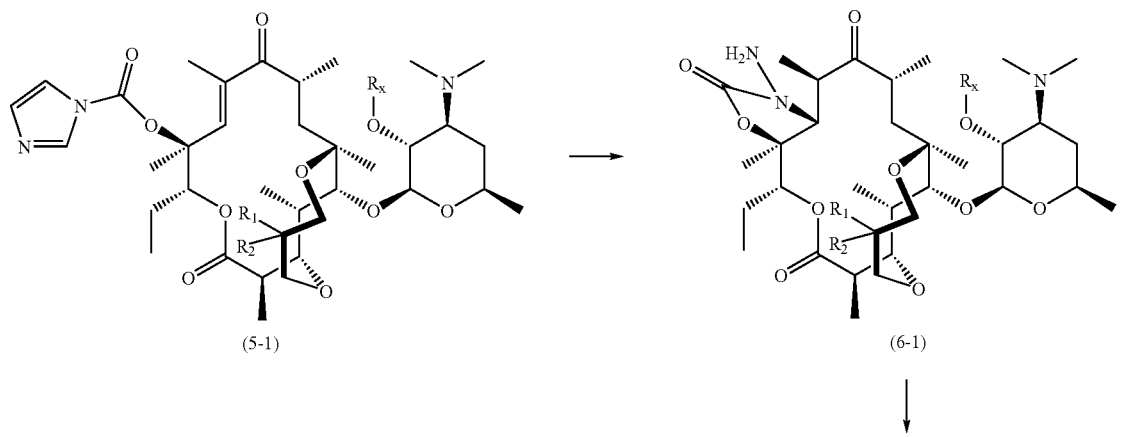

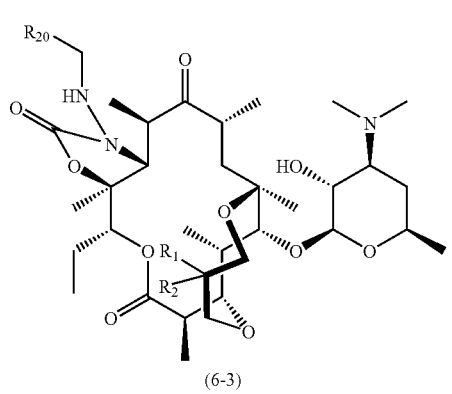

(6-3)

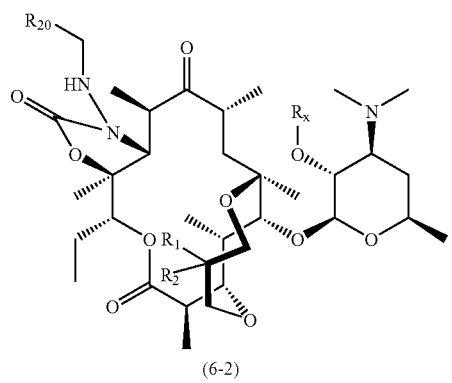

(6-2)

Carbazate analogues, or N11-amino derivatives, are available by the reaction of hydrazine or a substituted hydrazine with intermediate 12'O-imidazolocarbonyl derivatives. Scheme 6 shows a reaction between the imidazolocarbonyl derivatives of formula (5-1) and excess hydrazine hydrate that provides the 3-aminoxazolidinone-derivatives of formula (6-1). Reductive alkylation between the amino group and a heterocyclic aldehyde with sodium cyanoborate provide alkylated products such as structure (6-2). The 2'-hydroxyl-protection in the sugar moiety is removed by conditions as previously outlined in Scheme 2 to provide target compounds of formula (6-3).

Scheme 7

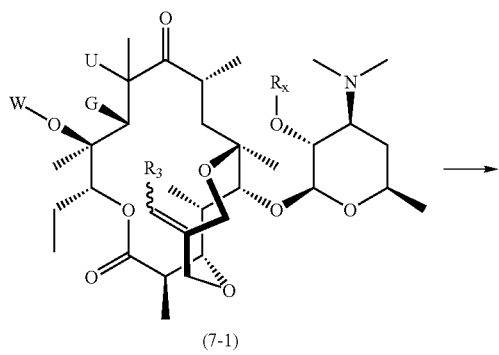

(7-1)

-continued (7-2)

Scheme 7 illustrates another process of the invention by which to prepare compound of the present invention. Conversion of alkenes (7-1) into ketones (7-2) can be accomplished by ozonolysis followed by decomposition of the ozonide with the appropriate reducing agents. The reaction is typically carried out in an inert solvent such as, but not limited to, methanol, ethanol, ethyl acetate, glacial acetic acid, chloroform, methylene chloride or hexane or mixtures thereof, preferably methanol, preferably at −78° C. to −20° C. Representative reducing agents are, for example, triphenylphosphine, trimethylphosphite, thiourea, and dimethyl sulfide, preferably triphenylphosphine. A more thorough discussion of ozonolysis and conditions therefor may be found In J. March, *Advanced Organic Chemistry*, $4^{th}$ ed., Wiley & Son, Inc, 1992. Alternatively, compounds of formula (7-1) can be prepared from compounds of formula (7-2) dihydroxydation with $OsO_4$ followed by $NaIO_4$ cleavage.

Scheme 8

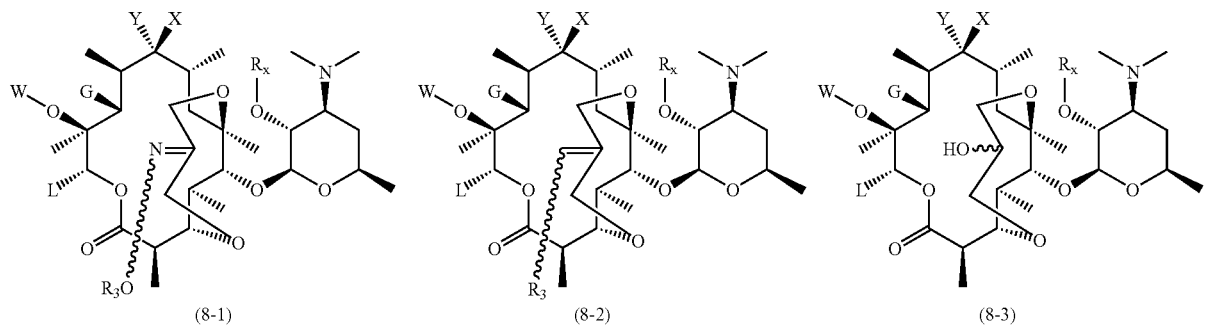

(8-1)   (8-2)   (8-3)

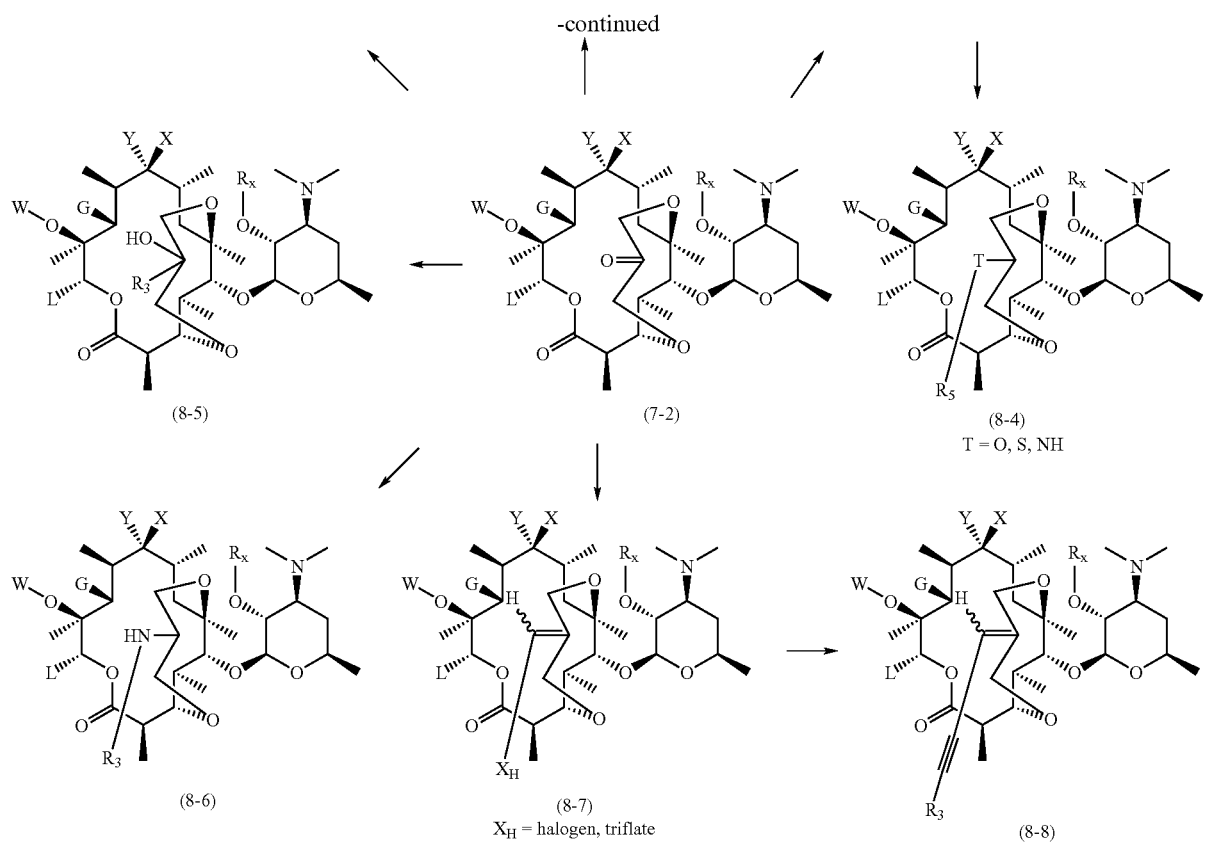

X$_H$ = halogen, triflate

T = O, S, NH

Compounds according to the invention of the formula (7-2) can be further functionalized in a variety of ways. Scheme 8 details a procedure for the conversion of the ketone of formula (7-2) into an oxime of formula (8-1). Oxime formation can be accomplished using the appropriate substituted hydroxylamine under either acidic or basic conditions in a variety of solvents. Representative acids include, but are not limited to, hydrochloric, phosphoric, sulfuric, p-toluenesulfonic, and pyridinium p-toluene sulfonate. Likewise, representative bases include, but are not limited to, triethylamine, pyridine, diisopropylethyl amine, 2,6-lutidine, and the like. Appropriate solvents include, but are not limited to, methanol, ethanol, water, tetrahydrofuran, 1,2-dimethoxyethane, and ethyl acetate. Preferably the reaction is carried out in ethanol using triethylamine as the base. The reaction temperature is generally 25° C., and reaction time is 1 to 12 hours.

It will be appreciated by one skilled in the art that ketones of formula (7-2) can be transformed into alkenes of formula (8-2) and (8-7) via Wittig reaction with the appropriate phosphonium salt in the presence of a base, see (a) Burke, *Tetrahedron Lett.*, 1987, 4143-4146, (b) Rathke and Nowak, *J. Org. Chem.*, 1985, 2624-2626, (c) Maryanoff and Reitz, *Chem. Rev.*, 1989, 863-927. Furthermore, vinyl halides of formula (8-7) can be functionalized by Sonogashira coupling with alkynes in the presence of a palladium catalyst, a copper halide and an amine base to give compounds of formula (8-8) (see (a) Sonogashira, *Comprehensive Organic Synthesis*, Volume 3, Chapters 2,4; (b) Sonogashira, *Synthesis* 1977, 777.). In a similar manner, alkenes of formula (8-2) can be obtained from vinyl halides (8-7) via Suzuki cross coupling with organoboron reagents in the presence of a palladium catalyst and a base, or via Stille cross coupling with organostananes in the presence of a palladium catalyst (see (a) Suzuki, *J. Organomet. Chem.* 1999, 576,147-168, (b) Stille, *Angew. Chem. Int. Ed. Engl.*, 1986, 508-524 (c) Farina, *J. Am. Chem. Soc.*, 1991, 9585-9595).

Furthermore, alcohols of type (8-3) can be prepared by reduction of the corresponding ketone of formula (7-2) under a variety of conditions (see Hudlicky, M. *Reductions in Organic Chemistry*, Ellis Horwood Limited: Chichester, 1984). The alcohols thus derived can be further modified to give compounds of formula (8-4). A process to generate compounds of formula (8-4) includes, but is not limited to, alkylation of the alcohol with an electrophile or conversion of the alcohol into a leaving group, such as a triflate, tosylate, phosphonate, halide, or the like, followed by displacement with a heteroatom nucleophile (e.g. an amine, alkoxide, sulfide or the like).

Yet another means by which to functionalize ketones of formula (7-2) is via addition of Grignard reagents to form alcohols of formula (8-5). The requisite Grignard reagents are readily available via the reaction of a variety of alkyl or aryl halides with magnesium under standard conditions (see B. S. Furniss, A. J. Hannaford, P. W. G. Smith, A. R. Tatchell, *Vogel's Textbook of Practical Organic Chemistry*, 5$^{th}$ ed., Longman, 1989). The addition is performed in an inert solvent, generally at low temperatures. Suitable solvents include, but are not limited to, tetrahydrofuran, diethylether, 1,4-dioxane, 1,2-dimethoxyethane, and hexanes. Preferably the solvent is tetrahydrofuran or diethylether. Preferably the reaction is run at −78° C. to 0° C.

In a similar way, reaction with other organometallic reagents gives rise to alcohols of formula (8-5). Examples of useful organometallic reagents include, but are not limited to, organo-aluminum, organo-lithium, organo-cerium, organo-zinc, organo-thallium, and organo-boron reagents. A more thorough discussion of organometallic reagents can be found In B. S. Furniss, A. J. Hannaford, P. W. G. Smith, A. R. Tatchell, *Vogel's Textbook of Practical Organic Chemistry*, 5$^{th}$ ed., Longman, 1989.

Ketone of formula (7-2) can be further utilized by conversion into amine of formula (8-6) via a reductive amination. Reductive amination is achieved by treating the ketone with an amine in the presence of a reducing agent to obtain the product amine (8-6). The reaction can be carried out either with or without added acid. Examples of acids that are commonly used include, but are not limited to, hydrochloric, phosphoric, sulfuric, acetic, and the like. Reducing agents that effect reductive amination include, but are not limited to, hydrogen and a catalyst, zinc and hydrochloric acid, sodium cyanoborohydride, sodium borohydride, iron pentacarbonyl, and alcoholic potassium hydroxide. Generally alcoholic solvents are used. The preferred conditions use sodium cyanoborohydride in methanol with added acetic acid.

It will be appreciated by one skilled in the art, that the unsaturated compounds represented by compounds (8-2) and (8-8) can be reduced to form the corresponding saturated compound (see Hudlicky, M., *Reductions in Organic Chemistry*, Ellis Horwood Limited: Chichester, 1984).

2,4; (c) Sonogashira, *Synthesis* 1977, 777). Under the Heck coupling conditions, regioisomers and stereoisomers of the double bond are possible. Alternatively, compound (9-1) can undergo a cross metathesis reaction with vinylaromatic derivatives using ruthenium catalysts to give compounds of formula (9-2) (see (a) *J. Org. Chem.* 2000, 65, 2204-2207; (b) Reviews: *Synlett.* 1999, 2, 267; (c) Reviews: Ivin, K. J.; Mol. J. C., *Olefin Metathesis and Metathesis Polymerization*, 2$^{nd}$ ed., Academic Press: New York, 1997; (d) *J. Org. Chem.* 1999, 64, 4798-4816; (e) *Angew. Chem., Int. Ed. Engl.* 1997, 36, 2036-2056; (f) *Tetrahedron* 1998, 54, 4413-4450).

All references cited herein, whether in print, electronic, computer readable storage media or other form, are expressly incorporated by reference in their entirety, including but not limited to, abstracts, articles, journals, publications, texts, treatises internet web sites, databases, patents, and patent publications.

EXAMPLES

The compounds and processes of the present invention will be better understood in connection with the following examples, which are intended as an illustration only and not Scheme 9

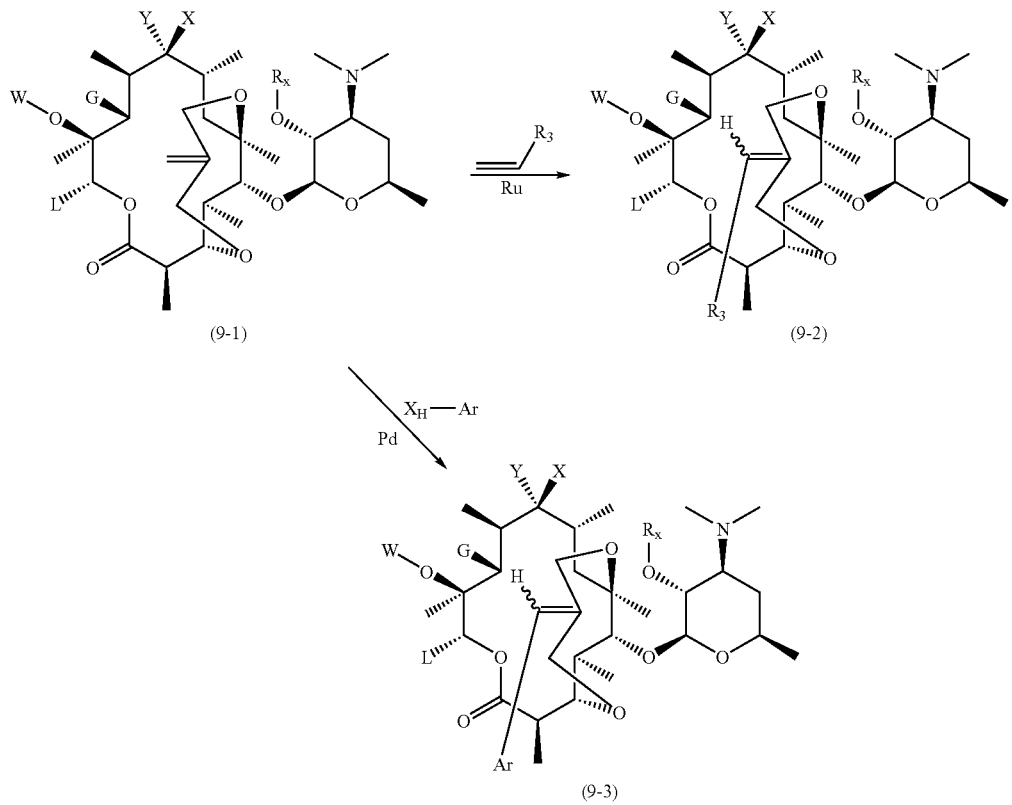

Compounds of the invention according to formula (9-1) are also capable of further functionalization to generate compounds of the present invention. Alkene (9-1) can be treated with an aryl halide or aryl triflate in the presence of a palladium catalyst [Pd(0) or Pd(II)] to provide compound (9-3): (See (a) Heck, *Palladium Reagents in Organic Synthesis*, Academic Press: New York, 1985, Chapter 1; (b) Sonogashira, *Comprehensive Organic Synthesis*, Volume 3, Chapters limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

Compound of formula II, wherein $R_1$ and $R_2$ taken together with the carbon atom to which they are attached are C=$CH_2$, G=OH and $R_6$=Rx=Ac, Step 1a.

To a flask containing a solution of commercially available Ery A oxime (1 eq.) in MeOH was slowly bubbled in anhydrous HCl gas (3.1 eq.) at 20 to 30° C. for 2 hrs. After HCl gas bubbling stops, the reaction mixture was stirred for 1 hr at room temperature. The mixture was then concentrated to about half the volume, and then quenched with dilute HCl solution. The resulting solution was extracted 4 times with dichloromethane. The aqueous solution was then basified with aqueous potassium carbonate solution until pH 9.5 to 10. The mixture was extracted 4 times with dichloromethane. The combine organic extracts were washed once with water, and then evaporated to dryness. The product was carried directly for the next step without further purification.

MS (ESI): m/z=591 [M+H].

Step 1b.

A solution of the compound from step (1a) in THF (12 L) was concentrated to a remaining volume about 9 L to azeotropically dry the material before acetylation reaction. To this clear THF solution was charged triethylamine (3.0 eq.), and then slowly charged $Ac_2O$ (2.3 eq.) at 20-30° C. over the period of about 30 min. Upon the completion of the addition, the reaction mixture was agitated at 25° C. for additional 3 hours. The reaction was diluted with EtOAc, subsequently washed 4 times with saturated aqueous $NaHCO_3$ solution, and 4 times with water. The organic solution was evaporated to dryness to afford the desired crude product which was purified by crystallization with EtOAc/Hex.

MS (ESI): m/z=675 [M+H].

Step 1c.

To a cloudy solution of compound from step (1b) in toluene was added carbonic acid 2-tert-butoxycarbonyloxymethyl-allyl ester tert-butyl ester (1.6 eq.) (prepared according to patent WO 03/097659 A1). The resulting mixture was degassed 3 times at 33° C. before $Pd_2(dba)_3$ (4 mol %) and dppb (8 mol %) were added and the resulting mixture was heated to reflux for 5 hours. After this time, the reaction was cooled back to room temperature and was concentrated under vacuo. The residue was passed through a short silica gel column eluting with 100% EtOAc to 95:5 (EtOAc:acetone) to give and the eluted product was concentrated and crystallized out from EtOAc to give the desired target.

MS (ESI): m/z 627.37 [M+H].

$^{13}$C NMR ($CDCl_3$, ppm) δ: 176.8, 171.3, 170.2, 168.0, 143.0, 118.9, 102.3, 81.0, 80.0, 77.6, 75.0, 74.4, 72.3, 71.9, 70.6, 69.2, 63.55, 63.47, 60.6, 43.6, 42.7, 40.9, 37.9, 34.9, 31.0, 28.5, 22.9, 22.1, 21.6, 21.3, 21.2, 20.0, 18.9, 16.9, 15.1, 14.4, 12.2, 10.6, 10.5.

Example 2

Compound of formula II, wherein $R_1$ and $R_2$ taken together with the carbon atom to which they are attached are C=$CH_2$, G=OH and R=Rx=Bz Step 2a.

A mixture of the compound from step (1a) of Example 1 and triethylamine (3.0 eq.) in THF was slowly added $Bz_2O$ (2.3 eq.) at 20-30° C. Upon the completion of the addition, the reaction mixture was stirred at room temperature for additional 15 hours. The reaction was diluted with EtOAc, subsequently was washed 3 times with saturated aqueous $NaHCO_3$ solution, and 3 times with water. The organic solution was evaporated to dryness to afford the desired crude product which is purified by crystallization with EtOAc/Hex.

Step 2b.

To a solution of compound from step (2a) in toluene was added carbonic acid 2-tert-butoxycarbonyloxymethyl-allyl ester tert-butyl ester (1.6 eq.) (prepared according to patent WO 03/097659 A1). The resulting mixture was degassed 3 times at 33° C. before $Pd_2(dba)_3$ (4 mol %) and dppb (8 mol %) are added and the resulting mixture was heated to reflux for 5 hours. After this time, the reaction was cooled back to room temperature and was concentrated under vacuo. The residue was passed through a short silica gel column eluting with 100% EtOAc to 95:5 (EtOAc:acetone), and the eluted product was concentrated and crystallized out from EtOAc to give the desired target.

Example 3

Compound of formula II, wherein $R_1$ and $R_2$ taken together with the carbon atom to which they are attached are C=$CH_2$, G=OH and $R_6$=Rx=$SiEt_3$ Step 3a.

A mixture of the compound from step (1a) of Example 1 and triethylamine (3.0 eq.) in THF is slowly added $Et_3SiCl$ (2.3 eq.) at 20-30° C. Upon the completion of the addition, the reaction mixture is stirred at room temperature for additional 3 hours. The reaction was diluted with EtOAc, subsequently is washed 3 times with saturated aqueous $NaHCO_3$ solution, and 3 times with water. The organic solution is evaporated to dryness to afford the desired crude product which is purified by crystallization with EtOAc/Hex.

Step 3b.

To a solution of compound from step (3a) in toluene is added carbonic acid 2-tert-butoxycarbonyloxymethyl-allyl ester tert-butyl ester (1.6 eq.) (prepared according to patent WO 03/097659 A1). The resulting mixture is degassed 3 times at 33° C. before $Pd_2(dba)_3$ (4 mol %) and dppb (8 mol %) are added and the resulting mixture is heated to reflux for 5 hours. After this time, the reaction is cooled back to room temperature and is concentrated under vacuo. The residue is passed through a short silica gel column eluting with 100% EtOAc to 95:5 (EtOAc:acetone), and the eluted product is concentrated and crystallized out from EtOAc to give the desired target.

Example 4

Compound of formula II, wherein $R_6$=(1-isopropoxycyclohexyl), $R_1$ and $R_2$ taken together with the carbon atom to which they are attached are C=$CH_2$, G=OH and Rx=Ac Step 4a.

A solution of compound from step (1b) of Example 1 in 1N aqueous HCl was heated to 60 C for one hour. The mixture was then cooled to room temperature and was neutralized with saturated $NaHCO_3$ and extracted with EtOAc. The combined organic extracts were washed with brine, dried, filtered and concentrated under vacuum to give the desired product.

Step 4b.

To a solution of compound from step (4a) in acetonitrile is added 1,1-diisopropoxy-cyclohexane (3 eq.) and formic acid (5 eq.). The mixture is heat to 40° C. for 8 hours. The mixture is then quenched with saturated $NaHCO_3$ to pH of 9 and is extracted with EtOAc. The combined EtOAc extracts are washed once with brine, dried, filtered and concentrated under vacuo to yield the desired product.

Example 5

Compound of formula II, wherein
$R_6$=(2-isopropoxy-2-propyl), $R_1$ and $R_2$ taken
together with the carbon atom to which they are
attached are C=$CH_2$, G=OH and Rx=Ac The title compound is prepared with the compound from step (4a) of Example 4 via the similar conditions described in step (4b) of Example 4 but with 2,2-diisopropoxy-propane instead of 1,1-diisopropoxy-cyclohexane.

Example 6

Compound of formula II, wherein $R_1$ and $R_2$ taken
together with the carbon atom to which they are
attached are C=$CH_2$, G=OH and R=Rx=H A suspension of compound from step (1c) of Example 1 in methanol and was heated to reflux for 2.5 hours. The mixture was then cooled and evaporated to dryness. The white solid residue was carried directly for the next step without further purification.

MS (ESI): m/z 643.33 [M+H].

$^{13}C$ NMR ($CDCl_3$, ppm) δ: 177.3, 170.2, 144.7, 116.9, 104.5, 81.2, 81.0, 75.6, 75.0, 72.6, 71.2, 70.9, 69.6, 66.0, 64.2, 43.8, 42.8, 40.5, 38.3, 33.8, 28.8, 25.8, 22.7, 22.0, 21.4, 19.2, 16.6, 15.0, 12.1, 10.9, 10.8.

Example 7

Compound of formula I, wherein X and Y taken
together with the carbon to which they are attached
are C=NH, $R_1$ and $R_2$ taken together with the
carbon atom to which they are attached are C=$CH_2$,
L=$CH_2CH_3$, W=U=Q=Rx=H and G=OH To a solution of compound from step (1c) of Example 1 in ethanol was added $TiCl_3$ at room temperature. After stirring at room temperature overnight, the mixture was diluted with a water and dichloromethane. The mixture was basified to pH of 9 with saturated sodium bicarbonate and the organic layer was separated, dried ($Na_2SO_4$), filtered and concentrated under vacuum. The residue was purified by column chromatography eluting with 95:5 ($CH_2Cl_2$:MeOH) to give the desired product as a white solid.

MS (ESI): m/z 627.30 [M+H], 314.27 [M+2H].

$^{13}C$ NMR ($CDCl_3$, ppm) δ: 193.9, 177.2, 144.6, 115.7, 104.7, 81.01, 80.96, 76.6, 74.8, 72.8, 71.1, 70.8, 69.7, 66.0, 63.6, 45.7, 44.2, 43.1, 40.5, 38.1, 35.0, 28.7, 22.2, 22.0, 21.4, 20.2, 16.3, 14.3, 11.8, 11.3, 11.0.

Example 8

Compound of formula I, wherein X=$NH_2$, $R_1$ and $R_2$
taken together with the carbon atom to which they
are attached are C=$CH_2$, L=$CH_2CH_3$,
Y=W=U=Q=Rx=H and G=OH To a clear mixture of compound from Example 6, ammonium acetate (15 eq.) and sodium cyanoborohydride (3.8 eq.) in methanol was added $TiCl_3$ (20% in 3% aqueous HCl) and the resulting solution was stirred at room temperature overnight. The solvent was then evaporated off and the residue was diluted with water and extracted with EtOAc. The aqueous layer was basified with saturated $NaHCO_3$ to pH of 9 and extracted 2 times with dichloromethane, dried over $Na_2SO_4$, filtered and concentrated under vacuum to give a white solid. The residue was triturated with acetonitrile and then was further purified by column chromatography eluting with 5% of 2M $NH_3$ in MeOH/$CH_2Cl_2$ to yield a white solid.

MS (ESI): m/z 629.18 [M+H], 315.22 [M+2H].

$^{13}C$ NMR ($CDCl_3$, ppm) δ: 177.4, 146.1, 113.3, 105.0, 81.0, 80.51, 80.48, 76.7, 75.2, 73.7, 71.4, 70.7, 69.8, 66.0, 64.1, 62.4, 53.7, 44.0, 43.4, 40.5, 36.4, 35.3, 31.8, 28.6, 22.5, 22.3, 22.0, 21.5, 16.9, 16.8, 12.2, 11.6, 10.9.

Example 9

Compound of formula III, wherein $R_1$ and $R_2$ taken
together with the carbon atom to which they are
attached are C=$CH_2$, G=OH and Rx=H To a stirred solution of compound from Example 6 (22 mmol) in ethanol was slowly added water (75 ml). To this mixture was added $NaNO_2$ (5 eq.) in one portion and then it was slowly treated with 1N aqueous HCl (110 ml). The reaction temperature was warmed to 70° C. over 20 min and was allowed to stir at this temperature for 2 hours. After the solution was cooled back to room temperature, it was basified with saturated $NaHCO_3$ to a pH of 9-10 and then extracted 5 times with dichloromethane. The combined organic extracts were washed once with brine, dried over $MgSO_4$, filtered and concentrated. The residue was purified by crystallization to afford the desired product.

MS (ESI): m/z 628.09 [M+H].

$^{13}C$ NMR ($CDCl_3$, ppm) δ: 220.6, 177.0, 143.9, 118.3, 104.5, 81.4, 80.7, 75.3, 75.1, 72.6, 70.8, 69.70, 69.66, 66.0, 63.7, 45.2, 43.7, 42.7, 40.5, 38.8, 38.5, 28.6, 22.7, 22.2, 21.4, 18.8, 16.6, 12.3, 12.1, 10.9, 10.6.

Example 10

Compound of formula III, wherein $R_1$ and $R_2$ taken
together with the carbon atom to which they are
attached are C=$CH_2$, G=OH and Rx=Ac To a solution of compound from Example 9 in $CH_2Cl_2$ was added $Ac_2O$ (1.2 eq.). The resulting solution was stirred at room temperature for 2.5 hours before it was diluted with EtOAc, washed 2 times with saturated $NaHCO_3$, once with brine, dried over $MgSO_4$ and concentrated under vacuum to give a white solid.

MS (ESI): m/z 670.10 [M+H].

$^{13}C$ NMR ($CDCl_3$, ppm) δ: 220.6, 176.9, 170.1, 143.8, 118.3, 102.4, 80.8, 80.5, 75.3, 75.1, 72.6, 72.0, 69.7, 69.3, 63.8, 63.5, 45.0, 43.6, 42.7, 40.9, 38.7, 38.4, 30.9, 22.8, 22.2, 21.6, 21.2, 18.7, 16.9, 12.2, 12.1, 10.7, 10.6.

Example 10a

Compound of formula I, wherein X and Y taken
together with the carbon to which they are attached
are C=NAc, $R_1$ and $R_2$ taken together with the
carbon atom to which they are attached are C=$CH_2$,
L=$CH_2CH_3$, W=U=Q=H, G=OH, and Rx=Ac The title compound was prepared with the title compound of Example 7 via similar conditions described in Example 10.

MS (ESI): m/z 711.39 [M+H].

Example 10b

Compound of formula I, wherein X and Y taken together with the carbon to which they are attached are C=NAc, $R_1$ and $R_2$ taken together with the carbon atom to which they are attached are C=$CH_2$, L=$CH_2CH_3$, W=U=Q=Rx=H and G=OH The title compound was prepared with the title compound of Example 10a via similar conditions described in Example 12.

MS (ESI): m/z 669.40 [M+H].

Example 11

Compound of formula V, wherein $R_1$ and $R_2$ taken together with the carbon atom to which they are attached are C=$CH_2$, and Rx=Ac To a solution of compound from Example 10, CDI (2.5 eq.) in THF-DMF was added NaH (2.5 eq.) in one portion at −40° C. The mixture was further stirred at −40° C. for another 30 min before it was quenched with aqueous $NaHCO_3$. The mixture was warmed to room temperature and diluted with EtOAc. The organic layer was separated and washed 2 more times with $NaHCO_3$, once with brine, dried over $MgSO_4$, filtered and concentrated under vacuum to give the desired product.

MS (ESI): m/z 696 [M+H].

Example 12

Compound of formula V, wherein $R_1$ and $R_2$ taken together with the carbon atom to which they are attached are C=$CH_2$, and Rx=H A solution of compound from Example 11 in MeOH was stirred at room temperature for 28 hours, the mixture was concentrated to dryness and the residue was purified by column chromatography eluting with 2-5% 2N $NH_3$/MeOH in dichloromethane.

MS (ESI): m/z 654 [M+H].

Example 13

Compound of formula VI, wherein $R_1$ and $R_2$ taken together with the carbon atom to which they are attached are C=$CH_2$, W=C(O)-(imidazol-1-yl) and Rx=Ac To a solution of compound from Example 10, CDI (4 eq.) in THF-DMF was added NaH (3 eq.) in one portion at −40° C. The mixture was warmed to room temperature over 2 and was further stirred at room temperature for an additional 15 hours. The mixture was then cooled back to 0° C. before it was quenched with aqueous $NaH_2PO_4$. The resulting mixture was extracted with EtOAc. The organic layer was separated and washed 2 more times with $NaH_2PO_4$. The combined organic layers were washed once with saturated $NaHCO_3$, once with brine, dried over $MgSO_4$, filtered and concentrated under vacuum to give the desired product.

MS (ESI): m/z 746 [M+H].

Example 14

Compound of formula VII, wherein $R_1$ and $R_2$ taken together with the carbon atom to which they are attached are C=$CH_2$, $R_{20}$=H, and Rx=Ac To a mixture of compound from example 10 (1.54 mmol), CDI (4.0 eq.), in THF (25 ml), and DMF (5 ml) was added NaHMDS (1.5 eq.) dropwise under nitrogen at room temperature. The resulting solution was further stirred at room temperature overnight. The yellow suspension was cannulated to a vessel containing 5 ml of liquid ammonia. The resulting mixture was sealed and stirred at room temperature for overnight. The mixture was then poured into a mixture of EtOAc (200 ml) and 5% $NaH_2PO_4$ (150 ml). The aqueous layer was extracted with EtOAc and the combined organic layers were washed twice with 5% $NaH_2PO_4$, once with saturated $NaHCO_3$, dried over $Na_2SO_4$, filtered and concentrated under vacuum to yield an off-white foam (92% yield).

MS (ESI): m/z 695.25 [M+H].

$^{13}C$ NMR ($CDCl_3$, ppm) δ: 218.1, 177.1, 170.1, 158.5, 144.0, 119.3, 102.2, 85.0, 80.7, 80.1, 74.3, 72.6, 71.9, 69.3, 63.4, 63.3, 60.6, 58.2, 45.2, 43.5, 42.5, 40.8, 38.7, 38.2, 30.9, 23.5, 22.2, 21.6, 21.3, 21.2, 18.9, 14.4, 14.1, 14.0, 11.8, 10.8, 10.2 ppm.

Example 15

Compound of formula VII, wherein $R_1$ and $R_2$ taken together with the carbon atom to which they are attached are C=$CH_2$, and $R_{20}$=Rx=H The title compound was prepared with the title compound of Example 14 via the similar conditions described in Example 12.

MS (ESI): m/z 653 [M+H].

Example 16

Compound of formula VII, wherein $R_1$ and $R_2$ taken together with the carbon atom to which they are attached are C=O, $R_{20}$=H, and Rx=Ac To a solution of compound from Example 1.4 in acetone was added $NaIO_4$(s) (2.2 eq.) and then water. To this mixture was then added 4% wt. solution of $OsO_4$ in water (12 mol %) dropwise at room temperature. White precipitates formed as reaction progressed. The mixture was then quenched with saturated $NaHCO_3$ and extracted with EtOAc. The combined organic extracts was dried over $Na_2SO_4$, filtered and concentrated under vacuum to give an off-white foam (92% yield).

MS (ESI): m/z 697.28 [M+H].

$^{13}C$ NMR ($CDCl_3$, ppm) δ: 217.1, 209.8, 177.5, 170.2, 157.6, 151.7, 103.2, 84.2, 81.7, 81.5, 79.9, 76.4, 71.8, 69.6, 67.9, 63.5, 58.5, 44.7, 44.0, 43.2, 40.8, 39.4, 36.3, 30.7, 22.6, 21.6, 21.2, 20.2, 14.4, 14.1, 13.3, 12.2, 11.0, 10.8.

Example 17

Compound of formula VII, wherein $R_1$ and $R_2$ taken together with the carbon atom to which they are attached are C=O and $R_{20}$=Rx=H The title compound was prepared with the title compound of Example 16 via the same conditions described in Example 12.

MS (ESI): m/z 655.20 [M+H].

$^{13}C$ NMR ($CDCl_3$, ppm) δ: 217.1, 210.0, 177.7, 157.7, 110.0, 105.1, 84.2, 82.0, 81.5, 80.3, 76.2, 70.5, 69.8, 67.9, 66.2, 58.6, 44.6, 44.0, 43.2, 40.5, 39.5, 36.5, 28.8, 22.5, 21.4, 21.1, 20.4, 13.9, 13.4, 12.3, 11.0, 10.9.

Example 18

Compound of formula VII, wherein $R_1$ and $R_2$ taken together with the carbon atom to which they are attached are C=$CH_2$, and $R_{20}$=(phenylbutyl), Rx=Ac To a solution of compound from Example 13 in DMF was treated with phenylbutylamine (6 eq.). The resulting mixture was stirred at room temperature for 4 days. The mixture was concentrated under vacuum to removed excess solvent and the residue was purified by HPLC to give the desired compound.

MS (ESI): m/z 827.37 [M+H].

Example 19

Compound of formula VII, wherein $R_1$ and $R_2$ taken together with the carbon atom to which they are attached are C=$CH_2$, and $R_{20}$=(phenylbutyl), Rx=H The title compound was prepared with the title compound of Example 18 via the same conditions described in Example 12.

MS (ESI): m/z 785.22 [M+H].

Example 20

Compound of formula VII, wherein $R_1$ and $R_2$ taken together with the carbon atom to which they are attached are C=$CH_2$, and $R_{20}$=(phenylpropyl), Rx=Ac The title compound was prepared from the title compound of Example 13 and phenylpropylamine via the similar conditions described in Example 18.

MS (ESI): m/z 813.18 [M+H].

Example 21

Compound of formula VII, wherein $R_1$ and $R_2$ taken together with the carbon atom to which they are attached are C=$CH_2$, and $R_{20}$=(phenylpropyl), Rx=H The title compound was prepared with the title compound of Example 20 via the similar conditions described in Example 12.

MS (ESI): m/z 771.19 [M+H].

Example 22

Compound of formula VII, wherein $R_1$ and $R_2$ taken together with the carbon atom to which they are attached are C=$CH_2$, and $R_{20}$=(phenylipentyl). Rx=Ac The title compound was prepared from the title compound of Example 13 and phenylpentylamine via the similar conditions described in Example 18.

MS (ESI): m/z 841 [M+H].

Example 23

Compound of formula VII, wherein $R_1$ and $R_2$ taken together with the carbon atom to which they are attached are C=$CH_2$, and $R_{20}$=(phenyltpentyl), Rx=H The title compound was prepared with the title compound of Example 22 via the similar conditions described in Example 12.

MS (ESI): m/z 799 [M+H].

Example 24

Compound of formula VII, wherein $R_1$ and $R_2$ taken together with the carbon atom to which they are attached are C=$CH_2$, and $R_{20}$=(4-pyridin-3-yl-1H-imidazol-1-ylbutyl), Rx=Ac The title compound was prepared from the title compound of Example 13 and 4-pyridin-3-yl-1H-imidazol-1-ylbutylamine (prepared according to patent EP 0680967) via the similar conditions described in Example 18.

MS (ESI): m/z 894.26 [M+H].

Example 25

Compound of formula VII, wherein $R_1$ and $R_2$ taken together with the carbon atom to which they are attached are C=$CH_2$, and $R_{20}$=(4-pyridin-3-yl-1H-imidazol-1-ylbutyl), Rx=H The title compound was prepared with the title compound of Example 24 via the similar conditions described in Example 12.

MS (ESI): m/z 851.97 [M+H].

Example 26

Compound of formula VII, wherein $R_1$ and $R_2$ taken together with the carbon atom to which they are attached are C=$CH_2$, and $R_{20}$=(4-pyridin-3-yl-1H-triazol-1-ylbutyl), Rx=Ac Step 26a.

To a solution of commercially available 2-(4-bromo-butyl)-isoindole-1,3-dione (7.1 mmol) in DMF (7 ml) was added sodium azide (5 eq.). After stirring at room temperature overnight, the mixture was diluted with water and extracted with EtOAc. The combined organic extracts were washed 3 times with water, once with brine, dried over $MgSO_4$, filtered and concentrated under vacuum to give the desired azide product in quantitative yield.

$^{13}$C NMR ($CDCl_3$, ppm) δ: 168.4, 134.0, 132.1, 123.3, 50.9, 37.3, 26.3, 26.3, 25.9.

Step 26b.

Compound from step 26a (4.1 mmol) and commercially available 3-ethynyl-pyridine were dissolved in BuOH (10 ml) and water (10 ml). To this mixture was then added copper (II) acetate (20 mol %) and sodium ascorbate (40 mol %) and the resulting solution was stirred at room temperature overnight. The mixture was extracted with $CH_2Cl_2$, and the organic layers were washed with water, dried over $Na_2SO_4$, filtered and concentrated under vacuum to give the desired triazole in quantitative yield.

MS (ESI): m/z 348.04 [M+H].

$^{13}$C NMR($CDCl_3$, ppm) δ: 168.4, 149.2, 147.1, 144.8, 134.1, 132.9, 131.9, 123.3, 120.0, 49.7, 36.8, 27.5, 25.5.

Step 26c.

To a solution of compound from step 26b (2 mmol) in 2N $NH_3$/MeOH (100 ml) was added $NH_2NH_2$ (130 □) and the resulting mixture was heated to reflux overnight. The excess solvents were then removed in vacuo and the residue was recrystallized in MeOH and $CH_2Cl_2$ to give the desired product.

MS (ESI): m/z 218.06 [M+H].

Step 26d.

The title compound was prepared from the title compound of Example 13 and compound from step (26c) via the similar conditions described in Example 18.

MS (ESI): m/z 895.07 [M+H].

Example 27

Compound of formula VII, wherein $R_1$ and $R_2$ taken together with the carbon atom to which they are attached are C=$CH_2$, and $R_{20}$=(4-pyridin-3-yl-1H-triazol-1-ylbutyl), Rx=H The title compound was prepared with compound from step (26d) of Example 26 via the same conditions described in Example 12.

MS (ESI): m/z 853.23 [M+H].

Example 28

Compound of formula VII, wherein $R_1$ and $R_2$ taken together with the carbon atom to which they are attached are C=$CH_2$, and $R_{20}$=(5-pyridin-3-yl-2H-tetrazol-2-ylbutyl), Rx=Ac Step 28a.

To a solution of commercially available 3-(1H-tetrazol-5-yl)-pyridine and 2-(4-Bromo-butyl)-isoindole-1,3-dione (1.0 eq.) in DMF was added $Cs_2CO_3$ at 50° C. The mixture was allowed to stirred at 50° C. for 14 hours before it was cooled back to room temperature and quenched with water and then extracted with EtOAc. The combined organic extracts were washed 2 times with water, once with brine, dried over MgSO4, filtered and concentrated under vacuum. The residue was purified by crystallization with EtOAc to give the desired product.

MS (ESI): m/z 349.04 [M+H].

Step 28b.

To a suspension of compound from step (28a) (1.95 mmol) in ethanol (12 ml) was added $NH_2NH_2.H_2O$ (2 eq.). The mixture was heated to reflux for 6.5 hours before it was cooled back to room temperature. To this mixture was then added 10 ml of 2N NaOH and the resulting solution was extracted with EtOAc. The combined EtOAc layers were washed with 2N NaOH, brine, dried over $MgSO_4$, filtered and concentrated under vacuo to give the desired target.

MS (ESI): m/z 219.09 [M+H].

Step 28c.

The title compound was prepared from the title compound of Example 13 and compound from step (28b) via the similar conditions described in Example 18.

MS (ES): m/z 896.08 [M+H].

Example 29

Compound of formula VII, wherein $R_1$ and $R_2$ taken together with the carbon atom to which they are attached are C=$CH_2$, and $R_{20}$=(5-pyridin-3-yl-2H-tetrazol-2-ylbutyl), Rx=H The title compound was prepared with compound from step (28c) of Example 28 via the same conditions described in Example 12.

MS (ESI): m/z 854.20 [M+H].

Example 30

Compound of formula VII, wherein $R_1$ and $R_2$ taken together with the carbon atom to which they are attached are C=O, and $R_{20}$=(phenylbutyl). Rx=Ac To a solution of compound from Example 18 (0.16 mmol) in acetone (3 ml) were added $NaIO_4$ (2.5 eq.) and water (3 ml). The resulting mixture was then treated with 4% aqueous $OsO_4$ (8 mol %) and was allowed to stirred at room temperature for 3 hours. The mixture was diluted with EtOAc and washed 2 times with saturated $NaHCO_3$, brine, dried over $MgSO_4$, filtered and concentrated under vacuo to give the title compound.

MS (ESI): m/z 829.24 [M+H].

Example 31

Compound of formula VII, wherein $R_1$ and $R_2$ taken together with the carbon atom to which they are attached are C=O, and $R_{20}$=(phenylbutyl), Rx=H The title compound was prepared with compound from Example 30 via similar conditions described in Example 12.

MS (ESI): m/z 787.19 [M+H].

Example 32

Compound of formula VII, wherein $R_1$ and $R_2$ taken together with the carbon atom to which they are attached are $CHCH_3$, and $R_{20}$=(phenylbutyl), Rx=H To a solution of compound from Example 19 (10 mg) in EtOAc (2 ml) was added 5 mg of 10% Pd—C. The mixture was stirred under hydrogen balloon for 10 hours before it was filtered through a pad of celite, and the filtrate was concentrated under vacuo. The residue was purified by column chromatography eluting from 98% to 97% EtOAc/2N $NH_3$-MeOH to give 8 mg of the title compound.

MS (ESI): m/z 787.22 [M+H].

Example 33

Compound of formula VII, wherein $R_1$ and $R_2$ taken together with the carbon atom to which they are attached are C=$CH_2$, and $R_{20}$=(4-quinolin-4-ylbutyl), Rx=Ac Step 33a.

A mixture of commercially available 2-(4-bromo-butyl)-isoindole-1,3-dione (37 mmol) and triphenyl phosphine (37 mmol) in toluene was heated to reflux for 3 days. The solution was then cooled to room temperature and the solid was collected through filtration. The solid residue was washed with toluene and hexane, dried in vacuum at 70° C. to give 15 g of the desired product (75%).

$^{13}C$ NMR ($CDCl_3$, ppm) δ: 168.1, 135.1, 135.1, 134.2, 133.7, 133.6, 131.8, 130.6, 130.5, 123.3, 118.3, 117.7, 38.1, 38.0, 21.9, 21.9, 21.0, 20.5.

Step 33b.

A mixture of compound from step (33a) (10 mmol) and commercially available quinoline-4-carbaldehyde (10 mmol) in 50 ml of THF was degassed at −78 C. To this solution was then added 10 ml of 1N KO$^t$Bu in THF. The mixture was allowed to stirred for 5 min at −78° C. before it was warmed to 0° C. After stirring for an additional 10 min at 0° C., the solution was quenched with 30 ml of saturated $NH_4Cl$ and the mixture was extracted EtOAc. The combined organic extracts were washed 2 times with water, once with brine, dried over $MgSO_4$, filtered and concentrated under vacuo. The residue was purified by column chromatography and crystallization with MeOH to give the desired target with 90% as E-isomer.

MS (ESI): m/z 329.02 [M+H].

$^{13}C$ NMR ($CDCl_3$, ppm) δ: 168.1, 149.9, 148.2, 142.5, 133.9, 132.1, 131.8, 129.8, 129.2, 127.7, 126.8, 126.3, 124.4, 123.1, 120.7, 37.2, 27.7.

Step 33c.

A solution of compound from step (33b) (2 mmol) and 10% Pd/C (70 mg) in MeOH was stirred under a hydrogen balloon for 4 hours. The mixture was filtered through a pad of celite to remove Pd/C and to this filtered solution was added hydrazine (128 μl). The resulting solution was heated to reflux overnight. The excess methanol was removed under vacuum and the residue was treated with 50 ml of 1% HCl and was filtered to remove the solid residue. The filtrate was basified to pH 12 with 1N NaOH and then saturated with NaCl(s). The resulting mixture was extracted with $CH_2Cl_2$ and the organic layers were dried over $Na_2SO_4$, filtered and concentrated under vacuo to yield the desired product (95%).

MS (ESI): m/z 201.08 [M+H].

$^{13}C$ NMR ($CDCl_3$, ppm) δ: 150.4, 148.6, 148.5, 130.5, 129.2, 127.8, 126.5, 123.8, 121.0, 42.3, 34.0, 32.2, 27.6.

Step 33d.

The title compound was prepared from the title compound of Example 13 and compound from step (33c) via the similar conditions described in Example 14.

MS (ESI): m/z 878.07 [M+H], 439.70 [M+2H].

Example 34

Compound of formula VII, wherein $R_1$ and $R_2$ taken together with the carbon atom to which they are attached are C=CH$_2$, and $R_{20}$=(4-quinolin-4-ylbutyl), Rx=H The title compound was prepared with compound from step (33d) of Example 33 via the similar conditions described in Example 12.

MS (ESI): m/z 836.21 [M+H].

$^{13}$C NMR (CDCl$_3$, ppm) δ: 215.1, 176.8, 156.9, 150.3, 150.2, 148.3, 148.3, 146.2, 130.3, 130.2, 129.0, 128.9, 127.5, 126.3, 126.3, 123.7, 123.5, 120.9, 120.8, 114.9, 104.6, 82.5, 80.9, 80.9, 80.5, 76.8, 74.8, 70.5, 69.6, 65.9, 65.0, 59.9, 43.4, 43.2, 42.9, 42.6, 41.9, 40.3, 32.0, 31.7, 28.2, 27.4, 27.1, 24.2, 22.2, 21.2, 18.9, 14.3, 12.9, 11.8, 11.1, 10.8.

Example 35

Compound of formula VII, wherein $R_1$ and $R_2$ taken together with the carbon atom to which they are attached are C=NO(CH$_2$Ph), $R_{20}$=H, and Rx=Ac To a solution of O-benzyl-hydroxylamine (1.9 eq.) and 1M HCl (2.2 eq.) in EtOH was added compound from Example 16 (0.14 mmol) in acetonitrile dropwise at room temperature. Solution turned slightly brown with some precipitate. After stirring for 10 min at room temperature the mixture was quenched with saturated NaHCO$_3$ and extracted with EtOAc. The combined organic extracts were washed with brine, dried, filtered and concentrated under vacuum to give the brownish foam. The residue was carried directly to the next step without purification.

MS (ESI): m/z 802.15 [M+H].

Example 36

Compound of formula VII, wherein $R_1$ and $R_2$ taken together with the carbon atom to which they are attached are C=NO(CH$_2$Ph), and $R_{20}$=Rx=H A solution of compound from Example 35 in methanol was stirred at room temperature overnight. HPLC analysis of reaction mixture showed the E:Z ratio was 2:1. White precipitate was filtered off to give the desired E-isomer. The mother liquor was concentrated to remove excess methanol and the residue was purified by HPLC to afford both E and Z isomers.

E-isomer

MS (ESI): m/z 760.10 [M+H].

$^{13}$C NMR (CDCl$_3$, ppm) δ: 217.0, 177.6, 158.0, 157.8, 137.9, 128.6, 128.2, 128.1, 104.8, 84.5, 80.8, 80.5, 79.2, 76.8, 76.5, 70.6, 69.6, 66.3, 66.1, 61.0, 58.3, 44.4, 44.2, 43.0, 40.6, 39.0, 37.4, 23.0, 21.5, 21.4, 19.9, 13.9, 13.5, 11.6, 11.4, 11.0.

Z-isomer

MS (ESI): m/z 760.10 [M+H].

$^{13}$C NMR (CDCl$_3$, ppm) δ: 217.1, 177.3, 158.5, 157.7, 137.7, 128.6, 128.5, 128.1, 103.4, 84.4, 82.3, 81.0, 80.9, 76.6, 76.3, 73.1, 70.0, 68.2, 67.2, 58.6, 44.4, 44.1, 43.3, 41.4, 40.5, 39.5, 37.3, 32.0, 22.6, 21.7, 21.0, 20.1, 14.1, 13.4, 12.3, 11.3, 11.1.

Example 37

Compound of formula VII, wherein $R_1$ and $R_2$ taken together with the carbon atom to which they are attached are C=NO(CH$_2$CH$_2$Ph), $R_{20}$=H, and Rx=Ac Step 37a.

To a clear solution of commercially available phenethyl bromide and N-BOC protected hydroxylamine in CH$_2$Cl$_2$ was added DBU dropwise at room temperature and the resulting solution was allowed to stir overnight at room temperature. The mixture was quenched with 1% HCl and extracted with EtOAc. The combined organic extracts were washed twice with 1% HCl and once with saturated NaHCO$_3$, dried over Na$_2$CO$_3$, filtered and concentrated under vacuum to give a clear light yellow oil.

$^{13}$C NMR (CDCl$_3$, ppm) δ: 157.3, 138.3, 129.1, 128.7, 126.6, 82.0, 60.7, 34.8, 28.5.

Step 37b.

Compound from step 37a was dissolved in 4M HCl in dioxane. The clear solution turned to white suspension within 2 minutes. The white precipitate was filtered off to give the desired target. This compound was directly used in the next step.

Step 37c.

The title compound was prepared with the title compound of Example 16 and compound from step (37b) via similar conditions outlined in Example 35.

MS (ESI): m/z 816.28 [M+H].

Example 38

Compound of formula VII, wherein $R_1$ and $R_2$ taken together with the carbon atom to which they are attached are C=NO(CH$_2$CH$_2$Ph), and $R_{20}$=Rx=H The title compound was prepared with the title compound of Example 37 via similar conditions described in Example 36. E:Z ratio was 2.7:1.

MS (ESI): m/z 774.23 [M+H].

E-isomer:

MS (ESI): m/z 774.23 [M+H].

$^{13}$C NMR (CDCl$_3$, ppm) δ: 217.0, 177.6, 157.8, 157.5, 138.7, 129.2, 128.6, 126.4, 84.5, 80.8, 80.6, 79.2, 76.9, 75.2, 70.5, 66.5, 66.0, 61.0, 58.3, 44.3, 44.2, 40.6, 39.1, 37.4, 35.8, 23.0, 21.5, 21.3, 19.9, 14.0, 13.5, 11.6, 11.4, 11.1.

Example 39

Compound of formula VII, wherein $R_1$ and $R_2$ taken together with the carbon atom to which they are attached are C=NO(CH$_2$CH$_2$CH$_2$Ph), $R_{20}$=H, and Rx=Ac The title compound was prepared with the title compound of Example 16 and O-(3-phenyl-propyl)-hydroxylamine (prepared similarly to steps 37a and 37b of Example 37 with commercially available phenylpropyl bromide) via similar conditions outlined in Example 35.

MS (ESI): m/z 830.30 [M+H].

Example 40

Compound of formula VII, wherein $R_1$ and $R_2$ taken together with the carbon atom to which they are attached are C=NO(CH$_2$CH$_2$CH$_2$Ph), and $R_{20}$=Rx=H The title compound was prepared with the title compound of Example 39 via similar conditions described in Example 36. E:Z ratio was 2:1.

MS (ESI): m/z 788.30 [M+H].

E-isomer:
MS (ESI): m/z 788.30 [M+H].
$^{13}$C NMR (CDCl$_3$, ppm) δ: 217.0, 177.6, 157.8, 157.1, 142.0, 128.8, 128.6, 126.0, 104.7, 84.5, 80.8, 80.5, 79.1, 76.9, 73.9, 70.6, 69.5, 66.3, 65.8, 61.0, 58.3, 44.3, 44.2, 43.0, 40.6, 39.0, 37.5, 32.3, 30.8, 23.0, 21.5, 21.4, 19.8, 13.9, 13.5, 11.6, 11.4, 11.1.

Example 41

Compound of formula VII, wherein R$_1$ and R$_2$ taken together with the carbon atom to which they are attached are C=NO[(CH$_2$)$_4$Ph], R=H, and Rx=Ac The title compound was prepared with the title compound of Example 16 and O-(3-phenyl-butyl)-hydroxylamine (prepared similarly to steps 37a and 37b of Example 373 with commercially available phenylbutyl bromide) via similar conditions outlined in Example 35.
MS (ESI): m/z 843.98 [M+H].

Example 42

Compound of formula VII, wherein R$_1$ and R$_2$ taken together with the carbon atom to which they are attached are C=NO[(CH$_2$)$_4$Ph], and R$_{20}$=Rx=H The title compound was prepared with the title compound of Example 41 via similar conditions described in Example 36. E:Z ratio was 4:1.
MS (ESI): m/z 802.04 [M+H].

E-isomer:
MS (ESI): m/z 802.04 [M+H].
$^{13}$C NMR (CDCl$_3$, ppm) δ: 217.0, 177.5, 157.8, 156.8, 142.6, 128.7, 128.5, 125.9, 104.0, 84.6, 80.7, 80.6, 78.9, 74.6, 70.3, 66.7, 65.8, 61.0, 58.2, 44.22, 44.16, 42.9, 40.7, 39.0, 37.5, 35.8, 28.8, 27.8, 23.0, 21.6, 21.2, 19.8, 14.0, 13.5, 11.5, 11.4, 11.2.

Example 43

Compound of formula VII, wherein R$_1$ and R$_2$ taken together with the carbon atom to which they are attached are C=NO[Ph], R$_{20}$=H, and Rx=Ac The title compound was prepared with the title compound of Example 16 and commercially available O-phenylhydroxylamine hydrochloride salt via similar conditions outlined in Example 35.
MS (ESI): m/z 788.00 [M+H].

Example 44

Compound of formula VII, wherein R$_1$ and R$_2$ taken together with the carbon atom to which they are attached are C=NO[Ph], and R$_{20}$=Rx=H The title compound was prepared with the title compound of Example 43 via similar conditions described in Example 36. E:Z ratio was 2:1.
MS (ESI): m/z 746.05 [M+H].

E-isomer:
MS (ESI): m/z 746.05 [M+H].
$^{13}$C NMR (CDCl$_3$, ppm) δ: 217.0, 177.6, 161.1, 159.1, 157.6, 129.5, 122.8, 114.9, 104.5, 84.3, 81.0, 80.6, 79.5, 70.4, 69.3, 66.6, 66.2, 61.0, 58.4, 44.5, 44.1, 43.1, 40.7, 39.2, 37.2, 22.9, 21.4, 21.3, 20.1, 14.0, 13.5, 11.8, 11.3, 11.0.

Example 45

Compound of formula VII, wherein R$_1$ and R$_2$ taken together with the carbon atom to which they are attached are C=NO[(CH$_2$)$_5$Ph], R$_{20}$=H, and Rx=Ac The title compound was prepared with the title compound of Example 16 and O-(3-phenyl-butyl)-hydroxylamine (prepared similarly to steps 37a and 37b of Example 37 with commercially available phenylpentyl bromide) via similar conditions outlined in Example 35.
MS (ESI): m/z 858.15 [M+H].

Example 46

Compound of formula VII, wherein R$_1$ and R$_2$ taken together with the carbon atom to which they are attached are C=NO[(CH$_2$)$_5$Ph], and R$_{20}$=Rx=H The title compound was prepared with the title compound of Example 45 via similar conditions described in Example 36. E:Z ratio was 3.8:1.
MS (ESI): m/z 816.12 [M+H].

E-isomer:
MS (ESI): m/z 816.12 [M+H].
$^{13}$C NMR (CDCl$_3$, ppm) δ: 217.0, 177.5, 157.8, 156.9, 143.0, 128.7, 128.5, 125.8, 104.4, 84.6, 80.7, 80.6, 79.0, 74.7, 70.5, 69.3, 66.5, 65.8, 61.0, 58.2, 44.2, 42.9, 40.6, 39.0, 37.5, 36.1, 31.5, 29.1, 25.8, 23.1, 21.5, 21.3, 19.8, 14.0, 13.5, 11.5, 11.4, 11.1.

Example 47

Compound of formula VII, wherein R$_1$ and R$_2$ taken together with the carbon atom to which they are attached are C=NO[6-pyrazol-1-yl-pyridin-3-ylmethyl], R$_{20}$=H, and Rx=Ac The title compound was prepared with the title compound of Example 16 and O-(6-pyrazol-1-yl-pyridin-3-ylmethyl)-hydroxylamine (prepared according to WO 03/097659 A1) via similar conditions outlined in Example 35.
MS (ESI): m/z 869.16 [M+H].

Example 48

Compound of formula VII, wherein R$_1$ and R$_2$ taken together with the carbon atom to which they are attached are C=NO[6-pyrazol-1-yl-pyridin-3-ylmethyl], and R$_{20}$=Rx=H The title compound was prepared with the title compound of Example 47 via similar conditions described in Example 36. E:Z ratio was 2:1.
MS (ESI): m/z 827.21 [M+H], 414.26 [M+2H].

E-isomer:
MS (ESI): m/z 827.21 [M+H], 414.26 [M+2H].
$^{13}$C NMR (CDCl$_3$, ppm) δ: 216.7, 177.9, 159.0, 158.0, 147.6, 142.2, 138.8, 131.4, 127.5, 112.4, 108.0, 104.7, 84.4, 80.8, 80.6, 79.2, 76.7, 73.3, 70.5, 66.4, 65.9, 58.4, 44.4, 44.1, 43.1, 40.6, 39.2, 37.3, 22.8, 21.4, 21.3, 20.0, 14.0, 13.6, 11.8, 11.3, 11.0.

Example 49

Compound of formula VII, wherein $R_1$ and $R_2$ taken together with the carbon atom to which they are attached are C=NO[4-isobutyl-phenyl], $R_{20}$=H, and Rx=Ac Step 49a.

A mixture of commercially available hydroxylphthalimide (1 mmol), 4-isobutyl-phenyl boronic acid (2 eq.), copper acetate (1 eq.) and 4 Å molecular sieves (265 mg) in dichloroethane (5 ml) was stirred at room temperature for 5 hours. The green suspension was evaporated to dryness and the residue was purified by column chromatography eluting with hexane/$CH_2Cl_2$ (1:1) to yield a light yellow solid (81%).

MS (ESI): m/z 295.98 [M+H].

$^{13}$C NMR (CDCl$_3$, ppm) δ: 163.3, 157.3, 138.4, 135.1, 130.4, 129.1, 124.2, 114.8, 44.8, 30.5, 22.5.

Step 49b.

Compound from step 49a was dissolved in 1N $NH_3$/MeOH and the resulting solution was sealed and stirred at room temperature overnight. The excess $NH_3$/MeOH was removed to give a white solid. This compound was directly used in the next step without further purification.

Step 49c.

The title compound was prepared with the title compound of Example 16 and compound from step 49b via similar conditions outlined in Example 35.

MS (ESI): m/z 844.11 [M+H].

Example 50

Compound of formula IV, wherein $R_1$ and $R_2$ taken together with the carbon atom to which they are attached are C=NO[4-isobutyl-phenyl], and $R_{20}$=Rx=H The title compound was prepared with the title compound of Example 49 via similar conditions described in Example 36. E:Z ratio was 2:1.

MS (ESI): m/z 802.13 [M+H].

E-isomer:

MS (ESI): m/z 802.13 [M+H].

$^{13}$C NMR (CDCl$_3$, ppm) δ: 216.9, 117.6, 160.7, 157.6, 157.3, 136.1, 130.0, 114.7, 104.3, 84.3, 80.9, 80.7, 79.5, 76.9, 70.3, 69.0, 66.2, 61.1, 58.4, 44.9, 44.4, 44.0, 43.1, 40.7, 39.2, 37.2, 30.6, 22.9, 22.5, 21.4, 20.1, 14.0, 13.5, 11.8, 11.3, 11.1.

Example 51

Compound of formula VII, wherein $R_1$ and $R_2$ taken together with the carbon atom to which they are attached are C=NO[biphenyl-4-yl], $R_{20}$=H, and Rx=Ac The title compound was prepared with the title compound of Example 16 and O-biphenyl-4-yl-hydroxylamine (prepared similarly to steps 49a and 49b) via similar conditions outlined in Example 35.

MS (ESI): m/z 864.08 [M+H].

Example 52

Compound of formula VII, wherein $R_1$ and $R_2$ taken together with the carbon atom to which they are attached are C=NO[biphenyl-4-yl], and $R_{20}$=Rx=H The title compound was prepared with the title compound of Example 51 via similar conditions described in Example 36. E:Z ratio was 2:1.

MS (ESI): m/z 822.09 [M+H].

E-isomer:

MS (ESI): m/z 822.09 [M+H].

$^{13}$C NMR (CDCl$_3$, ppm) δ: 217.0, 177.6, 161.3, 158.7, 157.6, 141.1, 135.9, 128.9, 128.2, 127.2, 127.0, 115.2, 104.2, 84.3, 81.0, 80.7, 79.6, 76.9, 70.3, 69.0, 66.8, 66.2, 61.0, 58.4, 44.4, 44.1, 43.1, 40.7, 39.2, 37.2, 22.9, 21.4, 21.2, 20.1, 14.0, 13.5, 11.9, 11.3, 11.1.

Example 53

Compound of formula VII, wherein $R_1$ and $R_2$ taken together with the carbon atom to which they are attached are C=NO[naphthalen-2-yl], $R_{20}$=H, and Rx=Ac The title compound was prepared with the title compound of Example 16 and O-naphthalen-2-yl-hydroxylamine (prepared similarly to steps 49a and 49b) via similar conditions outlined in Example 35.

MS (ESI): m/z 838.09 [M+H].

Example 54

Compound of formula VII, wherein $R_1$ and $R_2$ taken together with the carbon atom to which they are attached are C=NO[naphthalen-yl], and $R_{20}$=Rx=H The title compound was prepared with the title compound of Example 53 via similar conditions described in Example 36. E:Z ratio was 1.6:1.

MS (ESI): m/z 796.10 [M+H].

Example 55

Compound of formula VII, wherein $R_1$ and $R_2$ taken together with the carbon atom to which they are attached are C=NO[pyridine-3-yl], $R_{20}$=H, and Rx=Ac The title compound was prepared with the title compound of Example 16 and commercially available O-pyridin-3-yl-hydroxylamine (prepared similarly to steps 49a and 49b) via similar conditions outlined in Example 35.

MS (ESI): m/z 788.00 [M+H].

Example 56

Compound of formula VII, wherein $R_1$ and $R_2$ taken together with the carbon atom to which they are attached are C=NO[pyridine-3-yl], and $R_{20}$=Rx=H The title compound was prepared with the title compound of Example 55 via similar conditions described in Example 36. E:Z ratio was 2:1.

MS (ESI): m/z 788.96 [M+H], 395.11 [M+2H].

E-isomer:

MS (ESI): m/z 747.01 [M+H], 374.11 [M+2H].

$^{13}$C NMR (CDCl$_3$, ppm) δ: 217.0, 177.7, 162.6, 157.6, 155.4, 144.2, 137.8, 124.1, 122.1, 103.9, 84.3, 81.1, 80.7, 79.6, 76.9, 70.1, 68.5, 67.2, 66.0, 60.9, 58.4, 44.4, 44.0, 43.1, 40.9, 39.2, 37.1, 22.9, 21.4, 21.1, 20.1, 14.0, 13.5, 11.9, 11.2, 11.1.

Example 57

Compound of formula VIII, wherein $R_1$ and $R_2$ taken together with the carbon atom to which they are attached are C=NNH[Ph], $R_{20}$=H, and Rx=Ac The title compound was prepared with the title compound of Example 16 and commercially available phenylhydrazine hydrochloride salt via similar conditions outlined in Example 35.

MS (ESI): m/z 787.10 [M+H].

Example 58

Compound of formula VIII, wherein $R_1$ and $R_2$ taken together with the carbon atom to which they are attached are C=NNH[Ph], and $R_{20}$=Rx=H The title compound was prepared with the title compound of Example 57 via similar conditions described in Example 36. E:Z ratio was 1.5:1. The isomers were separated by HPLC.
MS (ESI): m/z 745.00 [M+H].

Example 59

Compound of formula VII, wherein $R_1$ and $R_2$ taken together with the carbon atom to which they are attached are C=CH[CH=CHPh]. $R_{20}$=H, and Rx=Ac A mixture of compound from Example 16 (0.15 mmol), (2-bromo-vinyl)-benzene (1.6 eq.), potassium carbonate (2.6 eq.), and POPd (14 mol %) in acetonitrile (3 ml) was degassed, sealed and heated to 100° C. overnight. The mixture was then cooled and filtered through a pad of celite and the filtrate was evaporated to dryness. The residue was purified by column chromatography eluting with 1:3 (acetone/hexane) to give an off-white foam.
MS (ESI): m/z 797.06 [M+H].

Example 60

Compound of formula VII, wherein $R_1$=H and $R_2$=$(CH_2)_3$Ph, and $R_{20}$=Rx=H To a solution of compound from Example 59 (0.1 mmol) in MeOH (4 ml) was added 10% Pd/C (95 mg). The mixture was subjected to hydrogen under 60 psi overnight. The mixture was then filtered through a pad of celite and then evaporated to dryness. The residue was purified by column chromatography eluting with 2% MeOH/$CH_2Cl_2$ and was further purified by crystallization with EtOH and water to give the desired product as white crystals.
MS (ESI): m/z 759.11 [M+H].
$^{13}$C NMR (CDCl$_3$, ppm) δ: 217.5, 177.3, 158.2, 142.3, 128.7, 128.6, 126.1, 103.7, 84.8, 82.1, 80.6, 80.2, 70.5, 68.9, 66.6, 66.0, 58.4, 44.8, 44.0, 42.7, 41.6, 40.8, 38.9, 38.6, 36.2, 29.8, 29.4, 23.3, 21.3, 21.2, 19.2, 14.0, 13.8, 11.44, 11.37, 10.4.

Example 61

Compound of formula VII, wherein $R_1$=H and $R_2$=$CH_3$, and $R_{20}$=Rx=

The title compound was prepared with compound from Example 14 via similar conditions described in Example 60.
MS (ESI): m/z 655.16 [M+H].
$^{13}$C NMR (CDCl$_3$, ppm) δ: 217.7, 177.4, 158.3, 104.1, 84.9, 82.4, 80.4, 80.3, 78.2, 76.8, 70.7, 69.4, 68.2, 66.3, 58.4, 45.0, 44.0, 42.6, 40.6, 39.2, 38.5, 37.0, 23.4, 21.4, 21.1, 19.0, 14.8, 13.9, 13.8, 11.6, 11.3, 11.2.

Example 62

Compound of formula VII, wherein $R_1$=H and $R_2$=OH, $R_{20}$=H, and Rx=Ac

A solution of compound from Example 16 (21 mg) in THF was added LiAl(O'Bu)$_3$H (1.5 eq.) at room temperature. The reaction was completed in 5 minutes. The mixture was quenched with water and extracted with EtOAc. The combined organic extracts were dried over $Na_2CO_3$, filtered and concentrated under vacuum to give the desired product (17 mg).
MS (ESI): m/z 699.15 [M+H].

Example 63

Compound of formula VII, wherein $R_1$=H and $R_2$=OH, and $R_{20}$=Rx=

The title compound was prepared with the title compound of Example 62 via similar conditions described in Example 36. Purified by column chromatography eluting with 2% MeOH/$CH_2Cl_2$.
MS (ESI): m/z 657.09 [M+H].
$^{13}$C NMR (CDCl$_3$, ppm) δ: 218.5, 177.2, 158.1, 103.2, 84.9, 81.7, 80.2, 78.0, 76.7, 74.2, 71.1, 70.3, 68.2, 67.0, 62.6, 57.9, 44.7, 44.0, 42.5, 39.1, 38.8, 32.2, 23.2, 21.8, 21.0, 19.4, 14.1, 13.8, 11.6, 11.4, 11.1.

Example 64

Compound of formula VII, wherein $R_1$ and $R_2$ taken together with the carbon atom to which they are attached are C=NO[3-benzyloxy-phenyl], $R_{20}$=H, and Rx=Ac The title compound was prepared with the title compound of Example 16 and commercially available O-(3-benzyloxy-phenyl)-hydroxylamine (prepared similarly to steps 49a and 49b) via similar conditions outlined in Example 35.
MS (ESI): m/z 893.93 [M+H].

Example 65

Compound of formula VII, wherein $R_1$ and $R_2$ taken together with the carbon atom to which they are attached are C=NO[3-benzyloxy-phenyl], and $R_{20}$=Rx=H The title compound was prepared with the title compound of Example 64 via similar conditions described in Example 36. E:Z ratio was 2:1.
MS (ESI): m/z 852.24 [M+H].

E-isomer:
MS (ESI): m/z 852.24 [M+H].
$^{13}$C NMR (CDCl$_3$, ppm) δ: 217.1, 177.7, 161.4, 160.3, 160.0, 157.6, 137.3, 130.0, 128.8, 128.1, 127.8, 109.5, 107.4, 105.1, 101.7, 84.2, 81.1, 80.5, 79.8, 76.7, 70.6, 70.3, 69.8, 66.3, 66.2, 61.0, 58.4, 44.6, 44.1, 43.2, 40.5, 39.3, 37.1, 28.8, 22.8, 21.4, 21.3, 20.2, 13.9, 13.5, 12.0, 11.2, 10.9.

Example 66

Compound of formula VII, wherein $R_1$ and $R_2$ taken together with the carbon atom to which they are attached are C=NO[p-chloro-phenyl], $R_{20}$=H, and Rx=Ac The title compound was prepared with the title compound of Example 16 and commercially available O-(p-chloro-phenyl)-hydroxylamine (prepared similarly to steps 49a and 49b) via similar conditions outlined in Example 35.
MS (ESI): m/z 822.15 [M+H].

Example 67

Compound of formula VII, wherein $R_1$ and $R_2$ taken together with the carbon atom to which they are attached are C=NO[p-chloro-phenyl], and $R_{20}$=Rx=H The title compound was prepared with the title compound of Example 66 via similar conditions described in Example 36. E:Z ratio was 2:1.

MS (ESI): m/z 780.12 [M+H].

E-isomer:
MS (ESI): m/z 780.12 [M+H].
$^{13}$C NMR (CDCl$_3$, ppm) δ: 217.2, 177.8, 161.9, 157.71, 157.66, 129.4, 127.5, 116.2, 105.1, 84.3, 81.2, 80.4, 79.7, 76.7, 70.6, 69.9, 66.1, 60.9, 58.4, 44.6, 44.1, 43.1, 40.5, 39.2, 37.1, 28.7, 22.8, 21.4, 21.3, 20.2, 13.9, 13.5, 11.9, 11.2, 10.9.

Example 68

Compound of formula VII, wherein $R_1$ and $R_2$ taken together with the carbon atom to which they are attached are C=NO[m-chloro-phenyl], $R_{20}$=H, and Rx=Ac The title compound was prepared with the title compound of Example 16 and commercially available O-(m-chloro-phenyl)-hydroxylamine (prepared similarly to steps 55a and 55b) via similar conditions outlined in Example 35.

MS (ESI): m/z 822.18 [M+H].

Example 69

Compound of formula VII, wherein $R_1$ and $R_2$ taken together with the carbon atom to which they are attached are C=NO[m-chloro-phenyl], and $R_{20}$=Rx=H The title compound was prepared with the title compound of Example 68 via similar conditions described in Example 36. E:Z ratio was 2:1.

MS (ESI): m/z 780.10 [M+H].

E-isomer:
MS (ESI): m/z 780.10 [M+H].
$^{13}$C NMR (CDCl$_3$, ppm) δ: 217.1, 177.7, 162.1, 159.7, 157.6, 134.9, 130.3, 122.8, 115.3, 113.1, 105.0, 84.2, 81.2, 80.5, 79.7, 76.7, 70.6, 69.8, 66.2, 66.1, 60.9, 58.4, 44.6, 44.1, 43.2, 40.5, 39.2, 37.1, 28.9, 22.8, 21.4, 21.3, 20.2, 13.9, 13.5, 11.9, 11.2, 10.9.

Example 70

Compound of formula VII, wherein $R_1$ and $R_2$ taken together with the carbon atom to which they are attached are C=NO[o-chloro-phenyl], $R_{20}$=H, and Rx=Ac The title compound was prepared with the title compound of Example 16 and commercially available O-(o-chloro-phenyl)-hydroxylamine (prepared similarly to steps 55a and 55b) via similar conditions outlined in Example 35.

MS (ESI): m/z 822.09 [M+H].

Example 71

Compound of formula VII, wherein $R_1$ and $R_2$ taken together with the carbon atom to which they are attached are C=NO[o-chloro-phenyl], and $R_{20}$=Rx=H The title compound was prepared with the title compound of Example 70 via similar conditions described in Example 36. E:Z ratio was 2:1.

MS (ESI): m/z 780.12 [M+H].

E-isomer:
MS (ESI): m/z 780.12 [M+H].
$^{13}$C NMR (CDCl$_3$, ppm) δ: 217.2, 177.5, 163.1, 157.7, 154.5, 130.2, 128.0, 123.4, 120.8, 116.3, 104.0, 84.3, 82.6, 81.5, 80.7, 76.4, 72.5, 70.2, 68.8, 58.8, 58.7, 44.5, 44.2, 43.4, 40.8, 39.5, 37.3, 22.6, 21.6, 21.1, 20.1, 14.0, 13.4, 12.4, 11.13, 11.07.

Z-isomer:
MS (ESI): m/z 780.12 [M+H].
$^{13}$C NMR (CDCl$_3$, ppm) δ: 217.1, 177.5, 163.0, 157.7, 154.5, 130.2, 127.9, 123.5, 121.4, 116.6, 104.7, 84.3, 81.1, 80.5, 79.7, 76.7, 70.5, 69.4, 66.5, 66.3, 60.9, 58.4, 44.5, 44.0, 43.2, 40.6, 39.2, 37.1, 22.8, 21.3, 20.2, 14.0, 13.5, 12.0, 11.2, 11.0.

Example 72

Compound of formula VII, wherein $R_1$ and $R_2$ taken together with the carbon atom to which they are attached are C=NO[biphenyl-3-yl], $R_{20}$=H, and Rx=Ac The title compound was prepared with the title compound of Example 16 and commercially available O-biphenyl-3-yl-hydroxylamine (prepared similarly to steps 49a and 49b) via similar conditions outlined in Example 35.

MS (ESI): m/z 864.15 [M+H].

Example 73

Compound of formula VII, wherein $R_1$ and $R_2$ taken together with the carbon atom to which they are attached are C=NO[biphenyl-3-yl], and $R_{20}$=Rx=H The title compound was prepared with the title compound of Example 72 via similar conditions described in Example 36. E:Z ratio was 2:1.

MS (ESI): m/z 822.18 [M+H].

E-isomer:
MS (ESI): m/z 822.18 [M+H].
$^{13}$C NMR (CDCl$_3$, ppm) δ: 217.1, 177.7, 161.5, 159.5, 157.6, 142.7, 129.8, 128.9, 127.5, 121.6, 113.7, 105.0, 84.2, 81.1, 80.5, 79.8, 76.7, 70.6, 69.8, 66.3, 66.2, 61.0, 58.4, 44.6, 44.1, 43.2, 40.5, 39.3, 37.1, 28.8, 22.8, 21.4, 21.3, 20.3, 13.9, 13.5, 12.0, 11.2, 10.9.

Example 74

Compound of formula VII, wherein $R_1$ and $R_2$ taken together with the carbon atom to which they are attached are C=NO[2-amino-benzooxazol-5-ylmethyl], $R_{20}$=H, and Rx=Ac The title compound was prepared with the title compound of Example 16 and commercially available O-(2-amino-benzooxazol-5-ylmethyl)-hydroxylamine (prepared according to literature procedure) via similar conditions outlined in Example 35.

MS (ESI): m/z 858.16 [M+H], 429.71 [M+2H].

Example 75

Compound of formula VII, wherein $R_1$ and $R_2$ taken together with the carbon atom to which they are attached are C=NO[2-amino-benzooxazol-5-ylmethyl], and $R_{20}$=Rx=H The title compound was prepared with the title compound of Example 74 via similar conditions described in Example 36. E:Z ratio was 2:1.

MS (ESI): m/z 816.12 [M+H], 408.68 [M+2H].

E-isomer:

MS (ESI): m/z 816.12 [M+H], 408.68 [M+2H].

$^{13}$C NMR (CDCl$_3$, ppm) δ: 215.5, 178.2, 162.8, 159.7, 158.7, 147.8, 143.0, 135.7, 118.3, 113.7, 108.6, 105.1, 84.9, 81.0, 79.6, 75.5, 70.6, 69.7, 66.6, 66.2, 60.6, 58.7, 45.1, 44.0, 43.6, 40.5, 39.7, 28.9, 22.2, 21.4, 21.1, 20.5, 13.7, 13.6, 12.5, 10.9, 10.8.

Example 76

Compound of formula VII, wherein R$_1$ and R$_2$ taken together with the carbon atom to which they are attached are C=NO[6'-amino-[2,2']bipyridinyl-4-ylmethyl], R$_{20}$=H, and Rx=Ac The title compound was prepared with the title compound of Example 16 and commercially available O-(6'-amino-[2,2']bipyridinyl-4-ylmethyl)-hydroxylamine (prepared according to literature procedure) via similar conditions outlined in Example 35.

MS (ESI): m/z 895.09 [M+H], 448.20 [M+2H].

Example 77

Compound of formula VII, wherein R$_1$ and R$_2$ taken together with the carbon atom to which they are attached are C=NO[6'-amino-[2,2']bipyridinyl-4-ylmethyl], and R$_{20}$=Rx=H The title compound was prepared with the title compound of Example 74 via similar conditions described in Example 36. E:Z ratio was 2:1.

MS (ESI): m/z 853.13 [M+H], 427.22 [M+2H].

E-isomer:

MS (ESI): m/z 853.13 [M+H], 427.22 [M+2H].

$^{13}$C NMR (CDCl$_3$, ppm) δ: 216.2, 178.0, 159.2, 158.6, 158.5, 148.9, 138.8, 136.4, 133.4, 120.8, 111.7, 109.4, 105.0, 84.3, 80.7, 80.5, 79.2, 76.5, 73.4, 70.6, 69.8, 66.10, 66.07, 60.5, 58.9, 44.6, 43.6, 43.3, 40.5, 39.4, 37.1, 28.7, 22.8, 21.4, 21.3, 20.2, 14.0, 13.6, 12.0, 11.1, 10.8.

Example 78

Compound of formula VII, wherein R$_1$ and R$_2$ taken together with the carbon atom to which they are attached are C=NO[phenyl], and R$_{20}$=(phenylbutyl), Rx=Ac The title compound was prepared with the title compound of Example 30 and commercially available O-phenyl-hydroxylamine via similar conditions outlined in Example 35.

MS (ESI): m/z 920.14 [M+H].

Example 79

Compound of formula VII, wherein R$_1$ and R$_2$ taken together with the carbon atom to which they are attached are C=NO[phenyl], and R$_{20}$=(phenylbutyl), Rx=H The title compound was prepared with the title compound of Example 78 via similar conditions described in Example 36. E:Z ratio was 4:1.

MS (ESI): m/z 878.03 [M+H].

Example 80

Compound of formula VII, wherein R$_1$ and R$_2$ taken together with the carbon atom to which they are attached are C=CH$_2$, and R$_{20}$=(3-phenylsulfanyl-propyl), Rx=H The title compound was prepared from the title compound of Example 13 and 3-phenylsulfanyl-propylamine via the similar conditions described in Example 18 and Example 12.

MS (ESI): m/z 803.08 [M+H].

Example 81

Compound of formula VII, wherein R$_1$ and R$_2$ taken together with the carbon atom to which they are attached are C=CH$_2$, and R$_{20}$=(benzylsulfanyl-ethyl), Rx=H The title compound was prepared from the title compound of Example 13 and 2-benzylsulfanyl-ethylamine hydrochloride salt via the similar conditions described in Example 18 and Example 12.

MS (ESI): m/z 803.10 [M+H].

Example 82

Compound of formula VII, wherein R$_1$ and R$_2$ taken together with the carbon atom to which they are attached are C=NO[prop-2-ynyl], R$_{20}$=H, and Rx=Ac The title compound was prepared with the title compound of Example 16 and O-prop-2-ynyl-hydroxylamine (prepared according to literature procedure) via similar conditions outlined in Example 35.

MS (ESI): m/z 750.10 [M+H].

Example 83

Compound of formula VII, wherein R$_1$ and R$_2$ taken together with the carbon atom to which they are attached are C=NO[prop-2-ynyl], and R$_{20}$=Rx=H The title compound was prepared with the title compound of Example 82 via similar conditions described in Example 36. E:Z ratio was 2:1.

MS (ESI): m/z 708.12 [M+H].

Example 84

Compound of formula VII, wherein R$_1$ and R$_2$ taken together with the carbon atom to which they are attached are C=NO[2-Thiazol-2-yl-benzyl], R$_{20}$=H, and Rx=Ac The title compound was prepared with the title compound of Example 16 and O-(2-Thiazol-2-yl-benzyl)-hydroxylamine (prepared according to literature procedure) via similar conditions outlined in Example 35.

MS (ESI): m/z 885.08 [M+H], 443.20 [M+2H].

Example 85

Compound of formula VII, wherein R$_1$ and R$_2$ taken together with the carbon atom to which they are attached are C=NO[2-Thiazol-2-yl-benzyl], and R$_{20}$=Rx=H The title compound was prepared with the title compound of Example 84 via similar conditions described in Example 36. E:Z ratio was 2.5:1.

MS (ESI): m/z 843.01 [M+H], 422.13 [M+2H].

E-isomer:

MS (ESI): m/z 843.01 [M+H], 422.13 [M+2H].

$^{13}$C NMR (CDCl$_3$, ppm) δ: 216.8, 177.6, 158.2, 157.8, 143.5, 136.5, 132.3, 130.3, 129.8, 129.0, 128.0, 120.0, 104.5, 84.4, 80.8, 80.6, 79.4, 76.7, 74.5, 70.5, 69.3, 66.6, 66.2, 61.1, 58.3, 44.4, 44.0, 43.1, 40.7, 39.1, 37.3, 29.9, 22.9, 21.4, 21.3, 20.0, 14.0, 13.4, 11.8, 11.3, 11.0.

Z-isomer:
MS (ESI): m/z 843.01 [M+H], 422.13 [M+2H].

Example 86

Compound of formula VII, wherein $R_1$ and $R_2$ taken together with the carbon atom to which they are attached are C=NO[3-Thiazol-2-yl-benzyl], $R_{20}$=H, and Rx=Ac The title compound was prepared with the title compound of Example 16 and O-(3-Thiazol-2-yl-benzyl)-hydroxylamine (prepared according to literature procedure) via similar conditions outlined in Example 35.
MS (ESI): m/z 885.07 [M+H], 443.18 [M+2H].

Example 87

Compound of formula VII, wherein $R_1$ and $R_2$ taken together with the carbon atom to which they are attached are C=NO[3-Thiazol-2-yl-benzyl], and $R_{20}$=Rx=H The title compound was prepared with the title compound of Example 86 via similar conditions described in Example 36. E:Z ratio was 2.5:1.
MS (ESI): m/z 842.93 [M+H], 422.09 [M+2H].

E-isomer:
MS (ESI): m/z 842.93 [M+H], 422.09 [M+2H].
$^{13}$C NMR (CDCl$_3$, ppm) δ: 217.0, 177.6, 168.6, 158.4, 157.8, 143.9, 138.9, 133.9, 129.9, 129.3, 126.4, 126.3, 119.1, 104.9, 84.5, 80.9, 80.5, 79.3, 76.8, 76.1, 70.6, 69.7, 66.3, 66.1, 61.0, 58.3, 44.4, 44.1, 43.1, 40.5, 39.1, 37.4, 29.9, 28.9, 23.0, 21.42, 21.37, 19.9, 14.0, 13.5, 11.7, 11.3, 11.0.

Z-isomer:
MS (ESI): m/z 842.93 [M+H], 422.09 [M+2H].
$^{13}$C NMR (CDCl$_3$, ppm) δ: 217.2, 177.5, 168.4, 159.2, 157.7, 144.0, 138.8, 134.0, 130.0, 129.3, 126.6, 126.4, 119.2, 104.7, 84.3, 82.5, 81.2, 80.6, 76.2, 73.0, 70.5, 69.5, 66.4, 58.62, 58.58, 44.6, 44.2, 43.4, 40.6, 39.5, 37.3, 29.9, 22.6, 21.6, 21.3, 20.1, 14.0, 13.4, 12.3, 11.1, 11.0.

Example 88

Compound of formula VII, wherein $R_1$ and $R_2$ taken together with the carbon atom to which they are attached are C=NO[4-Thiazol-2-yl-benzyl], $R_{20}$=H, and Rx=Ac The title compound was prepared with the title compound of Example 16 and O-(4-Thiazol-2-yl-benzyl)-hydroxylamine (prepared according to literature procedure) via similar conditions outlined in Example 35.
MS (ESI): m/z 884.99 [M+H], 443.14 [M+2H].

Example 89

Compound of formula VII, wherein $R_1$ and $R_2$ taken together with the carbon atom to which they are attached are C=NO[4-Thiazol-2-yl-benzyl], and $R_{20}$=Rx=H The title compound was prepared with the title compound of Example 88 via similar conditions described in Example 36. E:Z ratio was 2.5:1.
MS (ESI): m/z 842.95 [M+H], 422.11 [M+2H].

E-isomer:
MS (ESI): m/z 842.95 [M+H], 422.11 [M+2H].
$^{13}$C NMR (CDCl$_3$, ppm) δ: 216.9, 177.8, 168.5, 158.7, 158.0, 148.8, 144.2, 144.0, 140.1, 129.1, 128.5, 127.9, 127.1, 126.94, 126.86, 119.5, 119.1, 118.9, 105.0, 84.4, 80.4, 80.5, 79.3, 76.9, 76.2, 75.8, 70.6, 69.8, 66.1, 60.8, 58.4, 44.5, 44.0, 43.2, 40.5, 39.2, 37.3, 28.8, 22.9, 21.4, 20.0, 14.0, 13.5, 11.8, 11.3, 10.9.

Z-isomer:
MS (ESI): m/z 842.95 [M+H], 422.11 [M+2H].
$^{13}$C NMR (CDCl$_3$, ppm) δ: 217.3, 177.5, 168.3, 159.3, 157.7, 144.0, 139.8, 133.5, 128.9, 126.9, 119.0, 105.1, 84.3, 82.5, 81.3, 80.4, 76.2, 76.0, 73.0, 70.7, 70.0, 66.0, 58.6, 58.5, 44.7, 44.3, 43.4, 40.5, 39.4, 37.3, 28.4, 22.6, 21.6, 21.5, 20.1, 13.9, 13.4, 12.3, 11.0.

Example 90

Compound of formula VII, wherein $R_1$ and $R_2$ taken together with the carbon atom to which they are attached are C=NO[benzotriazol-1-ylmethyl], $R_{20}$=H, and Rx=Ac The title compound was prepared with the title compound of Example 16 and O-benzotriazol-1-ylmethyl-hydroxylamine (prepared according to literature procedure) via similar conditions outlined in Example 35.
MS (ESI): m/z 843.02 [M+H], 422.17 [M+2H].

Example 91

Compound of formula VII, wherein $R_1$ and $R_2$ taken together with the carbon atom to which they are attached are C=NO[benzotriazol-1-ylmethyl], and $R_{20}$=Rx=H The title compound was prepared with the title compound of Example 90 via similar conditions described in Example 36. E:Z ratio was 2:1.
MS (ESI): m/z 801.06 [M+H], 401.19 [M+2H].

E-isomer:
MS (ESI): m/z 801.06 [M+H], 401.19 [M+2H].
$^{13}$C NMR (CDCl$_3$, ppm) δ: 217.1, 177.7, 161.6, 157.8, 146.4, 133.4, 128.1, 124.4, 120.1, 110.8, 104.9, 84.4, 81.1, 80.3, 79.6, 78.9, 76.5, 70.5, 69.7, 66.3, 65.8, 60.9, 58.3, 44.5, 44.0, 43.1, 40.5, 39.2, 37.1, 22.8, 21.33, 21.26, 20.2, 13.9, 13.4, 11.9, 11.2, 10.8.

Z-isomer:
MS (ESI): m/z 801.06 [M+H], 401.19 [M+2H].
$^{13}$C NMR (CDCl$_3$, ppm) δ: 217.2, 177.5, 161.8, 157.7, 146.5, 133.5, 128.3, 124.5, 120.1, 111.0, 104.8, 84.2, 82.9, 81.3, 80.5, 78.8, 76.2, 72.6, 70.5, 69.5, 66.4, 58.6, 58.3, 44.7, 44.1, 43.3, 40.6, 39.4, 37.1, 22.5, 21.5, 21.4, 20.2, 13.9, 13.4, 12.3, 11.03, 11.00.

Example 92

Compound of formula VII, wherein $R_1$ and $R_2$ taken together with the carbon atom to which they are attached are
C=NO[1-methyl-1H-benzotriazol-5-ylmethyl], $R_{20}$=H, and Rx=Ac The title compound was prepared with the title compound of Example 16 and O-(1-methyl-1H-benzotriazol-5-ylmethyl)-hydroxylamine (prepared according to literature procedure) via similar conditions outlined in Example 35.
MS (ESI): m/z 857.04 [M+H], 429.18 [M+2H].

Example 93

Compound of formula VII, wherein $R_1$ and $R_2$ taken together with the carbon atom to which they are attached are C=NO[1-methyl-1H-benzotriazol-5-ylmethyl], and $R_{20}$=Rx=H The title compound was prepared with the title compound of Example 92 via similar conditions described in Example 36. E:Z ratio was 3.6:1.
MS (ESI): m/z 814.98 [M+H], 408.15 [M+2H].

E-isomer:
MS (ESI): m/z 814.98 [M+H], 408.15 [M+2H].
$^{13}$C NMR (CDCl$_3$, ppm) δ: 216.8, 177.7, 158.6, 157.9, 146.3, 134.4, 133.5, 127.7, 118.9, 109.4, 105.0, 84.5, 80.93, 80.92, 80.5, 79.2, 76.7, 76.0, 70.7, 69.8, 66.2, 66.0, 60.9, 58.3, 44.4, 44.2, 43.0, 40.5, 39.1, 37.4, 34.5, 28.7, 22.9, 21.44, 21.40, 19.9, 13.9, 13.5, 11.6, 11.3, 11.0.

Z-isomer:
MS (ESI): m/z 814.98 [M+H], 408.15 [M+2H].
$^{13}$C NMR (CDCl$_3$, ppm) δ: 217.0, 177.5, 159.2, 157.7, 134.1, 133.5, 128.2, 119.4, 109.4, 104.5, 84.3, 82.4, 81.2, 80.7, 76.24, 76.19, 72.9, 70.5, 69.3, 66.5, 58.6, 58.4, 44.6, 44.2, 43.3, 40.7, 39.4, 37.3, 34.5, 29.9, 22.6, 21.6, 21.3, 20.1, 14.0, 13.4, 12.3, 11.1, 11.0.

Example 94

Compound of formula VII, wherein $R_1$ and $R_2$ taken together with the carbon atom to which they are attached are C=NO[biphenyl-4-ylmethyl], $R_{20}$=H and Rx=Ac The title compound was prepared with the title compound of Example 16 and O-biphenyl-4-ylmethyl-hydroxylamine (prepared according to literature procedure) via similar conditions outlined in Example 35.
MS (ESI): m/z 877.92 [M+H].

Example 95

Compound of formula VII, wherein $R_1$ and $R_2$ taken together with the carbon atom to which they are attached are C=NO[biphenyl-4-ylmethyl], and $R_{20}$=Rx=H The title compound was prepared with the title compound of Example 94 via similar conditions described in Example 36. E:Z ratio was 3:1.
MS (ESI): m/z 835.92 [M+H].

E-isomer:
MS (ESI): m/z 835.92 [M+H].
$^{13}$C NMR (CDCl$_3$, ppm) δ: 216.8, 177.7, 158.6, 157.9, 146.3, 134.4, 133.5, 127.7, 118.9, 109.4, 105.0, 84.5, 80.93, 80.92, 80.5, 79.2, 76.7, 76.0, 70.7, 69.8, 66.2, 66.0, 60.9, 58.3, 44.4, 44.2, 43.0, 40.5, 39.1, 37.4, 34.5, 28.7, 22.9, 21.44, 21.40, 19.9, 13.9, 13.5, 11.6, 11.3, 11.0.

Example 96

Compound of formula VII, wherein $R_1$ and $R_2$ taken together with the carbon atom to which they are attached are C=NO[naphthalen-2-ylmethyl], $R_{20}$=H, and Rx=Ac The title compound was prepared with the title compound of Example 16 and O-naphthalen-2-ylmethyl-hydroxylamine (prepared according to literature procedure) via similar conditions outlined in Example 35.
MS (ESI): m/z 851.92 [M+H].

Example 97

Compound of formula VII, wherein $R_1$ and $R_2$ taken together with the carbon atom to which they are attached are C=NO[naphthalen-2-ylmethyl], and $R_{20}$=Rx=H The title compound was prepared with the title compound of Example 96 via similar conditions described in Example 36. E:Z ratio was 3:1.
MS (ESI): m/z 809.91 [M+H].

E-isomer:
MS (ESI): m/z 809.91 [M+H].
$^{13}$C NMR (CDCl$_3$, ppm) δ: 217.0, 177.6, 158.2, 157.8, 135.4, 133.5, 133.3, 128.30, 128.25, 127.9, 127.2, 126.23, 126.19, 126.1, 105.0, 84.5, 80.9, 80.5, 79.3, 76.9, 76.7, 70.7, 69.8, 66.14, 66.08, 61.0, 58.3, 44.4, 44.2, 43.1, 40.5, 39.1, 37.4, 29.9, 28.6, 23.0, 21.43, 21.40, 19.9, 13.9, 13.5, 11.7, 11.3, 11.0.

Example 98

Compound of formula VII, wherein $R_1$ and $R_2$ taken together with the carbon atom to which they are attached are C=NO[quinolin-2-ylmethyl], $R_{20}$=H, and Rx=Ac The title compound was prepared with the title compound of Example 16 and O-quinolin-2-ylmethyl-hydroxylamine (prepared according to literature procedure) via similar conditions outlined in Example 35.
MS (ESI): m/z 853.00 [M+H], 427.14 [M+2H].

Example 99

Compound of formula VII, wherein $R_1$ and $R_2$ taken together with the carbon atom to which they are attached are C=NO[quinolin-2-ylmethyl], and $R_{20}$=Rx=H The title compound was prepared with the title compound of Example 98 via similar conditions described in Example 36. E:Z ratio was 3:1.
MS (ESI): m/z 811.04 [M+H], 406.14 [M+2H].

E-isomer:
MS (ESI): m/z 811.04 [M+H], 406.14 [M+2H].
$^{13}$C NMR (CDCl$_3$, ppm) δ: 217.0, 177.8, 159.2, 158.9, 157.9, 147.8, 137.0, 129.7, 129.3, 128.0, 127.8, 126.5, 119.6, 105.0, 84.4, 81.0, 80.4, 79.4, 77.7, 76.7, 70.7, 69.9, 66.2, 66.1, 61.0, 58.4, 44.5, 44.1, 43.2, 40.5, 39.1, 37.3, 29.9, 28.6, 22.9, 21.40, 21.37, 20.0, 13.9, 13.4, 11.8, 11.3, 10.9.

Z-isomer:
MS (ESI): m/z 811.04 [M+H], 406.14 [M+2H].
$^{13}$C NMR (CDCl$_3$, ppm) δ: 217.2, 177.5, 159.5, 158.4, 157.8, 147.9, 137.0, 129.9, 129.4, 127.9, 126.7, 120.2, 104.9, 84.3, 82.2, 81.3, 80.6, 77.8, 76.3, 72.8, 70.6, 69.7, 66.2, 58.6, 58.3, 44.6, 44.3, 43.3, 40.5, 39.4, 37.4, 28.9, 22.6, 21.6, 21.4, 20.1, 14.0, 13.5, 12.2, 11.1, 11.0.

Example 100

Compound of formula VII, wherein $R_1$ and $R_2$ taken together with the carbon atom to which they are attached are C=NO[naphthalen-1-ylmethyl], $R_{20}$=H, and Rx=Ac The title compound was prepared with the title compound of Example 16 and O-naphthalen-1-ylmethyl-hydroxylamine (prepared according to literature procedure) via similar conditions outlined in Example 35.

MS (ESI): m/z 852.03 [M+H].

Example 101

Compound of formula VII, wherein $R_1$ and $R_2$ taken together with the carbon atom to which they are attached are C=NO[naphthalen-1-ylmethyl], and $R_{20}$=Rx=H The title compound was prepared with the title compound of Example 100 via similar conditions described in Example 36. E:Z ratio was 5.3:1.

MS (ESI): m/z 810.23 [M+H].

E-isomer:

MS (ESI): m/z 810.23 [M+H].
$^{13}$C NMR (CDCl$_3$, ppm) δ: 216.9, 177.5, 158.1, 157.8, 133.9, 133.3, 132.0, 129.1, 128.8, 127.3, 126.5, 125.9, 125.5, 124.3, 104.4, 84.5, 80.8, 80.5, 79.2, 76.8, 75.1, 70.4, 69.2, 66.6, 66.0, 61.1, 58.3, 44.3, 44.1, 43.0, 40.7, 39.1, 37.4, 29.9, 23.0, 21.4, 21.2, 20.0, 14.0, 13.5, 11.7, 11.3, 11.1.

Z-isomer:

MS (ESI): m/z 811.04 [M+H], 406.14 [M+2H].

Example 102

Compound of formula VII, wherein $R_1$ and $R_2$ taken together with the carbon atom to which they are attached are C=NO[biphenyl-2-ylmethyl], $R_{20}$=H, and Rx=Ac The title compound was prepared with the title compound of Example 16 and O-biphenyl-2-ylmethyl-hydroxylamine (prepared according to literature procedure) via similar conditions outlined in Example 35.

MS (ESI): m/z 878.40 [M+H].

Example 103

Compound of formula VII, wherein $R_1$ and $R_2$ taken together with the carbon atom to which they are attached are C=NO[biphenyl-2-ylmethyl], and $R_{20}$=Rx=H The title compound was prepared with the title compound of Example 102 via similar conditions described in Example 36. E:Z ratio was 2:1.

MS (ESI): m/z 836.32 [M+H].

E-isomer:

MS (ESI): m/z 836.32 [M+H].
$^{13}$C NMR (CDCl$_3$, ppm) δ: 217.0, 177.6, 157.9, 157.8, 142.2, 140.9, 134.9, 130.2, 129.7, 129.5, 128.3, 128.0, 127.6, 127.3, 105.1, 84.4, 80.8, 80.4, 79.4, 76.7, 74.5, 70.7, 69.9, 66.2, 66.1, 61.1, 58.3, 44.5, 44.1, 43.1, 40.5, 39.1, 37.4, 31.8, 29.9, 28.4, 22.94, 22.88, 21.43, 21.39, 20.0, 14.3, 13.9, 13.4, 11.7, 11.3, 10.9.

Z-isomer:

MS (ESI): m/z 836.32 [M+H].
$^{13}$C NMR (CDCl$_3$, ppm) δ: 217.3, 177.6, 158.8, 157.7, 142.3, 140.9, 134.8, 130.3, 129.9, 129.5, 128.3, 128.2, 127.6, 127.4, 105.1, 84.3, 82.7, 81.2, 80.5, 76.1, 74.4, 73.2, 70.7, 70.0, 66.0, 58.7, 58.6, 44.7, 44.2, 43.4, 40.4, 39.5, 37.3, 29.9, 28.4, 22.6, 21.6, 21.5, 20.2, 13.9, 13.4, 12.4, 11.02, 11.01.

Example 104

Compound of formula VII, wherein $R_1$ and $R_2$ taken together with the carbon atom to which they are attached are C=NO[biphenyl-3-ylmethyl], $R_{20}$=H, and Rx=Ac The title compound was prepared with the title compound of Example 16 and O-biphenyl-3-ylmethyl-hydroxylamine (prepared according to literature procedure) via similar conditions outlined in Example 35.

MS (ESI): m/z 878.41 [M+H].

Example 105

Compound of formula VII, wherein $R_1$ and $R_2$ taken together with the carbon atom to which they are attached are C=NO[biphenyl-3-ylmethyl], and $R_{20}$=Rx=H The title compound was prepared with the title compound of Example 104 via similar conditions described in Example 36. E:Z ratio was 6.9:1.

MS (ESI): m/z 836.37 [M+H].

E-isomer:

MS (ESI): m/z 836.37 [M+H].
$^{13}$C NMR (CDCl$_3$, ppm) δ: 217.0, 177.6, 158.2, 157.8, 141.5, 141.3, 138.4, 129.0, 128.9, 127.48, 127.46, 127.2, 127.1, 126.9, 105.1, 84.5, 80.9, 80.4, 79.3, 76.8, 76.6, 70.7, 69.9, 66.1, 61.0, 58.3, 44.5, 44.2, 43.0, 40.5, 39.1, 37.5, 28.4, 23.0, 21.4, 19.9, 13.9, 13.5, 11.6, 11.3, 11.0.

Z-isomer:

MS (ESI): m/z 836.37 [M+H].

Example 106

Compound of formula VII, wherein $R_1$ and $R_2$ taken together with the carbon atom to which they are attached are C=NO[quinolin-4-ylmethyl], $R_{20}$=H, and Rx=Ac The title compound was prepared with the title compound of Example 16 and O-quinolin-4-ylmethyl-hydroxylamine (prepared according to literature procedure) via similar conditions outlined in Example 35.

MS (ESI): m/z 853.38 [M+H], 427.33 [M+2H].

Example 107

Compound of formula VII, wherein $R_1$ and $R_2$ taken together with the carbon atom to which they are attached are C=NO[quinolin-4-ylmethyl], $R_{20}$=Rx=H The title compound was prepared with the title compound of Example 106 via similar conditions described in Example 36. E:Z ratio was 3.9:1.

MS (ESI): m/z 811.26 [M+H], 406.26 [M+2H].

E-isomer:

MS (ESI): m/z 811.26 [M+H], 406.26 [M+2H].

$^{13}$C NMR (CDCl$_3$, ppm) δ: 217.1, 177.7, 159.2, 157.8, 150.5, 148.4, 143.0, 130.4, 129.4, 127.0, 126.5, 123.6, 120.1, 105.1, 84.5, 81.0, 80.4, 79.4, 76.8, 73.1, 70.7, 70.0, 66.1, 65.9, 60.9, 58.3, 44.5, 44.2, 43.1, 40.5, 39.1, 37.4, 28.4, 22.9, 21.42, 21.39, 19.9, 13.9, 13.5, 11.7, 11.3, 10.9.

Z-isomer:

MS (ESI): m/z 811.26 [M+H], 406.26 [M+2H].

$^{13}$C NMR (CDCl$_3$, ppm) δ: 217.1, 177.3, 159.7, 157.5, 150.3, 142.7, 130.2, 129.3, 126.8, 126.3, 123.4, 120.0, 104.8, 84.1, 82.4, 81.1, 80.1, 76.0, 72.9, 72.6, 70.4, 69.7, 65.8, 58.4, 58.1, 44.4, 44.0, 43.1, 40.2, 39.2, 37.1, 28.1, 22.4, 21.3, 21.2, 19.9, 13.7, 13.2, 12.1, 10.8.

Example 108

Compound of formula VII, wherein $R_1$ and $R_2$ taken together with the carbon atom to which they are attached are C=NO[4-[1,2,4]triazol-1-yl-benzyl], $R_2$=H, and Rx=Ac The title compound was prepared with the title compound of Example 16 and O-(4-[1,2,4]triazol-1-yl-benzyl)-hydroxylamine (prepared according to literature procedure) via similar conditions outlined in Example 35.

MS (ESI): m/z 869.34 [M+H], 435.32 [M+2H].

Example 109

Compound of formula VII, wherein $R_1$ and $R_2$ taken together with the carbon atom to which they are attached are C=NO[4-[1,2,4]triazol-1-yl-benzyl], and $R_{20}$=Rx=H The title compound was prepared with the title compound of Example 108 via similar conditions described in Example 36. E:Z ratio was 3.7:1.

MS (ESI): m/z 827.36 [M+H], 414.30 [M+2H].

E-isomer:

MS (ESI): m/z 827.36 [M+H], 414.30 [M+2H].

$^{13}$C NMR (CDCl$_3$, ppm) δ: 217.0, 177.8, 158.6, 157.9, 152.8, 141.2, 138.3, 136.7, 129.3, 120.2, 105.1, 84.5, 81.0, 80.4, 79.2, 76.9, 75.5, 70.7, 69.9, 66.1, 65.9, 60.8, 58.3, 44.4, 44.2, 43.0, 40.4, 39.0, 37.5, 31.8, 28.4, 23.0, 22.9, 21.5, 21.4, 19.8, 14.3, 13.9, 13.5, 11.6, 11.3, 11.0.

Z-isomer:

MS (ESI): m/z 827.36 [M+H], 414.30 [M+2H].

$^{13}$C NMR (CDCl$_3$, ppm) δ: 217.4, 177.5, 159.4, 157.7, 152.9, 141.1, 138.1, 136.8, 129.8, 120.3, 105.1, 84.3, 82.4, 81.3, 80.4, 76.2, 75.6, 72.9, 70.7, 70.0, 66.0, 58.6, 58.3, 44.7, 44.3, 43.3, 40.5, 39.4, 37.4, 28.4, 22.6, 21.6, 21.5, 20.1, 13.9, 13.4, 12.2, 11.0.

Example 110

Compound of formula VII, wherein $R_1$ and $R_2$ taken together with the carbon atom to which they are attached are C=NO[5-p-tolyl-[1,3,4]oxadiazol-2-ylmethyl], $R_{20}$=H, and Rx=Ac The title compound was prepared with the title compound of Example 16 and O-(5-p-tolyl-[1,3,4]oxadiazol-2-ylmethyl)-hydroxylamine (prepared according to literature procedure) via similar conditions outlined in Example 35.

MS (ESI): m/z 884.36 [M+H], 442.84 [M+2H].

Example 111

Compound of formula VII, wherein $R_1$ and $R_2$ taken together with the carbon atom to which they are attached are C=NO[5-p-tolyl-[1,3,4]oxadiazol-2-ylmethyl], and $R_{20}$=Rx=H The title compound was prepared with the title compound of Example 110 via similar conditions described in Example 36. E:Z ratio was 1.8:1.

MS (ESI): m/z 842.37 [M+H], 421.84 [M+2H].

E-isomer:

MS (ESI): m/z 842.37 [M+H], 421.84 [M+2H].

$^{13}$C NMR (CDCl$_3$, ppm) δ: 216.9, 177.7, 165.8, 163.0, 160.7, 157.8, 142.6, 130.0, 127.3, 121.2, 105.2, 84.4, 81.0, 80.4, 79.7, 76.5, 70.7, 70.0, 66.05, 66.01, 65.6, 60.8, 58.3, 44.6, 44.0, 43.2, 40.4, 39.3, 37.1, 31.8, 28.4, 22.9, 22.8, 21.9, 21.4, 21.3, 20.1, 14.3, 13.9, 13.4, 11.9, 11.1, 10.8.

Z-isomer:

MS (ESI): m/z 842.37 [M+H], 421.84 [M+2H].

$^{13}$C NMR (CDCl$_3$, ppm) δ: 217.1, 177.3, 165.8, 162.7, 160.8, 157.5, 142.5, 129.8, 127.1, 121.0, 104.9, 84.0, 82.5, 81.1, 80.3, 75.9, 72.4, 70.4, 69.7, 65.8, 65.4, 58.4, 58.1, 44.5, 44.0, 43.1, 40.2, 39.2, 37.0, 28.1, 22.3, 21.7, 21.32, 21.26, 19.9, 14.2, 13.7, 13.2, 12.1, 10.78, 10.77.

Example 112

Compound of formula VII, wherein $R_1$ and $R_2$ taken together with the carbon atom to which they are attached are C=NO[quinoxalin-6-ylmethyl], $R_{20}$=H, and Rx=Ac The title compound was prepared with the title compound of Example 16 and O-quinoxalin-6-ylmethyl-hydroxylamine (prepared according to literature procedure) via similar conditions outlined in Example 35.

MS (ESI): m/z 854.44 [M+H], 427.88 [M+2H].

Example 113

Compound of formula VII, wherein $R_1$ and $R_2$ taken together with the carbon atom to which they are attached are C=NO[quinoxalin-6-ylmethyl], and $R_{20}$=Rx=H The title compound was prepared with the title compound of Example 112 via similar conditions described in Example 36. E:Z ratio was 5:1.

MS (ESI): m/z 812.32 [M+H], 406.79 [M+2H].

E-isomer:

MS (ESI): m/z 812.32 [M+H], 406.79 [M+2H].

$^{13}$C NMR (CDCl$_3$, ppm) δ: 216.5, 177.9, 159.1, 158.2, 145.2, 145.1, 143.0, 142.8, 141.2, 129.7, 129.1, 126.7, 105.2, 84.3, 80.86, 80.85, 80.6, 79.5, 76.3, 75.1, 70.7, 70.0, 66.1, 66.0, 60.7, 58.2, 44.7, 44.2, 43.2, 40.5, 39.3, 37.3, 31.8, 28.4, 22.9, 22.8, 21.4, 21.3, 20.1, 14.3, 13.9, 12.0, 11.2, 11.0.

Z-isomer:

MS (ESI): m/z 812.32 [M+H], 406.79 [M+2H].

$^{13}$C NMR (CDCl$_3$, ppm) δ: 217.3, 177.5, 159.7, 157.8, 145.4, 145.2, 143.2, 142.9, 140.6, 130.0, 129.8, 128.0, 105.1, 84.3, 82.5, 81.3, 80.5, 76.2, 75.6, 72.8, 70.7, 70.0, 66.0, 58.6, 58.3, 44.7, 44.3, 43.3, 40.5, 39.4, 37.3, 28.4, 22.6, 21.6, 21.5, 20.2, 13.9, 13.4, 12.3, 11.0.

Example 114

Compound of formula VII, wherein $R_1$ and $R_2$ taken together with the carbon atom to which they are attached are C=NO[3-pyrazol-1-yl-benzyl], $R_{20}$=H, and Rx=Ac The title compound was prepared with the title compound of Example 16 and O-(3-pyrazol-1-yl-benzyl)-hydroxylamine (prepared according to literature procedure) via similar conditions outlined in Example 35.
MS (ESI): m/z 868.43 [M+H], 434.88 [M+2H].

Example 115

Compound of formula VII, wherein $R_1$ and $R_2$ taken together with the carbon atom to which they are attached are C=NO[3-pyrazol-1-yl-benzyl], and $R_{20}$=Rx=H The title compound was prepared with the title compound of Example 114 via similar conditions described in Example 36. E:Z ratio was 3:1.
MS (ESI): m/z 826.40 [M+H], 413.86 [M+2H].

E-isomer:
MS (ESI): m/z 826.40 [M+H], 413.86 [M+2H].
$^{13}$C NMR (CDCl$_3$, ppm) δ: 217.2, 177.7, 158.5, 157.8, 141.2, 140.5, 139.5, 129.7, 127.2, 126.1, 118.9, 118.8, 107.7, 105.1, 84.5, 80.9, 80.4, 79.2, 76.8, 76.0, 70.7, 69.9, 66.04, 65.96, 60.9, 58.3, 44.4, 44.2, 43.0, 40.5, 39.0, 37.5, 29.9, 28.4, 23.0, 21.5, 19.9, 13.9, 13.5, 11.6, 11.3, 10.9.

Z-isomer:
MS (ESI): m/z 826.40 [M+H], 413.86 [M+2H].
$^{13}$C NMR (CDCl$_3$, ppm) δ: 217.1, 177.3, 159.0, 157.5, 141.1, 140.3, 139.2, 129.5, 126.9, 126.1, 118.9, 118.7, 107.6, 104.8, 84.1, 82.3, 81.0, 80.2, 75.9, 75.8, 72.7, 70.4, 69.7, 65.8, 58.4, 58.2, 44.5, 44.0, 43.1, 40.2, 39.2, 37.1, 29.7, 28.1, 22.3, 21.4, 21.2, 19.9, 13.7, 13.2, 12.1, 10.80, 10.78.

Example 116

Compound of formula VII, wherein $R_1$ and $R_2$ taken together with the carbon atom to which they are attached are C=NO[3-(3-methyl-pyrazol-1-yl)-benzyl], $R_{20}$=H, and Rx=Ac The title compound was prepared with the title compound of Example 16 and O-[3-(3-methyl-pyrazol-1-yl)-benzyl]-hydroxylamine (prepared according to literature procedure) via similar conditions outlined in Example 35.
MS (ESI): m/z 882.39 [M+H], 441.86 [M+2H].

Example 117

Compound of formula VII, wherein $R_1$ and $R_2$ taken together with the carbon atom to which they are attached are C=NO[3-(3-methyl-pyrazol-1-yl)-benzyl], and $R_{20}$=Rx=H The title compound was prepared with the title compound of Example 116 via similar conditions described in Example 36. E:Z ratio was 3.3:1.
MS (ESI): m/z 840.36 [M+H], 420.84 [M+2H].

E-isomer:
MS (ESI): m/z 840.36 [M+H], 420.84 [M+2H].
$^{13}$C NMR (CDCl$_3$, ppm) δ: 217.0, 177.7, 158.4, 157.8, 150.7, 140.5, 139.4, 129.6, 127.8, 125.6, 118.5, 118.4, 107.7, 105.1, 84.5, 80.9, 80.4, 79.2, 76.8, 76.1, 70.7, 69.9, 66.05, 66.02, 61.0, 58.2, 44.4, 44.2, 43.0, 40.5, 39.0, 37.4, 29.9, 28.4, 23.0, 21.4, 19.9, 14.0, 13.9, 13.5, 11.6, 11.3, 10.9.

Z-isomer:
MS (ESI): m/z 840.36 [M+H], 420.84 [M+2H].
$^{13}$C NMR (CDCl$_3$, ppm) δ: 217.1, 177.3, 159.0, 157.5, 150.6, 140.3, 139.1, 129.4, 127.5, 125.6, 118.5, 118.3, 107.6, 104.8, 84.1, 82.3, 81.0, 80.2, 75.93, 75.91, 72.8, 70.4, 69.7, 65.8, 58.4, 58.3, 44.5, 44.0, 43.1, 40.2, 39.2, 37.1, 29.7, 28.1, 22.3, 21.4, 21.2, 19.9, 13.8, 13.7, 13.2, 12.1, 10.80, 10.78.

Example 118

Compound of formula VII, wherein $R_1$ and $R_2$ taken together with the carbon atom to which they are attached are C=NO[3-imidazol-1-yl-benzyl], $R_{20}$=H, and Rx=Ac The title compound was prepared with the title compound of Example 16 and O-(3-imidazol-1-yl-benzyl)-hydroxylamine (prepared according to literature procedure) via similar conditions outlined in Example 35.
MS (ESI): m/z 868.43 [M+H], 434.89 [M+2H].

Example 119

Compound of formula VII, wherein $R_1$ and $R_2$ taken together with the carbon atom to which they are attached are C=NO[3-imidazol-1-yl-benzyl], and $R_{20}$=Rx=H The title compound was prepared with the title compound of Example 118 via similar conditions described in Example 36. E:Z ratio was 3.9:1.
MS (ESI): m/z 826.47 [M+H], 413.90 [M+2H].

E-isomer:
MS (ESI): m/z 826.47 [M+H], 413.90 [M+2H].
$^{13}$C NMR (CDCl$_3$, ppm) δ: 217.0, 177.8, 158.7, 157.9, 140.2, 137.7, 135.9, 130.6, 130.1, 126.8, 120.9, 120.8, 118.5, 105.1, 84.5, 81.0, 80.5, 79.1, 76.9, 75.6, 70.7, 69.9, 66.0, 65.8, 60.8, 58.3, 44.4, 44.3, 43.0, 40.5, 39.0, 37.5, 34.9, 31.8, 28.4, 25.5, 23.0, 22.9, 21.5, 21.4, 19.8, 14.4, 13.9, 13.5, 11.5, 11.3, 11.0.

Z-isomer:
MS (ESI): m/z 826.47 [M+H], 413.90 [M+2H].
$^{13}$C NMR (CDCl$_3$, ppm) δ: 217.1, 177.3, 159.2, 157.5, 139.9, 137.5, 135.6, 130.5, 130.0, 127.0, 121.0, 120.9, 118.3, 104.8, 84.1, 82.1, 81.1, 80.1, 76.0, 75.4, 72.6, 70.4, 69.7, 65.8, 58.4, 58.0, 44.4, 44.1, 43.1, 40.2, 39.2, 37.1, 28.1, 22.4, 21.4, 21.2, 19.9, 13.7, 13.2, 12.0, 10.8.

Example 120

Compound of formula VII, wherein $R_1$ and $R_2$ taken together with the carbon atom to which they are attached are C=NO[2-methyl-quinolin-4-ylmethyl], $R_{20}$=H, and Rx=Ac The title compound was prepared with the title compound of Example 16 and O-(2-methyl-quinolin-4-ylmethyl)-hydroxylamine (prepared according to literature procedure) via similar conditions outlined in Example 35.
MS (ESI): m/z 867.45 [M+H], 434.40 [M+2H].

Example 121

Compound of formula VII, wherein $R_1$ and $R_2$ taken together with the carbon atom to which they are attached are C=NO[2-methyl-quinolin-4-ylmethyl], and $R_{20}$=Rx=H The title compound was prepared with the title compound of Example 120 via similar conditions described in Example 36. E:Z ratio was 4.3:1.
MS (ESI): m/z 825.38 [M+H], 413.35 [M+2H].

E-isomer:
MS (ESI): m/z 825.38 [M+H], 413.35 [M+2H].
$^{13}$C NMR (CDCl$_3$, ppm) δ: 217.1, 177.7, 159.1, 159.0, 157.9, 148.2, 142.9, 129.45, 129.41, 126.1, 124.9, 123.5, 121.3, 105.1, 84.5, 81.0, 80.4, 79.4, 76.8, 73.4, 70.7, 70.0, 66.0, 65.9, 60.9, 58.3, 44.5, 44.2, 43.1, 40.5, 39.1, 37.4, 28.4, 25.7, 22.9, 21.43, 21.39, 19.9, 13.9, 13.5, 11.7, 11.3, 10.9.

Z-isomer:
MS (ESI): m/z 825.38 [M+H], 413.35 [M+2H].
$^{13}$C NMR (CDCl$_3$, ppm) δ: 217.2, 177.3, 159.6, 158.8, 157.5, 148.0, 142.4, 129.3, 129.2, 125.9, 124.7, 123.3, 121.1, 104.8, 84.1, 82.4, 81.1, 80.0, 75.9, 73.1, 72.7, 70.4, 69.7, 65.8, 58.4, 58.2, 44.4, 44.0, 43.1, 40.2, 39.2, 37.0, 28.1, 25.5, 22.3, 21.3, 21.2, 19.9, 13.7, 13.2, 12.1, 10.8.

Example 122

Compound of formula VII, wherein $R_1$ and $R_2$ taken together with the carbon atom to which they are attached are C=NO[1H-benzotriazol-5-ylmethyl], $R_{20}$=H, and Rx=Ac The title compound was prepared with the title compound of Example 16 and O-(1H-benzotriazol-5-ylmethyl)-hydroxylamine (prepared according to literature procedure) via similar conditions outlined in Example 35.
MS (ESI): m/z 843.43 [M+H].

Example 123

Compound of formula VII, wherein $R_1$ and $R_2$ taken together with the carbon atom to which they are attached are C=NO[1H-benzotriazol-5-ylmethyl], and $R_{20}$=Rx=H The title compound was prepared with the title compound of Example 122 via similar conditions described in Example 36. E:Z ratio was 2:1.
MS (ESI): m/z 801.39 [M+H].

E-isomer:
MS (ESI): m/z 801.39 [M+H].
$^{13}$C NMR (CDCl$_3$, ppm) δ: 216.8, 177.5, 158.5, 158.3, 136.4, 125.4, 115.7, 112.9, 104.7, 84.8, 80.8, 80.1, 78.9, 77.3, 77.0. 76.8, 76.6, 75.8, 70.5, 69.7, 65.71, 65.67, 60.6, 58.1, 44.04, 44.00, 42.7, 40.2, 38.6, 37.3, 28.2, 22.8, 21.3, 21.2, 19.4, 13.7, 13.3, 11.3, 11.1, 10.9.

Z-isomer:
MS (ESI): m/z 801.39 [M+H].

Example 124

Compound of formula VII, wherein $R_1$ and $R_2$ taken together with the carbon atom to which they are attached are C=NO[1-phenyl-1H-benzotriazol-4-ylmethyl], $R_{20}$=H, and Rx=Ac The title compound was prepared with the title compound of Example 16 and O-(1-phenyl-1H-benzotriazol-4-ylmethyl)-hydroxylamine (prepared according to literature procedure) via similar conditions outlined in Example 35.
MS (ESI): m/z 919.38 [M+H], 460.36 [M+2H].

Example 125

Compound of formula VII, wherein $R_1$ and $R_2$ taken together with the carbon atom to which they are attached are C=NO[1-phenyl-1H-benzotriazol-4-ylmethyl], and $R_{20}$=Rx=H The title compound was prepared with the title compound of Example 124 via similar conditions described in Example 36. E:Z ratio was 4.1:1.
MS (ESI): m/z 877.39 [M+H], 439.37 [M+2H].

E-isomer:
MS (ESI): m/z 877.39 [M+H], 439.37 [M+2H].
$^{13}$C NMR (CDCl$_3$, ppm) δ: 217.0, 177.8, 158.8, 157.8, 144.9, 137.4, 132.6, 130.9, 130.1, 128.8, 128.5, 123.2, 123.0, 109.9, 105.1, 84.4, 80.9, 80.4, 79.4, 76.5, 71.8, 70.7, 70.0, 66.2, 66.1, 61.1, 58.4, 44.6, 44.1, 43.1, 40.5, 39.1, 37.3, 29.9, 28.4, 22.9, 21.5, 21.4, 20.1, 13.9, 13.5, 11.8, 11.3, 10.9.

Z-isomer:
MS (ESI): m/z 877.39 [M+H], 439.37 [M+2H].
$^{13}$C NMR (CDCl$_3$, ppm) δ: 217.2, 177.4, 159.3, 157.5, 144.8, 137.1, 132.5, 130.5, 129.9, 128.7, 128.2, 123.4, 123.1, 109.9, 104.9, 84.0, 82.5, 81.0, 80.3, 75.8, 72.9, 71.6, 70.4, 69.7, 65.8, 58.5, 58.4, 44.5, 44.0, 43.2, 40.2, 39.2, 37.0, 29.7, 28.1, 22.3, 21.4, 21.3, 20.0, 13.7, 13.1, 12.2, 10.8.

Example 126

Compound of formula VII, wherein $R_1$ and $R_2$ taken together with the carbon atom to which they are attached are C=NO[6-amino-5-hydroxy-pyridin-2-ylmethyl], $R_{20}$=H, and Rx=Ac The title compound was prepared with the title compound of Example 16 and O-(6-amino-5-hydroxy-pyridin-2-ylmethyl)-hydroxylamine (prepared according to literature procedure) via similar conditions outlined in Example 35.
MS (ESI): m/z 834.44 [M+H], 417.88 [M+2H].

Example 127

Compound of formula VII, wherein $R_1$ and $R_2$ taken together with the carbon atom to which they are attached are C=NO[6-amino-5-hydroxy-pyridin-2-ylmethyl], and $R_{20}$=Rx=H The title compound was prepared with the title compound of Example 126 via similar conditions described in Example 36. E:Z ratio was 3:1.
MS (ESI): m/z 792.50 [M+H], 396.90 [M+2H].

E-isomer:
MS (ESI): m/z 792.50 [M+H], 396.90 [M+2H].

Z-isomer:
MS (ESI): m/z 792.50 [M+H], 396.90 [M+2H].

Example 128

Compound of formula VII, wherein $R_1$ and $R_2$ taken together with the carbon atom to which they are attached are C=NO[oxazolo[4,5-b]pyridin-5-ylmethyl], $R_{20}$=H, and Rx=Ac The title compound of Example 126 and p-toluenesulfonyl chloride was dissolved in trimethoxy-methane. The mixture was heated at 75° C. for 2 hours, and then was quenched with saturated NaHCO$_3$ and extracted with EtOAc. The combined organic extracts were washed with brine, dried, filtered and concentrated under vacuum to give the brownish foam. The residue was carried directly to the next step without purification.
MS (ESI): m/z 834.44 [M+H], 422.89 [M+2H].

Example 129

Compound of formula VII, wherein R$_1$ and R$_2$ taken together with the carbon atom to which they are attached are
C=NO[oxazolo[4,5-b]pyridin-5-ylmethyl], and R$_{20}$=Rx=H The title compound was prepared with the title compound of Example 128 via similar conditions described in Example 36. E:Z ratio was 3:1.
MS (ESI): m/z 802.51 [M+H], 401.91 [M+2H].

E-isomer:
MS (ESI): m/z 802.51 [M+H], 401.91 [M+2H].
$^{13}$C NMR (CDCl$_3$, ppm) δ: 217.1, 177.9, 159.2, 157.9, 156.1, 155.8, 154.2, 141.7, 129.3, 128.6, 119.6, 119.3, 105.1, 84.4, 81.0, 80.4, 79.4, 76.9, 76.6, 70.7, 70.0, 66.2, 66.1, 60.9, 58.3, 44.5, 44.1, 43.1, 40.5, 39.1, 37.3, 28.4, 22.9, 21.5, 21.4, 20.0, 13.9, 13.4, 11.8, 11.3, 10.9.

Z-isomer:
MS (ESI): m/z 802.51 [M+H], 401.91 [M+2H].
$^{13}$C NMR (CDCl$_3$, ppm) δ: 217.4, 177.6, 159.8, 157.8, 155.90, 155.87, 141.8, 128.6, 119.7, 119.6, 105.1, 84.3, 82.6, 81.3, 80.5, 76.1, 72.9, 70.6, 70.0, 66.0, 58.6, 58.5, 44.7, 44.3, 43.4, 40.5, 39.5, 37.3, 28.4, 22.6, 21.6, 21.5, 20.2, 13.9, 13.4, 12.3, 11.04, 11.00.

Example 130

Compound of formula VII, wherein R$_1$ and R$_2$ taken together with the carbon atom to which they are attached are C=NO[2-amino-oxazolo[4,5-b]pyridin-5-ylmethyl], R$_{20}$=H, and Rx=Ac The title compound of Example 126 and cyanogen bromide was dissolved in ethanol. The mixture was stirred at room temperature for 2 hours, and then was quenched with saturated NaHCO$_3$ and extracted with EtOAc. The combined organic extracts were washed with brine, dried, filtered and concentrated under vacuum to give the brownish foam. The residue was carried directly to the next step without purification.
MS (ESI): m/z 859.53 [M+H], 430.42 [M+2H].

Example 131

Compound of formula VII, wherein R$_1$ and R$_2$ taken together with the carbon atom to which they are attached are C=NO[2-amino-oxazolo[4,5-b]pyridin-5-ylmethyl], and R$_{20}$=Rx=H The title compound was prepared with the title compound of Example 130 via similar conditions described in Example 36. E:Z ratio was 2.1:1.
MS (ESI): m/z 817.50 [M+H], 409.39 [M+2H].

E-isomer:
MS (ESI): m/z 817.50 [M+H], 409.39 [M+2H].

Z-isomer:
MS (ESI): m/z 817.50 [M+H], 409.39 [M+2H].

Example 132

Compound of formula VII, wherein R$_1$ and R$_2$ taken together with the carbon atom to which they are attached are
C=NO[1-ethyl-1H-benzotriazol-4-ylmethyl], R$_{20}$=H, and Rx=Ac The title compound was prepared with the title compound of Example 16 and O-(1-ethyl-1H-benzotriazol-4-ylmethyl)-hydroxylamine (prepared according to literature procedure) via similar conditions outlined in Example 35.
MS (ESI): m/z 871.46 [M+H], 436.40 [M+2H].

Example 133

Compound of formula VII, wherein R$_1$ and R$_2$ taken together with the carbon atom to which they are attached are
C=NO[1-ethyl-1H-benzotriazol-4-ylmethyl], and R$_{20}$=Rx=H The title compound was prepared with the title compound of Example 132 via similar conditions described in Example 36. E:Z ratio was 3.2:1.
MS (ESI): m/z 829.49 [M+H], 415.41 [M+2H].

E-isomer:
MS (ESI): m/z 829.49 [M+H], 415.41 [M+2H].
$^{13}$C NMR (CDCl$_3$, ppm) δ: 216.9, 177.7, 158.6, 157.8, 144.6, 132.9, 130.5, 127.4, 122.4, 108.8, 105.1, 84.4, 80.9, 80.4, 79.3, 76.5, 71.8, 70.7, 69.9, 66.2, 66.1, 61.1, 58.3, 44.6, 44.1, 43.5, 43.1, 40.5, 39.1, 37.3, 28.4, 22.9, 21.44, 21.37, 20.1, 15.3, 13.9, 13.5, 11.8, 11.3, 10.9.

Z-isomer:
MS (ESI): m/z 829.49 [M+H], 415.41 [M+2H].
$^{13}$C NMR (CDCl$_3$, ppm) δ: 217.2, 177.4, 159.2, 157.5, 144.5, 132.7, 130.1, 127.1, 122.7, 109.8, 108.8, 104.9, 84.0, 82.5, 80.9, 80.3, 75.8, 72.9, 71.6, 70.4, 69.7, 65.8, 58.5, 58.4, 44.5, 44.0, 43.3, 43.2, 40.2, 39.3, 37.0, 28.1, 22.3, 21.4, 21.3, 20.0, 15.0, 13.7, 13.1, 12.2, 10.8.

Example 134

Compound of formula VII, wherein R$_1$ and R$_2$ taken together with the carbon atom to which they are attached are C=NOH, R$_{20}$=H, and Rx=Ac The title compound was prepared with the title compound of Example 16 and commercially available hydroxylamine hydrochloride via similar conditions outlined in Example 35.
MS (ESI): m/z 712.39 [M+H].

Example 135

Compound of formula VII, wherein R$_1$ and R$_2$ taken together with the carbon atom to which they are attached are C=NOH, and R$_{20}$=Rx=H The title compound was prepared with the title compound of Example 134 via similar conditions described in Example 36. E:Z ratio was 1:1.
MS (ESI): m/z 670.43 [M+H].

E-isomer:
MS (ESI): m/z 670.43 [M+H].
$^{13}$C NMR (CDCl$_3$, ppm) δ: 216.8, 177.3, 158.2, 158.0, 104.8, 84.5, 80.6, 80.3, 78.7, 76.6, 70.5, 69.6, 65.7, 65.4, 60.7, 58.0, 44.1, 43.9, 42.7, 40.2, 38.9, 37.4, 28.2, 22.9, 21.3, 21.2, 19.7, 13.8, 13.3, 11.22, 11.15, 10.8.

Z-isomer:

MS (ESI): m/z 670.43 [M+H].

$^{13}$C NMR (CDCl$_3$, ppm) δ: 216.9, 177.1, 158.4, 157.8, 104.7, 84.3, 81.1, 80.5, 80.2, 76.3, 72.1, 70.5, 69.6, 65.6, 58.2, 56.6, 44.2, 42.9, 40.2, 39.0, 37.5, 28.2, 22.6, 21.6, 21.2, 19.6, 13.7, 13.3, 11.6, 11.0, 10.8.

Example 136

Compound of formula VII, wherein R$_1$ and R$_2$ taken together with the carbon atom to which they are attached are
C=NO[6-tetrazol-1-yl-pyridin-3-ylmethyl], R$_{20}$=H, and Rx =Ac The title compound was prepared with the title compound of Example 16 and O-(6-tetrazol-1-yl-pyridin-3-ylmethyl)-hydroxylamine (prepared according to literature procedure) via similar conditions outlined in Example 35.

MS (ESI): m/z 871.52 [M+H].

Example 137

Compound of formula VII, wherein R$_1$ and R$_2$ taken together with the carbon atom to which they are attached are
C=NO[6-tetrazol-1-yl-pyridin-3-ylmethyl], and R$_2$n=Rx=H The title compound was prepared with the title compound of Example 136 via similar conditions described in Example 36. E:Z ratio was 3.5:1.

MS (ESI): m/z 829.48 [M+H].

E-isomer:

MS (ESI): m/z 829.48 [M+H].

$^{13}$C NMR (CDCl$_3$, ppm) δ: 216.9, 178.1, 159.4, 158.1, 148.0, 146.6, 140.8, 139.2, 135.6, 114.5, 105.1, 84.5, 81.1, 80.5, 79.1, 76.4, 72.8, 70.7, 70.0, 66.0, 65.7, 60.5, 58.2, 44.5, 44.4, 43.1, 40.5, 39.0, 37.4, 28.4, 22.9, 21.4, 19.9, 13.8, 13.7, 11.7, 11.3, 10.9.

Z-isomer:

MS (ESI): m/z 829.48 [M+H].

$^{13}$C NMR (CDCl$_3$, ppm) δ: 217.2, 177.3, 159.8, 157.5, 148.7, 146.5, 140.1, 139.7, 134.8, 114.1, 104.8, 84.1, 82.0, 81.2, 80.1, 76.0, 72.7, 72.3, 70.4, 69.7, 65.8, 58.4, 57.7, 44.4, 44.1, 43.1, 40.2, 39.1, 37.1, 28.1, 22.4, 21.33, 21.26, 19.9, 13.7, 13.2, 11.9, 10.84, 10.82.

Example 138

Compound of formula VII, wherein R$_1$ and R$_2$ taken together with the carbon atom to which they are attached are
C=NO[6-isoxazol-5-yl-pyridin-3-ylmethyl], R$_{20}$=H, and Rx=Ac The title compound was prepared with the title compound of Example 16 and O-(6-isoxazol-5-yl-pyridin-3-ylmethyl)-hydroxylamine (prepared according to literature procedure) via similar conditions outlined in Example 35.

MS (ESI): m/z 870.41 [M+H], 435.86 [M+2H].

Example 139

Compound of formula-VII, wherein R$_1$ and R$_2$ taken together with the carbon atom to which they are attached are
C=NO[6-isoxazol-5-yl-pyridin-3-ylmethyl], and R$_{20}$=Rx=H The title compound was prepared with the title compound of Example 138 via similar conditions described in Example 36. E:Z ratio was 3.3:1.

MS (ESI): m/z 828.39 [M+H], 414.86 [M+2H].

E-isomer:

MS (ESI): m/z 828.39 [M+H], 414.86 [M+2H].

$^{13}$C NMR (CDCl$_3$, ppm) δ: 216.4, 178.0, 168.8, 159.2, 158.1, 151.6, 149.1, 145.8, 136.5, 135.0, 120.9, 105.2, 102.1, 84.4, 80.9, 80.6, 79.2, 76.3, 73.3, 70.7, 70.0, 66.0, 65.8, 60.5, 58.4, 44.6, 44.2, 43.1, 40.5, 39.2, 37.3, 28.4, 22.8, 21.45, 21.38, 20.0, 13.8, 13.7, 11.9, 11.2, 10.9.

Z-isomer:

MS (ESI): m/z 828.39 [M+H], 414.86 [M+2H].

$^{13}$C NMR (CDCl$_3$, ppm) δ: 217.1, 177.3, 168.7, 159.6, 157.5, 151.1, 149.8, 146.0, 136.9, 134.2, 120.6, 104.8, 101.6, 84.1, 82.2, 81.1, 80.1, 75.9, 73.3, 72.5, 70.4, 69.7, 65.8, 58.4, 57.9, 44.4, 44.0, 43.1, 40.2, 39.2, 37.1, 28.1, 22.4, 21.22, 21.26, 29.9, 13.7, 13.2, 12.0, 10.81, 10.79.

Example 140

Compound of formula VII, wherein R$_1$ and R$_2$ taken together with the carbon atom to which they are attached are
C=NO[6-pyrazol-1-yl-pyridin-2-ylmethyl], R$_{20}$=H, and Rx=Ac The title compound was prepared with the title compound of Example 16 and O-(6-pyrazol-1-yl-pyridin-2-ylmethyl)-hydroxylamine (prepared according to literature procedure) via similar conditions outlined in Example 35.

MS (ESI): m/z 869.50 [M+H], 435.42 [M+2H].

Example 141

Compound of formula VII, wherein R$_1$ and R$_2$ taken together with the carbon atom to which they are attached are
C=NO[6-pyrazol-1-yl-pyridin-2-ylmethyl], and R$_{20}$=Rx=H The title compound was prepared with the title compound of Example 140 via similar conditions described in Example 36. E:Z ratio was 3.3:1.

MS (ESI): m/z 827.52 [M+H], 414.42 [M+2H].

E-isomer:

MS (ESI): m/z 827.52 [M+H], 414.42 [M+2H].

$^{13}$C NMR (CDCl$_3$, ppm) δ: 217.0, 177.8, 159.0, 157.8, 157.2, 151.2, 142.1, 139.4, 127.5, 119.0, 111.2, 107.8, 105.1, 84.4, 81.0, 80.4, 79.4, 76.7, 70.7, 70.0, 66.09, 66.06, 60.9, 58.4, 44.5, 44.2, 43.1, 40.5, 39.1, 37.4, 29.9, 28.4, 22.9, 21.5, 21.4, 20.0, 13.9, 13.5, 11.8, 11.3, 10.9.

Z-isomer:

MS (ESI): m/z 827.52 [M+H], 414.42 [M+2H].

$^{13}$C NMR (CDCl$_3$, ppm) δ: 217.1, 177.3, 159.4, 157.5, 156.7, 151.0, 142.0, 139.2, 127.2, 119.2, 111.2, 107.6, 104.8, 84.1, 82.2, 81.1, 80.1, 76.5, 76.0, 72.6, 70.4, 69.7, 65.8, 58.4, 58.2, 44.4, 44.1, 43.1, 40.2, 39.2, 37.1, 29.7, 28.1, 22.4, 21.4, 21.2, 19.9, 13.7, 13.2, 12.0, 10.82, 10.79.

Example 142

Compound of formula VII, wherein R$_1$ and R$_2$ taken together with the carbon atom to which they are attached are C=NO[1H-benzotriazol-4-ylmethyl], R$_{20}$=H, and Rx=Ac The title compound was prepared with the title compound of Example 16 and O-(1H-benzotriazol-4-ylmethyl)-hydroxylamine (prepared according to literature procedure) via similar conditions outlined in Example 35.
MS (ESI): m/z 843.50 [M+H], 422.41 [M+2H].

Example 143

Compound of formula VII, wherein $R_1$ and $R_2$ taken together with the carbon atom to which they are attached are C=NO[1H-benzotriazol-4-ylmethyl], and $R_{20}$=Rx=H The title compound was prepared with the title compound of Example 142 via similar conditions described in Example 36. E:Z ratio was 4.5:1.
MS (ESI): m/z 801.49 [M+H], 401.40 [M+2H].

E-isomer:
MS (ESI): m/z 801.49 [M+H], 401.40 [M+2H].
$^{13}$C NMR (CDCl$_3$, ppm) δ: 216.8, 178.1, 158.7, 158.1, 126.9, 124.3, 121.3, 119.1, 104.9, 85.1, 81.5, 80.6, 78.5, 77.4, 74.2, 70.7, 69.9, 66.0, 65.3, 60.8, 57.6, 44.2, 43.8, 43.0, 40.5, 39.5, 38.1, 28.4, 23.2, 21.9, 21.5, 19.4, 14.5, 13.4, 11.4, 11.1, 10.9.

Z-isomer:
MS (ESI): m/z 801.49 [M+H], 401.40 [M+2H].

Example 144

Compound of formula VII, wherein $R_1$ and $R_2$ taken together with the carbon atom to which they are attached are
C=NO[2,4-diamino-pteridin-6-ylmethyl], $R_{20}$=H, and Rx=Ac The title compound was prepared with the title compound of Example 16 and O-(2,4-diamino-pteridin-6-ylmethyl)-hydroxylamine (prepared according to literature procedure) via similar conditions outlined in Example 35.
MS (ESI): m/z 886.49 [M+H], 443.91 [M+2H].

Example 145

Compound of formula VII, wherein $R_1$ and $R_2$ taken together with the carbon atom to which they are attached are
C=NO[2,4-diamino-pteridin-6-ylmethyl], and $R_{20}$=Rx=H The title compound was prepared with the title compound of Example 144 via similar conditions described in Example 36. E:Z ratio was 2.3:1.
MS (ESI): m/z 844.47 [M+H], 422.89 [M+2H].

E-isomer:
MS (ESI): m/z 844.47 [M+H], 422.89 [M+2H].
$^{13}$C NMR (CDCl$_3$, ppm) δ: 216.8, 177.6, 163.3, 162.6, 159.6, 158.3, 155.2, 150.1, 146.8, 121.5, 104.9, 84.4, 80.8, 80.3, 78.9, 76.6, 74.9, 70.5, 69.7, 65.8, 65.5, 60.3, 58.3, 44.3, 43.9, 42.9, 40.2, 39.3, 37.2, 28.1, 22.6, 21.3, 21.2, 19.7, 13.8, 13.5, 11.5, 11.0, 10.6.

Z-isomer:
MS (ESI): m/z 844.47 [M+H], 422.89 [M+2H].
$^{13}$C NMR (CDCl$_3$, ppm) δ: 216.2, 176.8, 163.6, 162.7, 158.7, 157.8, 155.9, 151.7, 144.9, 122.0, 104.6, 84.6, 81.3, 80.2, 78.4, 76.6, 74.8, 71.0, 70.5, 69.7, 65.8, 58.4, 55.3, 44.3, 43.9, 42.7, 40.2, 38.5, 37.9, 28.1, 22.9, 21.7, 21.3, 19.3, 13.7, 13.6, 11.2, 10.9, 10.7.

Example 146

Compound of formula VII, wherein $R_1$ and $R_2$ taken together with the carbon atom to which they are attached are C=NO[quinoxalin-5-ylmethyl], $R_{20}$=H, and Rx=Ac The title compound was prepared with the title compound of Example 16 and O-quinoxalin-5-ylmethyl-hydroxylamine (prepared according to literature procedure) via similar conditions outlined in Example 35.
MS (ESI): m/z 854.26 [M+H], 427.80 [M+2H].

Example 147

Compound of formula VII, wherein $R_1$ and $R_2$ taken together with the carbon atom to which they are attached are C=NO[quinoxalin-5-ylmethyl], and $R_{20}$=Rx=H The title compound was prepared with the title compound of Example 146 via similar conditions described in Example 36. E:Z ratio was 2.5:1.
MS (ESI): m/z 812.28 [M+H], 406.80 [M+2H].

E-isomer:
MS (ESI): m/z 812.28 [M+H], 406.80 [M+2H].
$^{13}$C NMR (CDCl$_3$, ppm) δ: 217.0, 177.7, 158.5, 157.8, 145.1, 144.3, 143.1, 141.3, 136.8, 130.0, 129.3, 129.0, 105.1, 84.4, 80.9, 80.4, 79.3, 76.7, 71.8, 70.7, 69.9, 66.1, 66.0, 61.0, 58.3, 44.5, 44.2, 43.1, 40.5, 39.1, 37.4, 28.4, 22.9, 21.43, 21.41, 20.0, 13.9, 13.5, 11.7, 11.3, 10.9.

Z-isomer:
MS (ESI): m/z 812.28 [M+H], 406.80 [M+2H].
$^{13}$C NMR (CDCl$_3$, ppm) δ: 217.3, 177.5, 158.9, 157.8, 145.2, 144.4, 143.2, 141.4, 136.5, 130.0, 129.8, 129.6, 105.1, 84.3, 82.1, 81.2, 80.5, 76.2, 72.9, 72.0, 70.6, 69.9, 66.0, 58.6, 58.2, 44.6, 44.3, 43.3, 40.5, 39.4, 37.4, 28.4, 22.6, 21.7, 21.5, 20.1, 13.9, 13.5, 12.2, 11.1, 11.0.

Example 148

Compound of formula VII, wherein $R_1$ and $R_2$ taken together with the carbon atom to which they are attached are
C=NO[pyrido[2,3-b]pyrazin-6-ylmethyl], $R_{20}$=H, and Rx=Ac The title compound was prepared with the title compound of Example 16 and O-pyrido[2,3-b]pyrazin-6-ylmethyl-hydroxylamine (prepared according to literature procedure) via similar conditions outlined in Example 35.
MS (ESI): m/z 855.88 [M+H], 428.61 [M+2H].

Example 149

Compound of formula VII, wherein $R_1$ and $R_2$ taken together with the carbon atom to which they are attached are
C=NO[pyrido[2,3-b]pyrazin-6-ylmethyl], and $R_{20}$=Rx=H The title compound was prepared with the title compound of Example 148 via similar conditions described in Example 36. E:Z ratio was 3:1.
MS (ESI): m/z 813.85 [M+H], 407.58 [M+2H].

E-isomer:
MS (ESI): m/z 813.85 [M+H], 407.58 [M+2H].
$^{13}$C NMR (CDCl$_3$, ppm) δ: 217.0, 178.0, 164.0, 160.0, 157.9, 150.9, 148.0, 146.0, 139.2, 138.1, 124.0, 105.2, 84.3, 81.0, 80.4, 79.6, 76.6, 70.7, 70.0, 66.2, 66.1, 60.8, 58.4, 44.6, 44.0, 43.3, 40.5, 39.2, 37.2, 28.4, 22.8, 21.4, 21.3, 20.1, 13.9, 13.4, 12.0, 11.2, 10.8.

Z-isomer:
MS (ESI): m/z 813.85 [M+H], 407.58 [M+2H].

Example 150

Compound of formula VII, wherein $R_1$ and $R_2$ taken together with the carbon atom to which they are attached are C=NO[quinolin-5-ylmethyl], $R_{20}$=H, and Rx=Ac The title compound was prepared with the title compound of Example 16 and O-quinolin-5-ylmethyl-hydroxylamine (prepared according to literature procedure) via similar conditions outlined in Example 35.

MS (ESI): m/z 853.65 [M+H], 427.49 [M+2H].

Example 151

Compound of formula VII, wherein $R_1$ and $R_2$ taken together with the carbon atom to which they are attached are C=NO[quinolin-5-ylmethyl], and $R_{20}$=Rx=H The title compound was prepared with the title compound of Example 150 via similar conditions described in Example 36. E:Z ratio was 4.6:1.

MS (ESI): m/z 811.63 [M+H], 406.46 [M+2H].

E-isomer:
MS (ESI): m/z 811.63 [M+H], 406.46 [M+2H].
$^{13}$C NMR (CDCl$_3$, ppm) δ: 217.0, 177.6, 158.3, 157.9, 150.4, 148.7, 133.7, 132.9, 130.5, 129.1, 127.9, 127.3, 121.4, 104.0, 84.6, 80.8, 80.6, 79.1, 76.9, 74.4, 70.3, 68.8, 66.8, 65.8, 61.0, 58.2, 44.2, 44.1, 43.0, 40.7, 39.1, 37.4, 23.0, 21.5, 21.2, 19.8, 14.0, 13.5, 11.6, 11.4, 11.1.

Z-isomer:
MS (ESI): m/z 811.63 [M+H], 406.46 [M+2H].

Example 152

Compound of formula VII, wherein $R_1$ and $R_2$ taken together with the carbon atom to which they are attached are C=NO[pyrido[2,3-b]pyrazin-8-ylmethyl], $R_{20}$=H, and Rx=Ac The title compound was prepared with the title compound of Example 16 and O-pyrido[2,3-b]pyrazin-8-ylmethyl-hydroxylamine (prepared according to literature procedure) via similar conditions outlined in Example 35.

MS (ESI): m/z 855.61 [M+H], 428.47 [M+2H].

Example 153

Compound of formula VII, wherein $R_1$ and $R_2$ taken together with the carbon atom to which they are attached are C=NO[pyrido[2,3-b]pyrazin-8-ylmethyl], and $R_{20}$=Rx=H The title compound was prepared with the title compound of Example 152 via similar conditions described in Example 36. E:Z ratio was 3:1.

MS (ESI): m/z 813.60 [M+H], 407.46 [M+2H].

E-isomer:
MS (ESI): m/z 813.60 [M+H], 407.46 [M+2H].
$^{13}$C NMR (CDCl$_3$, ppm) δ: 217.1, 177.8, 159.5, 157.8, 154.5, 151.0, 147.92, 147.90, 145.2, 136.6, 122.9, 105.0, 84.4, 81.0, 80.4, 79.4, 76.8, 70.8, 70.6, 69.8, 66.2, 65.9, 60.8, 58.3, 44.4, 44.2, 43.1, 40.5, 39.1, 37.4, 28.8, 22.9, 21.41, 21.39, 19.9, 13.9, 13.5, 11.7, 11.3, 11.0.

Z-isomer:
MS (ESI): m/z 813.60 [M+H], 407.46 [M+2H].
$^{13}$C NMR (CDCl$_3$, ppm) δ: 217.3, 177.4, 159.8, 157.8, 154.5, 151.2, 148.0, 147.7, 145.2, 136.7, 123.2, 104.3, 84.3, 82.2, 81.3, 80.5, 76.3, 72.7, 70.9, 70.4, 69.2, 66.6, 58.6, 58.2, 44.5, 44.3, 43.3, 40.7, 39.4, 37.3, 22.6, 21.7, 21.3, 20.1, 14.0, 13.5, 12.2, 11.2, 11.1.

Example 154

Compound of formula VII, wherein $R_1$ and $R_2$ taken together with the carbon atom to which they are attached are C=NO[1H-[1,2,3]triazolo[4,5-b]pyridin-5-ylmethyl], $R_{20}$=H, and Rx=Ac The title compound was prepared with the title compound of Example 16 and O-(1H-[1,2,3]triazolo[4,5-b]pyridin-5-ylmethyl)-hydroxylamine (prepared according to literature procedure) via similar conditions outlined in Example 35.

MS (ESI): m/z 844.61 [M+H], 422.97 [M+2H].

Example 155

Compound of formula VII, wherein $R_1$ and $R_2$ taken together with the carbon atom to which they are attached are C=NO[1H-[1,2,3]triazolo[4,5-b]pyridin-5-ylmethyl], and $R_{20}$=Rx=H The title compound was prepared with the title compound of Example 154 via similar conditions described in Example 36. E:Z ratio was 7:1.

MS (ESI): m/z 802.60 [M+H], 401.96 [M+2H].

E-isomer:
MS (ESI): m/z 802.60 [M+H], 401.96 [M+2H].
$^{13}$C NMR (CD$_3$OD, ppm) δ: 217.0, 178.0, 159.7, 159.1, 125.2, 119.5, 104.2, 85.1, 81.0, 80.6, 79.1, 77.1, 76.7, 69.5, 68.5, 65.6, 65.4, 60.4, 58.5, 53.6, 43.9, 43.8, 42.7, 39.4, 38.8, 37.4, 30.0, 22.8, 21.1, 20.0, 18.5, 13.1, 12.4, 10.6, 10.5, 10.3.

Z-isomer:
MS (ESI): m/z 802.60 [M+H], 401.96 [M+2H].
$^{13}$C NMR (CD$_3$OD, ppm) δ: 216.8, 177.4, 159.6, 159.1, 125.4, 118.2, 104.5, 85.0, 82.3, 81.4, 80.3, 76.9, 76.5, 72.4, 70.2, 68.8, 65.2, 58.5, 57.8, 43.8, 43.7, 43.1, 39.9, 39.2, 37.5, 30.2, 22.5, 21.5, 20.1, 18.6, 13.2, 12.2, 11.4, 10.5, 10.2.

Example 156

Compound of formula VII, wherein $R_1$ and $R_2$ taken together with the carbon atom to which they are attached are C=NO[3H-[1,2,3]triazolo[4,5-b]pyridin-7-ylmethyl], $R_{20}$=H, and Rx=Ac The title compound was prepared with the title compound of Example 16 and O-(3H-[1,2,3]triazolo[4,5-b]pyridin-7-ylmethyl)-hydroxylamine (prepared according to literature procedure) via similar conditions outlined in Example 35.

MS (ESI): m/z 844.69 [M+H].

Example 157

Compound of formula VII, wherein $R_1$ and $R_2$ taken together with the carbon atom to which they are attached are C=NO[3H-[1,2,3]triazolo[4,5-b]pyridin-7-ylmethyl], and $R_{20}$=Rx=H The title compound was prepared with the title compound of Example 156 via similar conditions described in Example 36. E:Z ratio was 2:1.
MS (ESI): m/z 802.70 [M+H].

E-isomer:
MS (ESI): m/z 802.70 [M+H].

Z-isomer:
MS (ESI): m/z 802.70 [M+H].

Example 158

Compound of formula VII, wherein $R_1$ and $R_2$ taken together with the carbon atom to which they are attached are C=NO[[2,2']bipyridinyl-6-ylmethyl], $R_{20}$=H, and Rx=Ac The title compound was prepared with the title compound of Example 16 and 0-[2,2']bipyridinyl-6-ylmethyl-hydroxylamine (prepared according to literature procedure) via similar conditions outlined in Example 35.
MS (ESI): m/z 880.41 [M+H], 440.87 [M+2H].

Example 159

Compound of formula VII, wherein $R_1$ and $R_2$ taken together with the carbon atom to which they are attached are C=NO[[2,2']bipyridinyl-6-ylmethyl], and $R_{20}$=Rx=H The title compound was prepared with the title compound of Example 158 via similar conditions described in Example 36. E:Z ratio was 4:1.
MS (ESI): m/z 838.53 [M+H], 419.89 [M+2H].

E-isomer:
MS (ESI): m/z 838.53 [M+H], 419.89 [M+2H].
$^{13}$C NMR (CDCl$_3$, ppm) δ: 217.0, 177.8, 158.9, 157.8, 156.5, 155.7, 149.3, 137.6, 137.1, 123.8, 121.63, 121.57, 120.0, 105.1, 84.4, 80.9, 80.4, 79.4, 76.7, 70.7, 70.0, 66.2, 66.1, 61.0, 58.4, 44.5, 44.1, 43.1, 40.5, 39.1, 37.3, 29.9, 28.4, 22.9, 21.44, 21.38, 20.0, 13.9, 13.4, 11.8, 11.3, 10.9.

Z-isomer:
MS (ESI): m/z 838.53 [M+H], 419.89 [M+2H].
$^{13}$C NMR (CDCl$_3$, ppm) δ: 217.1, 177.6, 159.5, 157.8, 149.4, 137.7, 137.1, 123.9, 121.9, 121.6, 120.2, 105.1, 84.3, 82.5, 81.3, 80.5, 76.2, 72.9, 70.7, 70.0, 66.0, 58.6, 58.5, 44.7, 44.3, 43.4, 40.5, 39.5, 37.3, 29.9, 28.4, 22.6, 21.6, 21.5, 20.2, 13.9, 13.4, 12.3, 11.0.

Example 160

Compound of formula VII, wherein $R_1$ and $R_2$ taken together with the carbon atom to which they are attached are C=NO[6'-fluoro-[2,3']bipyridinyl-6-ylmethyl], $R_{20}$=H, and Rx=Ac The title compound was prepared with the title compound of Example 16 and O-(6'-fluoro-[2,3']bipyridinyl-6-ylmethyl)-hydroxylamine (prepared according to literature procedure) via similar conditions outlined in Example 35.
MS (ESI): m/z 898.24 [M+H], 449.79 [M+2H].

Example 161

Compound of formula VII, wherein $R_1$ and $R_2$ taken together with the carbon atom to which they are attached are C=NO[6'-fluoro-[2,3']bipyridinyl-6-ylmethyl], and $R_{20}$=Rx=H The title compound was prepared with the title compound of Example 160 via similar conditions described in Example 36. E:Z ratio was 2.3:1.
MS (ESI): m/z 856.56 [M+H], 428.91 [M+2H].

E-isomer:
MS (ESI): m/z 856.56 [M+H], 428.91 [M+2H].
$^{13}$C NMR (CDCl$_3$, ppm) δ: 217.1, 177.9, (165.1, 163.2), (159.0, 158.9), 157.9, 153.2, (146.5, 146.4), (140.4, 140.3), 137.9, 133.4, 120.6, 119.2, (109.8, 109.5), 105.1, 84.5, 81.0, 80.4, 79.3, 76.7, 70.7, 70.0, 66.1, 60.9, 58.3, 44.5, 44.2, 43.1, 40.5, 39.0, 37.4, 31.9, 28.4, 22.95, 22.88, 21.4, 20.0, 14.3, 13.9, 13.5, 11.7, 11.3, 10.9.

Z-isomer:
MS (ESI): m/z 856.56 [M+H], 428.91 [M+2H].
$^{13}$C NMR (CDCl$_3$, ppm) δ: 217.4, 177.5, (165.2, 163.3), (159.6, 158.6), 157.8, 153.5, (146.6, 146.4), (140.42, 140.35), 137.9, 133.4, 121.2, 119.4, (109.9, 109.6), 105.1, 84.3, 82.3, 81.3, 80.4, 76.3, 72.8, 70.7, 70.0, 66.0, 58.6, 58.3, 44.6, 44.3, 43.3, 40.5, 39.4, 37.4, 28.4, 22.6, 21.6, 21.5, 20.1, 13.9, 13.4, 12.2, 11.1, 11.0.

Example 162

Compound of formula VII, wherein $R_1$ and $R_2$ taken together with the carbon atom to which they are attached are C=NO[6-pyrimidin-5-yl-pyridin-2-ylmethyl], $R_{20}$=H, and Rx=Ac The title compound was prepared with the title compound of Example 16 and O-(6-pyrimidin-5-yl-pyridin-2-ylmethyl)-hydroxylamine (prepared according to literature procedure) via similar conditions outlined in Example 35.
MS (ESI): m/z 898.24 [M+H], 449.79 [M+2H].

Example 163

Compound of formula VII, wherein $R_1$ and $R_2$ taken together with the carbon atom to which they are attached are C=NO[6-pyrimidin-5-yl-pyridin-2-ylmethyl], and $R_{20}$=Rx=H The title compound was prepared with the title compound of Example 162 via similar conditions described in Example 36. E:Z ratio was 2.8:1.
MS (ESI): m/z 839.31 [M+H], 420.31 [M+2H].

E-isomer:
MS (ESI): m/z 839.31 [M+H], 420.31 [M+2H].
$^{13}$C NMR (CDCl$_3$, ppm) δ: 217.1, 177.9, 159.5, 159.2, 158.7, 157.9, 155.4, 151.5, 138.1, 132.6, 121.4, 119.5, 105.1, 84.5, 81.0, 80.4, 79.3, 76.6, 70.7, 70.0, 66.0, 60.9, 58.3, 44.5, 44.2, 43.1, 40.5, 39.0, 37.4, 28.4, 22.9, 21.44, 21.42, 20.0, 13.9, 13.5, 11.7, 11.3, 10.9.

Z-isomer:
MS (ESI): m/z 839.31 [M+H], 420.31 [M+2H].
$^{13}$C NMR (CDCl$_3$, ppm) δ: 217.4, 177.6, 159.7, 159.2, 158.8, 157.8, 155.5, 151.7, 138.0, 132.6, 121.9, 119.6, 105.1, 84.3, 82.5, 81.3, 80.4, 76.2, 72.8, 70.7, 70.0, 66.1, 58.6, 58.4, 44.7, 44.3, 43.3, 40.5, 39.4, 37.3, 28.4, 22.6, 21.6, 21.5, 20.1, 13.9, 13.4, 12.2, 11.1.

Example 164

Compound of formula VII, wherein $R_1$ and $R_2$ taken together with the carbon atom to which they are attached are C=NO[2'-chloro-[2,3']bipyridinyl-6-ylmethyl], $R_{20}$=H, and Rx=Ac The title compound was prepared with the title compound of Example 16 and O-(2'-chloro-[2,3']bipyridinyl-6-ylmethyl)-hydroxylamine (prepared according to literature procedure) via similar conditions outlined in Example 35.
MS (ESI): m/z 914.50 [M+H], 457.75 [M+2H].

Example 165

Compound of formula VII, wherein $R_1$ and $R_2$ taken together with the carbon atom to which they are attached are C=NO[2'-chloro-[2,3']bipyridinyl-6-ylmethyl], and $R_{20}$=Rx=H The title compound was prepared with the title compound of Example 164 via similar conditions described in Example 36. E:Z ratio was 2.2:1.
MS (ESI): m/z 872.63 [M+H], 436.81 [M+2H].

E-isomer:
MS (ESI): m/z 872.63 [M+H], 436.81 [M+2H].
$^{13}$C NMR (CDCl$_3$, ppm) δ: 217.1, 177.8, 159.1, 158.7, 157.9, 154.5, 149.4, 140.7, 137.0, 135.9, 123.7, 122.9, 120.8, 105.1, 84.4, 81.0, 80.4, 79.3, 76.6, 70.7, 70.0, 66.1, 66.0, 60.9, 58.3, 44.5, 44.2, 43.1, 40.4, 39.1, 37.4, 28.4, 22.9, 21.44, 21.41, 20.0, 13.9, 13.4, 11.7, 11.3, 10.9.

Z-isomer:
MS (ESI): m/z 872.63 [M+H], 436.81 [M+2H].
$^{13}$C NMR (CDCl$_3$, ppm) δ: 217.2, 177.5, 159.6, 158.3, 157.8, 154.7, 149.5, 140.7, 136.9, 135.8, 123.9, 123.0, 121.3, 105.1, 84.3, 82.4, 81.3, 80.5, 76.2, 72.8, 70.6, 70.0, 66.0, 58.6, 58.3, 44.7, 44.3, 43.3, 40.4, 39.4, 37.3, 28.4, 22.6, 21.6, 21.5, 20.1, 13.9, 13.4, 12.2, 11.1, 11.0.

Example 166

Compound of formula VII, wherein $R_1$ and $R_2$ taken together with the carbon atom to which they are attached are C=NO[2'-fluoro-[2,3']bipyridinyl-6-ylmethyl], $R_{20}$=H, and Rx=Ac The title compound was prepared with the title compound of Example 16 and O-(2'-fluoro-[2,3']bipyridinyl-6-ylmethyl)-hydroxylamine (prepared according to literature procedure) via similar conditions outlined in Example 35.
MS (ESI): m/z 898.78 [M+H], 449.89 [M+2H].

Example 167

Compound of formula VII, wherein $R_1$ and $R_2$ taken together with the carbon atom to which they are attached are C=NO[2'-fluoro-[2,3']bipyridinyl-6-ylmethyl], and $R_{20}$=Rx=H The title compound was prepared with the title compound of Example 166 via similar conditions described in Example 36. E:Z ratio was 2.2:1.
MS (ESI): m/z 856.82 [M+H], 428.91 [M+2H].

E-isomer:
MS (ESI): m/z 856.82 [M+H], 428.91 [M+2H].
$^{13}$C NMR (CDCl$_3$, ppm) δ: 217.1, 177.8, (162.0, 160.1), (159.0, 158.7), 157.9, (150.8, 150.7), (147.7, 147.6), 142.0, 137.6, (123.2, 123.1), (122.6, 122.4), 122.3, 121.0, 105.1, 84.5, 81.0, 80.4, 79.3, 76.7, 70.7, 70.0, 66.1, 60.9, 58.4, 44.5, 44.2, 40.5, 39.0, 37.4, 29.9, 28.4, 22.9, 21.4, 20.0, 13.9, 13.5, 11.7, 11.3, 10.9.

Z-isomer:
MS (ESI): m/z 856.82 [M+H], 428.91 [M+2H].
$^{13}$C NMR (CDCl$_3$, ppm) δ: 217.3, 177.5, (162.0, 160.1), 159.5, (158.4, 157.8), 151.0, (147.8, 147.7), 142.0, 137.5, (123.4, 123.3), 122.5, 122.3, 121.5, 105.1, 84.3, 82.3, 81.3, 80.4, 76.3, 72.8, 70.7, 70.0, 66.0, 58.6, 58.3, 44.6, 44.3, 43.3, 40.5, 39.4, 37.4, 29.9, 28.4, 22.6, 21.6, 21.5, 20.1, 13.9, 13.4, 12.2, 11.1, 11.0.

Example 168

Compound of formula VII, wherein $R_1$ and $R_2$ taken together with the carbon atom to which they are attached are C=NO[6-pyrazin-2-yl-pyridin-2-ylmethyl], $R_{20}$=H, and Rx=Ac The title compound was prepared with the title compound of Example 16 and O-(6-pyrazin-2-yl-pyridin-2-ylmethyl)-hydroxylamine (prepared according to literature procedure) via similar conditions outlined in Example 35.
MS (ESI): m/z 881.81 [M+H], 441.41 [M+2H].

Example 169

Compound of formula VII, wherein $R_1$ and $R_2$ taken together with the carbon atom to which they are attached are C=NO[6-pyrazin-2-yl-pyridin-2-ylmethyl], and $R_{20}$=Rx=H The title compound was prepared with the title compound of Example 168 via similar conditions described in Example 36. E:Z ratio was 2.5:1.
MS (ESI): m/z 839.70 [M+H], 420.35 [M+2H].

E-isomer:
MS (ESI): m/z 839.70 [M+H], 420.35 [M+2H].
$^{13}$C NMR (CDCl$_3$, ppm) δ: 217.0, 177.8, 159.0, 158.3, 157.9, 153.8, 151.4, 144.5, 143.8, 143.7, 137.9, 122.3, 120.4, 105.0, 84.4, 81.0, 80.5, 79.4, 76.7, 70.6, 70.0, 66.2, 66.1, 61.0, 58.4, 44.5, 44.1, 43.1, 40.5, 39.1, 37.3, 29.9, 28.8, 22.9, 21.4, 20.0, 13.9, 13.5, 11.8, 11.3, 10.9.

Z-isomer:
MS (ESI): m/z 839.70 [M+H], 420.35 [M+2H].
$^{13}$C NMR (CDCl$_3$, ppm) δ: 217.3, 177.5, 159.6, 158.1, 157.8, 153.9, 151.4, 144.6, 143.8, 137.8, 122.7, 120.5, 104.7, 84.3, 82.6, 81.3, 80.6, 76.2, 72.9, 70.5, 69.6, 66.3, 58.6, 58.5, 44.6, 44.3, 43.3, 40.6, 39.5, 37.3, 29.9, 29.2, 22.6, 21.6, 21.4, 20.1, 14.0, 13.4, 12.3, 11.1, 11.0.

Example 170

Compound of formula VII, wherein $R_1$ and $R_2$ taken together with the carbon atom to which they are attached are C=NO[[2,3']bipyridinyl-6-ylmethyl], $R_{20}$=H and Rx=Ac The title compound was prepared with the title compound of Example 16 and O-[2,3']bipyridinyl-6-ylmethyl-hydroxylamine (prepared according to literature procedure) via similar conditions outlined in Example 35.
MS (ESI): m/z 880.43 [M+H], 440.89 [M+2H].

Example 171

Compound of formula VII, wherein $R_1$ and $R_2$ taken together with the carbon atom to which they are attached are C=NO[[2,3']bipyridinyl-6-ylmethyl], and $R_{20}$=Rx=H The title compound was prepared with the title compound of Example 170 via similar conditions described in Example 36. E:Z ratio was 4:1.

MS (ESI): m/z 838.58 [M+H], 419.79 [M+2H].

E-isomer:

MS (ESI): m/z 838.58 [M+H], 419.79 [M+2H].

$^{13}$C NMR (CDCl$_3$, ppm) δ: 217.0, 177.8, 159.0, 158.9, 157.9, 154.3, 150.0, 148.6, 137.8, 135.1, 134.8, 123.8, 120.6, 119.5, 105.0, 84.5, 81.0, 80.5, 79.3, 76.7, 70.7, 69.8, 66.2, 66.1, 60.9, 58.4, 44.5, 44.2, 43.1, 40.5, 39.0, 37.4, 29.9, 28.7, 22.9, 21.4, 20.0, 13.9, 13.5, 11.7, 11.3, 10.9.

Z-isomer:

MS (ESI): m/z 838.58 [M+H], 419.79 [M+2H].

$^{13}$C NMR (CDCl$_3$, ppm) δ: 217.3, 177.5, 159.5, 158.6, 157.8, 154.6, 150.1, 148.6, 137.8, 135.1, 134.8, 123.8, 121.1, 119.7, 104.9, 84.3, 82.4, 81.3, 80.5, 76.3, 72.9, 70.6, 69.8, 66.2, 58.6, 58.4, 44.6, 44.3, 43.3, 40.5, 39.4, 37.3, 29.9, 28.8, 22.6, 21.6, 21.4, 20.1, 13.9, 13.4, 12.2, 11.1.

Example 172

Compound of formula VII, wherein $R_1$ and $R_2$ taken together with the carbon atom to which they are attached are C=NO[6-(5-bromo-pyrimidin-2-yl)-pyridin-2-ylmethyl], $R_{20}$=H, and Rx=Ac The title compound was prepared with the title compound of Example 16 and O-[6-(5-bromo-pyrimidin-2-yl)-pyridin-2-ylmethyl]-hydroxylamine (prepared according to literature procedure) via similar conditions outlined in Example 35.

MS (ESI): m/z 959.66 [M+H], 480.34 [M+2H].

Example 173

Compound of formula VII, wherein $R_1$ and $R_2$ taken together with the carbon atom to which they are attached are C=NO[6-(5-bromo-pyrimidin-2-yl)-pyridin-2-ylmethyl], and $R_{20}$=Rx=H The title compound was prepared with the title compound of Example 172 via similar conditions described in Example 36. E:Z ratio was 4:1.

MS (ESI): m/z 917.57 [M+H], 459.28 [M+2H].

E-isomer:

MS (ESI): m/z 917.57 [M+H], 459.28 [M+2H].

$^{13}$C NMR (CDCl$_3$, ppm) δ: 217.1, 177.9, 162.1, 159.3, 159.2, 158.6, 157.9, 153.4, 137.9, 123.2, 122.9, 120.1, 105.1, 84.4, 81.0, 80.4, 79.5, 76.6, 70.7, 70.0, 66.3, 66.1, 61.0, 58.4, 44.6, 44.1, 43.2, 40.5, 39.1, 37.3, 29.9, 28.4, 22.9, 21.45, 21.38, 20.1, 13.9, 13.4, 11.9, 11.3, 10.9.

Z-isomer:

MS (ESI): m/z 917.57 [M+H], 459.28 [M+2H].

$^{13}$C NMR (CDCl$_3$, ppm) δ: 217.4, 177.6, 162.0, 159.8, 159.2, 158.6, 157.7, 153.5, 137.9, 123.4, 122.9, 120.2, 104.9, 84.3, 82.8, 81.3, 80.6, 76.2, 73.0, 70.5, 69.7, 66.3, 58.8, 58.7, 44.7, 44.2, 43.4, 40.6, 39.5, 37.2, 29.9, 29.0, 22.5, 21.6, 21.4, 20.2, 14.0, 13.4, 12.4, 11.1, 11.0.

Example 174

Compound of formula VII, wherein $R_1$ and $R_2$ taken together with the carbon atom to which they are attached are C=NO[6-pyrimidin-2-yl-pyridin-2-ylmethyl], $R_{20}$=H, and Rx=Ac The title compound was prepared with the title compound of Example 16 and O-(6-pyrimidin-2-yl-pyridin-2-ylmethyl)-hydroxylamine (prepared according to literature procedure) via similar conditions outlined in Example 35.

MS (ESI): m/z 881.58 [M+H], 441.29 [M+2H].

Example 175

Compound of formula VII, wherein $R_1$ and $R_2$ taken together with the carbon atom to which they are attached are C=NO[6-pyrimidin-2-yl-pyridin-2-ylmethyl], and $R_{20}$=Rx=H The title compound was prepared with the title compound of Example 174 via similar conditions described in Example 36. E:Z ratio was 2:1.

MS (ESI): m/z 839.70 [M+H], 420.35 [M+2H].

E-isomer:

MS (ESI): m/z 839.70 [M+H], 420.35 [M+2H].

$^{13}$C NMR (CDCl$_3$, ppm) δ: 217.0, 159.1, 157.9, 137.8, 122.8, 120.5, 105.1, 84.4, 80.9, 80.5, 79.5, 76.3, 70.7, 69.9, 66.3, 66.2, 58.4, 44.6, 44.0, 43.2, 40.5, 39.2, 37.2, 28.6, 22.9, 21.4, 20.1, 13.9, 13.4, 11.9, 11.3, 10.9.

Z-isomer:

MS (ESI): m/z 839.70 [M+H], 420.35 [M+2H].

Example 176

Compound of formula VII, wherein $R_1$ and $R_2$ taken together with the carbon atom to which they are attached are C=NO[6'-amino-[2,2']bipyridinyl-6-ylmethyl], $R_{20}$=H, and Rx=Ac The title compound was prepared with the title compound of Example 16 and O-(6'-amino-[2,2']bipyridinyl-6-ylmethyl)-hydroxylamine (prepared according to literature procedure) via similar conditions outlined in Example 35.

MS (ESI): m/z 895.68 [M+H], 448.34 [M+2H].

Example 177

Compound of formula VII, wherein $R_1$ and $R_2$ taken together with the carbon atom to which they are attached are C=NO[6'-amino-[2,2']bipyridinyl-6-ylmethyl], and $R_{20}$=Rx=H The title compound was prepared with the title compound of Example 176 via similar conditions described in Example 36. E:Z ratio was 2:1.

MS (ESI): m/z 853.72 [M+H], 427.36 [M+2H].

E-isomer:

MS (ESI): m/z 853.72 [M+H], 427.36 [M+2H].

$^{13}$C NMR (CDCl$_3$, ppm) δ: 216.9, 177.7, 159.0, 158.2, 157.9, 157.7, 156.0, 155.0, 138.8, 137.5, 121.3, 120.0, 112.2, 109.0, 105.2, 84.4, 80.9, 80.5, 79.4, 76.7, 70.7, 70.0, 66.3, 66.1, 61.0, 58.4, 44.6, 44.1, 43.2, 40.5, 39.2, 37.3, 29.9, 28.4, 22.9, 21.5, 21.4, 20.1, 13.9, 13.5, 11.8, 11.3, 10.9.

Z-isomer:
MS (ESI): m/z 853.72 [M+H], 427.36 [M+2H].
$^{13}$C NMR (CDCl$_3$, ppm) δ: 217.3, 177.6, 159.5, 158.2, 157.8, 157.5, 156.2, 154.0, 138.8, 137.4, 121.5, 120.0, 112.2, 109.1, 105.1, 84.3, 82.6, 81.3, 80.5, 76.2, 73.0, 70.7, 70.0, 66.0, 58.66, 58.65, 44.7, 44.2, 43.4, 40.5, 39.5, 37.3, 29.9, 28.4, 22.6, 21.6, 21.5, 20.2, 13.9, 13.4, 12.4, 11.0.

Example 178

Compound of formula VII, wherein R$_1$ and R$_2$ taken together with the carbon atom to which they are attached are C=NO[6'-hydroxy-[2,2']bipyridinyl-6-ylmethyl], R$_{20}$=H, and Rx=Ac To an acetonitrile solution of the title compound of Example 176 was added 1M aqueous hydrochloride solution. The mixture was cooled to 0° C., and then was added sodium nitrite. After 30 minutes the mixture was quenched with saturated NaHCO$_3$ and extracted with EtOAc. The combined organic extracts were washed with brine, dried, filtered and concentrated under vacuum. The residue was purified by HPLC to afford both E and Z isomers. E:Z ratio was 14:1.
MS (ESI): m/z 854.43 [M+H], 427.72 [M+2H].

E-isomer:
MS (ESI): m/z 854.43 [M+H], 427.72 [M+2H].
$^{13}$C NMR (CDCl$_3$, ppm) δ: 217.1, 178.0, 163.1, 159.5, 158.5, 158.0, 147.3, 141.9, 140.9, 138.4, 122.5, 122.3, 118.7, 105.1, 103.2, 84.5, 81.1, 80.4, 79.2, 76.52, 76.49, 70.7, 70.0, 66.1, 60.9, 58.4, 44.5, 44.2, 43.1, 40.5, 39.0, 37.4, 28.4, 22.9, 21.5, 21.4, 20.0, 13.8, 11.8, 11.3, 10.8.

Z-isomer:
MS (ESI): m/z 854.43 [M+H], 427.72 [M+2H].

Example 179

Compound of formula VII, wherein R$_1$ and R$_2$ taken together with the carbon atom to which they are attached are C=NO[6-(6-amino-pyrazin-2-yl)-pyridin-2-ylmethyl], R$_{20}$=H, and Rx=Ac The title compound was prepared with the title compound of Example 16 and O-[6-(6-amino-pyrazin-2-yl)-pyridin-2-ylmethyl]-hydroxylamine (prepared according to literature procedure) via similar conditions outlined in Example 35.
MS (ESI): m/z 896.78 [M+H], 448.89 [M+2H].

Example 180

Compound of formula VII, wherein R$_1$ and R$_2$ taken together with the carbon atom to which they are attached are C=NO[6-(6-amino-pyrazin-2-yl)-pyridin-2-ylmethyl], and R$_{20}$=Rx=H The title compound was prepared with the title compound of Example 179 via similar conditions described in Example 36. E:Z ratio was 3.2:1.
MS (ESI): m/z 854.76 [M+H], 427.88 [M+2H].

E-isomer:
MS (ESI): m/z 854.76 [M+H], 427.88 [M+2H].
$^{13}$C NMR (CDCl$_3$, ppm) δ: 217.0, 177.8, 159.1, 158.1, 157.9, 154.3, 153.8, 148.6, 137.6, 132.8, 132.4, 121.8, 120.3, 105.1, 84.4, 81.0, 80.4, 79.4, 76.6, 70.7, 69.9, 66.2, 66.0, 60.9, 58.4, 44.6, 44.1, 43.1, 40.4, 39.1, 37.3, 29.9, 28.4, 22.9, 21.44, 21.36, 20.1, 13.9, 13.5, 11.8, 11.3, 10.9.

Z-isomer:
MS (ESI): m/z 854.76 [M+H], 427.88 [M+2H].
$^{13}$C NMR (CDCl$_3$, ppm) δ: 217.3, 177.5, 159.6, 158.0, 157.8, 154.4, 153.7, 148.6, 137.6, 132.9, 132.4, 122.1, 120.3, 105.1, 84.3, 82.6, 81.3, 80.5, 76.2, 73.0, 70.7, 69.9, 66.0, 58.6, 58.5, 44.7, 44.3, 43.4, 40.4, 39.5, 37.3, 29.9, 28.4, 22.6, 21.6, 21.5, 20.2, 13.9, 13.4, 12.3, 11.1.

Example 181

Compound of formula VII, wherein R$_1$ and R$_2$ taken together with the carbon atom to which they are attached are C=NO[6-cyano-pyridin-2-ylmethyl], R$_{20}$=H, and Rx=Ac The title compound was prepared with the title compound of Example 16 and O-(6-cyano-pyridin-2-ylmethyl)-hydroxylamine (prepared according to literature procedure) via similar conditions outlined in Example 35.
MS (ESI): m/z 828.54 [M+H].

Example 182

Compound of formula VII, wherein R$_1$ and R$_2$ taken together with the carbon atom to which they are attached are C=NO[6-cyano-pyridin-2-ylmethyl], and R$_{20}$=Rx=H The title compound was prepared with the title compound of Example 181 via similar conditions described in Example 36. E:Z ratio was 3:1.
MS (ESI): m/z 786.57 [M+H].

E-isomer:
MS (ESI): m/z 786.57 [M+H].
$^{13}$C NMR (CDCl$_3$, ppm) δ: 217.2, 178.0, 160.8, 159.8, 158.0, 137.9, 133.4, 127.5, 124.9, 117.4, 105.1, 84.5, 81.1, 80.4, 79.3, 76.6, 76.2, 70.7, 70.0, 66.1, 66.0, 60.8, 58.4, 44.5, 44.2, 43.1, 40.5, 39.0, 37.4, 29.9, 28.5, 22.9, 21.44, 21.41, 20.0, 13.9, 13.4, 11.7, 11.3, 10.9.

Z-isomer:
MS (ESI): m/z 786.57 [M+H].
$^{13}$C NMR (CDCl$_3$, ppm) δ: 217.5, 177.6, 160.5, 160.3, 157.8, 137.8, 133.6, 127.5, 125.4, 117.3, 105.1, 84.3, 82.6, 81.4, 80.4, 76.23, 76.16, 72.7, 70.7, 69.9, 66.1, 58.6, 58.3, 44.7, 44.3, 43.4, 40.5, 39.5, 37.3, 29.9, 28.5, 22.6, 21.6, 21.5, 20.2, 13.9, 13.4, 12.3, 11.0.

Example 183

Compound of formula VII, wherein R$_1$ and R$_2$ taken together with the carbon atom to which they are attached are C=NO[6-(6-chloro-pyridazin-3-yl)-pyridin-2-ylmethyl], R$_{20}$=H, and Rx=Ac The title compound was prepared with the title compound of Example 16 and O-[6-(6-chloro-pyridazin-3-yl)-pyridin-2-ylmethyl]-hydroxylamine (prepared according to literature procedure) via similar conditions outlined in Example 35.
MS (ESI): m/z 915.57 [M+H], 458.28 [M+2H].

Example 184

Compound of formula VII, wherein R$_1$ and R$_2$ taken together with the carbon atom to which they are attached are C=NO[6-(6-chloro-pyridazin-3-yl)-pyridin-2-ylmethyl], and R$_{20}$=Rx=H The title compound was prepared with the title compound of Example 183 via similar conditions described in Example 36. E:Z ratio was 5:1.
MS (ESI): m/z 873.69 [M+H], 437.35 [M+2H].

E-isomer:

MS (ESI): m/z 873.69 [M+H], 437.35 [M+2H].

$^{13}$C NMR (CDCl$_3$, ppm) δ: 217.1, 177.8, 159.0, 158.3, 158.2, 157.9, 157.0, 152.0, 138.0, 128.9, 127.5, 123.0, 120.5, 105.1, 84.5, 81.0, 80.4, 79.3, 76.9, 70.7, 70.0, 66.1, 66.0, 60.9, 58.3, 44.4, 44.2, 43.1, 40.5, 39.0, 37.5, 29.9, 28.4, 23.0, 21.4, 19.9, 13.9, 13.5, 11.6, 11.3, 11.0.

Z-isomer:

MS (ESI): m/z 873.69 [M+H], 437.35 [M+2H].

Example 185

Compound of formula VII, wherein $R_1$ and $R_2$ taken together with the carbon atom to which they are attached are C=NO[6-pyridazin-3-yl-pyridin-2-ylmethyl], and $R_{20}$=Rx=H To a methanol solution of the title compound of Example 185 was added palladium on carbon. The mixture was stirred under hydrogen at room temperature for 17 hours. Filtration through a pad of potassium carbonate and celite followed by removal of the solvent afforded the title compound.

MS (ESI): m/z 839.47 [M+H], 420.23 [M+2H].

$^{13}$C NMR (CDCl$_3$, ppm) δ: 216.7, 177.4, 158.7, 158.4, 157.8, 157.6, 152.8, 151.1, 137.7, 127.0, 124.8, 122.5, 120.3, 103.6, 84.3, 80.6, 80.5, 78.9, 76.2, 70.0, 68.3, 66.8, 65.7, 60.7, 58.1, 44.0, 43.9, 42.8, 40.6, 38.8, 37.2, 31.6, 29.7, 22.8, 22.7, 21.3, 20.9, 19.6, 14.1, 13.8, 13.3, 11.4, 11.1, 10.9.

Example 186

Compound of formula VII, wherein $R_1$ and $R_2$ taken together with the carbon atom to which they are attached are C=NO[3-cyanobenzyl], $R_{20}$=H, and Rx=Ac The title compound was prepared with the title compound of Example 16 and O-(3-cyanobenzyl)-hydroxylamine (prepared according to literature procedure) via similar conditions outlined in Example 35.

MS (ESI): m/z 827.80 [M+H].

Example 187

Compound of formula VII, wherein $R_1$ and $R_2$ taken together with the carbon atom to which they are attached are C=NO[3-cyanobenzyl], and $R_{20}$=Rx=H The title compound was prepared with the title compound of Example 186 via similar conditions described in Example 36. E:Z ratio was 3:1.

MS (ESI): m/z 785.53 [M+H].

E-isomer:

MS (ESI): m/z 785.53 [M+H].

$^{13}$C NMR (CDCl$_3$, ppm) δ: 217.1, 177.8, 159.1, 157.9, 139.7, 132.3, 131.7, 131.5, 129.4, 119.1, 112.7, 105.1, 84.5, 81.0, 80.4, 79.2, 76.8, 75.1, 70.7, 70.0, 66.1, 65.8, 60.8, 58.3, 44.4, 44.2, 43.0, 40.5, 39.0, 37.5, 29.9, 28.4, 23.0, 21.4, 19.9, 13.9, 13.5, 11.6, 11.3, 10.9.

Z-isomer:

MS (ESI): m/z 785.53 [M+H].

Example 188

Compound of formula VII, wherein $R_1$ and $R_2$ taken together with the carbon atom to which they are attached are C=NO[5-(6-amino-pyridin-2-yl)-thiophen-2-ylmethyl], $R_{20}$=H, and Rx=Ac The title compound was prepared with the title compound of Example 16 and O-[5-(6-amino-pyridin-2-yl)-thiophen-2-ylmethyl)-hydroxylamine (prepared according to literature procedure) via similar conditions outlined in Example 35.

MS (ESI): m/z 900.50 [M+H], 450.75 [M+2H].

Example 189

Compound of formula VII, wherein $R_1$ and $R_2$ taken together with the carbon atom to which they are attached are C=NO[5-(6-amino-pyridin-2-yl)-thiophen-2-ylmethyl], and $R_{20}$=Rx=H The title compound was prepared with the title compound of Example 188 via similar conditions described in Example 36. E:Z ratio was 2.7:1.

MS (ESI): m/z 858.51 [M+H], 429.76 [M+2H].

E-isomer:

MS (ESI): m/z 858.51 [M+H], 429.76 [M+2H].

$^{13}$C NMR (CDCl$_3$, ppm) δ: 216.8, 177.6, 159.1, 158.5, 158.0, 151.2, 145.6, 141.6, 138.5, 127.9, 124.2, 109.4, 107.2, 105.1, 84.4, 80.8, 80.5, 79.3, 76.6, 70.9, 70.7, 69.9, 66.2, 66.0, 61.0, 58.4, 44.5, 44.0, 43.1, 40.5, 39.3, 37.2, 28.4, 22.9, 21.45, 21.37, 20.1, 14.0, 13.5, 11.8, 11.2, 10.9.

Z-isomer:

MS (ESI): m/z 858.51 [M+H], 429.76 [M+2H].

$^{13}$C NMR (CDCl$_3$, ppm) δ: 217.2, 177.5, 159.5, 158.3, 157.8, 151.2, 146.1, 141.6, 138.5, 128.0, 123.9, 109.4, 107.2, 105.1, 84.3, 82.5, 81.2, 80.7, 76.1, 73.0, 71.2, 70.7, 69.9, 66.0, 58.6, 58.5, 44.7, 44.2, 43.4, 40.4, 39.5, 37.3, 28.4, 22.6, 21.6, 21.5, 20.2, 13.9, 13.4, 12.4, 11.03, 10.99.

Example 190

Compound of formula VII, wherein $R_1$ and $R_2$ taken together with the carbon atom to which they are attached are C=NO[6-(5-amino-pyrazin-2-yl)-pyridin-2-ylmethyl], $R_{20}$=H, and Rx=Ac The title compound was prepared with the title compound of Example 16 and O-[6-(5-amino-pyrazin-2-yl)-pyridin-2-ylmethyl]-hydroxylamine (prepared according to literature procedure) via similar conditions outlined in Example 35.

MS (ESI): m/z 896.53 [M+H], 448.77 [M+2H].

Example 191

Compound of formula VII, wherein $R_1$ and $R_2$ taken together with the carbon atom to which they are attached are C=NO[6-(5-amino-pyrazin-2-yl)-pyridin-2-ylmethyl], and $R_{20}$=Rx=H The title compound was prepared with the title compound of Example 190 via similar conditions described in Example 36. E:Z ratio was 2.5:1.

MS (ESI): m/z 854.58 [M+H], 427.79 [M+2H].

E-isomer:

MS (ESI): m/z 854.58 [M+H], 427.79 [M+2H].

$^{13}$C NMR (CDCl$_3$, ppm) δ: 216.9, 177.8, 158.9, 158.5, 157.6, 154.9, 154.6, 141.6, 141.1, 137.4, 131.2, 120.3, 118.7, 105.2, 84.5, 80.8, 80.5, 79.8, 76.6, 76.3, 70.7, 69.9, 66.4, 66.0, 61.0, 58.4, 44.8, 44.1, 43.2, 40.5, 39.3, 37.1, 28.4, 22.8, 21.4, 21.2, 20.2, 13.9, 13.5, 12.0, 11.2, 10.9.

Z-isomer:

MS (ESI): m/z 854.58 [M+H], 427.79 [M+2H].

$^{13}$C NMR (CDCl$_3$, ppm) δ: 216.6, 177.0, 159.1, 158.4, 157.4, 155.0, 154.5, 141.3, 140.6, 137.1, 131.1, 120.1, 118.5, 104.9, 84.2, 82.8, 81.0, 80.6, 76.5, 75.7, 73.0, 70.5, 69.7, 65.8, 58.6, 58.5, 44.5, 44.2, 43.0, 40.2, 39.2, 37.4, 28.2, 22.5, 21.6, 21.2, 19.8, 13.7, 13.4, 11.8, 11.2, 10.9.

Example 192

Compound of formula VII, wherein $R_1$ and $R_2$ taken together with the carbon atom to which they are attached are C=NO[5'-amino-[2,2']bipyridinyl-6-ylmethyl], $R_{20}$=H, and Rx=Ac The title compound was prepared with the title compound of Example 16 and O-(5'-amino-[2,2']bipyridinyl-6-ylmethyl)-hydroxylamine (prepared according to literature procedure) via similar conditions outlined in Example 35.
MS (ESI): m/z 895.56 [M+H], 448.28 [M+2H].

Example 193

Compound of formula VII, wherein $R_1$ and $R_2$ taken together with the carbon atom to which they are attached are C=NO[5'-amino-[2,2']bipyridinyl-6-ylmethyl], and $R_{20}$=Rx=H The title compound was prepared with the title compound of Example 192 via similar conditions described in Example 36. E:Z ratio was 2.6:1.
MS (ESI): m/z 853.54 [M+H], 427.27 [M+2H].

E-isomer:
MS (ESI): m/z 853.54 [M+H], 427.27 [M+2H].
$^{13}$C NMR (CDCl$_3$, ppm) δ: 217.0, 177.7, 158.7, 157.8, 157.5, 156.0, 147.4, 142.9, 137.4, 136.7, 122.3, 122.2, 120.3, 118.9, 105.1, 84.4, 80.9, 80.4, 79.4, 76.7, 70.7, 69.9, 66.2, 66.1, 61.0, 58.4, 44.5, 44.1, 43.1, 40.5, 39.1, 37.3, 28.5, 22.9, 21.43, 21.38, 20.0, 13.9, 13.5, 11.8, 11.3, 10.9.

Z-isomer:
MS (ESI): m/z 853.54 [M+H], 427.27 [M+2H].
$^{13}$C NMR (CDCl$_3$, ppm) δ: 217.1, 177.3, 159.1, 157.5, 157.0, 156.0, 147.1, 142.7, 137.2, 136.5, 122.1, 121.9, 120.4, 118.8, 104.6, 80.1, 82.3, 81.0, 80.3, 76.0, 72.7, 70.3, 69.5, 66.0, 58.4, 58.3, 44.4, 44.0, 43.1, 40.3, 39.2. 37.1, 28.6, 22.4, 21.4, 21.2, 19.9, 13.7, 13.2, 12.1, 10.8.

Example 194

Compound of formula VII, wherein $R_1$ and $R_2$ taken together with the carbon atom to which they are attached are C=NO[3'-amino-[2,2']bipyridinyl-6-ylmethyl], $R_{20}$=H, and Rx=Ac The title compound was prepared with the title compound of Example 16 and O-(3'-amino-[2,2']bipyridinyl-6-ylmethyl)-hydroxylamine (prepared according to literature procedure) via similar conditions outlined in Example 35.
MS (ESI): m/z 895.40 [M+H], 448.20 [M+2H].

Example 195

Compound of formula VII, wherein $R_1$ and $R_2$ taken together with the carbon atom to which they are attached are C=NO[3'-amino-[2,2']bipyridinyl-6-ylmethyl], and $R_{20}$=Rx=H The title compound was prepared with the title compound of Example 194 via similar conditions described in Example 36. E:Z ratio was 2.6:1.
MS (ESI): m/z 853.53 [M+H], 427.27 [M+2H].

E-isomer:
MS (ESI): m/z 853.53 [M+H], 427.27 [M+2H].
$^{13}$C NMR (CDCl$_3$, ppm) δ: 217.1, 177.8, 159.1, 158.8, 157.8, 155.0, 144.4, 138.0, 137.3, 137.2, 124.7, 124.6, 121.3, 119.9, 105.0, 84.4, 80.9, 80.4, 79.5, 76.9, 70.6, 69.8, 66.14, 66.09, 61.0, 58.3, 44.5, 44.1, 43.1, 40.5, 39.1, 37.3, 28.6, 22.9, 21.4, 20.0, 13.9, 13.4, 11.7, 11.3, 10.9.

Z-isomer:
MS (ESI): m/z 853.53 [M+H], 427.27 [M+2H].
$^{13}$C NMR (CDCl$_3$, ppm) δ: 217.3, 177.2, 159.2, 159.0, 157.5, 154.9, 144.1, 137.8, 137.1, 136.7, 124.6, 124.3, 121.2, 119.7, 104.6, 84.1, 82.5, 81.1, 80.2, 76.0, 72.8, 70.3, 69.3, 66.1, 58.4, 44.4, 44.1, 43.1, 40.3, 39.3, 37.1, 28.8, 22.3, 21.4, 21.1, 19.9, 13.7, 13.2, 12.1, 10.9, 10.8.

Example 196

Compound of formula VII, wherein $R_1$ and $R_2$ taken together with the carbon atom to which they are attached are C=NO[4'-amino-[2,2']bipyridinyl-6-ylmethyl], $R_{20}$=H, and Rx=Ac The title compound was prepared with the title compound of Example 16 and O-(4'-amino-[2,2']bipyridinyl-6-ylmethyl)-hydroxylamine (prepared according to literature procedure) via similar conditions outlined in Example 35.
MS (ESI): m/z 895.64 [M+H], 448.33 [M+2H].

Example 197

Compound of formula VII, wherein $R_1$ and $R_2$ taken together with the carbon atom to which they are attached are C=NO[4'-amino-[2,2']bipyridinyl-6-ylmethyl], and $R_{20}$=Rx=H The title compound was prepared with the title compound of Example 196 via similar conditions described in Example 36. E:Z ratio was 2:1.
MS (ESI): m/z 853.43 [M+H], 427.21 [M+2H].

E-isomer:
MS (ESI): m/z 853.43 [M+H], 427.21 [M+2H].
$^{13}$C NMR (CDCl$_3$, ppm) δ: 216.8, 177.5, 158.5, 157.7, 157.0, 153.8, 149.4, 137.3, 121.4, 119.9, 109.5, 107.3, 104.9, 84.3, 80.7, 80.2, 79.1, 76.6, 70.5, 69.7, 65.8, 60.7, 58.2, 44.2, 43.9, 42.8, 40.2, 38.9, 37.2, 28.2, 22.7, 21.2, 19.7, 13.7, 13.3, 11.4, 11.1, 10.7.

Z-isomer:
MS (ESI): m/z 853.43 [M+H], 427.21 [M+2H].

Example 198

Compound of formula VII, wherein $R_1$ and $R_2$ taken together with the carbon atom to which they are attached are C=NO[6-(3-amino-phenyl)-pyridin-2-ylmethyl], $R_{20}$=H, and Rx=Ac The title compound was prepared with the title compound of Example 16 and O-[6-(3-amino-phenyl)-pyridin-2-ylmethyl]-hydroxylamine (prepared according to literature procedure) via similar conditions outlined in Example 35.
MS (ESI): m/z 894.65 [M+H], 447.83 [M+2H].

Example 199

Compound of formula VII, wherein $R_1$ and $R_2$ taken together with the carbon atom to which they are attached are C=NO[6-(3-amino-phenyl)-pyridin-2-ylmethyl], and $R_{20}$=Rx=H The title compound was prepared with the title compound of Example 198 via similar conditions described in Example 36. E:Z ratio was 2.3:1.
MS (ESI): m/z 852.57 [M+H], 426.78 [M+2H].

E-isomer:

MS (ESI): m/z 852.57 [M+H], 426.78 [M+2H].

$^{13}$C NMR (CDCl$_3$, ppm) δ: 217.0, 177.8, 158.8, 158.1, 157.9, 157.2, 147.1, 140.8, 137.4, 129.7, 119.8, 119.6, 117.6, 115.9, 114.1, 105.1, 84.4, 80.9, 80.4, 79.4, 76.7, 70.7, 70.0, 66.2, 66.1, 61.0, 58.4, 44.5, 44.1, 43.1, 40.5, 39.1, 37.3, 28.4, 22.9, 21.45, 21.41, 20.1, 13.9, 13.5, 11.8, 11.3, 10.9.

Z-isomer:

MS (ESI): m/z 852.57 [M+H], 426.78 [M+2H].

$^{13}$C NMR (CDCl$_3$, ppm) δ: 217.2, 177.5, 159.2, 157.8, 157.4, 147.1, 140.7, 137.4, 129.8, 120.3, 119.8, 117.6, 115.9, 114.2, 105.0, 84.3, 82.1, 81.3, 80.5, 76.3, 72.8, 70.7, 69.9, 66.1, 58.7, 58.3, 44.6, 44.3, 43.3, 40.5, 39.4, 37.4, 28.5, 22.7, 21.6, 21.5, 20.1, 14.0, 13.4, 12.2, 11.1, 11.0

Example 200

Compound of formula VII, wherein R$_1$ and R$_2$ taken together with the carbon atom to which they are attached are C=NO[6-amino-pyridin-2-ylmethyl], R$_{20}$=H, and Rx=Ac The title compound was prepared with the title compound of Example 16 and O-(6-amino-pyridin-2-ylmethyl)-hydroxylamine (prepared according to literature procedure) via similar conditions outlined in Example 35.

MS (ESI): m/z 818.45 [M+H], 409.73 [M+2H].

Example 201

Compound of formula VII, wherein R$_1$ and R$_2$ taken together with the carbon atom to which they are attached are C=NO[6-amino-pyridin-2-ylmethyl], and R$_{20}$=Rx=H The title compound was prepared with the title compound of Example 200 via similar conditions described in Example 36. E:Z ratio was 2:1.

MS (ESI): m/z 776.41 [M+H], 388.70 [M+2H].

Example 202

Compound of formula VII, wherein R$_1$ and R$_2$ taken together with the carbon atom to which they are attached are C=NO[6-hydroxy-pyridin-2-ylmethyl], R$_{20}$=H, and Rx=Ac The title compound was prepared with the title compound of Example 201 via similar conditions described in Example 178. E:Z ratio was 2.9:1.

MS (ESI): m/z 777.37 [M+H], 389.19 [M+2H].

E-isomer:

MS (ESI): m/z 777.37 [M+H], 389.19 [M+2H].

$^{13}$C NMR (CDCl$_3$, ppm) δ: 217.0, 177.8, 163.9, 160.6, 157.9, 144.0, 141.2, 120.6, 105.1, 84.5, 81.2, 80.4, 79.2, 76.8, 71.8, 70.7, 70.0, 66.0, 65.7, 60.7, 58.2, 44.4, 44.1, 43.0, 40.5, 39.2, 37.4, 28.4, 22.9, 21.49, 21.46, 19.9, 14.0, 13.5, 11.6, 11.3, 10.9.

Z-isomer:

MS (ESI): m/z 777.37 [M+H], 389.19 [M+2H].

$^{13}$C NMR (CDCl$_3$, ppm) δ: 217.2, 177.2, 163.5, 161.1, 157.6, 143.8, 140.9, 120.3, 104.9, 84.1, 82.1, 81.2, 80.4, 75.9, 72.1, 71.7, 70.4, 69.7, 65.8, 58.4, 57.6, 44.5, 44.0, 43.1, 40.2, 39.2, 37.1, 28.1, 22.4, 21.4, 21.3, 19.9, 13.7, 13.2, 12.0, 10.82, 10.76.

Example 203

Compound of formula VII, wherein R$_1$ and R$_2$ taken together with the carbon atom to which they are attached are C=NO[6'-amino-[2,3']bipyridinyl-6-ylmethyl], R$_{20}$=H, and Rx=Ac The title compound was prepared with the title compound of Example 16 and O-(6'-amino-[2,3']bipyridinyl-6-ylmethyl)-hydroxylamine (prepared according to literature procedure) via similar conditions outlined in Example 35.

MS (ESI): m/z 895.49 [M+H], 448.24 [M+2H].

Example 204

Compound of formula VII, wherein R$_1$ and R$_2$ taken together with the carbon atom to which they are attached are C=NO[6'-amino-[2,3']bipyridinyl-6-ylmethyl], and R$_{20}$=Rx=H The title compound was prepared with the title compound of Example 203 via similar conditions described in Example 36. E:Z ratio was 2:1.

MS (ESI): m/z 853.43 [M+H], 427.21 [M+2H].

E-isomer:

MS (ESI): m/z 853.43 [M+H], 427.21 [M+2H].

$^{13}$C NMR (CDCl$_3$, ppm) δ: 216.9, 177.7, 159.0, 158.8, 158.24, 158.17, 155.1, 147.2, 137.4, 136.9, 126.0, 119.2, 118.2, 108.6, 105.1, 84.4, 80.9, 80.5, 79.5, 76.5, 70.7, 69.9, 66.3, 66.0, 61.0, 58.4, 44.6, 44.1, 43.1, 40.5, 39.2, 37.3, 28.4, 22.9, 21.44, 21.35, 20.1, 13.9, 13.5, 11.8, 11.3, 10.9.

Z-isomer:

MS (ESI): m/z 853.43 [M+H], 427.21 [M+2H].

Example 205

Compound of formula VII, wherein R$_1$ and R$_2$ taken together with the carbon atom to which they are attached are C=NO[pyridin-2-ylmethyl], R$_{20}$=H, and Rx=Ac The title compound was prepared with the title compound of Example 16 and O-pyridin-2-ylmethyl-hydroxylamine (prepared according to literature procedure) via similar conditions outlined in Example 35.

MS (ESI): m/z 803.64 [M+H], 402.32 [M+2H].

Example 206

Compound of formula VII, wherein R$_1$ and R$_2$ taken together with the carbon atom to which they are attached are C=NO[pyridin-2-ylmethyl], and R$_{20}$=Rx=H The title compound was prepared with the title compound of Example 205 via similar conditions described in Example 36. E:Z ratio was 1:1.

MS (ESI): m/z 761.41 [M+H], 381.20 [M+2H].

E-isomer:

MS (ESI): m/z 761.41 [M+H], 381.20 [M+2H].

$^{13}$C NMR (CDCl$_3$, ppm) δ: 217.0, 177.8, 158.9, 158.2, 157.9, 149.4, 136.9, 122.7, 121.7, 105.1, 84.4, 81.0, 80.4, 79.3, 76.6, 70.7, 70.0, 66.14, 66.07, 61.0, 58.4, 44.5, 44.1, 43.1, 40.5, 39.1, 37.4, 28.4, 22.9, 21.45, 21.41, 20.0, 13.9, 13.5, 11.7, 11.3, 10.9.

Z-isomer:

MS (ESI): m/z 761.41 [M+H], 381.20 [M+2H].

$^{13}$C NMR (CDCl$_3$, ppm) δ: 217.3, 177.5, 159.3, 157.9, 157.8, 149.5, 136.8, 122.9, 122.2, 105.1, 84.3, 82.2, 81.3, 80.5, 76.2, 72.8, 70.7, 70.0, 66.0, 58.6, 58.2, 44.7, 44.3, 43.3, 40.5, 39.4, 37.3, 28.4, 22.6, 21.6, 21.5, 20.1, 13.9, 13.5, 12.2, 11.1, 11.0.

Example 207

Compound of formula VII, wherein $R_1$ and $R_2$ taken together with the carbon atom to which they are attached are C=NO[1S-1-pyridin-2-yl-ethyl], $R_{20}$=H, and Rx=Ac The title compound was prepared with the title compound of Example 16 and O-(1S-1-pyridin-2-yl-ethyl)-hydroxylamine (prepared according to literature procedure) via similar conditions outlined in Example 35.

MS (ESI): m/z 817.45 [M+H], 409.23 [M+2H].

Example 208

Compound of formula VII, wherein $R_1$ and $R_2$ taken together with the carbon atom to which they are attached are C=NO[1S-1-pyridin-2-yl-ethyl], and $R_{20}$=Rx=H The title compound was prepared with the title compound of Example 207 via similar conditions described in Example 36. E:Z ratio was 1:1.

MS (ESI): m/z 775.43 [M+H], 388.21 [M+2H].

E-isomer:

MS (ESI): m/z 775.43 [M+H], 388.21 [M+2H].

$^{13}$C NMR (CDCl$_3$, ppm) δ: 217.0, 177.9, 162.6, 158.5, 157.9, 149.0, 137.1, 122.6, 120.2, 105.0, 84.4, 82.9, 80.9, 80.4, 79.2, 76.4, 70.7, 69.9, 66.2, 66.1, 61.0, 58.3, 44.5, 44.1, 43.1, 40.5, 38.9, 37.3, 28.5, 22.9, 21.43, 21.39, 21.0, 20.0, 13.8, 13.4, 11.8, 11.3, 10.8.

Z-isomer:

MS (ESI): m/z 775.43 [M+H], 388.21 [M+2H].

$^{13}$C NMR (CDCl$_3$, ppm) δ: 217.4, 177.5, 162.2, 158.9, 157.8, 149.3, 136.7, 122.6, 121.0, 105.2, 84.3, 82.5, 82.4, 81.2, 80.8, 76.1, 73.1, 70.7, 69.9, 66.0, 58.6, 58.4, 44.7, 44.3, 43.3, 40.5, 39.5, 37.3, 28.4, 22.6, 21.6, 21.5, 20.7, 20.2, 13.9, 13.4, 12.3, 11.1.

Example 209

Compound of formula VII, wherein $R_1$ and $R_2$ taken together with the carbon atom to which they are attached are C=NO[3-(1H-tetrazol-5-yl)-benzyl], $R_{20}$=H, and Rx=Ac The title compound was prepared with the title compound of Example 16 and O-[3-(1H-tetrazol-5-yl)-benzyl]-hydroxylamine (prepared according to literature procedure) via similar conditions outlined in Example 35.

MS (ESI): m/z 870.83 [M+H].

Example 210

Compound of formula VII, wherein $R_1$ and $R_2$ taken together with the carbon atom to which they are attached are C=NO[3-(1H-tetrazol-5-yl)-benzyl], and $R_{20}$=Rx=H The title compound was prepared with the title compound of Example 209 via similar conditions described in Example 36. E:Z ratio was 2:1.

MS (ESI): m/z 828.54 [M+H].

Example 211

Compound of formula VII, wherein $R_1$ and $R_2$ taken together with the carbon atom to which they are attached are C=CH$_2$, $R_{20}$=CH$_3$, and Rx=Ac The title compound was prepared with the title compound of Example 10 and commercially available methyl amine via similar conditions outlined in Example 14.

MS (ESI): m/z 709.56 [M+H].

$^{13}$C NMR (CDCl$_3$, ppm) δ: 214.9, 176.9, 169.9, 157.3, 145.8, 117.7, 102.2, 82.8, 81.1, 80.0, 78.2, 77.7, 74.2, 69.2, 64.9, 63.5, 63.0, 43.5, 43.2, 43.1, 41.6, 40.8, 38.9, 32.1, 31.8, 31.2, 24.3, 22.88, 22.85, 21.7, 21.2, 18.9, 14.6, 14.3, 12.3, 12.2, 11.2, 10.8.

Example 212

Compound of formula VII, wherein $R_1$ and $R_2$ taken together with the carbon atom to which they are attached are C=CH$_2$, $R_{20}$=CH$_3$, and Rx=H The title compound was prepared with the title compound of Example 211 via similar conditions described in Example 12.

MS (ESI): m/z 667.53 [M+H].

$^{13}$C NMR (CD$_3$OD, ppm) δ: 215.8, 177.2, 158.1, 146.5, 117.1, 104.2, 83.7, 81.1, 79.7, 78.5, 77.4, 73.9, 71.0, 69.1, 64.8, 64.7, 63.2, 43.3, 43.0, 42.7, 41.6, 39.5, 39.2, 31.2, 30.5, 23.7, 22.5, 20.3, 17.7, 13.4, 11.5, 11.1, 10.4, 10.3.

Example 213

Compound of formula VII, wherein $R_1$ and $R_2$ taken together with the carbon atom to which they are attached are C=O, $R_{20}$=CH, and Rx=Ac The title compound was prepared with the title compound of Example 212 via similar conditions described in Example 16.

MS (ESI): m/z 711.63 [M+H].

Example 214

Compound of formula VII, wherein $R_1$ and $R_2$ taken together with the carbon atom to which they are attached are C=O, $R_{20}$=CH$_3$, and Rx=H The title compound was prepared with the title compound of Example 213 via similar conditions described in Example 12.

MS (ESI): m/z 669.50 [M+H].

$^{13}$C NMR (CDCl$_3$, ppm) δ: 214.7, 209.9, 177.5, 157.3, 105.1, 82.7, 81.7, 81.2, 70.5, 69.7, 67.7, 66.4, 63.2, 44.3, 43.7, 43.2, 41.6, 40.6, 37.1, 32.3, 29.0, 22.8, 22.5, 21.4, 19.6, 14.6, 12.7, 12.5, 11.3, 11.0.

Example 215

Compound of formula VII, wherein $R_1$ and $R_2$ taken together with the carbon atom to which they are attached are C=NO[pyrido[2,3-b]pyrazin-8-ylmethyl], $R_{20}$=CH$_3$, and Rx=Ac The title compound was prepared with the title compound of Example 213 and O-pyrido[2,3-b]pyrazin-8-ylmethyl-hydroxylamine (prepared according to literature procedure) via similar conditions outlined in Example 35.

MS (ESI): m/z 869.73 [M+H], 435.52 [M+2H].

Example 216

Compound of formula VII, wherein $R_1$ and $R_2$ taken together with the carbon atom to which they are attached are C=NO[pyrido[2,3-b]pyrazin-8-ylmethyl], $R_{20}$=CH$_3$, and Rx=H The title compound was prepared with the title compound of Example 215 via similar conditions described in Example 36. E:Z ratio was 2.7:1.
MS (ESI): m/z 827.69 [M+H], 414.50 [M+2H].

E-isomer:
MS (ESI): m/z 827.69 [M+H], 414.50 [M+2H].
$^{13}$C NMR (CDCl$_3$, ppm) δ: 214.6, 177.7, 159.7, 157.4, 154.5, 151.1, 148.0, 147.8, 145.2, 136.6, 122.6, 105.0, 83.0, 81.4, 81.0, 80.0, 70.9, 70.6, 69.8, 66.3, 66.2, 63.0, 60.9, 44.2, 44.0, 43.0, 41.1, 40.5, 37.9, 32.4, 28.7, 23.01, 22.95, 21.4, 19.4, 14.5, 12.9, 12.0, 11.33, 11.26.

Z-isomer:
MS (ESI): m/z 827.69 [M+H], 414.50 [M+2H].
$^{13}$C NMR (CDCl$_3$, ppm) δ: 215.0, 177.3, 160.2, 157.3, 154.5, 151.1, 148.0, 147.8, 145.2, 136.7, 123.0, 104.6, 83.8, 82.7, 81.6, 81.4, 73.5, 70.8, 70.3, 69.2, 66.7, 63.2, 58.6, 44.0, 43.7, 43.3, 41.8, 40.7, 37.7, 32.3, 23.4, 22.3, 21.3, 19.5, 14.7, 12.9, 12.5, 11.5, 10.9.

Example 217

Compound of formula VII, wherein $R_1$ and $R_2$ taken together with the carbon atom to which they are attached are C=NO[6'-amino-[2,2']bipyridinyl-6-ylmethyl], $R_{20}$=CH$_3$, and Rx=Ac The title compound was prepared with the title compound of Example 213 and O-(6'-amino-[2,2']bipyridinyl-6-ylmethyl)-hydroxylamine (prepared according to literature procedure) via similar conditions outlined in Example 35.
MS (ESI): m/z 909.54 [M+H], 455.27 [M+2H].

Example 218

Compound of formula VII, wherein $R_1$ and $R_2$ taken together with the carbon atom to which they are attached are C=NO[6'-amino-[2,2']bipyridinyl-6-ylmethyl], $R_{20}$=CH$_3$, and Rx=H The title compound was prepared with the title compound of Example 217 via similar conditions described in Example 36. E:Z ratio was 3.1:1.
MS (ESI): m/z 867.18 [M+H], 434.09 [M+2H].

E-isomer:
MS (EST): m/z 867.18 [M+H], 434.09 [M+2H].
$^{13}$C NMR (CDCl$_3$, ppm) δ: 214.5, 177.6, 159.0, 158.2, 157.6, 157.3, 156.1, 154.9, 138.8, 137.4, 121.0, 120.0, 112.1, 109.1, 105.1, 83.0, 81.3, 81.1, 80.0, 70.7, 69.9, 66.5, 66.1, 63.0, 61.0, 44.3, 43.9, 43.0, 41.2, 40.5, 38.0, 32.2, 28.4, 23.1, 23.1, 21.4, 19.3, 14.4, 12.7, 12.0, 11.4, 11.3.

Z-isomer:
MS (ESI): m/z 867.18 [M+H], 434.09 [M+2H].
$^{13}$C NMR (CDCl$_3$, ppm) δ: 214.8, 177.1, 159.3, 157.9, 157.3, 157.1, 155.9, 154.6, 138.6, 137.2, 121.2, 120.0, 111.8, 108.9, 104.8, 83.6, 82.5, 81.4, 81.1, 73.4, 70.4, 69.6, 66.0, 62.9, 58.5, 43.8, 43.4, 43.2, 41.6, 40.3, 37.6, 32.1, 28.5, 23.2, 22.1, 21.2, 19.2, 14.4, 12.7, 12.2, 11.2, 10.6.

Example 219

Compound of formula VII, wherein $R_1$ and $R_2$ taken together with the carbon atom to which they are attached are C=N—NH—CO-Bz, $R_{20}$=and Rx=Ac The title compound was prepared with the title compound of Example 16 and commercially available benzoic hydrazide via similar conditions outlined in Example 35.
MS (ESI): m/z 815.71 [M+H].

Example 220

Compound of formula VII, wherein $R_1$ and $R_2$ taken together with the carbon atom to which they are attached are C=N—NH—CO-Bz, and $R_{20}$=Rx=H The title compound was prepared with the title compound of Example 219 via similar conditions described in Example 36. E:Z ratio was 2:1.
MS (ESI): m/z 773.71 [M+H].

Example 221

Compound of formula VII, wherein $R_1$ and $R_2$ taken together with the carbon atom to which they are attached are C=N—NH—CO-[pyridin-2-yl], $R_{20}$=H, and Rx=Ac The title compound was prepared with the title compound of Example 16 and commercially available 2-picolinyl hydrazide via similar conditions outlined in Example 35.
MS (ESI): m/z 816.45 [M+H].

Example 222

Compound of formula VII, wherein $R_1$ and $R_2$ taken together with the carbon atom to which they are attached are C=N—NH—CO-[pyridin-2-yl], and $R_{20}$=Rx=H The title compound was prepared with the title compound of Example 221 via similar conditions described in Example 36. E:Z ratio was 3:1.
MS (ESI): m/z 774.62 [M+H], 387.81 [M+2H].

E-isomer:
MS (ESI): m/z 774.62 [M+H], 387.81 [M+2H].
$^{13}$C NMR (CDCl$_3$, ppm) δ: 216.5, 178.1, 160.4, 157.9, 157.6, 149.2, 148.5, 137.8, 127.0, 123.2, 105.3, 84.2, 80.9, 80.6, 80.5, 76.7, 70.7, 70.0, 66.5, 66.1, 64.1, 58.3, 44.8, 43.7, 43.3, 40.5, 39.5, 37.2, 28.4, 22.7, 21.5, 21.4, 20.2, 14.0, 13.3, 12.2, 11.1, 10.9.

Z-isomer:
MS (ESI): m/z 774.62 [M+H], 387.81 [M+2H].
$^{13}$C NMR (CDCl$_3$, ppm) δ: 217.9, 176.9, 160.9, 159.0, 157.7, 149.4, 148.4, 138.0, 127.2, 123.5, 105.0, 84.4, 82.1, 80.5, 80.2, 76.8, 74.5, 70.7, 70.0, 66.0, 68.6, 57.1, 44.5, 44.3, 43.0, 40.4, 39.2, 37.7, 28.4, 22.9, 21.9, 21.5, 19.7, 14.0, 13.6, 11.5, 11.3, 11.0.

Example 223

Compound of formula VII, wherein $R_1$ and $R_2$ taken together with the carbon atom to which they are attached are C=N—NH—SO$_2$-phenyl, $R_{20}$=H, and Rx=Ac The title compound was prepared with the title compound of Example 16 and commercially available benzenesulfonyl hydrazide via similar conditions outlined in Example 35.
MS (ESI): m/z 851.64 [M+H].

Example 224

Compound of formula VII, wherein $R_1$ and $R_2$ taken together with the carbon atom to which they are attached are C=N—NH—SO$_2$-phenyl, and $R_{20}$=Rx=H The title compound was prepared with the title compound of Example 223 via similar conditions described in Example 36. E:Z ratio was 2:1.
MS (ESI): m/z 809.47 [M+H].

Example 225

Compound of formula VII, wherein $R_1$ and $R_2$ taken together with the carbon atom to which they are attached are C=CH[quinolin-3-yl], $R_{20}$=H, and Rx=Ac The title compound was prepared with the title compound of Example 16 and 3-bromo-quinoline via similar conditions described in Example 59.
MS (ESI): m/z 822.62 [M+H], 411.97 [M+2H].

Example 226

Compound of formula VII, wherein $R_1$ and $R_2$ taken together with the carbon atom to which they are attached are C=CH[quinolin-3-yl], $R_{20}$=Rx=H The title compound was prepared with the title compound of Example 225 via similar conditions described in Example 36. E:Z ratio was 1:1.
MS (ESI): m/z 780.69 [M+H], 390.97 [M+2H].

Example 227

Compound of formula VII, wherein $R_1$=H and $R_2$=CH$_2$[1,2,3,4-tetrahydro-quinolin-3-yl], and $R_{20}$=Rx=H The title compound was prepared with the title compound of Example 226 via similar conditions described in Example 60.
MS (ESI): m/z 786.74 [M+H], 394.02 [M+2H].

Examples 228

Compound of formula VII, wherein $R_1$ and $R_2$ taken together with the carbon atom to which they are attached are C=NO(CH$_2$CONHCH$_2$Ph), $R_{20}$=H, and Rx=Ac Step 228a.
To a clear solution of commercially available (BOC-aminooxy)acetic acid (573 mg), EDC (575 mg) and benzylamine (220 µl) in CH$_2$Cl$_2$ was added TEA (840 µl) at room temperature and the resulting mixture was allowed to stir overnight at room temperature. The mixture was extracted with EtOAc. The combined organic extracts were washed twice with 1% HCl and once with saturated NaHCO$_3$, dried over Na$_2$SO$_4$, filtered and concentrated under vacuum to give the desired compound.

Step 228b.
Compound from step 228a was dissolved in 50% TFA in CH$_2$Cl$_2$ at 0° C. The reaction mixture was stirred for 30 minutes. The white precipitate was filtered off to give the desired target.

Step 228c.
To a solution of the compound from step 228b (1.5 eq) and 1M HCl (2.0 eq.) in EtOH was added compound from Example 16 (0.14 mmol) at 0° C. The reaction mixture was stirred at 0° C. for 1 hour and quenched with 1M NaHCO$_3$ and extracted with CH$_2$Cl$_2$. The combined organic extracts were washed with brine, dried over Na$_2$SO$_4$, filtered and concentrated under vacuum to give the white foam. The residue was used directly to the next step without purification.
MS (ESI): m/z 859 [M+H].

Example 229

Compound of formula VII, wherein $R_1$ and $R_2$ taken together with the carbon atom to which they are attached are C=NO(CH$_2$CONHCH$_2$Ph), and $R_{20}$=Rx=H The solution of compound from Example 228 in methanol was stirred at 60° C. for 2 hours. The reaction mixture was concentrated and purified by preparative HPLC to give both E and Z isomers.

E-isomer
MS (ESI): m/z 817.32 [M+H].
$^{13}$C NMR (CDCl$_3$, ppm) δ: 216.4, 177.3, 169.1, 160.2, 157.4, 138.3, 128.6, 127.4, 127.2, 104.9, 84.3, 81.0, 80.2, 79.1, 76.4, 73.4, 70.4, 69.7, 65.8, 65.5, 60.5, 57.4, 44.2, 43.1, 42.8, 42.7, 40.2, 39.6, 37.3, 28.1, 22.5, 21.3, 21.2, 19.6, 14.2, 12.8, 11.4, 10.6, 10.5.

Z-isomer
MS (ESI): m/z 817.32 [M+H].
$^{13}$C NMR (CDCl$_3$, ppm) δ: 217.2, 177.2, 169.2, 161.1, 157.4, 138.0, 128.7, 127.5, 127.5, 104.8, 84.0, 82.3, 81.2, 80.0, 75.9, 73.2, 72.1, 70.3, 69.6, 65.7, 58.3, 57.8, 44.4, 44.0, 43.0, 42.8, 40.2, 39.2, 37.0, 28.1, 22.3, 21.2, 19.8, 13.6, 13.1, 12.0, 10.7.

Example 230

Compound of formula VII, wherein $R_1$ and $R_2$ taken together with the carbon atom to which they are attached are C=NO(CH$_2$CONHPh), $R_{20}$=H and Rx=Ac The title compound was prepared with the title compound of Example 16 and 0-(phenylcarbamoyl-methyl)-hydroxylamine (prepared similarly to steps 228a and 228b of Example 228 with commercially available (BOC-aminooxy) acetic acid and aniline) via similar conditions outlined in Step 228c of Example 228.
MS (ESI): m/z 845 [M+H].

Example 231

Compound of formula VII, wherein $R_1$ and $R_2$ taken together with the carbon atom to which they are attached are C=NO(CH$_2$CONHPh), and $R_{20}$=Rx=H The title compound was prepared with the title compound of Example 230 via similar conditions described in Example 229.

E-isomer
MS (ESI): m/z 803.35 [M+H].
$^{13}$C NMR (CDCl$_3$, ppm) δ: 216.7, 177.8, 167.3, 160.6, 157.6, 137.4, 129.1, 124.8, 120.7, 104.9, 84.6, 81.3, 80.6, 79.1, 76.9, 73.9, 70.5, 69.7, 66.1, 65.7, 60.7, 57.8, 44.4, 43.6, 43.1, 40.3, 39.7, 37.6, 28.7, 22.8, 21.6, 21.4, 19.8, 14.3, 13.2, 11.5, 10.9, 10.8

Z-isomer

MS (ESI): m/z 803.35 [M+H].

$^{13}$C NMR (CDCl$_3$, ppm) δ: 217.3, 177.3, 167.3, 161.8, 157.4, 136.9, 129.0, 124.7, 120.2, 104.8, 84.0, 82.4, 81.3, 80.0, 75.9, 73.5, 72.1, 70.3, 69.7, 65.7, 58.4, 57.9, 44.4, 44.1, 43.1, 40.2, 39.2, 37.0, 28.0, 22.3, 21.3, 21.2, 19.9, 13.6, 13.1, 12.0, 10.7.

Example 232

Compound of formula VII, wherein R$_1$ and R$_2$ taken together with the carbon atom to which they are attached are C=NO(CH$_2$OCH$_2$Ph), R$_{20}$=H and Rx=Ac The title compound was prepared with the title compound of Example 16 and O-(benzyloxy-methyl)-hydroxylamine via similar conditions outlined in Step 228c of Example 228.

MS (ESI): m/z 832 [M+H].

Example 233

Compound of formula VII, wherein R$_1$ and R$_2$ together with the carbon atom to which they are attached are C=NO(CH$_2$OCH$_2$Ph), and R$_{20}$=Rx=H The title compound was prepared with the title compound of Example 232 via similar conditions described in Example 229.

E-isomer

MS (ESI): m/z 790.43 [M+H].

$^{13}$C NMR (CDCl$_3$, ppm) δ: 216.7, 177.5, 159.5, 157.4, 137.6, 128.3, 127.8, 127.6, 104.9, 96.6, 84.1, 80.7, 80.1, 79.2, 76.4, 70.4, 70.3, 69.7, 65.8, 65.8, 60.8, 58.1, 44.3, 43.8, 42.8, 40.2, 38.9, 37.0, 28.1, 22.6, 21.2, 21.1, 19.8, 13.6, 13.2, 11.6, 11.0, 10.6

Z-isomer

MS (ESI): m/z 790.43 [M+H].

$^{13}$C NMR (CDCl$_3$, ppm) δ: 217.1, 177.3, 106.1, 157.5, 137.7, 128.3, 127.7, 127.6, 104.8, 96.9, 84.0, 82.3, 81.0, 80.3, 76.7, 75.9, 72.6, 70.7, 70.4, 69.7, 65.7, 58.3, 58.2, 44.5, 44.0, 43.1, 40.2, 39.2, 37.0, 28.1, 22.3, 21.3, 21.2, 19.9, 13.6, 13.1, 12.1, 10.7.

Example 234

Compound of formula VII, wherein R$_1$ and R$_2$ taken together with the carbon atom to which they are attached are C=NO(1-pyridin-2-yl-pyrroline-3R-yl), R$_{20}$=H, and Rx=Ac Step 234a.

The mixture of 3S-hydroxy pyrrolidine (8081 µl) and 2-fluoropyridine (388 mg) was heated at 90° C. in a pressure tube for 3 hours. The residue was purified by column chromatography to give the desired compound in 95% yield.

MS (ESI): m/z 165.06 [M+H].

Step 234b.

Compound from step 234a, hydroxyl thalamide (620 mg) and triphenyl phosphine (1.5 g) was dissolved in 15 ml THF. DIAD (600 µl) was added dropwise to this clear solution at 0° C. The reaction mixture was stirred for overnight. The residue was concentrated and purified by column chromatography to give the desired compound in 81% yield.

MS (ESI): m/z 310.06 [M+H].

Step 234c.

Compound from step 234b was heating with NH$_2$NH$_2$ (2 eq) in methanol at 50° C. for 2 hours. The residue was concentrated and purified by column chromatography to give the desired target (300 mg).

MS (ESI): m/z 180.0 [M+H].

Step 234d.

The title compound was prepared with the title compound of Example 16 and compound from step (234c) via similar conditions outlined in Step 228c of Example 228.

MS (ESI): m/z 858 [M+H].

Example 235

Compound of formula VII, wherein R$_1$ and R$_2$ taken together with the carbon atom to which they are attached are C=NO(1-pyridin-2-yl-pyrroline-3R-yl), and R$_{20}$=Rx=H The title compound was prepared with the title compound of Example 234 via similar conditions described in Example 229.

MS (ESI): m/z 816.32 [M+H].

$^{13}$C NMR (CDCl$_3$, ppm) δ: 216.8, 177.2, 158.3, 157.6, 157.1, 148.2, 137.0, 111.4, 106.5, 104.8, 84.2, 82.3, 80.6, 80.1, 79.0, 76.3, 70.4, 69.7, 65.8, 65.8, 60.9, 58.0, 51.7, 44.3, 44.2, 43.9, 42.8, 40.2, 38.8, 37.1, 30.7, 28.1, 22.6, 21.2, 21.1, 19.7, 13.6, 13.2, 11.4, 10.9, 10.6 Z-isomer MS (ESI): m/z 816.32 [M+H].

Example 236

Compound of formula VII, wherein R$_1$ and R$_2$ taken together with the carbon atom to which they are attached are C=NO(CH$_2$CH$_2$OPh), R$_{20}$=H, and Rx=Ac Step 236a.

To a solution of commercially available hydroxyl thalamide (1.96 g) and (2-bromoethoxy)-tert-butyldimethylsilane (2.15 ml) in THF was added DBU (2.25 ml) at room temperature and the resulting mixture was allowed to stir fro 3 days at room temperature. The mixture was concentrated and extracted with EtOAc. The combined organic extracts were washed with 1M NaHCO$_3$, H$_2$O and brine, dried over Na$_2$SO$_4$, filtered and concentrated under vacuum to give the crude compound. 1.9 g of desired compound (93% yield) was obtained after recrystalization fron hexanes.

Step 236b.

Compound (900 mg) from step 236a was dissolved in THF (20 ml). 36% HCl (1.0 ml) was added at room temperature. After 2 hours, the reaction mixture was neutralized with sodium bicarbonate and extracted with EtOAc. The combined organic extracts were washed with 1M NaHCO$_3$, H$_2$O and brine, dried over Na$_2$SO$_4$, filtered, concentrated and purified by column chromatography to give the desired target in 74% yield.

Step 236c.

Compound from step 236b (210 mg), phenol (94 mg) and triphenyl phosphine (394 mg) was dissolved in 2 ml THF. DIAD (207 µl) was added dropwise to this clear solution at 0° C. The reaction mixture was stirred for overnight. The residue was concentrated and purified by column chromatography to give the desired compound (80 mg).

Step 236d.

Compound from step 236c was heating with 2M NH$_3$ in methanol at 50° C. for 2 hours. The residue was concentrated and directly used in the next step.

Step 236e.

The title compound was prepared with the title compound of Example 16 and compound from step (236d) via similar conditions outlined in Step 228c of Example 228.

MS (ESI): m/z 832 [M+H].

Example 237

Compound of formula VII, wherein $R_1$ and $R_2$ taken together with the carbon atom to which they are attached are C=NO(CH$_2$CH$_2$OPh), and $R_{20}$=Rx=H The title compound was prepared with the title compound of Example 236 via similar conditions described in Example 229.

E-isomer

MS (ESI): m/z 790.44 [M+H].

$^{13}$C NMR (CDCl$_3$, ppm) δ: 216.8, 177.3, 158.8, 158.2, 157.5, 129.4, 120.8, 114.7, 104.8, 84.2, 80.6, 80.2, 79.0, 76.5, 72.6, 70.4, 69.7, 66.1, 65.8, 65.7, 60.7, 58.0, 44.2, 43.9, 42.8, 40.2, 38.8, 37.1, 28.1, 22.6, 21.2, 21.1, 19.7, 13.7, 13.2, 11.4, 11.0, 10.7.

Z-isomer

MS (ESI): m/z 790.44 [M+H].

$^{13}$C NMR (CDCl$_3$, ppm) δ: 217.0, 177.3, 159.0, 158.7, 157.5, 129.4, 120.9, 114.6, 104.8, 84.0, 82.1, 80.9, 80.3, 75.9, 72.7, 72.6, 70.4, 69.7, 66.2, 65.7, 58.3, 58.0, 44.4, 44.0, 43.1, 40.2, 39.1, 37.0, 28.1, 22.3, 21.3, 21.2, 19.8, 13.6, 13.1, 12.0, 10.8, 10.7.

Example 238

Compound of formula VII, wherein $R_1$ and $R_2$ taken together with the carbon atom to which they are attached are C=NO(CH$_2$CH$_2$SPh), $R_{20}$=H, and Rx=Ac Step 238a.

Compound from step 236b (105 mg) was dissolved in CH$_2$Cl$_2$. DIEA was added at 0° C., followed by adding methylsulfonyl chloride (78 μl) dropwise. The reaction mixture was stirred at 0° C. for 2 hours. The mixture was concentrated and extracted with EtOAc. The combined organic extracts were washed with 1M NaHCO$_3$, H$_2$O and brine, dried over MgSO$_4$, filtered and concentrated under vacuum to give the desired compound.

Step 238b.

Compound from step 238a was dissolved in DMF (3 ml). Sodium bicarbonate (100 mg) was added. Sodium thiophenoxide (660 mg) was added while the reaction mixture was heated to 70° C. After heating for 1 hour, the reaction mixture was extracted with EtOAc. The combined organic extracts were washed with 1M NaHCO$_3$, H$_2$O and brine, dried over MgSO$_4$, filtered and concentrated under vacuum to give the desired compound.

Step 238c.

Compound from step 238b was heating with 2M NH$_3$ in methanol at 50° C. for 2 hours. The residue was concentrated and directly used in the next step.

Step 238d.

The title compound was prepared with the title compound of Example 16 and compound from step (238c) via similar conditions outlined in Step 228c of Example 228.

MS (ESI): m/z 848 [M+H].

Example 239

Compound of formula VII, wherein $R_1$ and $R_2$ taken together with the carbon atom to which they are attached are C=NO(CH$_2$CH$_2$SPh), and $R_{20}$=Rx=H The title compound was prepared with the title compound of Example 238 via similar conditions described in Example 229.

E-isomer

MS (ESI): m/z 806.31 [M+H].

$^{13}$C NMR (CDCl$_3$, ppm) δ: 216.8, 177.4, 158.2, 157.5, 129.5, 128.9, 126.1, 104.8, 84.1, 80.6, 80.2, 79.1, 76.5, 72.5, 70.4, 69.6, 65.8, 65.7, 60.7, 58.0, 44.2, 43.9, 42.8, 40.1, 38.8, 37.1, 32.4, 28.2, 22.6, 21.2, 21.1, 19.7, 13.7, 13.2, 11.4, 11.0, 10.7.

Z-isomer

MS (ESI): m/z 806.31 [M+H].

$^{13}$C NMR (CDCl$_3$, ppm) δ: 217.1, 177.3, 159.0, 157.5, 129.3, 128.9, 126.1, 104.8, 84.0, 82.3, 80.9, 80.2, 75.9, 72.7, 72.5, 70.3, 69.6, 65.7, 58.4, 58.2, 44.4, 44.0, 43.1, 40.2, 39.2, 37.0, 32.5, 28.1, 22.3, 21.3, 21.2, 19.9, 13.6, 13.1, 12.1, 10.7

Example 240

Compound of formula VII, wherein $R_1$ and $R_2$ taken together with the carbon atom to which they are attached are
C=NO(naphthalen-2-ylcarbamoyl-methyl) $R_{20}$=H, and Rx=Ac The title compound was prepared with the title compound of Example 16 and O-(naphthalen-2-ylcarbamoyl-methyl)-hydroxylamine (prepared similarly to steps 228a and 228b of Example 228 with commercially available (BOC-aminooxy) acetic acid and 2-naphthylamine) via similar conditions outlined in Step 228c of Example 228.

MS (ESI): m/z 895 [M+H].

Example 241

Compound of formula VII, wherein $R_1$ and $R_2$ taken together with the carbon atom to which they are attached are
C=NO(naphthalen-2-ylcarbamoyl-methyl), and R—)=Rx=H The title compound was prepared with the title compound of Example 240 via similar conditions described in Example 229.

E-isomer

MS (ESI): m/z 853.4 [M+H].

$^{13}$C NMR (CDCl$_3$, ppm) δ: 216.5, 177.5, 167.2, 160.4, 157.4, 134.7, 133.8, 130.8, 128.6, 127.7, 127.5, 126.3, 124.7, 120.2, 117.2, 104.8, 84.5, 81.2, 80.3, 78.9, 73.8, 70.4, 69.7, 65.8, 65.5, 60.5, 57.4, 44.1, 43.2, 42.8, 40.2, 39.6, 37.5, 28.1, 22.6, 21.4, 21.2, 19.4, 14.2, 12.9, 11.3, 10.7, 10.6 Z-isomer MS (ESI): m/z 853.4 [M+H].

Example 242

Compound of formula VII, wherein $R_1$ and $R_2$ taken together with the carbon atom to which they are attached are
C=NO(biphenyl-4-ylcarbamoyl-methyl), $R_{20}$=H, and $R_x$=Ac The title compound was prepared with the title compound of Example 16 and O-(biphenyl-4-ylcarbamoyl-methyl)-hydroxylamine (prepared similarly to steps 228a and 228b of Example 228 with commercially available (BOC-aminooxy) acetic acid and biphenyl-4-amine) via similar conditions outlined in Step 228c of Example 228.
MS (ESI): m/z 921 [M+H].

Example 243

Compound of formula VII, wherein $R_1$ and $R_2$ taken together with the carbon atom to which they are attached are
C=NO(biphenyl-4-ylcarbamoyl-methyl) and $R_{20}$=Rx=H The title compound was prepared with the title compound of Example 242 via similar conditions described in Example 229.

E-isomer
MS (ESI): m/z 879.37 [M+H].
$^{13}$C NMR (CDCl$_3$, ppm) δ: 216.5, 177.5, 167.0, 160.3, 157.4, 140.6, 137.4, 136.6, 128.7, 127.5, 127.0, 126.9, 120.7, 104.6, 84.5, 81.1, 80.4, 78.9, 73.7, 70.2, 69.5, 65.9, 65.4, 60.5, 57.4, 44.1, 43.3, 42.8, 40.2, 39.6, 37.5, 28.4, 22.6, 21.4, 21.1, 19.5, 14.2, 12.9, 11.2, 10.7, 10.6.

Z-isomer
MS (ESI): m/z 879.37 [M+H].

Example 244

Compound of formula VII, wherein $R_1$ and $R_2$ taken together with the carbon atom to which they are attached are
C=NO(biphenyl-3-ylcarbamoyl-methyl) $R_{20}$=H, and Rx=Ac The title compound was prepared with the title compound of Example 16 and 0-(biphenyl-3-ylcarbamoyl-methyl)-hydroxylamine (prepared similarly to steps 228a and 228b of Example 228 with commercially available (BOC-aminooxy) acetic acid and biphenyl-3-amine) via similar conditions outlined in Step 228c of Example 228.
MS (ESI): m/z 921 [M+H].

Example 245

Compound of formula VII, wherein $R_1$ and $R_2$ taken together with the carbon atom to which they are attached are
C=NO(biphenyl-3-ylcarbamoyl-methyl), and $R_{20}$=Rx=H The title compound was prepared with the title compound of Example 244 via similar conditions described in Example 229.

E-isomer
MS (ESI): m/z 879.38 [M+H].
$^{13}$C NMR (CDCl$_3$, ppm) δ: 216.3, 177.3, 167.1, 160.3, 157.4, 141.8, 140.8, 137.7, 129.2, 128.6, 127.3, 127.2, 123.1, 119.3, 119.2, 104.8, 84.5, 81.2, 80.4, 78.9, 73.7, 70.4, 69.7, 65.8, 65.5, 60.5, 57.1, 44.1, 42.9, 42.7, 40.2, 40.0, 37.6, 28.1, 22.6, 21.5, 21.2, 19.4, 14.1, 12.8, 11.2, 10.6, 10.6 Z-isomer
MS (ESI): m/z 879.38 [M+H].

Examples 246

Compound of formula VII, wherein $R_1$ and $R_2$ taken together with the carbon atom to which they are attached are
C=NO(biphenyl-2-ylcarbamoyl-methyl), $R_{20}$=H, and Rx=Ac The title compound was prepared with the title compound of Example 16 and 0-(biphenyl-2-ylcarbamoyl-methyl)-hydroxylamine (prepared similarly to steps 228a and 228b of Example 228 with commercially available (BOC-aminooxy) acetic acid and biphenyl-2-amine) via similar conditions outlined in Step 228c of Example 228.
MS (ESI): m/z 921 [M+H].

Example 247

Compound of formula VII, wherein $R_1$ and $R_2$ taken together with the carbon atom to which they are attached are
C=NO(biphenyl-2-ylcarbamoyl-methyl), and $R_{20}$=Rx=H The title compound was prepared with the title compound of Example 246 via similar conditions described in Example 229.

E-isomer
MS (ESI): m/z 879.42 [M+H].
$^{13}$C NMR (CDCl$_3$, ppm) δ: 216.7, 177.5, 167.5, 160.9, 1157.4, 138.2, 134.2, 132.1, 130.0, 129.4, 128.8, 128.5, 127.8, 124.3, 121.0, 105.1, 83.9, 80.7, 80.2, 79.4, 76.2, 73.5, 70.4, 69.8, 65.8, 65.2, 60.4, 58.1, 44.4, 43.6, 42.9, 40.2, 39.0, 36.8, 28.2, 22.4, 21.3, 21.0, 19.9, 13.7, 13.1, 11.8, 10.8, 10.7
Z-isomer
MS (ESI): m/z 879.42 [M+H].

Example 248

Compound of formula VII, wherein $R_1$ and $R_2$ taken together with the carbon atom to which they are attached are C=NO
[(naphthalen-1-ylmethyl)-carbamoyl-methyl], $R_{20}$=H, and Rx=Ac The title compound was prepared with the title compound of Example 16 and 0-[(naphthalen-1-ylmethyl)-carbamoyl-methyl]-hydroxylamine (prepared similarly to steps 228a and 228b of Example 228 with commercially available (BOC-aminooxy) acetic acid and naphthyl-1-methylamine) via similar conditions outlined in Step 228c of Example 228.
MS (ESI): m/z 909 [M+H].

Example 249

Compound of formula VII, wherein $R_1$ and $R_2$ taken together with the carbon atom to which they are attached are C=NO[(naphthalen-1-ylmethyl)-carbamoyl-methyl], and $R_{20}$=Rx=H The title compound was prepared with the title compound of Example 248 via similar conditions described in Example 229.

E-isomer

MS (ESI): m/z 867.41 [M+H].

$^{13}$C NMR (CDCl$_3$, ppm) δ: 216.4, 177.2, 168.9, 160.1, 157.4, 133.8, 133.5, 131.3, 128.6, 128.5, 126.4, 125.8, 125.7, 125.4, 123.4, 104.8, 84.3, 81.0, 80.3, 79.0, 76.5, 73.4, 70.3, 69.6, 65.8, 65.5, 60.5, 57.4, 44.2, 43.1, 42.7, 40.8, 40.2, 39.6, 37.3, 28.2, 22.5, 21.3, 21.2, 19.6, 14.1, 12.8, 11.3, 10.6, Z-isomer MS (ESI): m/z 867.42 [M+H].

$^{13}$C NMR (CDCl$_3$, ppm) δ: 217.1, 177.2, 168.9, 161.1, 157.4, 133.8, 133.2, 131.3, 128.8, 128.6, 126.6, 126.3, 126.0, 125.4, 123.3, 104.8, 84.0, 82.1, 81.1, 80.0, 75.9, 73.2, 72.0, 70.3, 69.6, 65.7, 58.3, 57.7, 44.3, 43.9, 43.0, 41.1, 40.2, 39.1, 37.0, 31.5, 28.0, 22.6, 22.3, 21.2, 19.8, 14.1, 13.1, 12.0, 10.7

Example 250

Compound of formula VII, wherein R$_1$ and R$_2$ taken together with the carbon atom to which they are attached are
C=NO[(quinolin-4-ylmethyl)-carbamoyl-methyl], R$_{20}$=H, and Rx=Ac The title compound was prepared with the title compound of Example 16 and 0-[(quinolin-4-ylmethyl)-carbbmoyl-methyl]-hydroxylamine (prepared similarly to steps 228a and 228b of Example 228 with commercially available (BOC-aminooxy) acetic acid and quinolyl-1-methylamine) via similar conditions outlined in Step 228c of Example 228.

MS (ESI): m/z 910 [M+H].

Example 251 (EP-014653)

Compound of formula VII, wherein R$_1$ and R$_2$ taken together with the carbon atom to which they are attached are
C=NO[(quinolin-4-ylmethyl)-carbamoyl-methyl], and R$_{20}$=Rx=H The title compound was prepared with the title compound of Example 250 via similar conditions described in Example 229.

E-isomer

MS (ESI): m/z 868.41 [M+H].

$^{13}$C NMR (CDCl$_3$, ppm) δ: 216.1, 177.1, 169.4, 160.3, 157.4, 150.4, 148.1, 143.5, 130.1, 129.2, 126.8, 126.4, 123.0, 119.0, 104.9, 84.7, 81.2, 80.4, 78.8, 76.6, 73.5, 70.4, 69.7, 65.7, 65.5, 60.5, 56.8, 44.2, 42.7, 40.2, 39.5, 37.6, 28.1, 22.4, 21.5, 21.2, 19.4, 14.6, 12.5, 11.1, 10.5, 10.4 Z-isomer MS (ESI): m/z 868.40 [M+H].

$^{13}$C NMR (CDCl$_3$, ppm) δ: 217.3, 177.2, 169.3, 161.3, 157.4, 150.3, 148.2, 143.0, 130.3, 129.4, 127.0, 126.3, 122.9, 119.4, 104.8, 84.0, 81.9, 81.2, 80.0, 75.9, 73.1, 71.8, 70.3, 69.7, 65.7, 58.3, 57.4, 44.3, 44.0, 43.0, 40.2, 39.6, 39.1, 37.0, 28.0, 22.3, 21.2, 21.2, 19.8, 13.6, 13.1, 11.9, 10.8, 10.7

Example 252

Compound of formula VII, wherein R$_1$ and R$_2$ taken together with the carbon atom to which they are attached are C=NO(2-benzoylamino-ethyl), R$_{20}$=H, and Rx=Ac Step 252a.

Tert-butyl-N-(2-hydroxyethyl) carbamate (1.94 ml), hydroxyl thalamide (1.96 g) and triphenyl phosphine (4.72 g) was dissolved in 30 ml THF. DIAD (2.5 ml) was added dropwise to this clear solution at 0° C. The reaction mixture was stirred for overnight. The residue was concentrated and purified by column chromatography to give the desired compound (3.8 g).

Step 252b.

Compound (2.0 g) from step 252a was dissolved in 4M HCl in dioxane. The clear solution turned to white suspension. The white precipitate was filtered off to give the desired target (800 mg). This compound was directly used in the next step.

Step 252c.

To a clear solution of commercially available benzoic acid (183 mg), EDC (575 mg) and compound from step 252b (243 mg) in CH$_2$Cl$_2$ was added TEA (1.26 ml) at room temperature and the resulting mixture was allowed to stir overnight at room temperature. The mixture was extracted with EtOAc. The combined organic extracts were washed twice with 1% HCl and once with saturated NaHCO$_3$, dried over Na$_2$SO$_4$, filtered and concentrated under vacuum to give the desired compound.

Step 252d.

Compound from step 240c was heating with 2M NH$_3$ in methanol at 50° C. for 2 hours. The residue was concentrated and directly used in the next step.

Step 252e.

The title compound was prepared with the title compound of Example 16 and compound from step (252d) via similar conditions outlined in Step 228c of Example 228.

MS (ESI): m/z 859 [M+H].

Example 253

Compound of formula VII, wherein R$_1$ and R$_2$ taken together with the carbon atom to which they are attached are C=NO(2-benzoylamino-ethyl), and R=Rx=H The title compound was prepared with the title compound of Example 252 via similar conditions described in Example 229.

E-isomer

MS (ESI): m/z 817.45 [M+H].

$^{13}$C NMR (CDCl$_3$, ppm) δ: 216.6, 177.6, 167.5, 158.4, 157.6, 134.6, 131.2, 128.3, 127.2, 104.8, 84.3, 80.9, 80.3, 78.4, 76.5, 73.1, 70.4, 69.7, 65.8, 65.4, 60.6, 57.6, 44.1, 43.7, 42.8, 40.2, 39.9, 39.1, 37.5, 28.1, 22.6, 21.4, 21.2, 19.5, 13.9, 13.1, 11.1, 10.8, 10.5.

Z-isomer

MS (ESI): m/z 817.45 [M+H].

Example 254

Compound of formula VII, wherein R$_1$ and R$_2$ taken together with the carbon atom to which they are attached are
C=NO[2-(naphthlene-1-sulfonylamino)-ethyl], R$_{20}$=H, and Rx=Ac Step 254a.

To a clear solution of commercially available 1-naphthalenesulfonyl chloride (453 mg) and compound from step 252b (243 mg) in CH$_2$Cl$_2$ was added TEA (250>1) and pyridine (405 μl) at room temperature and the resulting mixture was allowed to stir overnight at room temperature. The mixture was extracted with EtOAc. The combined organic extracts were washed twice with 1% HCl and once with saturated NaHCO$_3$, dried over Na$_2$SO$_4$, filtered and concentrated under vacuum to give the desired compound.

Step 254b.

Compound from step 254a was heating with 2M $NH_3$ in methanol at 50° C. for 2 hours. The residue was concentrated and directly used in the next step.

Step 254c.

The title compound was prepared with the title compound of Example 16 and compound from step (254b) via similar conditions outlined in Step 228c of Example 228.

MS (ESI): m/z 945 [M+H].

Example 255

Compound of formula VII, wherein $R_1$ and $R_2$ taken together with the carbon atom to which they are attached are
C=NO[2-(naphthlene-1-sulfonylamino)-ethyl], and $R_{20}$=Rx=H The title compound was prepared with the title compound of Example 254 via similar conditions described in Example 229.

E-isomer

MS (ESI): m/z 903.43 [M+H].

$^{13}$C NMR (CDCl$_3$, ppm) δ: 216.7, 177.5, 158.5, 157.5, 134.8, 134.3, 134.1, 129.5, 129.0, 128.2, 126.7, 124.6, 124.2, 104.8, 84.3, 80.8, 80.3, 78.5, 76.5, 71.9, 70.4, 69.7, 65.8, 65.1, 60.4, 57.8, 44.0, 43.9, 43.0, 42.7, 40.2, 38.8, 37.4, 29.7, 28.1, 22.6, 21.3, 21.2, 19.5, 13.7, 13.2, 11.2, 10.8, 10.6.

Z-isomer

MS (ESI): m/z 903.43 [M+H].

Example 256

Compound of formula VII, wherein $R_1$ and $R_2$ taken together with the carbon atom to which they are attached are C=NO{2-[(quinoline-4-carbonyl)-amino]-ethyl}, $R_{20}$=H, and Rx=Ac The title compound was prepared with the title compound of Example 16 and O-{2-[(quinoline-4-carbonyl)-amino]-ethyl}-hydroxylamine (prepared similarly to steps 252c and 252d of Example 252 with commercially available 4-quinoline carboxylic acid and compound from step 252b) via similar conditions outlined in Step 228c of Example 228.

MS (ESI): m/z 910 [M+H].

Example 257

Compound of formula VII, wherein $R_1$ and $R_2$ taken together with the carbon atom to which they are attached are C=NO{2-[(quinoline-4-carbonyl)-amino]-ethyl}, and $R_{20}$=Rx=H The title compound was prepared with the title compound of Example 256 via similar conditions described in Example 229.

E-isomer

MS (ESI): m/z 868.48 [M+H].

$^{13}$C NMR (CDCl$_3$, ppm) δ: 216.8, 177.8, 167.8, 158.8, 157.8, 150.1, 148.8, 142.3, 130.0, 129.9, 127.7, 125.8, 124.9, 119.1, 105.0, 84.6, 81.3, 80.6, 78.4, 76.6, 73.0, 70.6, 69.9, 66.0, 65.5, 60.7, 57.6, 44.3, 43.7, 42.9, 40.4, 40.3, 39.4, 37.8, 28.3, 22.7, 21.7, 21.4, 19.6, 14.2, 13.2, 11.1, 10.7.

Z-isomer

MS (ESI): m/z 868.45 [M+H].

Example 258

Compound of formula VII, wherein $R_1$ and $R_2$ taken together with the carbon atom to which they are attached are C=NO(quinoxalin-2-yl-methyl), $R_{20}$=H, and Rx=Ac Step 258a.

To a solution of commercially available 2-methylquinoxaline (1.0 g) in CCl$_4$ was added NBS (1.23 g) and AIBN (45 mg) and the resulting mixture was heated at 80° C. for 2 hours. The reaction mixture was filtered and extracted with EtOAc. The combined organic extracts were washed 1M NaHCO$_3$, dried over MgSO$_4$, filtered and concentrated under vacuum to give the desired compound.

MS (ESI): m/z 222.89, 224.89[M+H].

Step 258b.

Compound from step 258a (1.7 g) was added to a solution of N-hydroxylphthalamide (571 mg) and DIEA (1.2 ml) in 10 ml acetonitrile. The reaction mixture was stirred at room temperature overnight. The reaction mixture was extracted with EtOAc. The combined organic extracts were washed with 1M NaHCO$_3$, H$_2$O and brine, dried over Na$_2$SO$_4$, filtered, concentrated and purified by column chromatography to give 400 mg of the desired target.

MS (ESI): m/z 305.94[M+H].

Step 258c.

Compound from step 258b was heating with 2M $NH_3$ in methanol at 50° C. for 2 hours. The residue was concentrated and directly used in the next step.

Step 258d.

The title compound was prepared with the title compound of Example 16 and compound from step (258c) via similar conditions outlined in Step 228c of Example 228.

MS (ESI): m/z 854 [M+H].

Example 259

Compound of formula VII, wherein $R_1$ and $R_2$ taken together with the carbon atom to which they are attached are C=NO(quinoxalin-2-yl-methyl), and $R_{20}$=Rx=H The title compound was prepared with the title compound of Example 258 via similar conditions described in Example 229.

E-isomer

MS (ESI): m/z 812.45[M+H].

$^{13}$C NMR (CDCl$_3$, ppm) δ: 215.9, 178.1, 159.8, 157.9, 154.2, 142.9, 141.7, 141.5, 130.2, 129.8, 129.4, 128.6, 105.0, 84.0, 80.7, 80.4, 79.0, 75.7, 75.5, 70.4, 69.7, 65.8, 65.7, 60.1, 58.0, 44.6, 44.0, 43.1, 40.2, 39.2, 36.9, 28.1, 22.2, 21.2, 20.9, 20.1, 13.5, 13.4, 12.0, 10.7, 10.5.

Z-isomer

MS (ESI): m/z 812.45 [M+H].

Example 260

Compound of formula VII, wherein $R_1$ and $R_2$ taken together with the carbon atom to which they are attached are C=NO(quinazolin-4-yl-methyl), $R_{20}$=H, and Rx=Ac Step 260a.

Formic acid (3.3 ml) was added dropwise to acetic anhydride (6.8 ml) at 0° C. The resulting solution was stirred at 0°

C. for 30 minutes and then warmed to 55° C. for 2.5 hours. The reaction mixture was cooled down to 0° C., and then −78° C. A solution of 2'-aminoacetophenone (5.0 g) and TEA (9.0 ml) in $CH_2Cl_2$ (20 ml) was added dropwise. The reaction mixture was allowed to stir at −78° C. for 2 hours and then warmed up to −10° C. for 20 minutes. The mixture was pooled into cold 1M $NaHCO_3$ (100 ml) and adjusted pH to 7. The resulting mixture was extracted with EtOAc. The combined, organic extracts were washed 1M $NaHCO_3$, dried over $MgSO_4$, filtered and concentrated under vacuum to give the crude compound. 3.68 g of desired compound was obtained after recrystalization from hexanes.

Step 260b.

Compound from step 260a (1.0 g) and 2M $NH_3$ in methanol (15 ml) was heated to 120° C. overnight. The reaction mixture was concentrated under vacuum. The residue was crystallized from hexanes to give the desired target in 96% yield.

MS (ESI): m/z 144.99[M+H].

Step 260c.

To a solution of compound from step 260b (650 mg) in $CCl_4$ was added NBS (803 mg) and AIBN (30 mg). The resulting mixture was heated at 80° C. for 2 hours. The reaction mixture was concentrated under vacuum to give the desired compound. This compound was directly used in the next step.

MS (ESI): m/z 222.90, 224.90[M+H].

Step 260d.

Compound from Step 260c (1.1 g) was added to a solution of N-hydroxyphthalamide (480 mg) and DIEA (1.1 ml) in 10 ml acetonitrile. The reaction mixture was stirred at room temperature overnight. The precipitate was filtered off to give the desired target.

MS (ESI): m/z 305.95[M+H].

Step 260e.

Compound from Step 260d was heating with $NH_2NH_2$ (1 eq) in ethanol at 65° C. for 2 hours. The reaction mixture was concentrated and directly used in the next step.

Step 260f.

The title compound was prepared with the title compound of Example 16 and compound from Step (260e) via similar conditions outlined in Step 228c of Example 228.

MS (ESI): m/z 854 [M+H].

Example 261

Compound of formula VII, wherein $R_1$ and $R_2$ taken together with the carbon atom to which they are attached are C=NO(quinazolin-4-yl-methyl), and $R_{20}$=Rx=H The title compound was prepared with the title compound of Example 260 via similar conditions described in Example 229.

E-isomer

MS (ESI): m/z 812.03[M+H].

$^{13}$C NMR ($CDCl_3$, ppm) δ: 216.7, 177.4, 165.5, 159.6, 157.5, 154.5, 150.4, 133.8, 129.0, 128.0, 125.1, 123.6, 104.9, 84.1, 80.6, 80.1, 79.2, 76.3, 75.2, 70.4, 69.7, 65.8, 65.7, 60.5, 58.0, 44.3, 42.8, 40.2, 38.9, 36.9, 28.1, 22.6, 21.1, 21.0, 19.8, 13.6, 13.2, 11.6, 11.0, 10.6.

Z-isomer

MS (ESI): m/z 812.03 [M+H].

Example 262

Compound of formula VII, wherein $R_1$ and $R_2$ taken together with the carbon atom to which they are attached are C=NO(benzo[1,2,5]thiadiazol-4-yl-methyl), $R_{20}$=H, and Rx=Ac The title compound was prepared with the title compound of Example 16 and O-(benzo [1,2,5] thiadiazol-4-yl-methyl)-hydroxylamine (prepared similarly to steps 260d and 260e of Example 260 with commercially available 4-bromomethyl-benzo [1,2,5]thiadiazole and N-hydroxyphthalamide) via similar conditions outlined in Step 228c of Example 228.

MS (ESI): m/z 860 [M+H].

Example 263

Compound of formula VII, wherein $R_1$ and $R_2$ taken together with the carbon atom to which they are attached are C=NO(benzo[1,2,5]thiadiazol-4-yl-methyl), and $R_{20}$=Rx=H The title compound was prepared with the title compound of Example 262 via similar conditions described in Example 229.

E-isomer

MS (ESI): m/z 818.82 [M+H].

$^{13}$C NMR ($CDCl_3$, ppm) δ: 216.8, 177.4, 158.6, 157.6, 154.9, 153.4, 130.8, 129.3, 127.3, 120.8, 104.8, 84.1, 80.6, 80.1, 79.2, 76.3, 72.2, 70.4, 69.7, 65.8, 60.7, 58.0, 44.2, 43.9, 42.8, 40.2, 38.8, 37.1, 28.1, 22.6, 21.2, 21.1, 19.7, 13.6, 13.2, 11.4, 10.9.

Z-isomer

MS (ESI): m/z 818.82[M+H].

Example 264

Compound of formula VII, wherein $R_1$ and $R_2$ taken together with the carbon atom to which they are attached are C=NO(pyrido[2,3-b]pyrazin-3-yl-methyl), $R_{20}$=H, and Rx=Ac Step 264a.

Commercially available methylglyoxal (4.95 g) and 2,3-diaminopyridine was dissolved in ethanol. The reaction mixture was stirred at room temperature for 1 hour. The reaction mixture was concentrated and purified by column chromatography to give 2.8 g of the desired target.

MS (ESI): m/z 145.98[M+H].

Step 264b.

The title compound was prepared with the title compound of Example 16 and 0-(pyrido[2,3-b]pyrazin-3-yl-methyl)-hydroxylamine (prepared similarly to steps 2603c, 260d and 260e of Example 260) via similar conditions outlined in Step 228c of Example 228.

MS (ESI): m/z 855 [M+H].

Example 265

Compound of formula VII, wherein $R_1$ and $R_2$ taken together with the carbon atom to which they are attached are C=NO(pyrido[2,3-b]pyrazin-3-yl-methyl), and $R_{20}$=Rx=H The title compound was prepared with the title compound of Example 264 via similar conditions described in Example 229.

E-isomer
MS (ESI): m/z 813.63 [M+H].
$^{13}$C NMR (CDCl$_3$, ppm) δ: 217.4, 178.5, 160.9, 159.1, 158.3, 154.2, 149.7, 145.2, 139.0, 137.0, 125.7, 105.0, 85.1, 81.2, 79.7, 79.1, 76.2, 75.0, 71.2, 69.2, 65.3, 64.6, 59.9, 58.4, 44.1, 43.0, 39.6, 39.3, 37.1, 30.5, 22.5, 20.8, 18.8, 12.8, 12.6, 10.9, 10.3, 10.2.

Z-isomer
MS (ESI): m/z 818.82[M+H].

Example 266

Compound of formula VII, wherein $R_1$ and $R_2$ taken together with the carbon atom to which they are attached are C=NO(cinnolin-4-yl-methyl), $R_{20}$=H, and Rx=Ac Step 266a.
To a solution of cinnoline-4-carboxylic acid (350 mg) in THF and methanol was added dropwise to SOCl$_2$ (1.5 ml) at 0° C. The resulting solution was stirred at 60° C. overnight. The reaction mixture was concentrated under vacuum and extracted with EtOAc. The combined organic extracts were washed 1M NaHCO$_3$, dried over MgSO$_4$, filtered and concentrated under vacuum to give the compound in 95% yield.
MS (ESI): m/z 188.92[M+H].

Step 266b.
Compound from step 266a (360 mg) was dissolved in methanol. Sodium borohydride (152 mg) was added partially. The reaction mixture was stirred at room temperature for 30 minutes and quenced with aqueous NH$_4$Cl. The resulting mixture was extracted with EtOAc. The combined organic extracts were washed 1M NaHCO$_3$, dried over MgSO$_4$, filtered and concentrated under vacuum to give the compound in 77% yield.
MS (ESI): m/z 160.96[M+H].

Step 266c.
Compound from step 266b (235 mg), hydroxyl thalamide (245 mg) and triphenyl phosphine (786 mg) was dissolved in 15 ml THF. DIAD (311 µl) was added dropwise to this clear solution at 0° C. The reaction mixture was stirred for overnight. The precipitate was filtered off to give the desired target.
MS (ESI): m/z 306.23[M+H].

Step 266d.
Compound from step 266c was heating with NH$_2$NH$_2$ (1 eq) in ethanol at 65° C. for 2 hours. The reaction mixture was concentrated and directly used in the next step.

Step 266e.
The title compound was prepared with the title compound of Example 16 and compound from Step (266d) via similar conditions outlined in Step 228c of Example 228.
MS (ESI): m/z 854 [M+H].

Example 267

Compound of formula VII, wherein $R_1$ and $R_2$ taken together with the carbon atom to which they are attached are C=NO(cinnolin-4-yl-methyl), and $R_{20}$=Rx=H The title compound was prepared with the title compound of Example 266 via similar conditions described in Example 229.

E-isomer
MS (ESI): m/z 812.64 [M+H].
$^{13}$C NMR (CDCl$_3$, ppm) δ: 217.2, 178.0, 160.2, 159.1, 149.8, 143.2, 132.5, 132.1, 131.2, 129.2, 124.8, 123.1, 104.9, 85.1, 81.1, 79.8, 79.2, 76.8, 71.1, 70.2, 69.1, 65.1, 64.6, 60.0, 58.4, 44.0, 43.9, 42.7, 39.6, 39.3, 37.3, 30.5, 22.7, 21.0, 18.5, 12.9, 12.5, 10.6, 10.4.

Z-isomer
MS (ESI): m/z 812.64 [M+H].

Example 268

Compound of formula VII, wherein $R_1$ and $R_2$ taken together with the carbon atom to which they are attached are C=NO[(6-amino-pyrido[2,3-b]pyrazin-3-yl)-methyl], $R_{20}$=H, and Rx=Ac Step 268a.
2,6-Dichloro-3-nitropyridine (1.0 g) was heating with 30 ml of 2M NH$_3$ in methanol at 100° C. for 48 hours. The reaction mixture was concentrated under vacuum. 20 ml of H$_2$O was added to the residue. The precipitate was filtered off and washed with water to give the desired target in 93% yield.

Step 268b.
A solution of compound from step 268a (750 mg) and 10% Pd/C (70 mg) in MeOH was stirred under hydrogen at 30 psi for 2 days. The mixture was filtered through a pad of celite to remove Pd/C and to this filtrate was added methylgloxal (878 mg). The resulting solution was stirred at room temperature for 1 hour. The reaction mixture was concentrated and purified by column chromatography to give 750 mg of the desired target.
MS (ESI): m/z 160.97[M+H].

Step 268c.
Compound from step 268b (200 mg) and succinic anhydride (125 mg) was refluxed in CHCl$_3$ for 2 days. HATU (456 mg) and DIEA (4181 µl) was added to the reaction mixture. The resulting clear solution was refluxed for 2 hours. The reaction mixture was concentrated and purified by column chromatography to give the desired target in 47% yield.
MS (ESI): m/z 242.91 [M+H].

Step 268d.
To a solution of compound from step 268c (250 mg) in CCl$_4$ was added NBS (178 mg) and BPO (24 mg). The resulting mixture was heated at 60° C. for 30 minutes. The reaction mixture was concentrated and purified by column chromatography to give the desired compound (100 mg).
MS (ESI): m/z 320.77, 322.77[M+H].

Step 268e.
Compound from step 268d (100 mg) was added to a solution of N-hydroxylphthalamide (51 mg) and DIEA (82 µl) in acetonitrile. The reaction mixture was stirred at room temperature overnight. The precipitate was filtered off to give the desired target (60 mg).
MS (ESI): m/z 405.24[M+H].

Step 268f.

Compound from step 268e was heating with $NH_2NH_2$ (2 eq) in ethanol at 65° C. for 2 hours. The reaction mixture was concentrated and directly used in the next step.

Step 268g.

The title compound was prepared with the title compound of Example 16 and compound from Step (268f) via similar conditions outlined in Step 228c of Example 228.

MS (ESI): m/z 870 [M+H].

Example 269

Compound of formula VII, wherein $R_1$ and $R_2$ taken together with the carbon atom to which they are attached are C=NO[(6-amino-pyrido[2,3-b]pyrazin-3-yl)-methyl], and $R_{20}$=Rx=H The title compound was prepared with the title compound of Example 268 via similar conditions described in Example 229.

E-isomer

MS (ESI): m/z 828.51[M+H], 414.91[M+2H].
$^{13}C$ NMR ($CDCl_3$, ppm) δ: 217.3, 178.3, 161.5, 160.3, 159.2, 156.0, 151.1, 138.5, 138.1, 133.4, 117.1, 105.0, 85.1, 81.2, 79.8, 79.2, 76.1, 74.9, 71.2, 69.2, 65.4, 64.6, 60.0, 58.4, 44.2, 44.1, 43.0, 39.6, 39.4, 37.0, 30.5, 22.4, 20.8, 20.2, 18.8, 12.8, 12.6, 11.0, 10.3.

Z-isomer

MS (ESI): m/z 828.51[M+H], 414.91[M+2H].

Example 270

Compound of formula VII, wherein $R_1$ and $R_2$ taken together with the carbon atom to which they are attached are C=NO([1,5]naphthyridin-4-yl-methyl), $R_{20}$=H, and Rx=Ac Step 270a.

The mixture of commercially available 3-amino-4-methylpyridine (3.0 g), sodium m-nitrobenzenesulfate (12.47 g), boric acid (2.74 g), $FeSO_4.7H_2O$ (1.0 g), conc. $H_2SO_4$ (15.5 ml), $H_2O$ (15.5 ml) and glycerol (9.1 ml) was heated to 140° C. for 24 hours. The dark reaction mixture was cooled down and adjusted pH to 7 with sodium hydroxide. The resulting mixture was filtered. The filtration was extracted with EtOAc. The combined organic extracts were washed with 1M $NaHCO_3$, dried over $MgSO_4$, filtered and concentrated and purified by column chromatography to give the desired compound (1.3 g).

MS (ESI): m/z 144.97[M+H].

Step 270b.

To a solution of compound from step 270a (300 mg) in $CCl_4$ was added NBS (374 mg) and AIBN (30 mg). The resulting mixture was heated at 80° C. for 1 hour. The reaction mixture was concentrated under vacuum to give the desired compound. This compound was directly used in the next step.

MS (ESI): m/z 222.82, 224.82[M+H].

Step 270c.

Compound from step 270b was added to a solution of N-hydroxylphthalamide (180 mg) and DIEA (348 µl) in 2 ml acetonitrile. The reaction mixture was stirred at room temperature overnight. The precipitate was filtered off to give the desired target (300 mg).

MS (ESI): m/z 305.82[M+H].

Step 270d.

Compound from step 270c was heating with $NH_2NH_2$ (1 eq) in ethanol at 65° C. for 2 hours. The reaction mixture was concentrated and directly used in the next step.

Step 270e.

The title compound was prepared with the title compound of Example 16 and compound from Step (270d) via similar conditions outlined in Step 228c of Example 228.

MS (ESI): m/z 854 [M+H].

Example 271

Compound of formula VII, wherein $R_1$ and $R_2$ taken together with the carbon atom to which they are attached are C=NO([1,5]naphthyridin-4-yl-methyl), and $R_{20}$=Rx=H The title compound was prepared with the title compound of Example 270 via similar conditions described in Example 229.

E-isomer

MS (ESI): m/z 812.61[M+H].
$^{13}C$ NMR ($CDCl_3$, ppm) δ: 217.2, 178.1, 159.8, 159.1, 151.1, 150.6, 146.8, 142.7, 141.4, 136.7, 124.9, 121.6, 104.8, 85.1, 81.2, 79.8, 79.2, 76.9, 71.1, 71.0, 69.1, 65.4, 64.7, 60.2, 58.5, 44.0, 43.8, 42.8, 39.5, 37.3, 30.4, 22.7, 21.1, 20.2, 18.5, 13.0, 12.4, 10.6, 10.4, 10.4.

Z-isomer

MS (ESI): m/z 812.61 [M+H].

Example 272

Compound of formula VII, wherein $R_1$ and $R_2$ taken together with the carbon atom to which they are attached are C=NO[(6-amino-[1,5]naphthyridin-4-yl)-methyl], $R_{20}$=H, and Rx=Ac Step 272a.

To the mixture of commercially available 2-chloro-5-aminopyridine (5.0 g), sodium m-nitrobenzenesulfate (17.5 g), boric acid (3.86 g), $FeSO_4.7H_2O$ (1.41 g), conc. $H_2SO_4$ (22 ml) and $H_2O$ (22 ml) was added dropwise methyl vinyl ketone (5 ml) at 135° C. The resulting mixture was heated for 24 hours. The dark reaction mixture was cooled down and adjusted pH to 7 with sodium hydroxide. The resulting mixture was filtered. The filtration was extracted with $CH_2Cl_2$. The combined organic extracts were washed with 1M $NaHCO_3$, dried over $Na_2SO_4$, filtered, concentrated and recrystallized to give the desired compound (1.0 g).

MS (ESI): m/z 160.95[M+H].

Step 272b.

A solution of the compound from step 272a in $POCl_3$ (30 ml) was stirred at 90° C. The mixture was concentrated under vacuum. To the residue was added crashed ice. The resulting mixture was neutralized with ammonium hydroxide to $pH_6$ and extracted with $CH_2Cl_2$. The combined organic extracts were washed with water and brine, dried over $Na_2SO_4$, filtered, concentrated under vacuum to give the desired compound (1.3 g).

MS (ESI): m/z 178.90, 180.90[M+H].

Step 272c.

The mixture of the compound from step 272b (1.0 g), acetamide (662 mg) and $K_2CO_3$ (387 mg) was heated to 200° C. for 1.5 hours. The reaction mixture was cooled down and extracted with $CH_2Cl_2$. The combined organic extracts were washed with 1M $NaHCO_3$ and brine, dried over $Na_2SO_4$, filtered, concentrated under vacuum to give the desired compound (600 mg).

MS (ESI): m/z 159.97[M+H].

Step 272d.

Compound from step 272c (600 mg) and succinic anhydride (377 mg) was refluxed in $CHCl_3$ for 2 days. HATU (912 mg) and DIEA (8021 µl) was added to the reaction mixture. The resulting clear solution was refluxed for 2 hours. The reaction mixture was concentrated and purified by column chromatography to give the desired target (550 mg)

MS (ESI): m/z 242.94[M+H].

Step 272e.

To a solution of compound from step 272d (200 mg) in $CCl_4$ was added NBS (150 mg) and AIBN (14 mg). The resulting mixture was heated at 90° C. for 5 hours. The reaction mixture was concentrated under vacuum and directly used in the next step.

MS (ESI): m/z 319.81, 321.81[M+H].

Step 272f.

Compound from step 272e was added to a solution of N-hydroxylphthalamide (147 mg) and DIEA (522 µl) in acetonitrile. The reaction mixture was stirred at room temperature overnight. The precipitate was filtered off to give the desired target (60 mg).

MS (ESI): m/z 402.85[M+H].

Step 272g.

Compound from step 272f was heating with $NH_2NH_2$ (2 eq) in ethanol at 65° C. for 2 hours. The reaction mixture was concentrated and directly used in the next step.

Step 272h.

The title compound was prepared with the title compound of Example 16 and compound from Step (272g) via similar conditions outlined in Step 228c of Example 228.

MS (ESI): m/z 869 [M+H].

Example 273

Compound of formula VII, wherein $R_1$ and $R_2$ taken together with the carbon atom to which they are attached are C=NO[(6-amino-[1,5]naphthyridin-4-yl)-methyl], and $R_{20}$=Rx=H The title compound was prepared with the title compound of Example 272 via similar conditions described in Example 229.

E-isomer

MS (ESI): m/z 827.70[M+H], 414.51[M+2H].

$^{13}C$ NMR ($CDCl_3$, ppm) δ: 217.3, 178.0, 159.4, 159.1, 158.4, 144.5, 142.6, 141.1, 138.8, 137.2, 121.1, 116.2, 104.9, 85.1, 81.2, 79.7, 79.1, 77.1, 71.3, 71.2, 69.2, 65.3, 64.6, 60.2, 58.5, 48.6, 44.0, 43.8, 42.7, 39.6, 39.3, 37.4, 30.5, 22.7, 21.1, 20.2, 18.4, 13.0, 12.4, 10.6, 10.4.

Z-isomer

MS (ESI): m/z 827.70[M+H], 414.51[M+2H].

Example 274

Compound of formula VII, wherein $R_1$ and $R_2$ taken together with the carbon atom to which they are attached are C=NO ([1,8]naphthyridin-4-yl-methyl), $R_{20}$=H, and Rx=Ac Step 274a.

The title compound was prepared similarly to step 270a of Example 270 with commercially available 2-amino-4-methylpyridine (3.0 g).

MS (ESI): m/z 144.97[M+H].

Step 274b.

To a solution of the compound from Step 274a (400 mg) in dioxane was added $SeO_2$ at 100° C. The reaction mixture was heated at 100° C. for 30 minutes and then filtered. To the filtrate was added methanol and sodium borohydride (205 mg). After 30 minutes, the reaction was quenched with 5% citric acid and adjusted pH to 7. The mixture was extracted with $CH_2Cl_2$. The organic extracts were washed with brine, dried over $MgSO_4$, filtered and concentrated to give the desired compound.

MS (ESI): m/z 160.99[M+H].

Step 274c.

The title compound was prepared with the title compound of Example 16 and O-([1,8]naphthyridin-4-yl-methyl)-hydroxylamine (prepared similarly to steps 266c and 266d of Example 266) via similar conditions outlined in Step 228c of Example 228.

MS (ESI): m/z 855 [M+H].

Example 275

Compound of formula VII, wherein $R_1$ and $R_2$ taken together with the carbon atom to which they are attached are C=NO ([1,8]naphthyridin-4-yl-methyl), and $R_{20}$=Rx=H The title compound was prepared with the title compound of Example 274 via similar conditions described in Example 229.

E-isomer

MS (ESI): m/z 813.63 [M+H].

$^{13}C$ NMR ($CDCl_3$, ppm) δ: 217.4, 178.5, 160.9, 159.1, 158.3, 154.2, 149.7, 145.2, 139.0, 137.0, 125.7, 105.0, 85.1, 81.2, 79.7, 79.1, 76.2, 75.0, 71.2, 69.2, 65.3, 64.6, 59.9, 58.4, 44.1, 43.0, 39.6, 39.3, 37.1, 30.5, 22.5, 20.8, 18.8, 12.8, 12.6, 10.9, 10.3, 10.2.

Z-isomer

MS (ESI): m/z 818.82[M+H].

Example 276

Compound of formula VII, wherein $R_1$ and $R_2$ taken together with the carbon atom to which they are attached are C=NO[3-(4-fluorophenyl)-phenyl], $R_{15}$=Rx=H Step 276a.

The compound was prepared from hydroxylphthalimide and 3-bromo-phenyl boronic acid via similar conditions described in Example 49a.

Step 276b.

A mixture of the compound from step 276a (200 mg, 0.628 mmol), 4-fluorophenyl tributyltin (269 mg, 0.698 mmol) and toluene (4 ml) was degassed with nitrogen, then treated with $Pd(PPh_3)_4$ (36 mg, 5% eq.). The resulting mixture was stirred at 100° C. for 16 h, cooled to rt, diluted with ethyl acetate, filtered. The filtrate was concentrated and subjected to silica gel column purification (Hexane:EtOAc=20:1 to 5:1) to afford the compound step 276b (130 mg) which was used directly in next step.

Step 276c

The title compound was prepared from the title compound of step 276b and the title compound of Example 16 via similar conditions described in Example 35 and Example 36.

MS (ESI): m/z 840.67 [M+H].

Example 277

Compound of formula VII, wherein $R_1$ and $R_2$ taken together with the carbon atom to which they are attached are C=NO[3-thiophen-2-yl-phenyl], $R_{15}$=H, and Rx=Ac Step 277a.

The compound was prepared from thiophen-2yl tributyltin (0.5 ml, 1.51 mmol) and compound of Example 276a (400 mg, 1.26 mmol) via similar conditions described in Example 276b.

MS (ESI): m/z 322.13 [M+H].

Step 277b.

The title compound was prepared from the title compound of step 277a and the title compound of Example 16 via similar conditions described in Example 35.

MS (ESI): m/z 870.69 [M+H].

Example 278

Compound of formula VII, wherein $R_1$ and $R_2$ taken together with the carbon atom to which they are attached are C=NO[3-thiophen-2-yl-phenyl], $R_{15}$=R=H The title compound was prepared with the title compound of Example 277 via similar conditions described in Example 36.

MS (ESI): m/z 828.63 [M+H].

Example 279

Compound of formula VII, wherein $R_1$ and $R_2$ taken together with the carbon atom to which they are attached are C=CHCOOMe, $R_{15}$H, and Rx=Ac A mixture of compound example 16 (500 mg, 0.718 mmol) and methyl (triphrnylphosphoranylidene)acetate (721 mg, 2.16 mmol) and toluene (10 ml) was stirred at 100° C. for 3.5 h, cooled to rt, diluted with ETOAc (20 ml), and sat. aq. Sodium bicarbonate (10 ml) was added. The mixture was extracted with EtOAc (80 ml). The organic phase was washed with half-saturated aq. NaCl, dried (MgSO$_4$) and concentrated. The residue was subjected to silica gel column purification (dichloromethane:methanol=98:2) to afford the title compound.

MS (ESI): m/z 753.57 [M+H].

Example 280

Compound of formula VII, wherein $R_1$ and $R_2$ taken together with the carbon atom to which they are attached are C=CHCOOMe, $R_{15}$=Rx=H The title compound was prepared with the title compound of Example 279 via similar conditions described in Example 36.

MS (ESI): m/z 711.41 [M+H].

Example 281

Compound of formula VII, wherein $R_1$ and $R_2$ taken together with the carbon atom to which they are attached are C=CHCOOCH$_2$Ph, $R_{15}$—H, and Rx=Ac The compound was prepared from compound of example 16 (200 mg, 0.29 mmol) and benzyl (triphenylphosphoranylidene) acetate (370 mg, 0.9 mmol) via similar conditions described in Example 279.

MS (ESI): m/z 829.49 [M+H].

Example 282

Compound of formula VII, wherein $R_1$ and $R_2$ taken together with the carbon atom to which they are attached are C=CHCOOCH$_2$Ph, $R_{15}$=Rx=H The title compound was prepared with the title compound of Example 281 via similar conditions described in Example 36.

MS (ESI): m/z 787.25 [M+H].

Example 283

Compound of formula VII, wherein $R_1$ and $R_2$ taken together with the carbon atom to which they are attached are C=CHCONHCH$_2$Ph, $R_{15}$=H, and Rx=Ac Step 283a.

The compound was prepared from compound of example 16 (200 mg, 0.29 mmol) and tert-butyl (triphrnylphosphoranylidene)acetate (339 mg, 0.9 mmol) via similar conditions described in Example 279.

MS (ESI): m/z 795.5 [M+H].

Step 283b.

A solution of compound of step 283a (236 mg) in dichloromethane (4 ml) at 0° C. was treated with trifluoroacetic acid (1 ml). The resulting mixture was stirred at rt for 1 h, concentrated to dryness to give TFA salt of compound of step b which was directly used in next step.

MS (ESI): m/z 739.25 [M+H].

Step 283c.

A mixture of compound step 283b, toluene (3 ml), thionyl chloride (1 ml) was stirred at 50° C. for 1 h, cooled to rt, concentrated to dryness. The residue was then dissolved in dichloromethane (2 ml) and added to a solution of benzylamine (20 ul, 0.18 mmol) and triethyl amine 80 ul, 0.57 mmol) in dichloromethane (2 ml). The resulting mixture was stirred at rt for 16 h, diluted with EtOAc, washed with sat. aq. sodium bicarbonate, sat. aq. NaCl, dried (MgSO4) and concentrated. The residue was purified by silica gel column (dichloromethane:methanol=98:2) to afford the title compound.

MS (ESI): m/z 828.4 [M+H].

Example 284

Compound of formula VII, wherein $R_1$ and $R_2$ taken together with the carbon atom to which they are attached are C=CHCONHCH$_2$Ph, $R_{15}$=Rx=H The title compound was prepared with the title compound of Example 283 via similar conditions described in Example 36.

MS (ESI): m/z 786.38 [M+H].

E-isomer

MS (ESI): m/z 786.49 [M+H].

Z-isomer

MS (ESI): m/z 786.49 [M+H].

Example 285

Compound of formula VII, wherein $R_1$ and $R_2$ taken together with the carbon atom to which they are attached are C=CHCOOPh, $R_{15}$=H, and Rx=Ac The compound was prepared from compound of step 283b and phenol via similar procedures described in example 283.
MS (ESI): m/z 815.44 [M+H].

Example 286

Compound of formula VII, wherein $R_1$ and $R_2$ taken together with the carbon atom to which they are attached are C=CHCOOPh, $R_{15}$=Rx=H The title compound was prepared from the title compound of Example 285 via similar procedures described in Example 36.
MS (ESI): m/z 773.49 [M+H].

Example 287

Compound of formula VII, wherein $R_1$ and $R_2$ taken together with the carbon atom to which they are attached are C=CHCONHPh, $R_{15}$=H, and Rx=Ac The compound was prepared from compound of step 283b and aniline via similar procedures described in example 283.
MS (ESI): m/z 814.38 [M+H].

Example 288

Compound of formula VII, wherein $R_1$ and $R_2$ taken together with the carbon atom to which they are attached are C=CHCONHPh, $R_{15}$=Rx=H The title compound was prepared from the title compound of Example 287 via similar procedures described in Example 36.
MS (ESI): m/z 772.36 [M+H].

Example 289

Compound of formula VII, wherein $R_1$ and $R_2$ taken together with the carbon atom to which they are attached are C=CHCONH[naphthalene-1-yl], $R_{15}$=H, and Rx=Ac The compound was prepared from compound of example step 283b and naphthalene-1-ylamine via similar procedures described in example 283.
MS (ESI): m/z 864.53 [M+H].

Example 290

Compound of formula VII, wherein $R_1$ and $R_2$ taken together with the carbon atom to which they are attached are C=CHCONH[naphthalen-1-yl], $R_{15}$=Rx=H The title compound was prepared from the title compound of Example 289 via similar procedures described in Example 36.
MS (ESI): m/z 822.61 [M+H].

Example 291

Compound of formula VII, wherein $R_1$ and $R_2$ taken together with the carbon atom to which they are attached are C=CHCONH[naphthalene-2-yl], $R_{15}$=H, and Rx=Ac The compound was prepared from compound of example step 283b and naphthalene-2-ylamine via similar procedures described in example 283.
MS (ESI): m/z 864.55 [M+H].

Example 292

Compound of formula VII, wherein $R_1$ and $R_2$ taken together with the carbon atom to which they are attached are C=CHCONH[naphthalen-2-yl], $R_{15}$=Rx=H The title compound was prepared from the title compound of Example 291 via similar procedures described in Example 36.
MS (ESI): m/z 822.61 [M+H].

Example 293

Compound of formula VII, wherein $R_1$ and $R_2$ taken together with the carbon atom to which they are attached are C=CHCONH[quinolin-3-yl], $R_{15}$=H, and Rx=Ac The compound was prepared from compound of example step 283b and 3-aminoquinoline via similar procedures described in example 283.
MS (ESI): m/z 865.61 [M+H].

Example 294

Compound of formula VII, wherein $R_1$ and $R_2$ taken together with the carbon atom to which they are attached are C=CHCONH[quinolin-3-yl], $R_{15}$=Rx=H The title compound was prepared from the title compound of Example 293 via similar procedures described in Example 36.
MS (ESI): m/z 823.73 [M+H].

Example 295

Compound of formula VII, wherein $R_1$ and $R_2$ taken together with the carbon atom to which they are attached are C=CHCH$_2$O[guinolin-4-yl], $R_{15}$=H, and Rx=Ac Step 295a.
To a solution of compound of example 279 (430 mg, 56% purity) in THF (5 ml) at 0° C. was added slowly DIBAl-H (10M in hexane, 3.2 ml, 3.2 mmol). The resulting solution was stirred at 0° C. for 2 h, quenched with aq. sodium potassium tartrate, extracted with EtOAc (100 ml). The organic phase was washed with sat. aq. sodium bicarbonate (20 ml), sat. aq. NaCl (20 ml), dried (MgSO4) and concentrated. The residue was purified through silica gel column (dichoromethane: 2M ammonia in dichloromethane=98:2 to 95:5) to give the compound of step 295a.
MS (ESI): m/z 685.28 [M+H].

Step 295b

To a solution of compound of step 295a (60 mg, 0.088 mmol), 4-hydroxyquinoline (15 mg, 0.105 mmol), triphenylphosphine (46 mg, 0.176 mmol) in anhydrous THF (5 ml) was added slowly diethyl azodicarboxylate (28 ul, 0.176 mmol). The resulting solution was stirred at rt for 1 h, concentrated. The residue was purified through silica gel column (dichoromethane: 2M ammonia in dichloromethane=98:2) to give the compound of step 295b (65 mg).

MS (ESI): m/z 812.39 [M+H].

Step 295c

A solution of compound of step 295b (65 mg, 0.08 mmol) in dichloromethane (3 ml) was treated with acetic anhydride (9 ul, 1.2 eq.). The resulting solution was stirred at rt for 16 h. To this reaction mixture was added Dess-Martin reagent (45 mg, 1.3 eq.). The resulting mixture was stirred at rt for 1 h, diluted with EtOAc, washed with sat. aq. sodium bicarbonate, sat. aq. NaCl, dried (MgSO4) and concentrated. The residue was purified through silica gel column (dichoromethane: methanol=98:2) to give the title compound (25 mg).

MS (ESI): m/z 852.37 [M+H].

Example 296

Compound of formula VII, wherein $R_1$ and $R_2$ taken together with the carbon atom to which they are attached are C=CHCH$_2$O[guinolin-4-yl], $R_{20}$=Rx=H The title compound was prepared with the title compound of Example 295 via similar conditions described in Example 36.

MS (ESI): m/z 810.53 [M+H].

Example 297

Compound of formula VII, wherein $R_1$ and $R_2$ taken together with the carbon atom to which they are attached are C=CHCH$_2$NHPh, $R_{15}$=H, and Rx=Ac

Step 297a.

A solution of compound of example 295 step 295a (40 mg, 0.058 mmol) in dichloromethane (3 ml) was treated with MnO$_2$ (activated, 85%, 70 mg, 0.68 mmol). The mixture was stirred at rt for 5 h. More MnO$_2$ (activated, 85%, 70 mg, 0.68 mmol) 0° C. was added. The resulting mixture was stirred at rt for another 13 h, filtered, washed with dichloromethane. The filtrate was concentrated to dryness to give the compound of step a (30 mg).

MS (ESI): m/z 683.58 [M+H].

Step 297b

The compound was prepared from compound of example step 297a (30 mg, 0.0439) via similar procedures described in example 295 step 295c.

MS (ESI): m/z 723.73 [M+H].

Step 297c

To a solution of compound of step 297b (<0.043 mmol) and aniline (10 ul, 2.5 eq.) in ethanol (2 ml) was added NaBH$_3$CN (2 mg, 0.032 mmol). The mixture was stirred at rt for 0.5 h. More NaBH$_3$CN (2 mg, 0.032 mmol) was added. The mixture was stirred at rt for another 0.5 h, diluted with EtOAc, washed with sat. aq. sodium bicarbonate, sat. aq. NaCl, dried (MgSO$_4$) and concentrated to dryness to give the title compound.

MS (ESI): m/z 800.74 [M+H].

Example 298

Compound of formula VII, wherein $R_1$ and $R_2$ taken together with the carbon atom to which they are attached are C=CHCH$_2$NHPh, $R_{15}$=Rx=H The title compound was prepared with the title compound of Example 297 via similar conditions described in Example 36.

MS (ESI): m/z 758.72 [M+H].

Example 299

Compound of formula VII, wherein $R_1$ and $R_2$ taken together with the carbon atom to which they are attached are C=CHCH$_2$NH[quinolin-3-yl], $R_{15}$=H, and Rx=Ac The compound was prepared from compound of example 297 step 297b and 3-aminoquinoline via similar procedures described in example 297 step 297c MS (ESI): m/z 851.49 [M+H].

Example 300

Compound of formula VII, wherein $R_1$ and $R_2$ taken together with the carbon atom to which they are attached are C=CHCH$_2$NH[quinolin-3-yl], $R_{15}$=Rx=H The title compound was prepared with the title compound of Example 299 via similar conditions described in Example 36.

MS (ESI): m/z 809.72 [M+H].

Example 301

Compound of formula VII, wherein $R_1$=phenylpropyl and $R_2$=OH, $R_{20}$=H and Rx=Ac To a solution of the compound from Example 16 (50 mg) in THF was added dropwise phenylpropylmagnesium bromide (0.72 ml) at −78° C. The resulting mixture was stirred at −78° C. for 5 minutes and then kept at 0 to 5° C. for 50 minutes. The reaction was quenched with aqeous NH$_4$Cl. The resulting mixture was extracted with CH$_2$Cl$_2$, washed with 1M NaHCO$_3$, brine, dried over Na$_2$SO$_4$, filtered and concentrated under vacuum to give desired compound.

MS (ESI): m/z 817.82[M+H].

Example 302

Compound of formula VII, wherein $R_1$=phenylpropyl and $R_2$=OH and =Rx=H

The title compound (R-isomer) was prepared with the title compound of Example 301 via similar conditions described in Example 229.

MS (ESI): m/z 775.79[M+H].
$^{13}$C NMR (CDCl$_3$, ppm) δ: 219.2, 176.8, 157.5, 142.1, 128.4, 128.3, 125.8, 105.0, 84.2, 81.6, 79.9, 79.0, 78.3, 75.8, 75.8, 70.5, 69.6, 65.8, 65.6, 57.9, 44.7, 44.4, 42.5, 40.2, 39.1, 38.3, 38.2, 36.3, 29.7, 28.1, 24.5, 22.7, 21.5, 21.2, 19.5, 13.7, 13.4, 11.2, 11.0.

Example 303

Compound of formula VII, wherein $R_1$=OPh and $R_2$=H, $R_{20}$=H, and Rx=ac

To a solution of the compound from Example 62 (50 mg), phenol (11 mg) and triphenylphosphine (38 mg) in THF (2 ml) was added dropwise DEAD (17.3 µl) at 0° C. The resulting mixture was stirred overnight at room temperature. The reaction mixture was concentrated and purified by column chromatography to give the desired compound.
MS (ESI): m/z 775.44[M+H].

Example 304

Compound of formula VII, wherein $R_1$=OPh and $R_2$=H, and $R_{20}$=Rx=H

The title compound (R-isomer) was prepared with the title compound of Example 301 via similar conditions described in Example 229.
MS (ESI): m/z 733.55 [M+H].
$^{13}$C NMR (CDCl$_3$, ppm) δ: 218.1, 177.7, 157.9, 157.6, 129.9, 121.5, 115.5, 105.1, 84.5, 80.9, 80.5, 78.7, 76.3, 74.3, 71.0, 70.7, 69.9, 66.0, 61.5, 58.6, 44.8, 44.6, 43.0, 40.4, 39.0, 37.8, 28.4, 23.0, 21.6, 21.4, 19.8, 13.8, 13.7, 11.3, 10.9.

Example 305

Compound of formula VII, wherein $R_1$=O (quinolin-4-yl) and $R_2$=H, $R_{20}$=H, and Rx=Ac The title compound was prepared with the title compound of Example 62 (50 mg) and quinolin-4-ol (16 mg) via similar conditions described in Example 229.
MS (ESI): m/z 825.52[M+H].

Example 306

Compound of formula VII, wherein $R_1$=O (quinolin-4-yl) and $R_2$=H, and $R_{20}$=Rx=H The title compound (R-isomer) was prepared with the title compound of Example 305 via similar conditions described in Example 229.
MS (ESI): m/z 784.54[M+H].
$^{13}$C NMR (CDCl$_3$, ppm) δ: 218.3, 177.8, 160.1, 157.9, 151.7, 149.7, 129.9, 129.3, 125.7, 121.9, 121.7, 105.2, 101.7, 84.4, 81.1, 80.8, 78.8, 76.3, 74.7, 70.7, 70.4, 69.9, 66.0, 60.8, 58.6, 44.9, 44.6, 43.1, 40.4, 39.1, 37.8, 28.3, 22.9, 21.6, 21.4, 19.9, 13.8, 13.7, 11.5.

Example 307

Compound of formula VII, wherein $R_1$=benzylamino and $R_2$=H, $R_{20}$=H, and Rx=Ac To a solution of the compound from Example 16 (70 mg), benzylamine (17 µl) and acetic acid (15 µl) in acetonitrile was added sodium cyanoborohydride (9.4 mg) at room temperature. The resulting mixture was stirred overnight at room temperature for 1 hour and quenched with 1M NaHCO$_3$. The reaction mixture was extracted with CH$_2$Cl$_2$. The combind organic extracts was washed with 1M NaHCO$_3$ and brine, dried over Na$_2$SO$_4$, filtered, and concentrated under vacuum to give the desired compound.
MS (ESI): m/z 788.52[M+H].

Example 308

Compound of formula VII, wherein $R_2$=benzylamino and $R_2$=H, and $R_{20}$=Rx=H The title compound was prepared with the title compound of Example 307 via similar conditions described in Example 229.

R-isomer
MS (ESI): m/z 746.92[M+H].
$^{13}$C NMR (CDCl$_3$, ppm) δ: 217.9, 177.4, 157.9, 139.8, 128.8, 127.9, 127.4, 104.9, 84.5, 81.0, 80.1, 76.8, 76.5, 71.7, 70.7, 69.8, 66.0, 63.8, 58.4, 55.0, 51.4, 44.8, 44.4, 42.7, 40.4, 38.6, 38.3, 28.4, 23.2, 21.8, 21.4, 19.6, 13.7, 11.5, 11.0, 10.7.

S-isomer
MS (ESI): m/z 746.92[M+H].
$^{13}$C NMR (CDCl$_3$, ppm) δ: 218.2, 177.1, 157.9, 140.4, 128.6, 128.2, 127.3, 104.9, 84.6, 81.6, 80.2, 79.2, 76.6, 73.5, 70.7, 69.8, 66.0, 62.1, 58.2, 57.1, 51.5, 44.8, 44.5, 42.7, 40.4, 38.9, 38.7, 28.4, 23.1, 21.4, 21.4, 19.7, 14.0, 13.7, 11.5, 11.3, 11.2.

Example 309

Compound of formula VII, wherein $R_1$=NCH$_3$(benzyl) and $R_2$=H, and $R_{20}$=Rx=H To a solution of the compound from Example 308 (R-isomer) (11 mg), formylaldehyde (18 µl) and acetic acid (5 µl) in acetonitrile was added sodium cyanoborohydride (2 mg) at room temperature. The resulting mixture was stirred at room temperature for 10 minutes and quenched with 1M NaHCO$_3$. The reaction mixture was extracted with CH$_2$Cl$_2$. The combind organic extracts was washed with 1M NaHCO$_3$, H$_2$O and brine, dried over Na$_2$SO$_4$, filtered, and concentrated under vacuum to give the desired compound.

R-isomer
MS (ESI): m/z 760.84[M+H].
$^{13}$C NMR (CDCl$_3$, ppm) δ: 217.8, 177.4, 157.8, 139.5, 128.6, 128.3, 127.3, 105.0, 84.5, 81.3, 80.1, 76.4, 70.7, 69.7, 68.0, 66.1, 10.0, 59.7, 58.5, 58.4, 44.7, 44.6, 42.8, 40.4, 38.7, 38.4, 38.0, 29.9, 28.5, 23.1, 21.8, 21.4, 19.7, 13.7, 13.7, 11.4, 11.1, 10.9.

Example 310

Compound of formula VII, wherein $R_1$=phenylethylamino and $R_2$H, $R_{20}$=H, and Rx=Ac The title compound was prepared with the title compound of Example 16 (50 mg) and phenylethylamine (11 µl) via similar conditions described in Example 307.
MS (ESI): m/z 802.81[M+H].

Example 311

Compound of formula VII, wherein $R_1$=phenylethylamino and $R_2$=H, and $R_{20}$=Rx=H The title compound was prepared with the title compound of Example 310 via similar conditions described in Example 229.

R-isomer
MS (ESI): m/z 760.43[M+H].
$^{13}$C NMR (CDCl$_3$, ppm) δ: 217.8, 177.3, 157.9, 139.5, 128.7, 128.5, 126.2, 104.7, 84.4, 80.7, 79.8, 76.1, 71.7, 70.5, 69.5, 65.8, 63.5, 58.2, 55.9, 48.8, 44.5, 44.2, 42.6, 40.2, 38.4, 37.9, 36.2, 28.1, 22.9, 21.5, 21.1, 19.3, 13.5, 13.5, 11.2, 10.8, 10.6.

S-isomer
MS (ESI): m/z 760.43[M+H].
$^{13}$C NMR (CDCl$_3$, ppm) δ: 217.5, 176.8, 157.8, 139.9, 128.7, 128.4, 126.1, 104.6, 84.4, 81.5, 80.1, 80.1, 76.4, 74.3, 70.5, 69.6, 65.8, 62.8, 58.1, 58.0, 48.9, 44.4, 44.2, 42.5, 40.2, 38.7, 38.5, 36.5, 28.1, 22.9, 21.3, 21.2, 19.3, 13.9, 13.3, 11.2, 11.1, 11.1.

Example 312

Compound of formula VII, wherein
$R_1$=phenylpropylamino and $R_2$=H, $R_{20}$=H, and Rx=Ac The title compound was prepared with the title compound of Example 16 (70 mg) and 3-phenylpropylamine (22 µl) via similar conditions described in Example 307.
MS (ESI): m/z 816.45[M+H].

Example 313

Compound of formula VII, wherein
$R_1$=phenylpropylamino and $R_2$=H, and $R_{20}$=Rx=H The title compound was prepared with the title compound of Example 312 via similar conditions described in Example 229.

R-isomer
MS (ESI): m/z 774.91[M+H].
$^{13}$C NMR (CDCl$_3$, ppm) δ: 218.0, 177.6, 158.2, 142.2, 128.6, 128.5, 126.0, 125.9, 104.9, 84.6, 81.0, 80.0, 76.4, 72.0, 70.7, 69.8, 66.0, 63.8, 58.4, 56.5, 48.9, 47.8, 47.3, 44.8, 44.5, 42.8, 40.4, 38.6, 38.2, 34.0, 33.8, 32.2, 32.1, 28.4, 23.2, 21.7, 21.4, 19.5, 13.8, 13.7, 11.4, 11.1, 10.8.

S-isomer
MS (ESI): m/z 774.91[M+H].
$^{13}$C NMR (CDCl$_3$, ppm) δ: 217.6, 176.8, 157.8, 142.1, 128.4, 128.3, 125.7, 104.7, 84.4, 81.5, 80.5, 80.0, 76.4, 74.7, 70.5, 69.6, 65.8, 62.7, 58.2, 58.0, 46.9, 44.4, 44.3, 42.5, 40.2, 38.7, 38.4, 38.4, 33.4, 31.7, 28.1, 22.9, 21.2, 21.2, 19.3, 13.9, 13.3, 11.2, 11.2, 11.1.

Example 314

Compound of formula VII, wherein
$R_1$=2-naphthalen-1-yl-ethylamino and $R_2$=H, $R_{20}$=H, and Rx=Ac The title compound was prepared with the title compound of Example 16 (100 mg) and 2-naphthalen-1-yl-ethylamine (38 mg) via similar conditions described in Example 307.
MS (ESI): m/z 852.50[M+H].

Example 315

Compound of formula VII, wherein
$R_1$=2-naphthalen-1-yl-ethylamino and $R_2$=H, and $R_{20}$=Rx=H The title compound was prepared with the title compound of Example 314 via similar conditions described in Example 229.

R-isomer
MS (ESI): m/z 810.50[M+H].
$^{13}$C NMR (CDCl$_3$, ppm) δ: 217.7, 177.3, 157.9, 135.6, 133.9, 131.9, 128.7, 127.0, 126.5, 125.9, 125.5, 125.5, 123.6, 104.7, 84.4, 80.7, 79.8, 76.1, 71.8, 70.5, 69.6, 65.8, 63.4, 58.2, 56.0, 48.0, 44.5, 44.3, 42.6, 40.2, 38.5, 37.9, 33.4, 28.1, 22.9, 21.5, 21.1, 19.4, 13.5, 13.4, 11.1, 10.8, 10.7.

S-isomer
MS (ESI): m/z 810.50[M+H].
$^{13}$C NMR (CDCl$_3$, ppm) δ: 217.8, 177.0, 158.0, 136.3, 134.1, 132.2, 128.9, 127.1, 126.7, 126.1, 125.7, 125.7, 124.0, 104.9, 84.7, 81.9, 80.5, 80.3, 76.6, 74.7, 70.7, 69.8, 66.0, 62.8, 58.7, 58.3, 48.7, 44.6, 44.5, 42.8, 40.4, 39.0, 38.7, 34.2, 28.4, 23.1, 21.5, 21.4, 19.6, 14.1, 13.6, 11.5, 11.4, 11.3.

Example 316

Compound of formula VII, wherein
$R_1$=2-naphthalen-2-yl-ethylamino and $R_2$=H, $R_{20}$=H, and Rx=Ac The title compound was prepared with the title compound of Example 16 (100 mg) and 2-naphthalen-2-yl-ethylamine (38 mg) via similar conditions described in Example 307.
MS (ESI): m/z 852.50[M+H].

Example 317

Compound of formula VII, wherein
$R_1$=2-naphthalen-2-yl-ethylamino and $R_2$=H, and $R_{20}$=Rx=H The title compound was prepared with the title compound of Example 316 via similar conditions described in Example 229.

R-isomer
MS (ESI): m/z 810.51 [M+H].
$^{13}$C NMR (CDCl$_3$, ppm) δ: 217.8, 177.3, 158.0, 137.0, 133.6, 132.2, 128.2, 128.0, 127.6, 127.5, 127.2, 127.1, 126.9, 125.9, 125.2, 104.7, 84.4, 80.7, 79.8, 76.2, 71.7, 70.5, 69.5, 65.8, 63.5, 58.2, 55.8, 48.6, 44.5, 44.2, 42.6, 40.2, 38.4, 37.9, 36.3, 28.1, 23.0, 21.5, 21.1, 19.3, 13.5, 11.2, 10.8, 10.6.

S-isomer
MS (ESI): m/z 810.51 [M+H].
$^{13}$C NMR (CDCl$_3$, ppm) δ: 217.6, 177.0, 158.0, 137.6, 133.8, 132.4, 128.2, 127.8, 127.7, 127.5, 127.2, 126.1, 125.4, 104.9, 84.7, 81.8, 80.6, 80.3, 76.7, 74.7, 70.7, 69.8, 66.0, 63.0, 58.6, 58.2, 49.1, 44.6, 44.5, 42.7, 40.4, 38.9, 38.7, 37.1, 28.4, 23.1, 21.5, 21.4, 19.5, 14.1, 13.5, 11.4, 11.3.

Example 318

Compound of formula VII, wherein $R_1$=NCH (2-naphthalen-2-yl-ethyl) and $R_2$=H, and $R_{20}$=Rx=H The title compound (R-isomer) was prepared with the title compound of Example 317 via similar conditions described in Example 229.
MS (ESI): m/z 824.36[M+H].
$^{13}$C NMR (CDCl$_3$, ppm) δ: 217.8, 177.4, 157.8, 139.5, 128.6, 128.3, 127.3, 105.0, 84.5, 81.3, 80.1, 76.4, 70.7, 69.7, 68.0, 66.1, 10.0, 59.7, 58.5, 58.4, 44.7, 44.6, 42.8, 40.4, 38.7, 38.4, 38.0, 29.9, 28.5, 23.1, 21.8, 21.4, 19.7, 13.7, 13.7, 11.4, 11.1, 10.9.

Example 319

Compound of formula VII, wherein $R_1$=O (3-guinolin-3-yl-prop-2-ene-1-yl) and $R_2$=H, $R_{20}$=H, and Rx=Ac Step 319a.
To a solution of compound of Example 16 (1.0 g), TEA (602 µl) and DMAP (175 mg) in CH$_2$Cl$_2$ was added partially BOC anhydride (1.6 g). After 30 minutes the reaction mixture was extracted with EtOAc. The combind organic extracts were washed with 1M NaHCO$_3$ and brine, dried over Na$_2$SO$_4$, filtered, concentrated under vacuum. The residue was purified by column chromatography to give the desired target in 88% yield.
MS (ESI): m/z 797.29[M+H].

Step 319b.

To a solution of compound from Step 319a (1.01 g) in THF was added dropwise 1.0M lithium tri-tert-butoxide aluminumhydride (1.7 ml) at −20° C. After 30 minutes the reaction mixture was quenched with 3N HCl and diluted with $CH_2Cl_2$. The resulting mixture was stirred with $Na_2SO_4$ for 30 minutes, filtered and concentrated under vacuum to give the desired compound in 100% yield.

MS (ESI): m/z 799.50[M+H].

Step 319c.

To a solution of compound from Step 319b (500 mg) and 2,6-lutidine (110 μl) in $CH_2Cl_2$ was added dropwise trfluoromethanesulfonic anhydride (165 μl) at −78° C. After 2 hours the reaction mixture was quenched with aqueous $NH_4Cl$ and extracted with EtOAc. The organic extracts were washed with $H_2O$ and brine, dried, filtered and concentrated under vacuum to give the desired compound directly used in the next step.

MS (ESI): m/z 931.57[M+H].

Step 319d.

A solution of 30% DMSO in water (3 ml) and THF (3 ml) was added to the compound from Step 319c. The resulting solution was stayed at room temperature for 2 hours. The reaction mixture was concentrated and extracted with EtOAc. The organic extracts were washed with $H_2O$ and brine, dried, filtered, concentrated and purified by column chromatography to give the desired target in 56% yield.

MS (ESI): m/z 799.73[M+H].

Step 319e.

A solution of compound from Step 319d (80 mg), carbonic acid tert-butyl ester 1-quinolin-3-yl-allyl ester (57 mg) and dppb (26 mg) was degassed. $Pd_2(dba)_3$ (27 mg) was added in. The resulting mixture was heated at 70° C. overnight, concentrated and purified by column chromatography to give the desired compound.

MS (ESI): m/z 966.33[M+H].

Step 319f.

Compound from step 319e was dissolved in 50% TFA in $CH_2Cl_2$ at 0° C. After 30 minutes the reaction mixture was concentrated to give the desired target.

MS (ESI): m/z 866.41[M+H].

Example 320

Compound of formula VII, wherein $R_1$=O (3-guinolin-3-yl-prop-2-ene-1-yl) and $R_2$=H, and $R_{20}$=Rx=H The title compound was prepared with the title compound of Example 319 via similar conditions described in Example 229. The ratio of R:S was 4:1.

R-isomer

MS (ESI): m/z 824.36[M+H].

$^{13}C$ NMR ($CDCl_3$, ppm) δ: 218.0, 177.6, 158.1, 149.6, 147.8, 133.0, 129.7, 129.4, 129.3, 128.3, 128.2, 128.1, 127.1, 105.1, 84.6, 81.0, 80.4, 79.0, 76.2, 71.8, 70.7, 70.6, 69.8, 66.0, 62.2, 58.5, 44.7, 44.6, 42.9, 40.4, 38.8, 37.8, 28.3, 22.9, 21.6, 21.4, 19.7, 13.8, 13.6, 11.2, 11.0.

S-isomer

MS (ESI): m/z 824.36[M+H].

Example 321

Compound of formula VII, wherein $R_1$=O (3-guinolin-4-yl-prop-2-ene-1-yl) and $R_2$=H, $R_{20}$=H, and Rx=Ac Step 321a.

To a solution of quinoline-4-carbaldehyde (1.0 g) in THF was added dropwise vinylmagnesium chloride (4.0 ml) at −78° C. The resulting yellow mixture was warmed up to 0° C. for 15 minutes. The mixture was cooled dowmn to −78° C. again and added dropwise a solution of BOC anhydride (1.46 g) in methelenechloride. The resulting mixture was allowed to stir at 0° C. for 1 hour and quenched with aq. $NH_4Cl$. The reaction mixture was extracted with EtOAc. The combind organic extracts were washed with aq. $NH_4Cl$, water and brine, dried over $MgSO_4$, filtered, concentrated under vacuum. The residue was purified by column chromatography to give the desired target (830 mg).

MS (ESI): m/z 286.15[M+H].

Step 321b.

The title compound was prepared with the compound from Step 319d (60 mg) of Example 319 and the compound from Step 321a (65 mg) via similar conditions outlined in Steps 319e and 319f of Example 319.

MS (ESI): m/z 966.66 [M+H].

Example 322

Compound of formula VII, wherein $R_1$=O (3-quinolin-4-yl-prop-2-ene-1-yl) and $R_2$=H, and $R_{20}$=Rx=H The title compound was prepared with the title compound of Example 321 via similar conditions described in Example 229. The ratio of R:S was 4:1.

R-isomer

MS (ESI): m/z 824.84[M+H].

$^{13}C$ NMR ($CDCl_3$, ppm) δ: 217.8, 177.4, 157.9, 150.2, 148.6, 142.5, 132.8, 130.0, 129.3, 126.5, 126.4, 126.2, 123.7, 117.7, 104.9, 84.4, 80.8, 80.2, 78.8, 76.1, 71.5, 70.5, 70.2, 69.6, 65.8, 62.0, 58.3, 53.4, 44.5, 44.4, 42.7, 40.2, 38.6, 37.6, 29.7, 28.1, 22.8, 21.4, 21.1, 19.5, 13.6, 13.3, 11.1, 11.0, 10.8.

S-isomer

MS (ESI): m/z 824.84[M+H].

Example 323

Compound of formula VII, wherein $R_1$=OH and $R_2$=H, $R_{20}$=H, and Rx=Ac

Step 323a.

To a solution of compound of Example 16 (200 mg) and 2,6-lutidine (100 μl) in $CH_2Cl_2$ was added dropwise trfluoromethanesulfonic anhydride (74 μl) at −78° C. After 2 hours the reaction mixture was quenched with aqueous $NH_4Cl$ and extracted with EtOAc.

The organic extracts were washed with $H_2O$ and brine, dried, filtered and concentrated under vacuum to give the desired compound directly used in the next step.

MS (ESI): m/z 831.44[M+H].

Step 323b.

A solution of 10% water in DMSO (2.1 ml) was added to the compound from Step YS-71a. The resulting solution was stayed at room temperature for 2 hours. The reaction mixture was concentrated and extracted with EtOAc. The organic extracts were washed with $H_2O$ and brine, dried, filtered, concentrated and purified by column chromatography to give the desired target in 50% yield.

MS (ESI): m/z 699.46[M+H].

Example 324

Compound of formula VII, wherein $R_1$=OCONHPh and $R_2$=H, $R_{20}$=H, and Rx=Ac To a solution of compound of Example 323 (50 mg) and TEA (3 eq) in dichloromethane was added dropewise phenylisocyanate (26 μl) at room temperature overnight. The reaction mixture was extracted with $CH_2Cl_2$. The combind organic extracts were washed with 1M NaHCO$_3$, water and brine, dried over Na$_2$SO$_4$, filtered, concentrated under vacuum to give the desired compound.
MS (ESI): m/z 818.47[M+H].

Example 325

Compound of formula VII, wherein R$_1$=OCONHPh and R$_2$=H, and R$_{20}$=Rx=H

The title compound (R-isomer) was prepared with the title compound of Example 324 via similar conditions described in Example 229.
MS (ESI): m/z 776.28[M+H].
$^{13}$C NMR (CDCl$_3$, ppm) δ: 216.9, 177.2, 157.6, 152.2, 137.6, 129.1, 123.6, 118.6, 105.0, 84.2, 80.9, 80.3, 76.1, 72.6, 70.5, 69.7, 65.8, 61.3, 58.2, 44.7, 44.0, 42.8, 40.2, 38.9, 37.3, 28.1, 22.7, 21.2, 19.6, 13.6, 13.2, 11.5, 11.0, 11.0.

Example 326

Compound of formula VII, wherein R$_1$=OCONHCH$_2$Ph and R$_2$=H, R$_{20}$=H, and Rx=Ac The title compound was prepared with compound of Example 323 (50 mg) and benzylisocyanate (30 μl) via the similar conditions described in Example 324.
MS (ESI): m/z 832.51 [M+H].

Example 327

Compound of formula VII, wherein R$_1$=OCONHCH$_2$Ph and R$_2$=H, and R$_{20}$=Rx=H The title compound (R-isomer) was prepared with the title compound of Example 326 via similar conditions described in Example 229.
MS (ESI): m/z 790.36[M+H].
$^{13}$C NMR (CDCl$_3$, ppm) δ: 216.8, 177.2, 157.6, 155.2, 138.2, 128.7, 127.6, 127.6, 104.9, 84.2, 80.8, 80.5, 80.2, 76.1, 72.3, 70.4, 69.6, 65.7, 61.6, 58.1, 45.2, 44.6, 44.0, 42.7, 40.2, 38.9, 37.4, 28.1, 22.7, 21.2, 19.5, 13.6, 13.2, 11.4, 11.0, 10.9.

Example 328

Compound of formula VII, wherein R$_1$=OSO$_2$CH$_3$ and R$_2$=H, R$_{20}$=H, and Rx=Ac To a solution of compound of Example 62 (1.5 g) and TEA (3 eq) in dichloromethane was added dropewise methanesulfonyl chloride (258 μl) at 0° C. The reaction mixture was stirred for 2 hours and extracted with EtOAc. The combind organic extracts were washed with 1M NaHCO$_3$, water and brine, dried over Na$_2$SO$_4$, filtered, concentrated under vacuum to give the desired compound in 100% yield.
MS (ESI): m/z 777.37[M+H].

Example 329

Compound of formula VII, wherein R$_1$=N$_3$, and R$_2$=H, R$_{20}$=H, and Rx=Ac To a solution of compound of Example 328 (1.7 g) in DMF was added sodium azide (715 mg). The reaction mixture was stirred at 75° C. overnight and extracted with EtOAc. The combind organic extracts were washed with 1M NaHCO$_3$, water and brine, dried over Na$_2$SO$_4$, filtered, concentrated under vacuum to give the desired compound in 96% yield.
MS (ESI): m/z 724.34[M+H].

Example 330

Compound of formula VII, wherein R$_1$=N$_3$, and R$_2$=H, and R$_{20}$=Rx=H

The title compound was prepared with the title compound of Example 329 via similar conditions described in Example 229.
R-
MS (ESI): m/z 682.49[M+H].
$^{13}$C NMR (CDCl$_3$, ppm) δ: 217.5, 177.4, 157.6, 105.0, 84.1, 80.7, 80.6, 80.2, 76.0, 71.7, 70.4, 69.7, 65.8, 61.6, 60.1, 58.3, 44.7, 44.1, 42.8, 40.2, 38.8, 37.3, 28.2, 22.6, 21.2, 19.7, 13.6, 13.3, 11.4, 10.9, 10.8.

Example 331

Compound of formula VII, wherein R$_1$=NH$_2$, and R$_2$=H, R$_{20}$=H, and Rx=Ac A solution of compound of Example 329 (1.5 g), 1N HCl (1 eq) and 10% Pd/C (150 mg) in MeOH was stirred under hydrogen at 40 psi overnight. The mixture was filtered through a pad of celite to remove Pd/C and concentrated under vacuum to give the desired target in 96% yield.
MS (ESI): m/z 698.52[M+H].

Example 332

Compound of formula VII, wherein R$_1$=NH$_2$, and R$_2$=H, and R$_{20}$=Rx=H

The title compound was prepared with the title compound of Example 331 and 1M K$_2$CO$_3$ via similar conditions described in Example 229.
R-
MS (ESI): m/z 656.48[M+H].
$^{13}$C NMR (CDCl$_3$, ppm) δ: 217.7, 177.3, 157.9, 104.6, 84.4, 80.7, 79.8, 76.7, 76.1, 74.2, 70.4, 69.4, 66.2, 65.9, 58.2, 49.5, 44.5, 44.2, 42.6, 40.2, 38.5, 37.9, 28.4, 22.9, 21.5, 21.1, 19.4, 13.5, 13.4, 11.2, 10.8, 10.7.

Example 333

Compound of formula VII, wherein R$_1$=NHCO$_2$CH$_2$Ph, and R$_2$=H, R$_{20}$=H, and Rx=Ac To a solution of compound of Example 331 (60 mg) and TEA (3 eq) in dichloromethane was added carbonic acid benzyl ester N-hydroxysuccinimide ester (43 mg) at room temperature overnight. The reaction mixture was extracted with CH$_2$Cl$_2$. The combind organic extracts were washed with 1M NaHCO$_3$, water and brine, dried over Na$_2$SO$_4$, filtered, concentrated under vacuum to give the desired compound.
MS (ESI): m/z 832.27[M+H].

Example 334

Compound of formula VII, wherein R$_1$=NHCO$_2$CH$_2$Ph, and R$_2$=H, and R$_{20}$=Rx=H The title compound was prepared with the title compound of Example 333 via similar conditions described in Example 229.
MS (ESI): m/z 790.45[M+H].

Example 335

Compound of formula VII, wherein $R_1$=NHCOPh, and $R_2$=H, $R_{20}$=H, and Rx=Ac A mixture of compound of Example 331 (60 mg), benzoic acid (21 mg), HOBt (27 mg), EDC (33 mg) and TEA (5 eq) in dichloromethane was stirred at room temperature overnight. The reaction mixture was extracted with $CH_2Cl_2$. The combind organic extracts were washed with 1M $NaHCO_3$, water and brine, dried over $Na_2SO_4$, filtered, concentrated under vacuum to give the desired compound.

MS (ESI): m/z 802.27[M+H].

Example 336

Compound of formula VII, wherein $R_1$=NHCOPh, and $R_2$=H, and $R_{20}$=Rx=H

The title compound was prepared with the title compound of Example 335 via similar conditions described in Example 229.

MS (ESI): m/z 760.47[M+H].
$^{13}$C NMR (CDCl$_3$, ppm) δ: 217.1, 177.5, 166.7, 157.9, 134.2, 131.9, 128.8, 127.1, 105.3, 84.6, 82.8, 80.4, 79.7, 76.4, 71.8, 70.7, 69.9, 66.0, 64.2, 58.4, 50.5, 44.8, 44.4, 43.0, 40.4, 39.0, 38.3, 28.3, 23.0, 21.8, 21.2, 19.5, 13.9, 13.5, 11.6, 11.3, 11.3.

Example 337

Compound of formula VII, wherein $R_1$=NHCOCH$_2$Ph, and $R_2$=H, $R_{20}$=H, and Rx=Ac The title compound was prepared with compound of Example 331 (60 mg) and benzene acetic acid (21 mg) via the similar conditions described in Example 335.

MS (ESI): m/z 816.36[M+H].

Example 338

Compound of formula VII, wherein $R_1$=NHCOCH$_2$Ph, and $R_2$=H, and $R_{20}$=Rx=H The title compound was prepared with the title compound of Example 337 via similar conditions described in Example 229.

MS (ESI): m/z 774.61 [M+H].
$^{13}$C NMR (CDCl$_3$, ppm) δ: 217.0, 177.5, 170.6, 157.9, 134.9, 129.6, 129.3, 127.6, 105.1, 84.6, 81.8, 80.2, 78.4, 76.3, 70.9, 70.7, 69.8, 66.0, 63.6, 58.3, 49.4, 44.6, 44.4, 43.9, 42.9, 40.4, 39.0, 38.0, 28.3, 23.0, 21.8, 21.4, 19.6, 13.8, 13.5, 11.3, 11.2, 11.0.

Example 339

Compound of formula VII, wherein $R_1$=NHCONHCH$_2$Ph and $R_2$=H, $R_{20}$=H, and Rx=Ac The title compound was prepared with compound of Example 331 (40 mg) and benzylisocyanate (13 μl) via the similar conditions described in Example 324.

MS (ESI): m/z 831.73[M+H].

Example 340

Compound of formula VII, wherein $R_1$=OCONHCH$_2$Ph and $R_2$=H, and =Rx=H

The title compound was prepared with the title compound of Example 339 via similar conditions described in Example 229.

MS (ESI): m/z 789.72[M+H].
$^{13}$C NMR (CDCl$_3$, ppm) δ: 217.0, 177.3, 157.7, 157.1, 139.0, 128.6, 127.6, 127.4, 104.8, 84.3, 81.5, 80.0, 78.2, 76.1, 71.7, 70.5, 69.6, 65.8, 63.9, 58.1, 49.9, 44.6, 44.4, 44.2, 42.7, 40.1, 38.8, 37.9, 28.2, 22.7, 21.5, 21.2, 19.3, 13.6, 13.3, 11.0, 10.9.

Example 341

Compound of formula VII, wherein $R_1$=NHCONHPh and $R_2$=H, $R_{20}$=H, and Rx=Ac The title compound was prepared with compound of Example 331 (40 mg) and phenylisocyanate (1 μl) via the similar conditions described in Example 324.

MS (ESI): m/z 817.70[M+H].

Example 342

Compound of formula VII, wherein $R_1$=OCONHPh and $R_2$=H, and $R_{20}$=Rx=H

The title compound was prepared with the title compound of Example 341 via similar conditions described in Example 229.

MS (ESI): m/z 775.70[M+H].
$^{13}$C NMR (CDCl$_3$, ppm) δ: 217.0, 177.6, 158.2, 155.2, 138.8, 129.4, 123.8, 120.9, 104.9, 84.9, 82.0, 80.2, 78.4, 76.4, 71.5, 70.7, 69.7, 66.0, 64.5, 58.3, 50.2, 44.5, 44.4, 42.9, 40.3, 39.0, 38.2, 28.5, 23.1, 21.8, 21.3, 19.4, 13.9, 13.5, 11.3, 11.1.

Example 343

Compound of formula VII, wherein $R_1$=NHSO$_2$CH$_2$Ph, and $R_2$=H, $R_{20}$=H, and Rx=Ac A mixture of compound of Example 331 (40 mg), α-toluenesulfonyl chloride (20 mg), pyridine (1 ml) and TEA (201 μl) in dichloromethane was stirred at room temperature overnight. The reaction mixture was extracted with $CH_2Cl_2$. The combind organic extracts were washed with 1M $NaHCO_3$, water and brine, dried over $Na_2SO_4$, filtered, concentrated under vacuum to give the desired compound.

MS (ESI): m/z 852.32[M+H].

Example 344

Compound of formula VII, wherein $R_2$=NHSO$_2$CH$_2$Ph, and $R_2$=H, and =Rx=H

The title compound was prepared with the title compound of Example 343 via similar conditions described in Example 229.

MS (ESI): m/z 810.51[M+H].
$^{13}$C NMR (CDCl$_3$, ppm) δ: 216.9, 177.5, 157.8, 130.9, 129.2, 129.0, 105.3, 84.4, 81.6, 80.5, 76.3, 73.0, 70.6, 69.9, 66.0, 64.6, 59.4, 58.4, 53.5, 44.8, 44.2, 43.0, 40.4, 39.0, 37.7, 28.3, 22.9, 21.7, 21.4, 19.6, 13.8, 13.5, 11.4, 11.2.

Example 345

Compound of formula VII, wherein $R_1$=NHSO$_2$Ph and $R_2$=H, $R_{20}$=H, and Rx=Ac The title compound was prepared with compound of Example 331 (40 mg) and benzenesulfonyl chloride (131 μl) via the similar conditions described in Example 343.

MS (ESI): m/z 838.57[M+H].

Example 346

Compound of formula VII, wherein $R_1$=NHSO$_2$Ph and $R_2$=H, and $R_{20}$=Rx=H The title compound was prepared with the title compound of Example 345 via similar conditions described in Example 229.
MS (ESI): m/z 796.35[M+H].
$^{13}$C NMR (CDCl$_3$, ppm) δ: 217.0, 177.1, 157.5, 140.0, 132.9, 129.3, 127.0, 105.0, 84.1, 81.3, 80.4, 76.6, 76.1, 72.8, 70.4, 69.7, 65.8, 63.9, 58.2, 52.9, 44.6, 44.0, 42.7, 40.1, 38.7, 37.5, 28.2, 22.6, 21.3, 21.2, 19.5, 13.6, 13.3, 11.2, 11.0, 11.0

Example 347

Compound of formula VII, wherein $R_1$=NHSO$_2$(pyridin-2-yl) and $R_2$=H, $R_{20}$=H, and Rx=Ac The title compound was prepared with compound of Example 331 and pyridine-2-sulfonyl chloride via the similar conditions described in Example 343.
MS (ESI): m/z 839.65[M+H].

Example 348

Compound of formula VII, wherein $R_1$=NHSO$_2$(pyridin-2-yl) and $R_2$=H, and $R_2$=Rx=H The title compound was prepared with the title compound of Example 347 via similar conditions described in Example 229.
MS (ESI): m/z 797.76[M+H].
$^{13}$C NMR (CDCl$_3$, ppm) δ: 216.8, 177.1, 157.6, 157.2, 150.2, 138.2, 126.8, 122.5, 104.8, 84.3, 81.3, 80.3, 79.1, 76.1, 71.8, 70.4, 69.5, 65.9, 64.5, 58.1, 53.0, 44.3, 44.2, 42.5, 40.1, 38.5, 37.8, 29.7, 28.4, 22.8, 21.4, 21.1, 19.2, 13.5, 13.1, 11.1, 11.0, 10.9

Example 349

Compound of formula VII, wherein $R_1$=NHSO$_2$(pyridin-3-yl) and $R_2$=H, $R_{20}$=H, and Rx=Ac The title compound was prepared with compound of Example 331 and pyridine-3-sulfonyl chloride via the similar conditions described in Example 343.
MS (ESI): m/z 839.70[M+H].

Example 350

Compound of formula VII, wherein $R_1$=NHSO$_2$(pyridin-3-yl) and $R_2$=H, and $R_{20}$=Rx=H The title compound was prepared with the title compound of Example 349 via similar conditions described in Example 229.
MS (ESI): m/z 797.76[M+H].

Example 351

Compound of formula VII, wherein $R_1$=NHSO$_2$(biphenyl-3-yl) and $R_2$=H, $R_{20}$=H, and Rx=Ac The title compound was prepared with compound of Example 331 and biphenyl-3-sulfonyl chloride via the similar conditions described in Example 343.
MS (ESI): m/z 914.64[M+H].

Example 352

Compound of formula VII, wherein $R_1$=NHSO$_2$(biphenyl-3-yl) and $R_2$=H, and $R_{20}$=Rx=H The title compound was prepared with the title compound of Example 351 via similar conditions described in Example 229.
MS (ESI): m/z 872.78[M+H].
$^{13}$C NMR (CDCl$_3$, ppm) δ: 217.2, 177.3, 157.8, 142.8, 141.1, 139.5, 131.7, 129.9, 129.2, 128.4, 127.5, 125.8, 125.6, 105.4, 84.3, 81.7, 81.4, 80.6, 76.2, 73.4, 70.7, 70.0, 66.1, 64.1, 58.5, 53.5, 45.0, 44.2, 43.0, 39.1, 37.6, 28.4, 22.8, 21.5, 21.4, 19.8, 13.8, 13.4, 11.6, 11.3, 11.1.

Example 353

Compound of formula VII, wherein $R_1$=NHSO$_2$(quinolin-5-yl) and $R_2$=H, $R_2$=H, and Rx=Ac The title compound was prepared with compound of Example 331 and quinoline-5-sulfonyl chloride via the similar conditions described in Example 343.
MS (ESI): m/z 889.80[M+H].

Example 354

Compound of formula VII, wherein $R_1$=NHSO$_2$(quinolin-5-yl) and $R_2$=H, and $R_{20}$=Rx=H The title compound was prepared with the title compound of Example 353 via similar conditions described in Example 229.
MS (ESI): m/z 847.54[M+H].
$^{13}$C NMR (CDCl$_3$, ppm) δ: 217.1, 177.1, 157.8, 151.0, 143.3, 137.5, 135.8, 133.8, 132.0, 129.2, 126.1, 122.4, 105.2, 84.3, 81.6, 80.5, 79.1, 76.1, 71.6, 70.7, 69.9, 66.1, 64.7, 58.3, 53.4, 44.6, 44.3, 42.6, 40.7, 38.7, 38.0, 28.4, 22.9, 21.7, 21.4, 19.5, 13.7, 13.5, 11.3, 11.1, 10.8.

Example 355

Compound of formula VII, wherein $R_1$=NHSO$_2$(biphenyl-4-yl) and $R_2$=H, $R_{20}$=H, and Rx=Ac The title compound was prepared with compound of Example 331 and biphenyl-4-sulfonyl chloride via the similar conditions described in Example 343.
MS (ESI): m/z 914.83[M+H].

Example 356

Compound of formula VII, wherein $R_1$=NHSO$_2$(biphenyl-4-yl) and $R_2$=H, and $R_{20}$=Rx=H The title compound was prepared with the title compound of Example 355 via similar conditions described in Example 229.
MS (ESI): m/z 872.35[M+H].
$^{13}$C NMR (CDCl$_3$, ppm) δ: 217.3, 177.3, 157.8, 146.0, 139.5, 138.9, 129.2, 128.7, 128.1, 127.7, 127.6, 105.3, 84.4, 81.6, 80.8, 80.6, 76.3, 73.2, 70.7, 70.0, 66.1, 64.2, 58.5, 53.2, 44.9, 44.3, 43.0, 40.4, 39.0, 37.7, 28.4, 22.8, 21.6, 21.4, 19.7, 13.8, 13.5, 11.5, 11.3, 11.1.

Example 357

Compound of formula VII, wherein $R_1$=NHSO$_2$(5-isoxazol-5-yl-thiophen-2-yl) and $R_2$=H, $R_{20}$=H, and Rx=Ac The title compound was prepared with compound of Example 331 and 5-isoxazol-5-yl-thiophene-2-sulfonyl chloride via the similar conditions described in Example 343.
MS (ESI): m/z 911.79[M+H].

Example 358

Compound of formula VII, wherein $R_1$=NHSO$_2$(5-isoxazol-5-yl-thiophen-2-yl) and $R_2$=H, and $R_{20}$=Rx=H The title compound was prepared with the title compound of Example 357 via similar conditions described in Example 229.
MS (ESI): m/z 869.50[M+H].
$^{13}$C NMR (CDCl$_3$, ppm) δ: 217.3, 177.3, 162.7, 157.9, 151.1, 143.1, 135.1, 133.2, 126.8, 105.2, 100.9, 84.4, 41.5, 80.7, 80.3, 76.3, 72.6, 70.6, 69.9, 66.1, 64.2, 58.5, 53.5, 44.7, 44.3, 42.9, 40.4, 38.9, 37.8, 28.5, 22.9, 21.6, 21.4, 19.7, 13.8, 13.5, 11.4, 11.2, 11.1.

Example 359.

Compound of formula VII, wherein $R_1$=NHSO$_2$(naphthalen-1-yl) and $R_2$H, $R_{20}$=H, and Rx=Ac The title compound was prepared with compound of Example 331 and naphthalene-1-sulfonyl chloride via the similar conditions described in Example 343.
MS (ESI): m/z 888.38[M+H].

Example 360

Compound of formula VII, wherein $R_1$=NHSO$_2$(naphthalen-1-yl) and $R_2$=H, and $R_{20}$=Rx=H The title compound was prepared with the title compound of Example 359 via similar conditions described in Example 229.
MS (ESI): m/z 846.67[M+H].
$^{13}$C NMR (CDCl$_3$, ppm) δ: 217.3, 177.2, 157.7, 134.9, 134.5, 134.5, 130.3, 129.5, 128.5, 128.1, 127.0, 124.5, 124.3, 105.4, 84.3, 81.6, 81.2, 80.5, 76.7, 76.1, 73.3, 70.7, 70.0, 66.0, 64.0, 58.4, 53.5, 45.0, 44.1, 42.9, 40.7, 39.0, 37.5, 28.4, 22.8, 21.5, 21.4, 19.8, 13.8, 13.4, 11.4, 11.2, 11.1.

Example 361

Compound of formula VII, wherein $R_1$=NHSO$_2$(naphthalen-2-yl) and $R_2$=H, $R_{20}$=H and Rx=Ac The title compound was prepared with compound of Example 331 and naphthalene-2-sulfonyl chloride via the similar conditions described in Example 343.
MS (ESI): m/z 888.38[M+H].

Example 362

Compound of formula VII, wherein $R_1$=NHSO$_2$(naphthalen-2-yl) and $R_2$=H, and $R_{20}$=Rx=H The title compound was prepared with the title compound of Example 361 via similar conditions described in Example 229.
MS (ESI): m/z 846.70[M+H].
$^{13}$C NMR (CDCl$_3$, ppm) δ: 217.2, 177.2, 157.8, 137.0, 135.1, 132.4, 129.9, 129.7, 129.1, 128.8, 128.1, 127.8, 122.2, 105.3, 84.4, 81.6, 80.6, 80.2, 76.1, 72.9, 70.7, 70.0, 66.0, 64.3, 58.4, 53.0, 44.8, 44.3, 42.9, 40.4, 38.9, 37.8, 28.4, 22.7, 21.6, 21.4, 19.7, 13.8, 13.5, 11.4, 11.2, 11.0.

Example 363

Compound of formula VII, wherein $R_1$=NHSO$_2$(thiophen-2-yl) and $R_2$=H, $R_{20}$=H, and Rx=Ac The title compound was prepared with compound of Example 331 and thiophene-2-sulfonyl chloride via the similar conditions described in Example 343.
MS (ESI): m/z 844.41[M+H].

Example 364

Compound of formula VII, wherein $R_1$=NHSO$_2$(thiophen-2-yl) and $R_2$=H, and $R_{20}$=Rx=H The title compound was prepared with the title compound of Example 363 via similar conditions described in Example 229.
MS (ESI): m/z 802.37[M+H].
$^{13}$C NMR (CDCl$_3$, ppm) δ: 217.1, 177.1, 157.6, 140.8, 132.8, 132.3, 127.5, 105.0, 84.2, 81.3, 80.5, 80.4, 76.1, 72.7, 70.4, 69.8, 65.8, 63.9, 58.2, 53.3, 44.6, 44.0, 42.7, 40.2, 38.7, 37.5, 28.1, 22.7, 21.3, 21.2, 19.5, 13.6, 13.3, 11.3, 11.0, 11.0.

Example 365

Compound of formula VII, wherein $R_1$=NHSO$_2$(5-isoxazol-3-yl-thiophen-2-yl) and $R_2$=H, $R_{20}$=H, and Rx=Ac The title compound was prepared with compound of Example 331 and 5-isoxazol-3-yl-thiophene-2-sulfonyl chloride via the similar conditions described in Example 343.
MS (ESI): m/z 911.42[M+H].

Example 366

Compound of formula VII, wherein $R_1$=NHSO$_2$(5-isoxazol-3-yl-thiophen-2-yl) and $R_2$=H, and $R_{20}$=Rx=H The title compound was prepared with the title compound of Example 365 via similar conditions described in Example 229.
MS (ESI): m/z 869.61 [M+H].
$^{13}$C NMR (CDCl$_3$, ppm) δ: 217.1, 177.1, 162.4, 157.6, 150.9, 134.8, 133.0, 126.6, 126.4, 105.0, 100.7, 100.2, 84.2, 81.2, 80.5, 80.1, 76.1, 72.4, 70.4, 69.8, 65.8, 63.9, 58.2, 53.3, 44.5, 44.1, 42.7, 40.2, 38.7, 37.5, 28.1, 22.6, 21.3, 21.2, 19.4, 14.2, 13.5, 13.3, 11.2, 11.0, 10.9.

Example 367

Compound of formula VII, wherein $R_1$=NHSO$_2$(2-phenyl-ethene-1-yl) and $R_2$=H, $R_{20}$=H, and Rx=Ac The title compound was prepared with compound of Example 331 and 2-phenyl-ethenesulfonyl chloride via the similar conditions described in Example 343.
MS (ESI): m/z 864.47[M+H].

Example 368

Compound of formula VII, wherein $R_1$=NHSO$_2$ (2-phenyl-ethene-1-yl) and $R_2$=H, and $R_{20}$=Rx=H The title compound was prepared with the title compound of Example 367 via similar conditions described in Example 229.

MS (ESI): m/z 822.45[M+H].

$^{13}$C NMR (CDCl$_3$, ppm) δ: 217.1, 177.4, 157.8, 142.4, 132.7, 131.1, 129.3, 128.7, 125.0, 105.2, 84.4, 81.5, 80.6, 79.8, 76.2, 73.0, 70.7, 70.0, 66.0, 64.7, 58.4, 52.7, 44.7, 44.4, 42.9, 40.4, 38.9, 37.9, 28.4, 22.8, 21.7, 21.4, 19.6, 13.8, 13.6, 11.4, 11.2, 10.9.

Example 369

Compound of formula VII, wherein $R_1$=NHSO$_2$ (benzofuran-2-yl) and $R_2$=H, $R_{20}$=H, and Rx=Ac The title compound was prepared with compound of Example 331 and benzofuran-2-sulfonyl chloride via the similar conditions described in Example 343.

MS (ESI): m/z 878.54[M+H].

Example 370

Compound of formula VII, wherein $R_1$=NHSO$_2$ (benzofuran-2-yl) and $R_2$=H, and $R_{20}$=Rx=H The title compound was prepared with the title compound of Example 369 via similar conditions described in Example 229.

MS (ESI): m/z 836.66[M+H].

$^{13}$C NMR (CDCl$_3$, ppm) δ: 217.2, 177.2, 157.8, 156.0, 149.7, 128.1, 126.1, 124.5, 123.3, 113.3, 112.5, 105.2, 84.4, 81.7, 80.8, 80.7, 76.2, 73.0, 70.7, 70.0, 66.1, 64.5, 58.5, 53.8, 44.8, 44.3, 42.9, 40.4, 39.0, 37.8, 29.9, 28.5, 22.8, 21.5, 21.4, 19.6, 13.8, 13.5, 11.5, 11.3, 11.1, 10.9.

Example 371

Compound of formula VII, wherein $R_1$=NHSO$_2$ (benzothiazol-6-yl) and $R_1$=H, $R_{20}$=H, and Rx=Ac The title compound was prepared with compound of Example 331 and benzothiazole-6-sulfonyl chloride via the similar conditions described in Example 343.

MS (ESI): m/z 895.52[M+H].

Example 372

Compound of formula VII, wherein $R_1$=NHSO$_2$ (benzothiazol-6-yl) and $R_2$=H and $R_{20}$=Rx=H The title compound was prepared with the title compound of Example 371 via similar conditions described in Example 229.

MS (ESI): m/z 853.41[M+H].

$^{13}$C NMR (CDCl$_3$, ppm) δ: 217.2, 177.2, 158.3, 157.8, 155.9, 137.6, 134.5, 124.8, 124.6, 122.5, 105.2, 84.4, 81.5, 80.6, 79.9, 76.1, 72.5, 70.6, 69.9, 66.1, 64.2, 58.4, 53.0, 44.7, 44.3, 42.9, 40.4, 38.9, 37.8, 29.9, 28.5, 22.8, 21.6, 21.4, 19.6, 13.8, 13.5, 11.3, 11.2, 11.1.

Example 373

Compound of formula VII, wherein $R_1$=NHSO$_2$ (4-pyrazol-1-yl-phenyl) and $R_2$=H, $R_{20}$=H, and Rx=Ac The title compound was prepared with compound of Example 331 and 4-pyrazol-1-yl-benzenesulfonyl chloride via the similar conditions described in Example 343.

MS (ESI): m/z 904.57[M+H].

Example 374

Compound of formula VII, wherein $R_1$=NHSO$_2$ (4-pyrazol-1-yl-phenyl) and $R_2$=H and $R_{20}$=Rx=H The title compound was prepared with the title compound of Example 373 via similar conditions described in Example 229.

MS (ESI): m/z 852.34[M+H].

$^{13}$C NMR (CDCl$_3$, ppm) δ: 217.2, 177.2, 157.8, 143.4, 142.4, 137.5, 128.9, 127.2, 119.2, 109.0, 105.2, 84.4, 81.5, 80.6, 79.9, 76.3, 72.6, 70.7, 69.9, 66.0, 64.2, 58.4, 52.9, 44.7, 44.3, 42.9, 40.4, 38.9, 37.8, 28.4, 22.9, 21.6, 21.4, 19.6, 13.8, 13.5, 11.3, 11.2, 11.1.

Example 375

Compound of formula VII, wherein $R_1$=NHSO$_2$ (6-phenoxy-pyridin-3-yl) and $R_2$=H, $R_{20}$=H, and Rx=Ac The title compound was prepared with compound of Example 331 and 6-phenoxy-pyridine-3-sulfonyl chloride via the similar conditions described in Example 343.

MS (ESI): m/z 931.57[M+H].

Example 376

Compound of formula VII, wherein $R_1$=NHSO$_2$ (6-phenoxy-pyridin-3-yl) and $R_2$=H, and $R_{20}$=Rx=H The title compound was prepared with the title compound of Example 375 via similar conditions described in Example 229.

MS (ESI): m/z [M+H].

$^{13}$C NMR (CDCl$_3$, ppm) δ: 217.2, 177.3, 166.3, 157.8, 153.2, 147.7, 138.6, 131.5, 130.0, 125.8, 121.7, 111.7, 105.3, 84.4, 81.5, 80.7, 80.7, 76.2, 73.1, 70.7, 70.0, 66.0, 64.0, 58.5, 53.1, 44.9, 44.3, 43.0, 40.4, 39.0, 37.7, 28.4, 22.8, 21.6, 21.4, 19.7, 13.8, 13.5, 11.5, 11.2, 11.2.

Example 377

Compound of formula VII, wherein $R_1$=NHSO$_2$ (benzo[b]thiophen-2-yl) and $R_2$=H, $R_{20}$=H, and Rx=Ac The title compound was prepared with compound of Example 331 and benzo[b]thiophene-2-sulfonyl chloride via the similar conditions described in Example 343.

MS (ESI): m/z 894.40[M+H].

Example 378

Compound of formula VII, wherein $R_1$=NHSO$_2$ (benzo[b]thiophen-2-yl) and $R_2$=H, and $R_{20}$=Rx=H The title compound was prepared with the title compound of Example 377 via similar conditions described in Example 229.

MS (ESI): m/z 852.66[M+H].

$^{13}$C NMR (CDCl$_3$, ppm) δ: 217.0, 177.0, 157.6, 141.8, 140.5, 137.5, 130.3, 127.4, 125.9, 125.5, 122.7, 105.0, 84.2, 81.3, 80.4, 80.3, 76.0, 72.6, 70.4, 69.7, 65.8, 64.1, 58.2, 53.3, 44.5, 44.02, 42.7, 40.2, 38.7, 37.6, 29.7, 28.2, 22.5, 21.3, 21.2, 19.4, 13.5, 13.3, 11.2, 11.0, 10.8.

Example 379

Compound of formula VII, wherein $R_1$=NHSO$_2$ (3-bromo-phenyl) and $R_{20}$=H, $R_{20}$=H, and Rx=Ac The title compound was prepared with compound of Example 331 and 3-bromo-benzenesulfonyl chloride via the similar conditions described in Example 343.
MS (ESI): m/z 916.51, 918.51[M+H].

Example 380

Compound of formula VII, wherein $R_1$=NHSO$_2$ (3-pyridin-3-yl-phenyl) and $R_2$=H, $R_{20}$=H and Rx=Ac The mixture of the compound of Example 379 (50 mg), 3-pyridineboronic acid (20.3 mg), cesium carbonate (90 mg), KF (90 mg) and DME was degassed and added PdCl$_2$(dppf).DCM (5 mg). The reaction mixture was heated at 90° C. overnight. The reaction mixture was extracted with CH$_2$Cl$_2$. The combind organic extracts were washed with 1M NaHCO$_3$, water and brine, dried over Na$_2$SO$_4$, filtered, concentrated under vacuum and purified by column chromatography to give the desired compound.
MS (ESI): m/z 915.67[M+H].

Example 381

Compound of formula VII, wherein $R_1$=NHSO$_2$ (3-pyridin-3-yl-phenyl) and $R_2$=H, and $R_{20}$=Rx=H The title compound was prepared with the title compound of Example 380 via similar conditions described in Example 229.
MS (ESI): m/z 873.50[M+H].
$^{13}$C NMR (CDCl$_3$, ppm) δ: 217.3, 177.3, 157.8, 149.5, 148.5, 141.6, 139.5, 135.2, 134.9, 131.7, 130.3, 126.8, 125.6, 123.9, 105.2, 84.4, 81.5, 80.6, 80.6, 76.2, 72.9, 70.6, 69.9, 66.1, 64.1, 58.4, 53.2, 44.8, 44.3, 42.9, 40.4, 39.0, 37.7, 29.9, 28.4, 22.8, 21.5, 21.4, 19.7, 13.8, 13.5, 11.5, 11.2, 11.2.

Example 382

Compound of formula VII, wherein $R_1$=NHSO$_2$ (3-pyrazin-2-yl-phenyl) and $R_2$=H, $R_{20}$=H, and Rx=Ac The mixture of the compound of Example 379 (50 mg), 2-(tributyistanny) pyrazine (100 µl) in toluene was degassed and added Pd(PPh$_3$)$_4$ (5 mg). The reaction mixture was heated at 110° C. overnight. The reaction mixture was concentrated under vacuum and purified by column chromatography to give the desired compound.
MS (ESI): m/z 916.77[M+H].

Example 383

Compound of formula VII, wherein $R_1$=NHSO$_2$ (3-pyrazin-2-yl-phenyl) and $R_2$=H, and $R_{20}$=Rx=H The title compound was prepared with the title compound of Example 382 via similar conditions described in Example 229.
MS (ESI): m/z 874.53[M+H].
$^{13}$C NMR (CDCl$_3$, ppm) δ: 217.0, 177.0, 157.6, 150.8, 144.3, 143.8, 142.2, 141.4, 137.7, 130.9, 130.0, 128.1, 125.4, 105.0, 84.1, 81.4, 80.4, 80.4, 76.0, 72.8, 70.4, 69.7, 65.9, 63.9, 58.2, 53.0, 44.6, 44.0, 42.7, 40.2, 38.8, 37.4, 28.3, 22.6, 21.3, 21.2, 19.5, 13.6, 13.3, 11.2, 11.0, 10.9.

Example 384

Compound of formula VII, wherein $R_1$=NHSO$_2$ (3-pyridin-2-yl-phenyl) and $R_2$=H, $R_{20}$=H, and Rx=Ac The title compound was prepared with the title compound of Example 379 with 2-(tributyistanny) pyridine via similar conditions described in Example 382.
MS (ESI): m/z 915.59[M+H].

Example 385

Compound of formula VII, wherein $R_1$=NHSO$_2$ (3-pyridin-2-yl-phenyl) and $R_2$=H, and $R_{20}$=Rx=H The title compound was prepared with the title compound of Example 384 via similar conditions described in Example 229.
MS (ESI): m/z 873.57[M+H].
$^{13}$C NMR (CDCl$_3$, ppm) δ: 217.2, 177.3, 157.8, 155.5, 150.1, 141.2, 140.9, 137.3, 131.3, 129.9, 127.4, 125.5, 123.2, 121.0, 105.3, 84.3, 81.7, 81.1, 80.6, 76.2, 73.3, 70.6, 69.9, 66.1, 64.1, 58.5, 53.5, 44.9, 44.2, 43.0, 40.4, 39.1, 37.6, 28.5, 22.8, 21.5, 21.4, 19.8, 13.8, 13.5, 11.6, 11.2, 11.1.

Example 386

Compound of formula VII, wherein $R_1$=NHSO$_2$ [3-(6-amino-pyridin-3-yl)-phenyl] and R=$R_{20}$=H, and Rx=Ac Step 386a.
The mixture of 2-amino-6-bromo-pyridine (5.0 g) and phthalic abhydride (4.3 g) in xylenens was heated to 150° C. The precipates were filtered off to give the desired product in 88% yield.
MS (ESI): m/z 303.07, 305.06[M+H].

Step 386b.
The mixture of the compound from Step 386a (1.0 g), Hexamethylditin (7091 µl) in DME was degassed and added Pd(PPh$_3$)$_4$ (191 mg). The reaction mixture was heated at 90° C. for 5 hours. The reaction mixture was concentrated under vacuum and purified by column chromatography to give the desired compound (856 mg).
MS (ESI): m/z 387.04[M+H].

Step 386c.
The title compound was prepared with the title compound of Example 379 with the compound from Step 386b via similar conditions described in Example 382.
MS (ESI): m/z 1060.64[M+H].

Example 387

Compound of formula VII, wherein $R_1$=NHSO$_2$ [3-(6-amino-pyridin-3-yl)-phenyl] and $R_2$=H, and $R_{20}$=Rx=H The title compound was prepared with the title compound of Example 386 via similar conditions described in Example 229.
MS (ESI): m/z 888.52[M+H], 444.76[M+2H].

$^{13}$C NMR (CDCl$_3$, ppm) δ: 217.1, 177.3, 158.7, 157.9, 154.0, 141.2, 140.7, 138.8, 131.2, 129.6, 126.9, 125.6, 111.1, 108.3, 105.3, 84.3, 81.7, 80.7, 80.5, 76.2, 73.1, 70.7, 69.9, 66.1, 64.0, 58.5, 53.4, 44.9, 44.2, 43.0, 40.4, 39.1, 37.7, 28.5, 22.8, 21.5, 21.4, 19.8, 13.9, 13.5, 11.6, 11.2.

Example 388

Compound of formula VII, wherein R$_1$=NHSO$_2$ (3,4-dichloro-phenyl) and R$_2$=H, R$_{20}$=H, and Rx=Ac The title compound was prepared with compound of Example 331 and 3,4-dichloro-benzenesulfonyl chloride via the similar conditions described in Example 343.

MS (ESI): m/z 906.42, 908.43[M+H].

Example 389

Compound of formula VII, wherein R$_1$=NHSO$_2$ (3,4-dichloro-phenyl) and R$_2$=H, and R$_{20}$=Rx=H The title compound was prepared with the title compound of Example 368 via similar conditions described in Example 229.

MS (ESI): m/z 864.36, 866.36[M+H].

$^{13}$C NMR (CDCl$_3$, ppm) δ: 217.2, 177.3, 157.9, 140.4, 137.9, 134.1, 131.5, 129.1, 126.4, 105.2, 84.4, 81.5, 80.7, 80.1, 76.2, 70.7, 70.0, 66.0, 64.1, 58.4, 53.1, 44.8, 44.3, 42.9, 40.4, 39.0, 37.7, 28.4, 22.8, 21.6, 21.4, 19.7, 13.8, 13.5, 11.4, 11.1.

Example 390

Compound of formula VII, wherein R$_1$=NHSO$_2$ (3,4-difluoro-phenyl) and R$_2$=H, R$_{20}$=H, and Rx=Ac The title compound was prepared with compound of Example 331 and 3,4-difluoro-benzenesulfonyl chloride via the similar conditions described in Example 343.

MS (ESI): m/z 874.48[M+H].

Example 391

Compound of formula VII, wherein R$_1$=NHSO$_2$ (3,4-difluoro-phenyl) and R$_2$=H, and R$_{20}$=Rx=H The title compound was prepared with the title compound of Example 390 via similar conditions described in Example 229.

MS (ESI): m/z 832.41[M+H].

$^{13}$C NMR (CDCl$_3$, ppm) δ: 217.0, 177.1, 157.6, 137.1, 124.3, 118.4, 118.2, 116.9, 116.8, 104.9, 84.2, 81.2, 80.4, 79.7, 76.0, 72.3, 70.4, 69.7, 65.8, 63.9, 58.2, 52.8, 44.5, 44.1, 42.7, 40.2, 38.7, 37.5, 29.7, 28.2, 22.7, 21.4, 21.2, 19.4, 13.5, 13.3, 11.1, 10.9, 10.9.

Example 392

Compound of formula VII, wherein R$_1$=NHSO$_2$ (4-fluoro-phenyl) and R$_2$=H, R$_{20}$=H, and Rx=Ac The title compound was prepared with compound of Example 331 and 4-fluoro-benzenesulfonyl chloride via the similar conditions described in Example 343.

MS (ESI): m/z 856.49[M+H].

Example 393

Compound of formula VII, wherein R$_1$=NHSO$_2$ (4-fluoro-phenyl) and R$_2$=H, and R$_{20}$=Rx=H The title compound was prepared with the title compound of Example 392 via similar conditions described in Example 229.

MS (ESI): m/z 814.42[M+H].

$^{13}$C NMR (CDCl$_3$, ppm) δ: 217.2, 177.3, 166.4, 164.4, 157.8, 130.0, 116.8, 116.6, 105.2, 84.5, 81.4, 80.6, 79.7, 76.3, 72.3, 70.6, 69.9, 64.2, 58.4, 52.8, 44.7, 44.3, 42.8, 40.4, 38.9, 37.8, 28.4, 22.9, 21.6, 21.4, 19.6, 13.7, 13.5, 11.3, 11.2, 11.2.

Example 394

Compound of formula VII, wherein R$_1$=NHSO$_2$ (3-fluoro-phenyl) and R$_2$=H, R$_{20}$=H, and Rx=Ac The title compound was prepared with compound of Example 331 and 3-fluoro-benzenesulfonyl chloride via the similar conditions described in Example 343.

MS (ESI): m/z 856.48[M+H].

Example 395

Compound of formula VII, wherein R$_1$=NHSO$_2$ (3-fluoro-phenyl) and R$_2$=H, and R$_{20}$=Rx=H The title compound was prepared with the title compound of Example 394 via similar conditions described in Example 229.

MS (ESI): m/z 814.40[M+H].

$^{13}$C NMR (CDCl$_3$, ppm) δ: 217.0, 177.1, 163.5, 161.5, 157.6, 142.3, 131.1, 122.8, 120.2, 120.0, 114.4, 114.2, 105.0, 84.2, 81.3, 80.4, 80.1, 76.0, 72.5, 70.4, 69.7, 65.8, 63.9, 58.2, 52.9, 44.6, 44.1, 42.7, 40.2, 38.7, 37.5, 28.2, 22.6, 21.3, 21.2, 19.5, 13.5, 13.3, 11.2, 10.9.

Example 396

Compound of formula VII, wherein R$_1$=NHSO$_2$ (4-methoxy-phenyl) and R$_2$=H, R$_{20}$=H, and Rx=Ac The title compound was prepared with compound of Example 331 and 4-methoxy-benzenesulfonyl chloride via the similar conditions described in Example 343.

MS (ESI): m/z 868.51[M+H].

Example 397

Compound of formula VII, wherein R$_1$=NHSO$_2$ (4-methoxy-phenyl) and R$_2$=H, and R$_{20}$=Rx=H The title compound was prepared with the title compound of Example 396 via similar conditions described in Example 229.

MS (ESI): m/z 826.55[M+H].

$^{13}$C NMR (CDCl$_3$, ppm) δ: 217.0, 177.1, 163.0, 157.6, 131.5, 129.2, 114.4, 104.9, 84.2, 81.3, 80.3, 80.1, 76.1, 72.6, 70.4, 69.6, 65.9, 64.0, 58.2, 55.6, 52.7, 44.5, 44.0, 42.7, 40.2, 38.7, 37.5, 29.7, 28.3, 22.6, 21.3, 21.2, 19.4, 13.6, 13.3, 11.2, 11.0.

Example 398

Compound of formula VII, wherein R$_1$=NHSO$_2$ (3-methoxy-phenyl) and R$_2$=H, R$_{20}$=H, and Rx=Ac The title compound was prepared with compound of Example 331 and 3-methoxy-benzenesulfonyl chloride via the similar conditions described in Example 343.

MS (ESI): m/z 868.50[M+H].

Example 399

Compound of formula VII, wherein $R_1$=NHSO$_2$ (3-methoxy-phenyl) and $R_2$=H, and $R_{20}$=Rx=H The title compound was prepared with the title compound of Example 398 via similar conditions described in Example 229.

MS (ESI): m/z 826.35[M+H].

$^{13}$C NMR (CDCl$_3$, ppm) δ: 217.0, 177.1, 160.0, 157.6, 141.2, 130.3, 119.2, 119.1, 111.8, 105.0, 84.1, 81.3, 80.4, 80.3, 76.0, 72.8, 70.4, 69.7, 65.8, 63.9, 58.2, 55.7, 53.0, 44.6, 44.0, 42.7, 40.2, 38.8, 37.4, 28.2, 22.6, 21.3, 21.2, 19.5, 13.6, 13.3, 11.3, 11.0, 10.9.

Example 400

Compound of formula VII, wherein $R_1$=NHSO$_2$ (3-chloro-phenyl) and $R_2$=H, $R_{20}$=H, and Rx=Ac The title compound was prepared with compound of Example 331 and 3-chloro-benzenesulfonyl chloride via the similar conditions described in Example 343.

MS (ESI): m/z 872.43, 874.43[M+H].

Example 401

Compound of formula VII, wherein $R_1$=NHSO$_2$ (3-chloro-phenyl) and $R_2$=H, and $R_{20}$=Rx=H The title compound was prepared with the title compound of Example 400 via similar conditions described in Example 229.

MS (ESI): m/z 830.36, 832.37[M+H].

$^{13}$C NMR (CDCl$_3$, ppm) δ: 217.3, 177.3, 157.8, 142.2, 135.6, 133.2, 130.8, 127.2, 125.4, 105.2, 84.3, 81.5, 80.6, 80.5, 76.2, 72.8, 70.6, 69.9, 66.1, 64.1, 58.8, 53.2, 44.8, 44.3, 42.9, 40.4, 39.0, 37.7, 28.4, 22.8, 21.5, 21.4, 19.7, 13.8, 13.5, 11.5, 11.2, 11.2.

Example 402

Compound of formula VII, wherein $R_1$=NCH$_3$SO$_2$ (benzo[b]thiophen-2-yl) and $R_2$=H, and $R_{20}$=Rx=H Step 402a.

The mixture of the compound of Example 329 (0.5 g) and 40% CH$_3$NH$_2$/H$_2$O (1 ml) in DMF was stirred at 60° C. overnight. The reaction mixture was extracted with DCM, washed with 1M NaHCO3 and brine, dried, filtered and concentrated to give the desired products.

MS (ESI): m/z 670.29[M+H].

Step 402b.

The title compound was prepared with compound from Step 402a and benzo[b]thiophene-2-sulfonyl chloride via the similar conditions described in Example 343.

R-isomer

MS (ESI): m/z 866.40[M+H].

$^{13}$C NMR (CDCl$_3$, ppm) δ: 217.3, 177.4, 157.7, 141.8, 139.9, 137.9, 129.6, 127.4, 126.0, 125.7, 122.9, 105.6, 84.3, 81.6, 81.4, 80.5, 76.1, 70.7, 70.6, 69.9, 66.0, 60.3, 58.5, 56.9, 45.4, 44.0, 43.1, 40.4, 39.3, 37.0, 30.8, 29.9, 28.3, 22.6, 21.6, 21.4, 20.2, 13.9, 13.4, 11.8, 11.3, 11.0.

S-isomer

MS (ESI): m/z 866.40[M+H].

Example 403

Compound of formula VII, wherein $R_1$ and $R_2$ taken together with the carbon atom to which they are attached are CHNHCOOCH$_2$[6-pyrazol-1-yl-pyridin-3-yl], $R_{15}$=H, and Rx=Ac To a mixture of (6-(1H-pyrazol-1-yl)pyridin-3-yl)methanol (48 mg, 0.274 mmol), succinimidyl carbonate (70 mg, 0.273 mmol) and DMF (1 ml) was added triethylamine (115 ul, 0.822 mmol). The resulting mixture was stirred at rt for 1 h, and HCl salt of compound of Example 331 (60 mg, 0.0817 mmol) was added. The mixture was stirred at rt for 23 h, diluted with EtOAc (80 ml), washed with sat. aq. sodium bicarbonate (3×15 ml), falf-sat. NaCl (15 ml), dried (MgSO4) and concentrated to dryness to give the title compound.

MS (ESI): m/z 899.62 [M+H].

Example 404

Compound of formula VII, wherein $R_1$ and $R_2$ taken together with the carbon atom to which they are attached are CHNHCOOCH$_2$[6-pyrazol-1-yl-pyridin-3-yl], $R_{15}$=Rx=H The title compound was prepared with the title compound of Example 403 via similar conditions described in Example 36.

MS (ESI): m/z 857.59 [M+H].

Example 405

Compound of formula VII, wherein $R_1$ and $R_2$ taken together with the carbon atom to which they are attached are CHNHCOOCH$_2$[6-pyrazol-1-yl-pyridin-2-yl], $R_{15}$=H, and Rx=Ac The title compound was prepared from (6-(1H-pyrazol-1-yl)pyridin-2-yl)methanol and HCl salt of compound of Example 331 via similar procedures described in example of 403.

MS (ESI): m/z 899.61 [M+H].

Example 406

Compound of formula VII, wherein $R_1$ and $R_2$ taken together with the carbon atom to which they are attached are CHNHCOOCH$_2$[6-pyrazol-1-yl-pyridin-2-yl], $R_{15}$=Rx=H The title compound was prepared with the title compound of Example 405 via similar conditions described in Example 36.

MS (ESI): m/z 857.55 [M+H].

Example 407

Compound of formula VII, wherein $R_1$ and $R_2$ taken together with the carbon atom to which they are attached are CHNHCOOCH$_2$[quinolin-3-yl], $R_{15}$=H, and Rx=Ac Step 407a.

To a solution of quinoline-3-carbaldehyde (3.6 g, 22.9 mmol) in methanol (22 ml) at 5° C. was added in portions sodium borohydride (870 mg, 22.9 mmol). The mixture was stirred at rt for 1 h, diluted with ETOAc (200 ml), washed with falf-sat. NaCl (50 ml), dried (MgSO4) and concentrated to dryness to give the compound of step a (100% yield).

MS (ESI): m/z 160.10 [M+H].

Step 407b.

The title compound was prepared from compound step 407a and HCl salt of compound of example 331 via similar procedures described in example of 403.
MS (ESI): m/z 883.78 [M+H].

Example 408

Compound of formula VII, wherein $R_1$ and $R_2$ taken together with the carbon atom to which they are attached are CHNHCOOCH$_2$[guinolin-3-yl], $R_{15}$=Rx=H The title compound was prepared with the title compound of Example 407 via similar conditions described in Example 36.
MS (ESI): m/z 841.68 [M+H].

Example 409

Compound of formula VII, wherein $R_1$ and $R_2$ taken together with the carbon atom to which they are attached are CHNHCOOCH$_2$[quinolin-4-yl], $R_{15}$=H, and Rx=Ac Step 409a.

The compound was prepared from quinoline-4-carbaldehyde via similar conditions described in Example 407.
MS (ESI): m/z 160.09 [M+H].

Step 409b.

The title compound was prepared from compound step 409a and HCl salt of compound of example 331 via similar procedures described in example of 403.
MS (ESI): m/z 883.04 [M+H].

Example 410

Compound of formula VII, wherein $R_1$ and $R_2$ taken together with the carbon atom to which they are attached are CHNHCOOCH$_2$[quinolin-4-yl], $R_{15}$=Rx=H The title compound was prepared with the title compound of Example 409 via similar conditions described in Example 36.
MS (ESI): m/z 841.70 [M+H].

Example 411

Compound of formula VII, wherein $R_1$ and $R_2$ taken together with the carbon atom to which they are attached are CHNHCO[quinolin-4-yl], $R_{15}$=H, and Rx=Ac To a solution of HCl salt of compound of example 331 (73 mg, 0.1 mmol), quinoline-4-carboxylic acid (21 mg, 0.12 mmol), 1-hydrixybenzotriazole (HOBt) (16 mg, 0.12 mmol), triethylamine (50 ul, 0.36 mmol) in DMF (1 m) was added N-(3-dimethylaminopropyl)-N'-ethylcarbodiimide (EDC) (25 mg, 0.13 mmol). The resulting mixture was stirred at rt for 5 h, diluted with EtOAc (60 ml), washed with sat. aq. sodium bivarbonate (2×15 ml), sat. NaCl (15 ml), dried (MgSO4) and concentrated. The residue was purified through a silica gel column (Hexane:EtOAc=5:5 to 4:6) to give the title compound (85 mg).
MS (ESI): m/z 853.62 [M+H].

Example 412

Compound of formula VII, wherein $R_1$ and $R_2$ taken together with the carbon atom to which they are attached are CHNHCO[quinolin-4-yl], $R_{15}$=Rx=H The title compound was prepared with the title compound of Example 411 via similar conditions described in Example 36.
MS (ESI): m/z 811.69 [M+H].

Example 413

Compound of formula VII, wherein $R_1$ and $R_2$ taken together with the carbon atom to which they are attached are CHNHCO[quinolin-3-yl], $R_{15}$=H, and Rx=Ac The title compound was prepared from HCl salt of compound of example 331 and quinoline-3-carboxylic acid via similar procedures as described in example 411.
MS (ESI): m/z 853.71[M+H].

Example 414

Compound of formula VII, wherein $R_1$ and $R_2$ taken together with the carbon atom to which they are attached are CHNHCO[guinolin-3-yl], $R_{15}$=Rx=H The title compound was prepared with the title compound of Example 413 via similar conditions described in Example 36.
MS (ESI): m/z 811.49 [M+H].

Example 415

Compound of formula VII, wherein $R_1$ and $R_2$ taken together with the carbon atom to which they are attached are CHNHCOCH$_2$[quinolin-3-yl], $R_{15}$=H, and Rx=Ac Step 415a.

To a solution of compound of example 407 step 407a (2.5 g, 15.7 mmol) in dichloromethane (17 ml) at rt was added thionyl chloride (1.5 ml, 1.3 eq.) at such a rate that a gentle reflux was maintained. After the addition was completed, the mixture was stirred for 0.5 h. EtOAc (200 ml) was added and the mixture was basified with sat. aq, sodium bicarbonate to pH 8~9. After extraction, the organic phase was washed with sat. aq. sodium bicarbonate, brine, dried (MgSO4) and concentrated to dryness to give the compound step a (2.53 g).
MS (ESI): m/z 178.08 [M+H].

Step 415b.

To a mixture of compound step 415a (500 mg, 2.8 mmol) and DMF (15 ml) at rt was added an aq. solution of KCN (370 mg in 3.5 ml of water). The resulting mixture was stirred at rt for 18 h, diluted with EtOAc (100 ml), washed with sat. aq. sodium bicarbonate (3×25 ml), sat. NaCl (25 ml), dried (MgSO4) and concentrated. The residue was purified by silica gel column (dichloromethane:methanol=1:0 to 99:1) to give compound step 415b.
MS (ESI): m/z 169.11 [M+H].

Step 415c.

A mixture of compound step 415b (20 mg, 0.119 mmol) and aq. HCl (6N, ml) was stirred at 100 1C for 4 h, cooled to rt, and lyophilized to give HCl salt of compound step c which was directly used in next step.
MS (ESI): m/z 188.13 [M+H].

Step 415d.

The title compound was prepared from compound step 415c and HCl salt of compound of example 331 via similar procedures as described in example 403.

MS (ESI): m/z 867.54[M+H].

Example 416

Compound of formula VII, wherein $R_1$ and $R_2$ taken together with the carbon atom to which they are attached are CHNHCOCH$_2$[quinolin-3-yl], $R_{15}$=Rx=H The title compound was prepared with the title compound of Example 415 via similar conditions described in Example 36.

MS (ESI): m/z 825.61 [M+H].

Example 417

Compound of formula VII, wherein $R_1$ and $R_2$ taken together with the carbon atom to which they are attached are CHNHCOCH$_2$[naphthalen-1-yl], $R_{15}$=H, and Rx=Ac The title compound was prepared from HCl salt of compound of example 331 and naphthalen-1-yl-acetic acid via similar procedures as described in example 411.

MS (ESI): m/z 866.65 [M+H].

Example 418

Compound of formula VII, wherein $R_1$ and $R_2$ taken together with the carbon atom to which they are attached are CHNHCOCH$_2$[naphthalen-1-yl], $R_{15}$=Rx=H The title compound was prepared with the title compound of Example 417 via similar conditions described in Example 36.

MS (ESI): m/z 824.55 [M+H].

Example 419

Compound of formula VII, wherein $R_1$ and $R_2$ taken together with the carbon atom to which they are attached are [6-pyrazol-1-yl-pyridin-3-yl], $R_{15}$=H, and Rx=Ac Step 419a.

The compound was prepared from (6-(1H-pyrazol-1-yl)pyridin-3-yl)methanol via similar procedures as described in example 415 steps 415a and 415b.

MS (ESI): m/z 185.12 [M+H].

Step 419b.

The HCl salt of compound step b was prepared from compound step a via similar procedures as described in example 415 step 415c.

MS (ESI): m/z 204.10 [M+H].

Step 419c.

The title compound was prepared from HCl salt of compound step 419b and HCl salt of compound of example 331 via similar procedures as described in example 411.

MS (ESI): m/z 883.58 [M+H].

Example 420

Compound of formula VII, wherein $R_1$ and $R_2$ taken together with the carbon atom to which they are attached are [6-pyrazol-1-yl-pyridin-3-yl], $R_{15}$=Rx=H The title compound was prepared with the title compound of Example 419 via similar conditions described in Example 36.

MS (ESI): m/z 841.58 [M+H].

Example 421

Compound of formula VII, wherein $R_1$ and $R_2$ taken together with the carbon atom to which they are attached are [6-pyrazol-1-yl-pyridin-2-yl], $R_{15}$=H and Rx=Ac Step 421a.

The compound was prepared from compound of (6-(1H-pyrazol-1-yl)pyridin-2-yl)methanol via similar procedures as described in example 415 steps a and b.

MS (ESI): m/z 185.10 [M+H].

Step 421b.

The HCl salt of compound step b was prepared from compound step 421a via similar procedures as described in example 415 step 415c.

MS (ESI): m/z 204.11 [M+H].

Step 421c.

The title compound was prepared from HCl salt of compound step 421b and HCl salt of compound of example 331 via similar procedures as described in example 411.

MS (ESI): m/z 883.59 [M+H].

Example 422

Compound of formula VII, wherein $R_1$ and $R_2$ taken together with the carbon atom to which they are attached are [6-pyrazol-1-yl-pyridin-2-yl], $R_{15}$=Rx=H The title compound was prepared with the title compound of Example 421 via similar conditions described in Example 36.

MS (ESI): m/z 841.56 [M+H].

Example 423

Compound of formula VII, wherein $R_1$ and $R_2$ taken together with the carbon atom to which they are attached are CHCH$_2$CONHPh, $R_{15}$=Rx=H The title compound was prepared from the title compound of Example 288 via similar procedures described in Example 32.

MS (ESI): m/z 774.44 [M+H].

Example 424

Compound of formula VII, wherein $R_1$ and $R_2$ taken together with the carbon atom to which they are attached are CHCH$_2$CONH[naphthalene-1-yl], R=Rx=H The title compound was prepared from the title compound of Example 290 via similar procedures described in Example 32.

MS (ESI): m/z 824.65 [M+H].

Example 425

Compound of formula VII, wherein $R_1$ and $R_2$ taken together with the carbon atom to which they are attached are CHCH$_2$CONH[naphthalene-2-yl], $R_{15}$=Rx=H The title compound was prepared from the title compound of Example 292 via similar procedures described in Example 32.

MS (ESI): m/z 824.65 [M+H].

Example 426

Compound of formula VIII, wherein $R_1$ and $R_2$ taken together with the carbon atom to which they are attached are C=CH$_2$, $R_{20}$=H, and Rx=Ac To a solution of compound from Example 13 in DMF was added hydrazine (4 eq.) and the resulting solution was stirred at room temperature overnight. To this mixture was then added potassium t-butoxide and further stirred at room temperature for 1.5 hours before it was diluted with water and extracted with CH$_2$Cl$_2$ (3×). The organic extracts were dried over Na$_2$SO$_4$, filtered and concentrated under vacuum to give the title compound.

MS (ESI): m/z 710.27 [M+H].

Example 427

Compound of formula VIII, wherein $R_1$ and $R_2$ taken together with the carbon atom to which they are attached are C=CH$_2$, and $R_{20}$=Rx=H The title compound was prepared with the title compound of Example 426 via the same conditions described in Example 12.

MS (ESI): m/z 668.15 [M+H].

$^{13}$C NMR (CDCl$_3$, ppm) δ: 216.8, 177.3, 156.6, 146.1, 117.0, 104.6, 81.9, 80.9, 80.9, 80.8, 77.6, 77.5, 77.0, 76.9, 76.7, 72.8, 70.8, 69.8, 66.1, 64.1, 63.4, 44.3, 43.7, 42.8, 40.9, 40.5, 39.0, 28.4, 23.3, 23.1, 21.5, 19.2, 14.3, 13.7, 11.6, 11.1, 10.9.

Example 428

Compound of formula VIII, wherein $R_1$ and $R_2$ taken together with the carbon atom to which they are attached are C=CH$_2$, $R_{20}$=(phenylpropyl), and Rx=Ac To a mixture of compound from Example 426, 3-phenyl-propionaldehyde (2.4 eq.), and acetic acid (4 eq.) in methanol was added NaBH$_3$CN (4 eq.). The mixture was stirred at room temperature for 3 days. The excess methanol was removed and the mixture was extracted in CH$_2$Cl$_2$. The combined organic extracts were washed with 1N NaOH, water, brine, dried over Na$_2$SO$_4$, filtered and concentrated under vacuum. The residue was purified by column chromatography eluting with Hexanes/CH$_2$Cl$_2$ to give the title compound.

MS (ESI): m/z 786.25 [M+H], 393.78 [M+2H]

$^{13}$C NMR (CDCl$_3$, ppm) δ: 216.0, 177.1, 156.1, 146.0, 142.2, 128.5, 128.3, 125.7, 114.3, 104.6, 81.3, 80.7, 80.6, 80.0, 77.3, 77.0, 76.8, 76.1, 74.0, 70.5, 69.6, 65.9, 64.9, 58.5, 48.5, 43.8, 43.1, 42.9, 41.6, 40.3, 38.4, 33.2, 29.7, 28.2, 23.3, 22.3, 21.2, 19.3, 14.2, 12.8, 12.3, 10.9, 10.8.

Example 429

Compound of formula IX, wherein $R_1$ and $R_2$ taken together with the carbon atom to which they are attached are C=CH$_2$, $R_{20}$=H, and Rx=Ac The title compound was prepared with the title compound of Example 13 via the similar conditions described in Example 426 but with NH$_2$OH.HCl instead of hydrazine.

MS (ESI): m/z 711.24 [M+H].

Example 430

Compound of formula IX, wherein $R_1$ and $R_2$ taken together with the carbon atom to which they are attached are C=CH$_2$, and $R_{20}$=Rx=H The title compound was prepared with the title compound of Example 429 via the same conditions described in Example 12.

MS (ESI): m/z 669.16 [M+H].

Example 431

Compound of formula IX, wherein $R_1$ and $R_2$ taken together with the carbon atom to which they are attached are C=CH$_2$, $R_{20}$=(phenylpropyl) and Rx=Ac The title compound was prepared from the title compound of Example 13 and commercially available O-(3-phenyl-propyl)-hydroxylamine via the similar conditions described in Example 18.

MS (ESI): m/z 829.03 [M+H].

Example 432

Compound of formula II, wherein $R_1$ and $R_2$ taken together with the carbon atom to which they are attached are C(OH)CH$_2$OH, W=$R_{20}$=H, and $R_6$=Rx=Bz A mixture of the title compound from Example 2 (1.18 mmol), NMO (4 eq.), pyridine (1 eq.), and osmium tetroxide (20 mol %) in acetone/water (20 ml:5 ml) was allowed to stir at room temperature overnight. The excess acetone and the residue was diluted with EtOAc and the resulting mixture was washed once with sodium bisulfite solution, twice with NaHCO$_3$, once with water and once with brine, dried over Na$_2$SO$_4$, filtered and concentrated under vacuo. The residue was purified by column chromatography to give the desired title compound in 70% yield.

MS (ESI): m/z 885.10 [M+H].

Example 433

Compound of formula II, wherein $R_1$ and $R_2$ taken together with the carbon atom to which they are attached are C(OH)CH$_2$OH, and W=$R_{20}$=$R_6$=Rx=H A mixture of the title compound from Example 432 (30 mg) and 1N KOH (6 eq.) in methanol (1 ml) was stirred at room temperature overnight. The mixture was purified by column chromatography eluting with 10% 2N NH$_3$/methanol to give 19 mg of the desired title compound.

MS (ESI): m/z 677.09 [M+H].

Example 434

Compound of formula V, wherein $R_1$ and $R_2$ taken together with the carbon atom to which they are attached are C=O, and Rx=Ac The title compound was prepared with the title compound of Example 11 via similar conditions described in Example 16.

MS (ESI): m/z 698.46 [M+H].

Example 435

Compound of formula V, wherein $R_1$ and $R_2$ taken together with the carbon atom to which they are attached are C=O, and Rx=H The title compound was prepared with the title compound of Example 434 via similar conditions described in Example 12.

MS (ESI): m/z 656.33 [M+H].

$^{13}$C NMR (CDCl$_3$, ppm) δ: 212.4, 209.7, 176.6, 153.2, 105.4, 85.8, 82.3, 81.5, 81.0, 80.1, 76.3, 70.6, 70.0, 67.9, 66.0, 44.6, 43.1, 42.4, 41.3, 40.5, 37.2, 28.4, 22.8, 22.7, 21.4, 19.9, 14.6, 12.4, 12.0, 11.0, 10.8.

Example 436

Compound of formula V, wherein $R_1$ and $R_2$ taken together with the carbon atom to which they are attached are C=NO[6'-amino-[2,2']bipyridinyl-6-ylmethyl], and Rx=Ac The title compound was prepared with the title compound of Example 434 and O-(6'-amino-[2,2']bipyridinyl-6-ylmethyl)-hydroxylamine (prepared according to literature procedure) via similar conditions outlined in Example 35.

MS (ESI): m/z 896.49 [M+H], 448.74 [M+2H].

Example 437

Compound of formula V, wherein $R_1$ and $R_2$ taken together with the carbon atom to which they are attached are C=NO[6'-amino-[2,2']bipyridinyl-6-ylmethyl], and Rx=H The title compound was prepared with the title compound of Example 436 via similar conditions described in Example 36. E:Z ratio was 2:1.

MS (ESI): m/z 854.51 [M+H], 427.75 [M+2H].

E-isomer:

MS (ESI): m/z 854.51 [M+H], 427.75 [M+2H].

$^{13}$C NMR (CDCl$_3$, ppm) δ: 212.5, 177.1, 158.8, 158.2, 157.8, 155.9, 155.0, 153.3, 138.8, 137.6, 121.3, 119.9, 112.1, 109.0, 105.2, 86.1, 81.2, 80.7, 80.5, 79.7, 76.5, 70.7, 69.9, 66.6, 66.0, 61.3, 44.6, 43.2, 43.0, 40.5, 40.2, 37.9, 29.9, 28.4, 23.4, 22.8, 21.4, 19.5, 14.7, 12.3, 12.0, 11.0, 10.9.

Z-isomer:

MS (ESI): m/z 854.51 [M+H], 427.75 [M+2H].

$^{13}$C NMR (CDCl$_3$, ppm) δ: 212.4, 176.1, 159.1, 157.9, 157.4, 155.9, 154.7, 153.1, 138.6, 137.2, 121.2, 119.7, 111.9, 108.8, 104.9, 85.8, 82.5, 81.1, 80.9, 80.0, 76.1, 73.0, 70.4, 69.7, 65.8, 58.4, 43.9, 43.2, 41.9, 41.5, 40.2, 37.6, 29.7, 28.2, 22.9, 22.6, 21.2, 19.5, 14.6, 12.7, 11.9, 10.9, 10.7.

Example 438

Compound of formula X, wherein X and Y taken together with the carbon atom to which they are attached are C=NOH, $R_1$ and $R_2$ taken together with the carbon atom to which they are attached are C=CH$_2$, and Rx=Ac An EtOH and water (1:1, v/v) solution of the title compound of Example 14 and hydroxylamine hydrochloride was stirred at 90° C. for 24 hours. The mixture was quenched with saturated NaHCO$_3$ and extracted with EtOAc. The combined organic extracts were washed with brine, dried, filtered and concentrated under vacuum. The residue was carried directly to the next step without purification.

MS (ESI): m/z 710.39 [M+H].

Example 439

Compound of formula X, wherein X and Y taken together with the carbon atom to which they are attached are C=NOH, $R_1$ and $R_2$ taken together with the carbon atom to which they are attached are C=CH$_2$, and Rx=H The title compound was prepared with the title compound of Example 438 via similar conditions described in Example 36. E:Z ratio was 7.6:1.

MS (ESI): m/z 668.45 [M+H].

E-isomer:

MS (ESI): m/z 668.45 [M+H].

$^{13}$C NMR (CDCl$_3$, ppm) δ: 177.4, 169.3, 158.9, 144.9, 117.6, 104.6, 85.1, 80.9, 80.8, 76.8, 75.1, 72.7, 70.9, 66.1, 63.9, 60.6, 43.8, 42.6, 40.5, 38.5, 33.6, 28.5, 23.6, 21.9, 21.4, 19.5, 16.7, 13.7, 11.8, 11.0, 10.6.

Z-isomer:

MS (ESI): m/z 668.45 [M+H].

Example 440

Compound of formula X, wherein X and Y taken together with the carbon atom to which they are attached are C=NOCH$_3$, $R_1$ and $R_2$ taken together with the carbon atom to which they are attached are C=CH$_2$, and Rx=Ac The title compound was prepared with the title compound of Example 14 and O-methyl-hydroxylamine hydrochloride via similar conditions described in Example 438.

MS (ESI): m/z 724.80 [M+H].

Example 441

Compound of formula X, wherein X and Y taken together with the carbon atom to which they are attached are C=NOCH, $R_1$ and $R_2$ taken together with the carbon atom to which they are attached are C=CH$_2$ and Rx=H The title compound was prepared with the title compound of Example 440 via similar conditions described in Example 36. E:Z ratio was 1.4:1.

MS (ESI): m/z 682.70 [M+H].

E-isomer:

MS (ESI): m/z 682.70 [M+H].

$^{13}$C NMR (CDCl$_3$, ppm) δ: 177.4, 168.2, 158.9, 144.9, 117.5, 104.6, 85.0, 80.9, 80.8, 76.9, 75.1, 72.6, 70.8, 69.7, 66.1, 63.6, 61.9, 60.6, 43.8, 42.6, 40.5, 38.5, 33.5, 29.9, 28.5, 26.4, 23.6, 21.8, 21.4, 19.4, 16.9, 13.7, 11.8, 11.0, 10.5.

Z-isomer:

MS (ESI): m/z 682.70 [M+H].

$^{13}$C NMR (CDCl$_3$, ppm) δ: 177.4, 164.3, 158.9, 145.3, 116.7, 104.6, 86.0, 80.9, 80.8, 77.2, 75.9, 72.7, 70.8, 69.7, 66.1, 62.7, 61.7, 58.5, 43.7, 42.5, 40.5, 38.5, 35.5, 34.9, 29.9, 28.5, 24.0, 21.8, 21.4, 20.3, 14.4, 11.9, 11.7, 10.9, 10.4.

Example 442

Compound of formula X, wherein X and Y taken together with the carbon atom to which they are attached are C=NOCH$_2$CH$_3$, R$_1$ and R$_2$ taken together with the carbon atom to which they are attached are C=CH$_2$, and Rx=Ac The title compound was prepared with the title compound of Example 14 and O-ethyl-hydroxylamine hydrochloride via similar conditions described in Example 438.

MS (ESI): m/z 738.03 [M+H].

Example 443

Compound of formula X, wherein X and Y taken together with the carbon atom to which they are attached are C=NOCH$_2$CH$_3$, R$_1$ and R$_2$ taken together with the carbon atom to which they are attached are C=CH$_2$, and Rx=H The title compound was prepared with the title compound of Example 442 via similar conditions described in Example 36. E:Z ratio was 1.6:1.

MS (ESI): m/z 696.14 [M+H].

E-isomer:

MS (ESI): m/z 696.14 [M+H].

$^{13}$C NMR (CDCl$_3$, ppm) δ: 177.4, 167.8, 158.9, 144.9, 117.5, 104.6, 85.0, 81.0, 80.7, 75.1, 72.6, 70.8, 69.7, 69.4, 66.1, 63.5, 60.7, 43.8, 42.6, 40.5, 38.5, 33.4, 29.9, 28.5, 26.4, 23.6, 21.8, 21.5, 19.5, 16.9, 14.8, 13.7, 11.8, 11.0, 10.5.

Z-isomer:

MS (ESI): m/z 696.14 [M+H].

$^{13}$C NMR (CDCl$_3$, ppm) δ: 177.4, 164.0, 158.9, 145.4, 116.5, 104.7, 86.0, 81.0, 80.7, 76.0, 72.8, 70.8, 69.7, 69.6, 66.1, 62.8, 58.6, 43.7, 42.5, 40.5, 38.5, 35.5, 34.9, 29.9, 28.5, 24.0, 21.8, 21.4, 20.4, 14.9, 14.4, 11.9, 11.7, 10.9, 10.4.

Example 444

Compound of formula X, wherein X and Y taken together with the carbon atom to which they are attached are C=NOCH$_2$CH$_3$, R$_1$ and R$_2$ taken together with the carbon atom to which they are attached are C=NO[quinoxalin-6-ylmethyl], and Rx=H The title compound was prepared with the title compound of Example 113 via similar conditions described in Example 438. E:Z ratio was 2:1.

MS (ESI): m/z 827.25 [M+H], 414.29 [M+2H].

E-isomer:

MS (ESI): m/z 827.25 [M+H], 414.29 [M+2H].

Z-isomer:

MS (ESI): m/z 827.25 [M+H], 414.29 [M+2H].

Examples (445)-(606) of the formula B

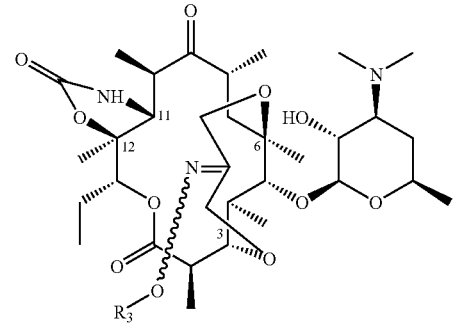

wherein R$_3$ is delineated for each example in Table 3.

Examples 445-606 are made from the title compound of Example 16 and the appropriate hydroxylamine of formula R$_3$—O—NH$_2$ via similar method delineated in Example 35.

In all of the following examples a mixture of E and Z isomers are present which may be separated by crystallization or HPLC.

The substituted hydroxylamines used in the following examples are either commercially available or can be made according to PCT Application WO 03/097659 A1 and US Application US 2004/0157787 A1.

What is claimed:

1. Compounds represented by formula (I):

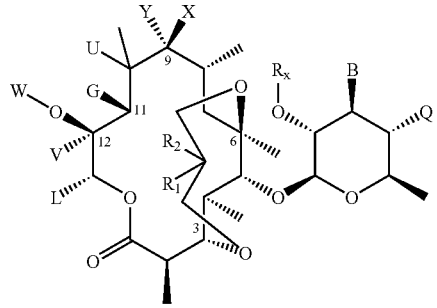

or the pharmaceutically acceptable salts, esters and prodrugs thereof, wherein R$_1$ is selected from the group consisting of:
  a) hydrogen;
  b) deuterium;
  c) —CH2OH;
  d) aryl;
  e) substituted aryl;
  f) heteroaryl;
  g) substituted heteroaryl; and
  h) —C$_1$-C$_6$ alkyl, —C$_2$-C$_6$ alkenyl, or —C$_2$-C$_6$ alkynyl containing 0, 1, 2, or 3 heteroatoms selected from O, S or N, optionally substituted with one or more substituents selected from halogen, aryl, substituted aryl, heteroaryl, or substituted heteroaryl;

R$_2$ is selected from the group consisting of:
  a) hydrogen;
  b) hydroxy; and
  c) activated hydroxy;

when R$_1$ is H, R$_2$ is selected from the group consisting of:
  a) hydrogen;

b) hydroxy;
c) activated hydroxy;
d) $N_3$;
e) $NH_2$;
f) CN;
g) protected hydroxy;
h) protected amino;
i) -A-$R_3$, where A is O, S, S(O), $SO_2$, NH, $NCH_3$, NH(CO), NH(CO)NH or $NHSO_2$; and $R_3$ is independently selected from the group consisting of:
   (i) hydrogen;
   (ii) aryl;
   (iii) substituted aryl;
   (iv) heteroaryl;
   (v) substituted heteroaryl;
   (vi) —$C_1$-$C_6$ alkyl, —$C_2$-$C_6$ alkenyl, or —$C_2$-$C_6$ alkynyl containing 0, 1, 2, or 3 heteroatoms selected from O, S or N, optionally substituted with one or more substituents selected from halogen, aryl, substituted aryl, heteroaryl, or substituted heteroaryl;
   provided that when A=S(O) or $SO_2$, $R_3$ cannot be hydrogen; and
(j)

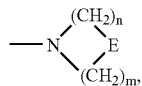

wherein L is absent, O, S, S(O), $S(O)_2$, $NR_3$, $N(CO)R_3$, $NSO_2R_3$, or $CHR_3$; n=1, 2, or 3; and m=2 or 3, where $R_3$ is as previously defined;
or alternatively, $R_1$ and $R_2$ taken together with the carbon atom to which they are attached is:
a) C=O;
b) C($OR_4$)($OR_5$), where $R_4$ and $R_5$ are selected from the group consisting of $C_1$-$C_{12}$ alkyl, aryl or substituted aryl; or taken together are —$(CH_2)_m$—, and where m is 2 or 3;
c) C($SR_4$)($SR_5$), where $R_4$ and $R_5$ are as previously defined above;
d) C=$CHR_3$, where $R_3$ is as previously defined;
e) C=CNH; or
f) C=N-Z-$R_3$, where Z is absent, O, NH, NH(CO), NH(CO)NH or $NHSO_2$; and $R_3$ is as previously defined;
X and Y are:
a) when one of X and Y is a hydrogen, the other is selected from:
   (i) hydrogen;
   (ii) deuterium;
   (iii) hydroxy;
   (iv) protected hydroxy;
   (v) amino;
   (vi) protected amino; or
   (vii)

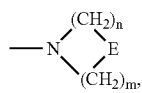

wherein L is absent, O, S, S(O), $S(O)_2$, $NR_3$, $N(CO)R_3$, $NSO_2R_3$, or $CHR_3$; n=1, 2, or 3; and m=2 or 3, where $R_3$ is as previously defined;
b) X and Y taken together with the carbon atom to which they are attached is:
   (i) C=O;

(ii) C=N—$OR_6$, wherein $R_6$ is selected from the group consisting of:
   1. hydrogen;
   2. —$CH_2O(CH_2)_2OCH_3$;
   3. —$CH_2O(CH_2O)_nCH_3$, wherein n is as previously defined;
   4. —$C_1$-$C_{12}$ alkyl, containing 0, 1, 2, or 3 heteroatoms, optionally substituted with one or more substituents selected from the group consisting of halogen, aryl, substituted aryl, heteroaryl and substituted heteroaryl;
   5. $C_3$-$C_{12}$ cycloalkyl;
   6. C(O)—$C_1$-$C_{12}$ alkyl;
   7. C(O)—($C_3$-$C_{12}$ cycloalkyl);
   8. C(O)—$R_3$, wherein R3 is as previously defined; and
   9. —Si($R_a$)($R_b$)($R_c$), wherein $R_a$, $R_b$ and $R_c$ are each independently selected from the group consisting of $C_1$-$C_{12}$ alkyl, aryl and substituted aryl; or
(iii) C=N—O—C($R_7$)($R_8$)—O—$R_9$, wherein $R_7$ and $R_8$ taken together with the carbon atom to which they are attached form a $C_3$ to $C_{12}$ cycloalkyl group or each independently is selected from the group consisting of: hydrogen and $C_1$-$C_{12}$ alkyl; and $R_9$ is selected from the group consisting of:
   1. —$C_{1-C12}$ alkyl, optionally substituted with one or more substituents selected from the group consisting of halogen, aryl, substituted aryl, heteroaryl and substituted heteroaryl;
   2. —$C_3$-$C_{12}$ cycloalkyl; and
   3. —Si($R_a$)($R_b$)($R_c$), wherein $R_a$, $R_b$ and $R_c$ are as previously defined;
W is selected from the group consisting of:
a) hydrogen;
b) methyl;
c) allyl; and
d) —$OCH_2SCH_3$
G is selected from the group consisting of:
a) hydroxy;
b) —O-aryl; —O-substituted aryl; —O-heteroaryl; —O-substituted heteroaryl; and
c) —$OC_1$-$C_6$ alkyl, —$OC_2$-$C_6$ alkenyl, or —$OC_2$-$C_6$ alkynyl containing 0, 1, 2, or 3 heteroatoms selected from O, S or N, optionally substituted with one or more substituents selected from halogen, aryl, substituted aryl, heteroaryl, or substituted heteroaryl;
U is hydrogen;
when U and G are taken together to form a bond, W is selected from the group consisting of:
a) hydrogen; and
b) —C(O)LGp, where LGp is a leaving group selected from Cl, imidazole, triazole, cyano, and p-nitrobenzene;
or alternatively, structure

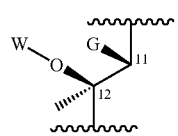

of formula (I) taken together is:

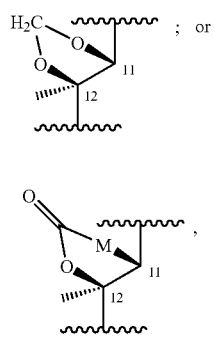

where M is O or N-J-$R_{20}$, and where J is absent, O, NH, NH(CO), or N=CH; and $R_{20}$ is selected from the group consisting of:
i. hydrogen;
ii. aryl; substituted aryl; heteroaryl; substituted heteroaryl; and
iii. —$C_1$-$C_6$ alkyl, —$C_2$-$C_6$ alkenyl, or —$C_2$-$C_6$ alkynyl containing 0, 1, 2, or 3 heteroatoms selected from O, S or N, optionally substituted with one or more substituents selected from halogen, aryl, substituted aryl, heteroaryl, or substituted heteroaryl;

B is $NR_{30}R_{40}$; wherein $R_{30}$ and $R_{40}$ is independently selected from the group consisting of hydrogen, acyl, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, saturated or unsaturated heterocyclic group; or can be taken together with the nitrogen atom to which they are attached to form a substituted or unsubstituted heterocyclic or heteroaromatic ring;

V is selected from the group consisting of hydrogen, azido, cyano, nitro, aldehyde, carboxylic acid, amide, a substituted or unsubstituted, saturated or unsaturated aliphatic group;

Q is selected from the group consisting of:
(a) hydrogen;
(b) protected hydroxy; and
(c) $OR_{21}$, where $R_{21}$ is selected from the group consisting of:
(i) hydrogen;
(ii) aryl; substituted aryl; heteroaryl; substituted heteroaryl;
(iii) —$C_1$-$C_6$ alkyl, —$C_2$-$C_6$ alkenyl, or —$C_2$-$C_6$ alkynyl containing 0, 1, 2, or 3 heteroatoms selected from O, S or N, optionally substituted with one or more substituents selected from halogen, aryl, substituted aryl, heteroaryl, or substituted heteroaryl; and
(iv) —$C_3$-$C_{12}$ cycloalkyl containing 0, 1, 2, or 3 heteroatoms selected from O, S or N, optionally substituted with one or more substituents selected from halogen, aryl, substituted aryl, heteroaryl, or substituted heteroaryl;

L is selected from the group consisting of:
(a) —$CH_2CH_3$;
(b) —$CH(OH)CH_3$; and
(c) —$C_1$-$C_6$ alkyl, —$C_2$-$C_6$ alkenyl, or —$C_2$-$C_6$ alkynyl optionally substituted with one or more substituents selected from the group consisting of aryl, substituted aryl, heteroaryl, and substituted heteroaryl; and Rx is hydrogen, hydroxy protecting group or hydroxy prodrug group.

2. A compound according to claim 1 represented by formula (II):

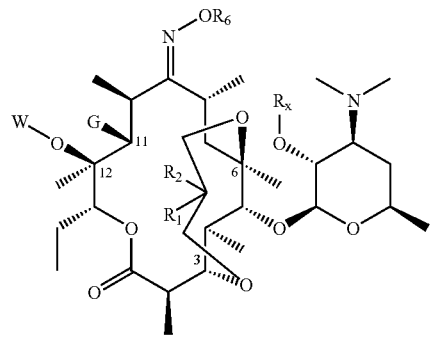

where W, $R_1$, $R_2$, $R_{20}$, $R_6$ and $R_x$ are as previously defined in claim 1.

3. A compound according to claim 1 represented by formula (III):

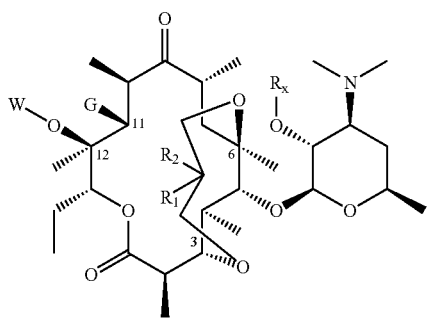

where W, $R_1$, $R_2$, $R_{20}$ and $R_x$ are as previously defined in claim 1.

4. A compound according to claim 1 represented by formula (IV):

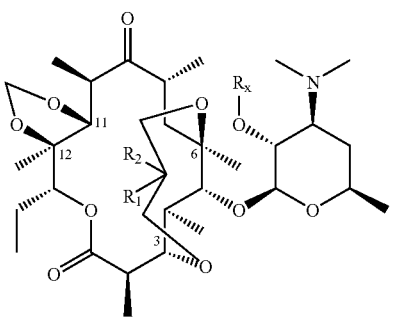

where $R_1$, $R_2$ and $R_x$ are as previously defined in claim 1.

5. A compound according to claim 1 represented by formula (V):

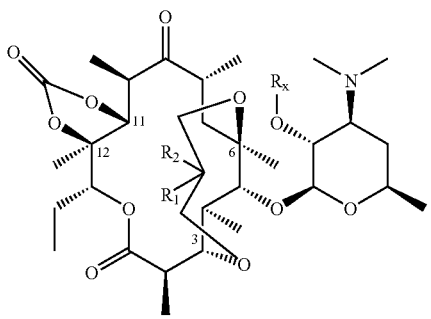

(V)

where $R_1$, $R_2$ and $R_x$ are as previously defined in claim 1.

6. A compound according to claim 1 represented by formula (VI):

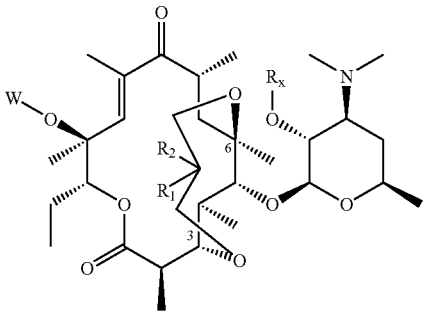

(VI)

where W, $R_1$, $R_2$ and $R_x$ are as previously defined in claim 1.

7. A compound according to claim 1 represented by formula (VII):

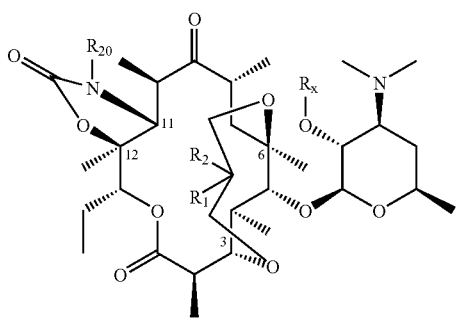

(VII)

where $R_1$, $R_2$, $R_x$ and $R_{20}$ are as previously defined in claim 1.

8. A compound according to claim 1 represented by formula (VIII):

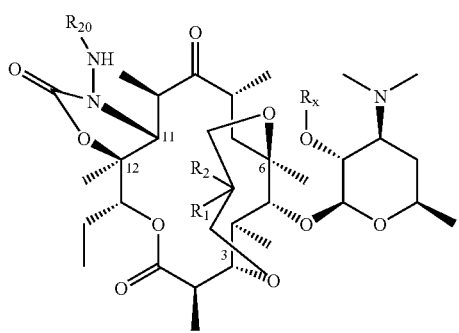

(VIII)

where $R_1$, $R_2$, $R_x$ and $R_{20}$ are as previously defined in claim 1.

9. A compound according to claim 1 represented by formula (IX):

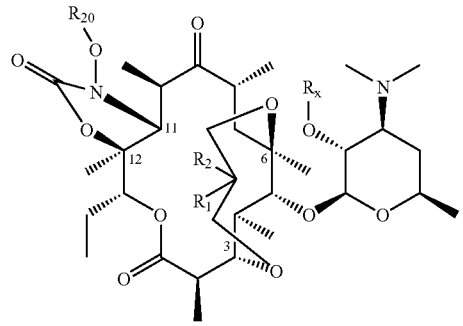

(IX)

where $R_1$, $R_2$, $R_x$ and $R_{20}$ are as previously defined in claim 1.

10. A compound according to claim 1 represented by formula (X):

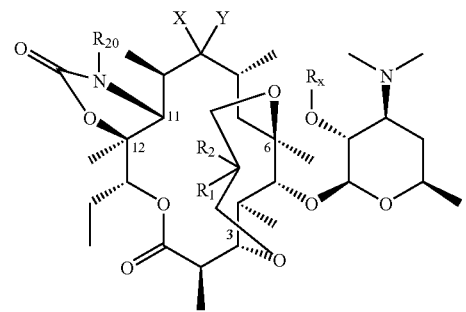

(X)

where $R_1$, $R_2$, X, Y, $R_x$ and $R_{20}$ are as previously defined in claim 1.

11. A compound of claim 1 having the Formula A, selected from compounds 1-10b of Table 1:

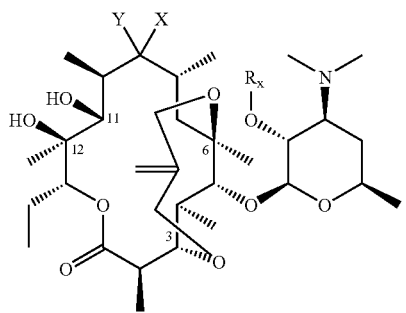

(A)

TABLE 1

| Compound | CXY | Rx |
|---|---|---|
| (1) | C=NOAc | Ac |
| (2) | C=NOBz | Bz |
| (3) | C=NOSiEt$_3$ | SiEt$_3$ |
| (4) | ![cyclohexyl-isopropoxy C=NO] | Ac |

TABLE 1-continued

| Compound | CXY | Rx |
|---|---|---|
| (5) | C—NO—C(CH₃)₂—O—iPr (structure) | Ac |
| (6) | C=NOH | H |
| (7) | C=NH | H |
| (8) | CH(NH₂) | H |
| (9) | C=O | H |
| (10) | C=O | Ac |
| (10a) | C=NAc | Ac |
| (10b) | C=NAc | H. |

12. A compound of claim 5, wherein $R_1$ and $R_2$ taken together with the carbon atom to which they are attached is C=CH$_2$, and Rx is Ac or H.

13. A compound of claim 6, wherein $R_1$ and $R_2$ taken together with the carbon atom to which they are attached is C=CH$_2$, W is C(O)-(imidazol-1-yl) and Rx is H.

14. A compound of claim 7, selected from compounds 14 to 300 of Table 2:

TABLE 2

| Compound | R$_{20}$ | CR$_1$R$_2$ | Rx |
|---|---|---|---|
| (14) | H | C=CH$_2$ | Ac |
| (15) | H | C=CH$_2$ | H |
| (16) | H | C=O | Ac |
| (17) | H | C=O | H |
| (18) | –(CH₂)₄–Ph | C=CH$_2$ | Ac |
| (19) | –(CH₂)₄–Ph | C=CH$_2$ | H |
| (20) | –(CH₂)₃–Ph | C=CH$_2$ | Ac |
| (21) | –(CH₂)₃–Ph | C=CH$_2$ | H |
| (22) | –(CH₂)₅–Ph | C=CH$_2$ | Ac |
| (23) | –(CH₂)₅–Ph | C=CH$_2$ | H |
| (24) | –(CH₂)₄–(4-(pyridin-3-yl)imidazol-1-yl) | C=CH$_2$ | Ac |
| (25) | –(CH₂)₄–(4-(pyridin-3-yl)imidazol-1-yl) | C=CH$_2$ | H |

TABLE 2-continued
| Compound | R20 | CR1R2 | Rx |
|---|---|---|---|
| (26) | 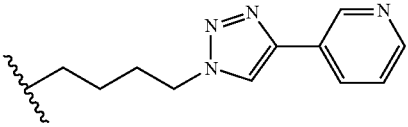 | C=CH2 | Ac |
| (27) | 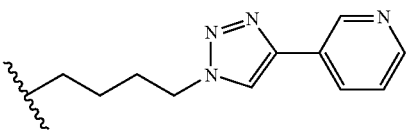 | C=CH2 | H |
| (28) | 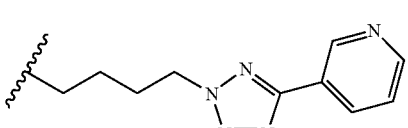 | C=CH2 | Ac |
| (29) | 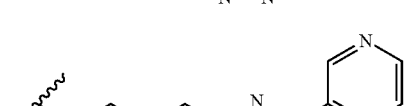 | C=CH2 | H |
| (30) | 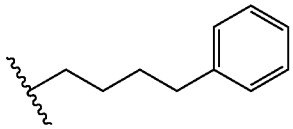 | C=O | Ac |
| (31) | 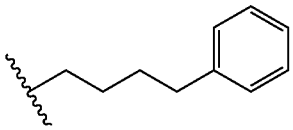 | C=O | H |
| (32) | 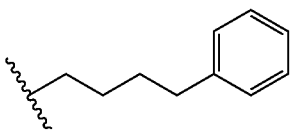 | CHCH3 | H |
| (33) | 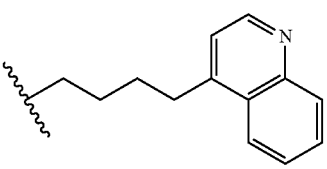 | C=CH2 | Ac |
| (34) | 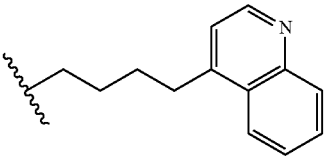 | C=CH2 | H |
| (35) | H | C=NO[CH2Ph] | Ac |
| (36) | H | C=NO[CH2Ph] | H |
| (37) | H | C=NO[(CH2)2Ph] | Ac |
| (38) | H | C=NO[(CH2)2Ph] | H |
| (39) | H | C=NO[(CH2)3Ph] | Ac |
| (40) | H | C=NO[(CH2)3Ph] | H |
| (41) | H | C=NO[(CH2)4Ph] | Ac |
| (42) | H | C=NO[(CH2)4Ph] | H |

TABLE 2-continued

| Compound | R₂₀ | CR₁R₂ | Rx |
|---|---|---|---|
| (43) | H | C=NO[Ph] | Ac |
| (44) | H | C=NO[Ph] | H |
| (45) | H | C=NO[(CH₂)₅Ph] | Ac |
| (46) | H | C=NO[(CH₂)₅Ph] | H |
| (47) | H | C=N—O—CH₂-(pyridyl-pyrazole) | Ac |
| (48) | H | C=N—O—CH₂-(pyridyl-pyrazole) | H |
| (49) | H | C=N—O-(4-isobutylphenyl) | Ac |
| (50) | H | C=N—O-(4-isobutylphenyl) | H |
| (51) | H | C=N—O-(biphenyl) | Ac |
| (52) | H | C=N—O-(biphenyl) | H |
| (53) | H | C=N—O-(naphthyl) | Ac |
| (54) | H | C=N—O-(naphthyl) | H |
| (55) | H | C=N—O-(pyridyl) | Ac |
| (56) | H | C=N—O-(pyridyl) | H |
| (57) | H | C=NNH[Ph] | Ac |
| (58) | H | C=NNH[Ph] | H |
| (59) | H | C=CH[CH=CHPh] | Ac |
| (60) | H | CH(CH₂)₃Ph | H |
| (61) | H | CHCH₃ | H |
| (62) | H | CHOH | Ac |
| (63) | H | CHOH | H |
| (64) | H | C=N—O-(phenyl-O-benzyl) | Ac |

TABLE 2-continued
| Compound | R$_{20}$ | CR$_1$R$_2$ | Rx |
|---|---|---|---|
| (65) | H | 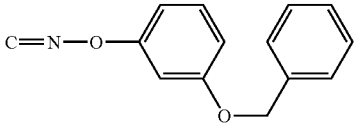 | H |
| (66) | H | 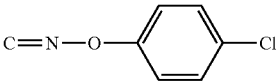 | Ac |
| (67) | H | 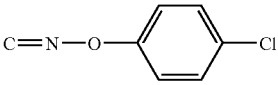 | H |
| (68) | H | 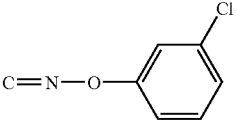 | Ac |
| (69) | H | 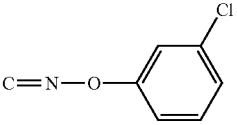 | H |
| (70) | H | 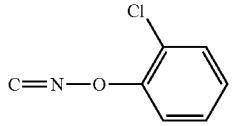 | Ac |
| (71) | H | 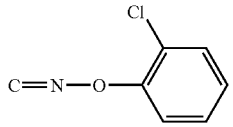 | H |
| (72) | H | 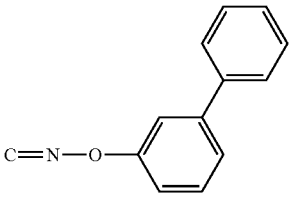 | Ac |
| (73) | H | 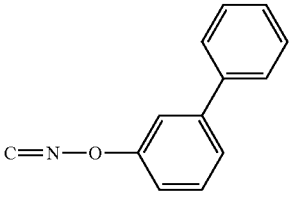 | H |
| (74) | H | 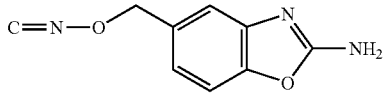 | Ac |
| (75) | H | 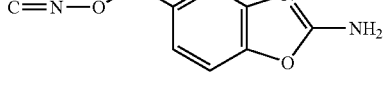 | H |

TABLE 2-continued
| Compound | R$_{20}$ | CR$_1$R$_2$ | Rx |
|---|---|---|---|
| (76) | H | 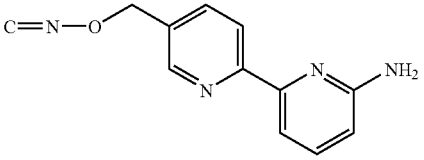 | Ac |
| (77) | H | 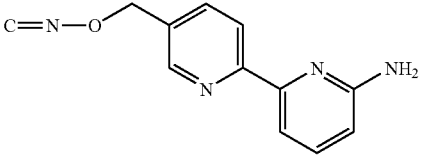 | H |
| (78) | 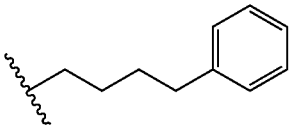 | C=NO[Ph] | Ac |
| (79) | 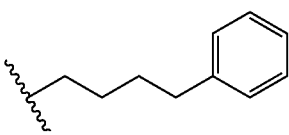 | C=NO[Ph] | H |
| (80) | 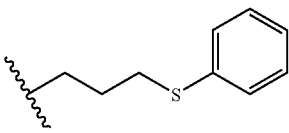 | C=CH$_2$ | H |
| (81) | 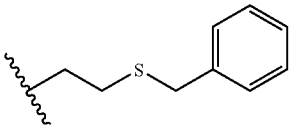 | C=CH$_2$ | H |
| (82) | H | 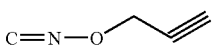 | Ac |
| (83) | H | 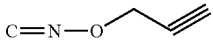 | H |
| (84) | H | 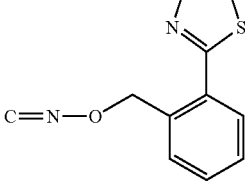 | Ac |
| (85) | H | 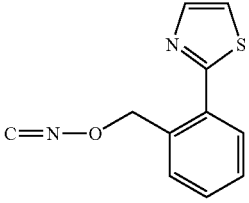 | H |

TABLE 2-continued
| Compound | R20 | CR1R2 | Rx |
|---|---|---|---|
| (86) | H | 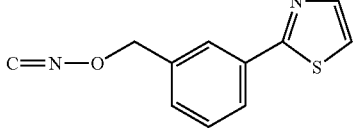 | Ac |
| (87) | H | 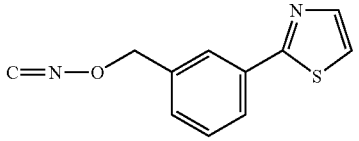 | H |
| (88) | H | 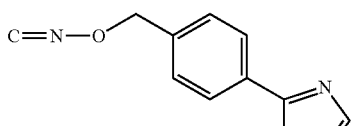 | Ac |
| (89) | H | 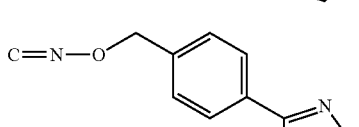 | H |
| (90) | H | 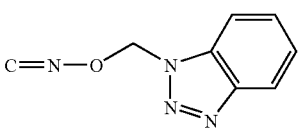 | Ac |
| (91) | H | 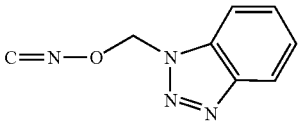 | H |
| (92) | H | 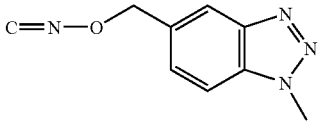 | Ac |
| (93) | H | 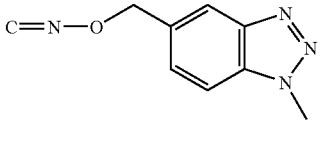 | H |
| (94) | H | 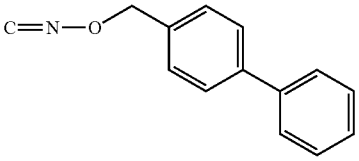 | Ac |
| (95) | H | 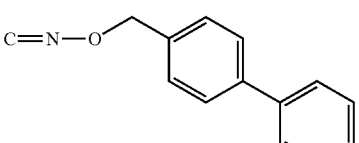 | H |

TABLE 2-continued
| Compound | R$_{20}$ | CR$_1$R$_2$ | Rx |
|---|---|---|---|
| (96) | H | 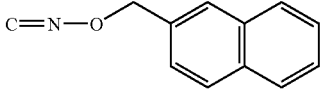 | Ac |
| (97) | H | 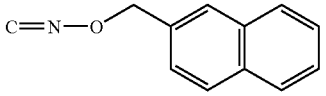 | H |
| (98) | H | 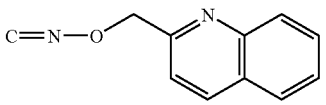 | Ac |
| (99) | H | 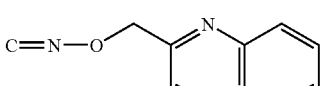 | H |
| (100) | H | 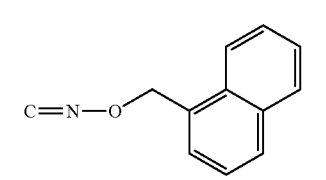 | Ac |
| (101) | H | 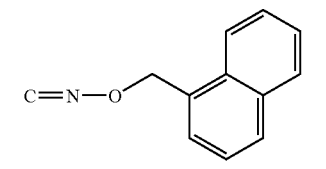 | H |
| (102) | H | 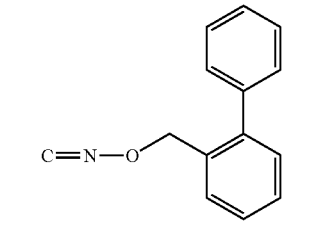 | Ac |
| (103) | H | 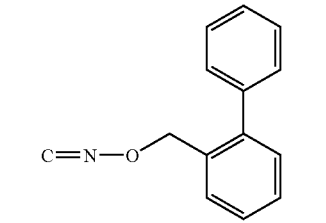 | H |
| (104) | H | 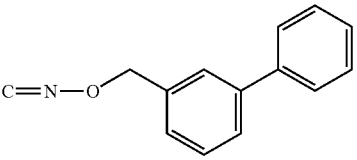 | Ac |

TABLE 2-continued

| Compound | R20 | CR1R2 | Rx |
|---|---|---|---|
| (105) | H | C=N—O—CH2-(3-phenylphenyl) | H |
| (106) | H | C=N—O—CH2-(quinolin-4-yl) | Ac |
| (107) | H | C=N—O—CH2-(quinolin-4-yl) | H |
| (108) | H | C=N—O—CH2-(4-(1,2,4-triazol-1-yl)phenyl) | Ac |
| (109) | H | C=N—O—CH2-(4-(1,2,4-triazol-1-yl)phenyl) | H |
| (110) | H | C=N—O—CH2-(5-(4-methylphenyl)-1,3,4-oxadiazol-2-yl) | Ac |
| (111) | H | C=N—O—CH2-(5-(4-methylphenyl)-1,3,4-oxadiazol-2-yl) | H |
| (112) | H | C=N—O—CH2-(quinoxalin-6-yl) | Ac |
| (113) | H | C=N—O—CH2-(quinoxalin-6-yl) | H |
| (114) | H | C=N—O—CH2-(3-(pyrazol-1-yl)phenyl) | Ac |

TABLE 2-continued
| Compound | R20 | CR1R2 | Rx |
|---|---|---|---|
| (115) | H | 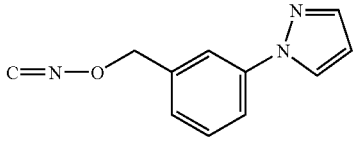 | H |
| (116) | H | 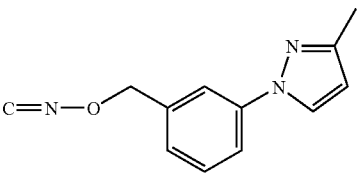 | Ac |
| (117) | H | 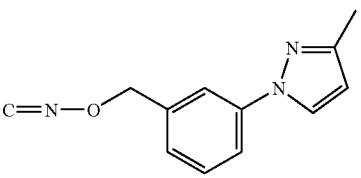 | H |
| (118) | H | 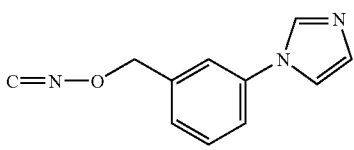 | Ac |
| (119) | H | 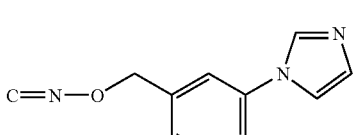 | H |
| (120) | H | 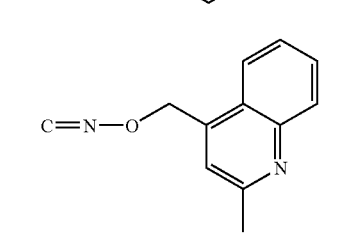 | Ac |
| (121) | H | 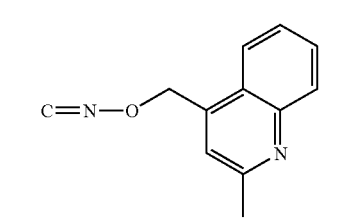 | H |
| (122) | H | 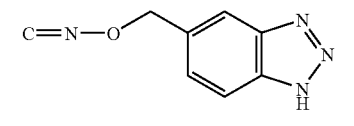 | Ac |
| (123) | H | 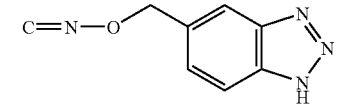 | H |

TABLE 2-continued

| Compound | R₂₀ | CR₁R₂ | Rx |
|---|---|---|---|
| (124) | H | C=N—O—CH₂—(benzotriazole-N-phenyl) | Ac |
| (125) | H | C=N—O—CH₂—(benzotriazole-N-phenyl) | H |
| (126) | H | C=N—O—CH₂—(2-amino-3-hydroxypyridin-6-yl) | Ac |
| (127) | H | C=N—O—CH₂—(2-amino-3-hydroxypyridin-6-yl) | H |
| (128) | H | C=N—O—CH₂—(oxazolo[4,5-b]pyridin-5-yl) | Ac |
| (129) | H | C=N—O—CH₂—(oxazolo[4,5-b]pyridin-5-yl) | H |
| (130) | H | C=N—O—CH₂—(2-amino-oxazolo[4,5-b]pyridin-5-yl) | Ac |
| (131) | H | C=N—O—CH₂—(2-amino-oxazolo[4,5-b]pyridin-5-yl) | H |
| (132) | H | C=N—O—CH₂—(1-ethyl-benzotriazol-7-yl) | Ac |
| (133) | H | C=N—O—CH₂—(1-ethyl-benzotriazol-7-yl) | H |
| (134) | H | C=N—OH | Ac |
| (135) | H | C=N—OH | H |

TABLE 2-continued

| Compound | R₂₀ | CR₁R₂ | Rx |
|---|---|---|---|
| (136) | H | *pyridine with tetrazole, C=N-O-CH₂-* | Ac |
| (137) | H | *pyridine with tetrazole, C=N-O-CH₂-* | H |
| (138) | H | *pyridine with isoxazole, C=N-O-CH₂-* | Ac |
| (139) | H | *pyridine with isoxazole, C=N-O-CH₂-* | H |
| (140) | H | *pyridine with pyrazole, C=N-O-CH₂-* | Ac |
| (141) | H | *pyridine with pyrazole, C=N-O-CH₂-* | H |
| (142) | H | *benzotriazole, C=N-O-CH₂-* | Ac |
| (143) | H | *benzotriazole, C=N-O-CH₂-* | H |
| (144) | H | *pteridine-2,4-diamine, C=N-O-CH₂-* | Ac |

TABLE 2-continued
| Compound | R20 | CR1R2 | Rx |
|---|---|---|---|
| (145) | H | 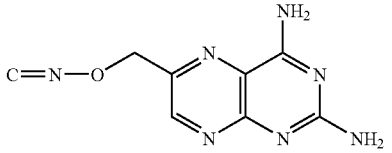 | H |
| (146) | H | 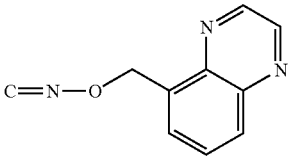 | Ac |
| (147) | H | 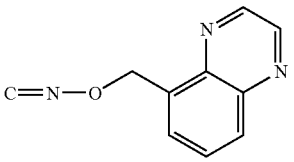 | H |
| (148) | H | 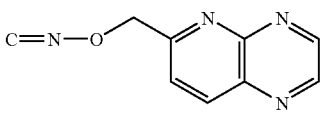 | Ac |
| (149) | H | 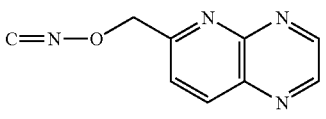 | H |
| (150) | H | 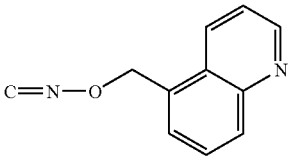 | Ac |
| (151) | H | 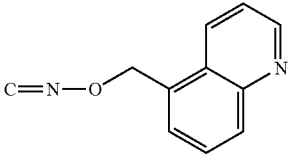 | H |
| (152) | H | 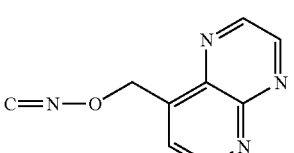 | Ac |
| (153) | H | 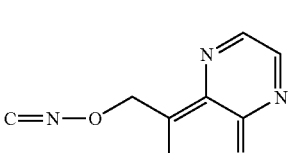 | H |
| (154) | H | 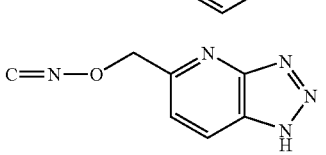 | Ac |

TABLE 2-continued

| Compound | R$_{20}$ | CR$_1$R$_2$ | Rx |
|---|---|---|---|
| (155) | H | C=N-O-CH$_2$-[triazolopyridine] | H |
| (156) | H | C=N-O-CH$_2$-[triazolopyridine] | Ac |
| (157) | H | C=N-O-CH$_2$-[triazolopyridine] | H |
| (158) | H | C=N-O-CH$_2$-[bipyridine] | Ac |
| (159) | H | C=N-O-CH$_2$-[bipyridine] | H |
| (160) | H | C=N-O-CH$_2$-[pyridyl-(6-fluoropyridyl)] | Ac |
| (161) | H | C=N-O-CH$_2$-[pyridyl-(6-fluoropyridyl)] | H |
| (162) | H | C=N-O-CH$_2$-[pyridyl-pyrimidinyl] | Ac |
| (163) | H | C=N-O-CH$_2$-[pyridyl-pyrimidinyl] | H |

TABLE 2-continued
| Compound | R20 | CR1R2 | Rx |
|---|---|---|---|
| (164) | H | 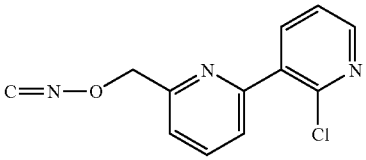 | Ac |
| (165) | H | 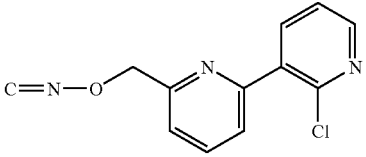 | H |
| (166) | H | 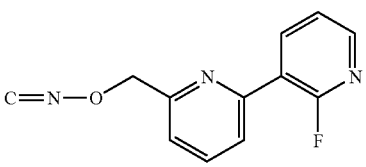 | Ac |
| (167) | H | 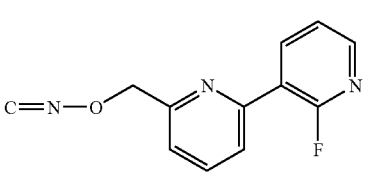 | H |
| (168) | H | 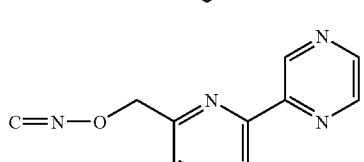 | Ac |
| (169) | H | 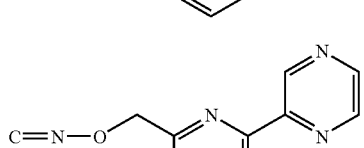 | H |
| (170) | H | 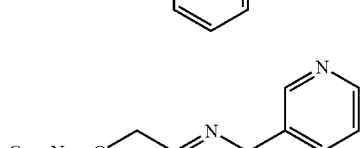 | Ac |
| (171) | H | 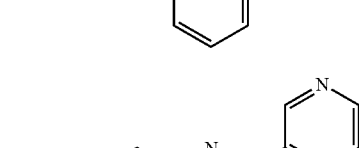 | H |
| (172) | H | 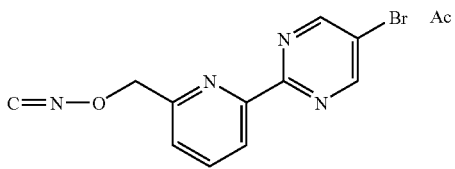 | Ac |

TABLE 2-continued
| Compound | R20 | CR1R2 | Rx |
|---|---|---|---|
| (173) | H | 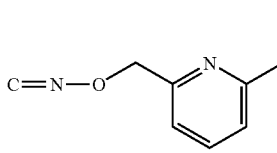 | H |
| (174) | H | 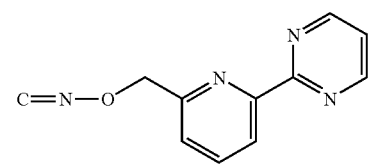 | Ac |
| (175) | H | 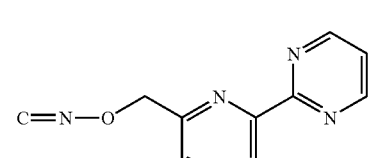 | H |
| (176) | H | 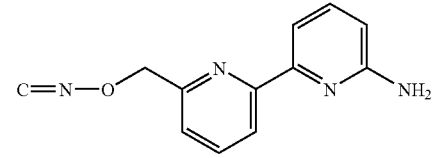 | Ac |
| (177) | H | 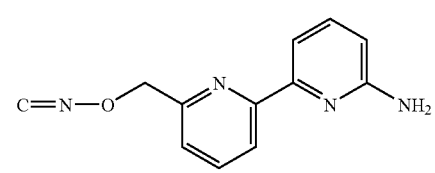 | H |
| (178) | H | 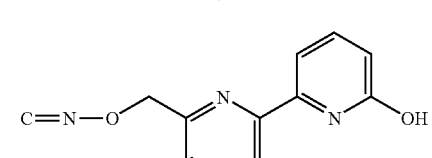 | H |
| (179) | H | 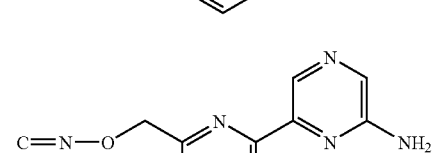 | Ac |
| (180) | H | 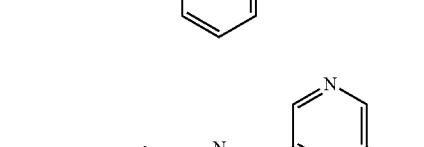 | H |
| (181) | H | 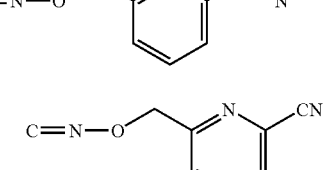 | Ac |

TABLE 2-continued
| Compound | R20 | CR1R2 | Rx |
|---|---|---|---|
| (182) | H | 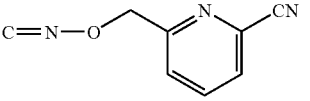 | H |
| (183) | H | 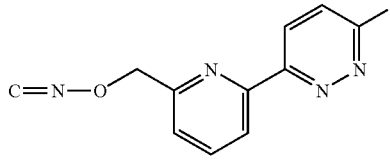 | Ac |
| (184) | H | 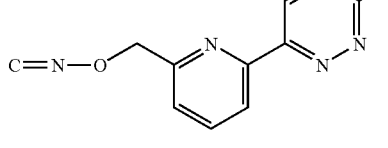 | H |
| (185) | H | 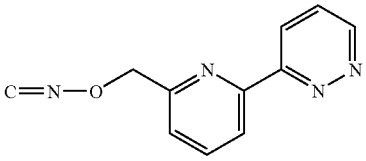 | H |
| (186) | H | 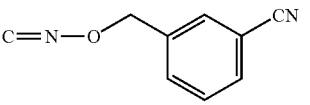 | Ac |
| (187) | H | 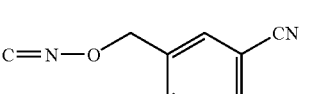 | H |
| (188) | H | 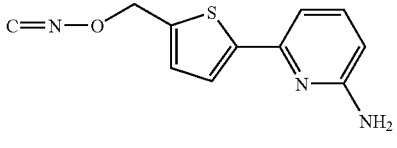 | Ac |
| (189) | H | 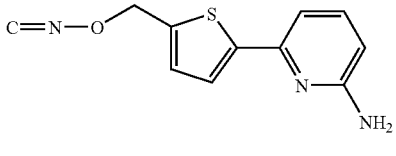 | H |
| (190) | H |  | Ac |
| (191) | H | 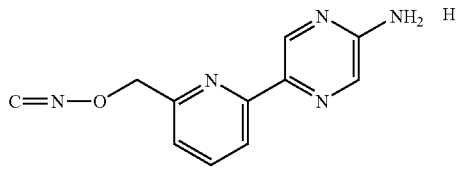 | H |

TABLE 2-continued

| Compound | R$_{20}$ | CR$_1$R$_2$ | Rx |
|---|---|---|---|
| (192) | H | pyridine-oxime-bipyridyl-NH$_2$ structure | Ac |
| (193) | H | pyridine-oxime-bipyridyl-NH$_2$ structure | H |
| (194) | H | pyridine-oxime-bipyridyl-NH$_2$ structure | Ac |
| (195) | H | pyridine-oxime-bipyridyl-NH$_2$ structure | H |
| (196) | H | pyridine-oxime-bipyridyl-NH$_2$ structure | Ac |
| (197) | H | pyridine-oxime-bipyridyl-NH$_2$ structure | H |
| (198) | H | pyridine-oxime-pyridyl-phenyl-NH$_2$ structure | Ac |
| (199) | H | pyridine-oxime-pyridyl-phenyl-NH$_2$ structure | H |

TABLE 2-continued
| Compound | R20 | CR1R2 | Rx |
|---|---|---|---|
| (200) | H | 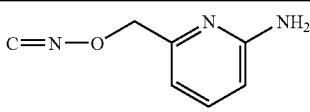 | Ac |
| (201) | H | 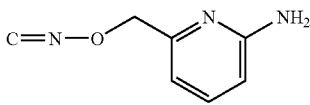 | H |
| (202) | H | 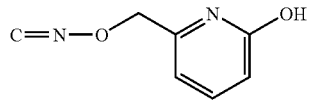 | H |
| (203) | H | 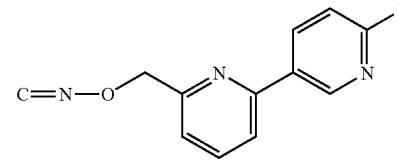 | Ac |
| (204) | H | 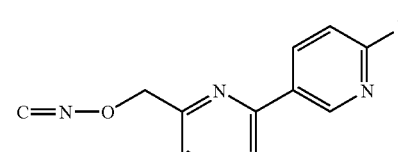 | H |
| (205) | H | 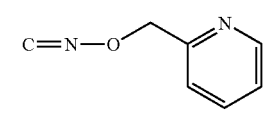 | Ac |
| (206) | H | 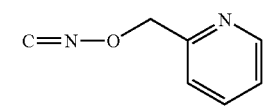 | H |
| (207) | H | 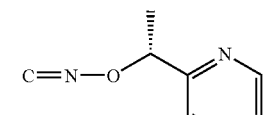 | Ac |
| (208) | H | 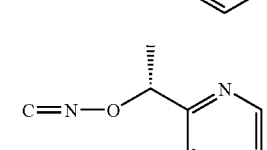 | H |
| (209) | H | 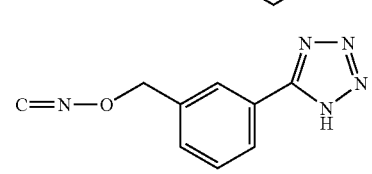 | Ac |
| (210) | H | 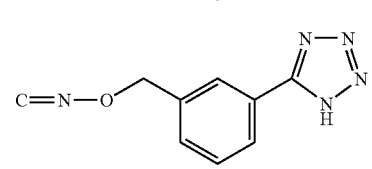 | H |

TABLE 2-continued

| Compound | R₂₀ | CR₁R₂ | Rx |
|---|---|---|---|
| (211) | CH₃ | C=CH₂ | Ac |
| (212) | CH₃ | C=CH₂ | H |
| (213) | CH₃ | C=O | Ac |
| (214) | CH₃ | C=O | H |
| (215) | CH₃ | C=N—O—CH₂—(pyrido[2,3-b]pyrazine) | Ac |
| (216) | CH₃ | C=N—O—CH₂—(pyrido[2,3-b]pyrazine) | H |
| (217) | CH₃ | C=N—O—CH₂—(6'-amino-2,2'-bipyridinyl) | Ac |
| (218) | CH₃ | C=N—O—CH₂—(6'-amino-2,2'-bipyridinyl) | H |
| (219) | H | C=N—NH—C(O)—phenyl | Ac |
| (220) | H | C=N—NH—C(O)—phenyl | H |
| (221) | H | C=N—NH—C(O)—(2-pyridyl) | Ac |
| (222) | H | C=N—NH—C(O)—(2-pyridyl) | H |
| (223) | H | C=N—NH—S(O)₂—phenyl | Ac |

TABLE 2-continued
| Compound | R₂₀ | CR₁R₂ | Rx |
|---|---|---|---|
| (224) | H | 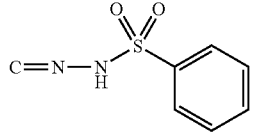 | H |
| (225) | H | 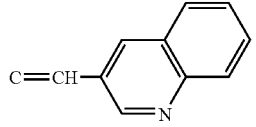 | Ac |
| (226) | H | 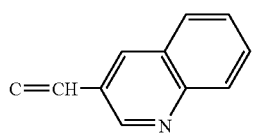 | H |
| (227) | H | 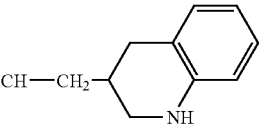 | H |
| (228) | H | 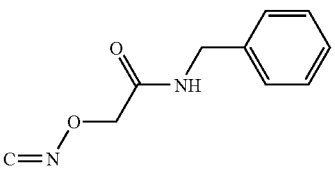 | Ac |
| (229) | H | 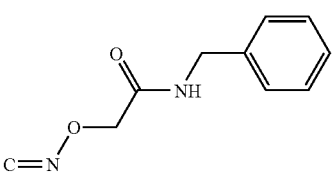 | H |
| (230) | H | 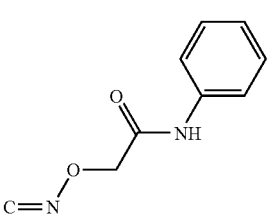 | Ac |
| (231) | H | 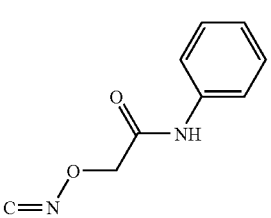 | H |
| (232) | H | 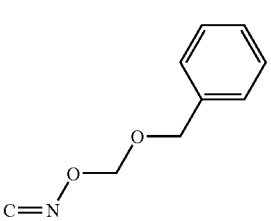 | Ac |

TABLE 2-continued
| Compound | R20 | CR1R2 | Rx |
|---|---|---|---|
| (233) | H | 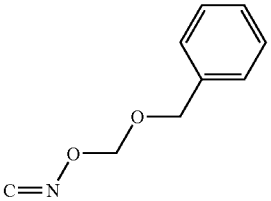 | H |
| (234) | H | 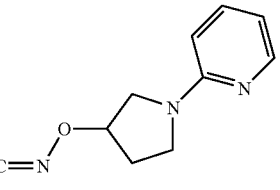 | Ac |
| (235) | H | 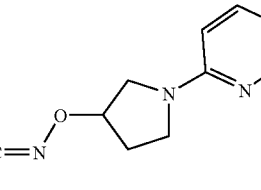 | H |
| (236) | H | 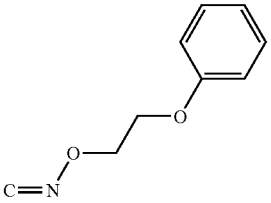 | Ac |
| (237) | H | 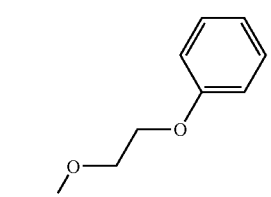 | H |
| (238) | H | 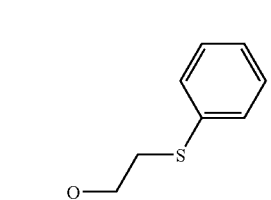 | Ac |
| (239) | H | 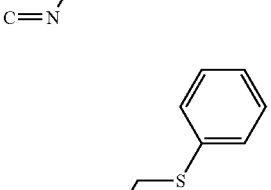 | H |

TABLE 2-continued
| Compound | R20 | CR1R2 | Rx |
|---|---|---|---|
| (240) | H | 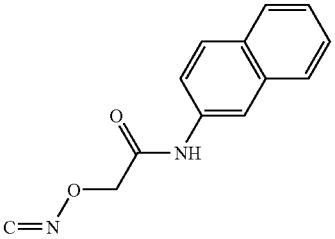 | Ac |
| (241) | H | 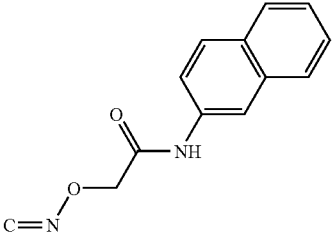 | H |
| (242) | H | 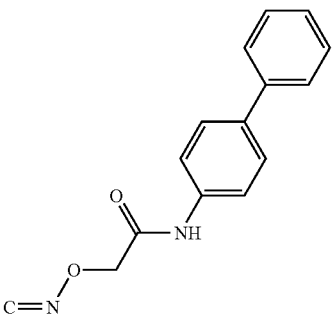 | Ac |
| (243) | H | 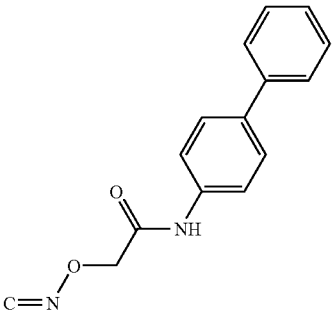 | H |
| (244) | H | 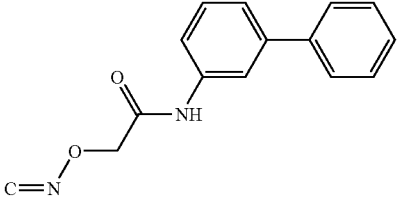 | Ac |
| (245) | H | 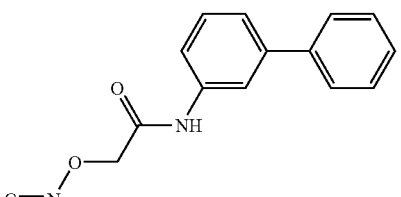 | H |

TABLE 2-continued
| Compound | R20 | CR1R2 | Rx |
|---|---|---|---|
| (246) | H | 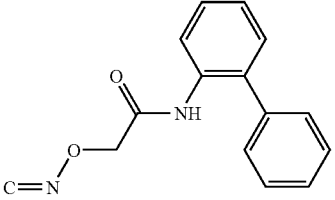 | Ac |
| (247) | H | 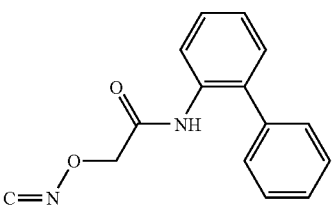 | H |
| (248) | H | 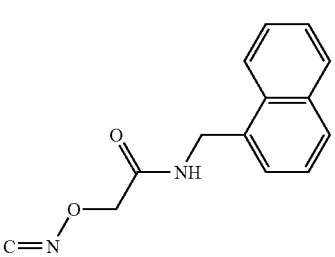 | Ac |
| (249) | H | 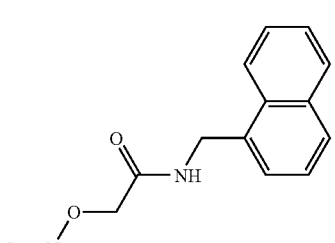 | H |
| (250) | H | 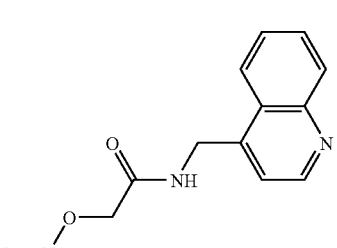 | Ac |
| (251) | H | 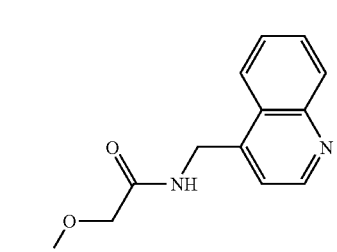 | H |

TABLE 2-continued

| Compound | R20 | CR1R2 | Rx |
|---|---|---|---|
| (252) | H | 2-(benzamido)ethoxyimino | Ac |
| (253) | H | 2-(benzamido)ethoxyimino | H |
| (254) | H | 2-(naphthalene-1-sulfonamido)ethoxyimino | Ac |
| (255) | H | 2-(naphthalene-1-sulfonamido)ethoxyimino | H |
| (256) | H | 2-(quinoline-4-carboxamido)ethoxyimino | Ac |
| (257) | H | 2-(quinoline-4-carboxamido)ethoxyimino | H |
| (258) | H | (quinoxalin-2-yl)methoxyimino | Ac |

TABLE 2-continued

| Compound | R$_{20}$ | CR$_1$R$_2$ | Rx |
|---|---|---|---|
| (259) | H | quinoxalin-2-yl-CH=N-O-CH$_2$ | H |
| (260) | H | quinazolin-4-yl-CH=N-O-CH$_2$ | Ac |
| (261) | H | quinazolin-4-yl-CH=N-O-CH$_2$ | H |
| (262) | H | 2,1,3-benzothiadiazol-4-yl-CH=N-O-CH$_2$ | Ac |
| (263) | H | 2,1,3-benzothiadiazol-4-yl-CH=N-O-CH$_2$ | H |
| (264) | H | pyrido[2,3-b]pyrazin-3-yl-CH=N-O-CH$_2$ | Ac |
| (265) | H | pyrido[2,3-b]pyrazin-3-yl-CH=N-O-CH$_2$ | H |
| (266) | H | cinnolin-4-yl-CH=N-O-CH$_2$ | Ac |

TABLE 2-continued

| Compound | R20 | CR1R2 | Rx |
|---|---|---|---|
| (267) | H | (4-cinnolinyl-methyleneaminooxy group) | H |
| (268) | H | (7-amino-pyrido[2,3-b]pyrazin-3-yl-methyleneaminooxy group) | Ac |
| (269) | H | (7-amino-pyrido[2,3-b]pyrazin-3-yl-methyleneaminooxy group) | H |
| (270) | H | (1,5-naphthyridin-4-yl-methyleneaminooxy group) | Ac |
| (271) | H | (1,5-naphthyridin-4-yl-methyleneaminooxy group) | H |
| (272) | H | (2-amino-1,5-naphthyridin-8-yl-methyleneaminooxy group) | Ac |
| (273) | H | (2-amino-1,5-naphthyridin-8-yl-methyleneaminooxy group) | H |
| (274) | H | (1,5-naphthyridin-4-yl-methyleneaminooxy group) | Ac |

TABLE 2-continued
| Compound | R20 | CR1R2 | Rx |
|---|---|---|---|
| (275) | H | 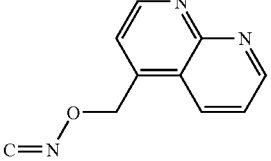 | H |
| (276) | H | 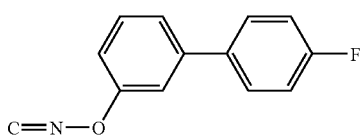 | H |
| (277) | H | 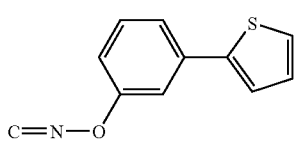 | Ac |
| (278) | H | 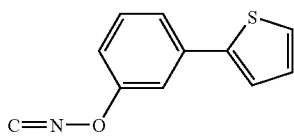 | H |
| (279) | H | 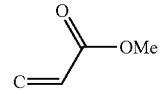 | Ac |
| (280) | H | 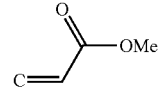 | H |
| (281) | H | 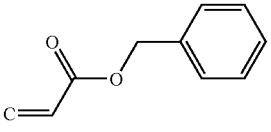 | Ac |
| (282) | H | 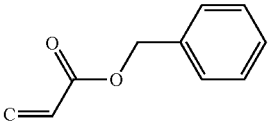 | H |
| (283) | H | 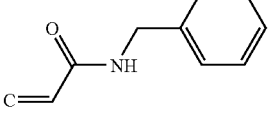 | Ac |
| (284) | H | 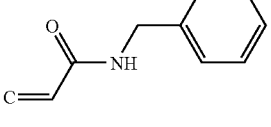 | H |
| (285) | H | 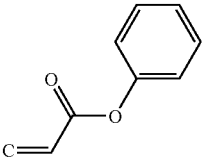 | Ac |

TABLE 2-continued

| Compound | $R_{20}$ | $CR_1R_2$ | Rx |
|---|---|---|---|
| (286) | H | phenyl acrylate (C=C–C(=O)–O–C₆H₅) | H |
| (287) | H | N-phenyl acrylamide (C=C–C(=O)–NH–C₆H₅) | Ac |
| (288) | H | N-phenyl acrylamide (C=C–C(=O)–NH–C₆H₅) | H |
| (289) | H | N-(naphthalen-1-yl) acrylamide | Ac |
| (290) | H | N-(naphthalen-1-yl) acrylamide | H |
| (291) | H | N-(naphthalen-2-yl) acrylamide | Ac |
| (292) | H | N-(naphthalen-2-yl) acrylamide | H |
| (293) | H | N-(quinolin-3-yl) acrylamide | Ac |

TABLE 2-continued
| Compound | R20 | CR1R2 | Rx |
|---|---|---|---|
| (294) | H | 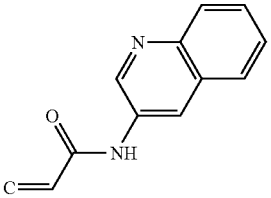 | H |
| (295) | H | 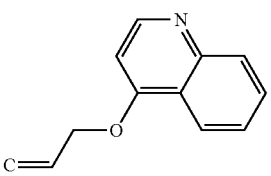 | Ac |
| (296) | H | 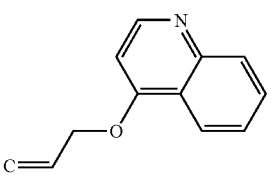 | H |
| (297) | H | 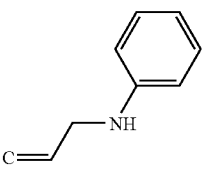 | Ac |
| (298) | H | 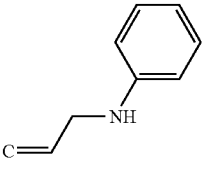 | H |
| (299) | H | 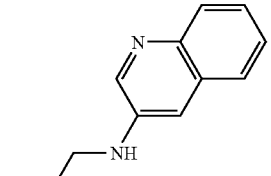 | Ac |
| (300) | H | 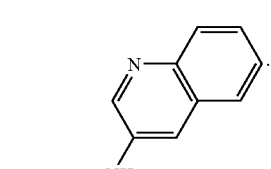 | H |

15. A compound of claim 7, selected from compounds 301 to 425 of Table 3:

TABLE 3

| Compound | R₂₀ | R₁ | R₂ | Rx |
|---|---|---|---|---|
| (301) | H | phenethyl (-CH₂CH₂-C₆H₅) | OH | Ac |
| (302) | H | phenethyl (-CH₂CH₂-C₆H₅) | OH | H |
| (303) | H | phenoxy (-O-C₆H₅) | H | Ac |
| (304) | H | phenoxy (-O-C₆H₅) | H | H |
| (305) | H | quinolin-4-yloxy | H | Ac |
| (306) | H | quinolin-4-yloxy | H | H |
| (307) | H | benzylamino (-NH-CH₂-C₆H₅) | H | Ac |
| (308) | H | benzylamino (-NH-CH₂-C₆H₅) | H | H |
| (309) | H | N-methyl-benzylamino | H | H |
| (310) | H | phenethylamino (-NH-CH₂CH₂-C₆H₅) | H | Ac |
| (311) | H | phenethylamino (-NH-CH₂CH₂-C₆H₅) | H | H |
| (312) | H | 3-phenylpropylamino | H | Ac |
| (313) | H | 3-phenylpropylamino | H | H |
| (314) | H | 2-(naphthalen-1-yl)ethylamino | H | Ac |
| (315) | H | 2-(naphthalen-1-yl)ethylamino | H | H |
| (316) | H | 2-(naphthalen-2-yl)ethylamino | H | Ac |
| (317) | H | 2-(naphthalen-2-yl)ethylamino | H | H |
| (318) | H | N-methyl-2-(naphthalen-2-yl)ethylamino | H | H |
| (319) | H | (E)-3-(quinolin-3-yl)prop-2-en-1-yloxy | H | Ac |

TABLE 3-continued
| Compound | R20 | R1 | R2 | Rx |
|---|---|---|---|---|
| (320) | H |  | H | H |
| (321) | H | 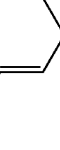 | H | Ac |
| (322) | H | 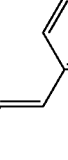 | H | H |
| (323) | H | OH (R—) | H | Ac |
| (324) | H | 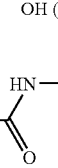 | H | Ac |
| (325) | H | 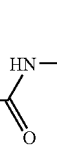 | H | H |
| (326) | H |  | H | Ac |
| (327) | H |  | H | H |
| (328) | H | OSO$_2$CH$_3$ (S—) | H | Ac |
| (329) | H | N$_3$ | H | Ac |
| (330) | H | N$_3$ | H | H |
| (331) | H | NH$_2$ | H | Ac |
| (332) | H | NH$_2$ | H | H |
TABLE 3-continued
| Compound | R20 | R1 | R2 | Rx |
|---|---|---|---|---|
| (333) | H | (benzyl carbamate) | H | Ac |
| (334) | H | (benzyl carbamate) | H | H |
| (335) | H | (benzamide) | H | Ac |
| (336) | H | (benzamide) | H | H |
| (337) | H | (phenylacetamide) | H | Ac |
| (338) | H | (phenylacetamide) | H | H |
| (339) | H | (benzylurea) | H | Ac |
| (340) | H | (benzylurea) | H | H |

TABLE 3-continued

| Compound | R20 | R1 | R2 | Rx |
|---|---|---|---|---|
| (341) | H | (phenylurea-NH-) | H | Ac |
| (342) | H | (phenylurea-NH-) | H | H |
| (343) | H | (benzylsulfonamide) | H | Ac |
| (344) | H | (benzylsulfonamide) | H | H |
| (345) | H | (phenylsulfonamide) | H | Ac |
| (346) | H | (phenylsulfonamide) | H | H |
| (347) | H | (pyridin-2-ylsulfonamide) | H | Ac |
| (348) | H | (pyridin-2-ylsulfonamide) | H | H |
| (349) | H | (pyridin-3-ylsulfonamide) | H | Ac |
| (350) | H | (pyridin-3-ylsulfonamide) | H | H |
| (351) | H | (biphenyl-3-ylsulfonamide) | H | Ac |
| (352) | H | (biphenyl-3-ylsulfonamide) | H | H |
| (353) | H | (quinolin-8-ylsulfonamide) | H | Ac |
| (354) | H | (quinolin-8-ylsulfonamide) | H | H |
| (355) | H | (biphenyl-4-ylsulfonamide) | H | Ac |
| (356) | H | (biphenyl-4-ylsulfonamide) | H | H |

TABLE 3-continued

| Compound | R20 | R1 | R2 | Rx |
|---|---|---|---|---|
| (357) | H | 5-(isoxazol-5-yl)thiophene-2-sulfonamide | H | Ac |
| (358) | H | 5-(isoxazol-5-yl)thiophene-2-sulfonamide | H | H |
| (359) | H | naphthalene-1-sulfonamide | H | Ac |
| (360) | H | naphthalene-1-sulfonamide | H | H |
| (361) | H | naphthalene-2-sulfonamide | H | Ac |
| (362) | H | naphthalene-2-sulfonamide | H | H |
| (363) | H | thiophene-2-sulfonamide | H | Ac |
| (364) | H | thiophene-2-sulfonamide | H | H |

TABLE 3-continued

| Compound | R20 | R1 | R2 | Rx |
|---|---|---|---|---|
| (365) | H | 5-(isoxazol-3-yl)thiophene-2-sulfonamide | H | Ac |
| (366) | H | 5-(isoxazol-3-yl)thiophene-2-sulfonamide | H | H |
| (367) | H | (E)-2-phenylethenesulfonamide | H | Ac |
| (368) | H | (E)-2-phenylethenesulfonamide | H | H |
| (369) | H | benzofuran-2-sulfonamide | H | Ac |
| (370) | H | benzofuran-2-sulfonamide | H | H |
| (371) | H | benzothiazole-6-sulfonamide | H | Ac |
| (372) | H | benzothiazole-6-sulfonamide | H | H |

TABLE 3-continued

| Compound | R20 | R1 | R2 | Rx |
|---|---|---|---|---|
| (373) | H | 4-(pyrazol-1-yl)phenylsulfonamide | H | Ac |
| (374) | H | 4-(pyrazol-1-yl)phenylsulfonamide | H | H |
| (375) | H | 6-phenoxypyridine-3-sulfonamide | H | Ac |
| (376) | H | 6-phenoxypyridine-3-sulfonamide | H | H |
| (377) | H | benzo[b]thiophene-2-sulfonamide | H | Ac |
| (378) | H | benzo[b]thiophene-2-sulfonamide | H | H |
| (379) | H | 3-bromophenylsulfonamide | H | Ac |

TABLE 3-continued

| Compound | R20 | R1 | R2 | Rx |
|---|---|---|---|---|
| (380) | H | 3-(pyridin-3-yl)phenylsulfonamide | H | Ac |
| (381) | H | 3-(pyridin-3-yl)phenylsulfonamide | H | H |
| (382) | H | 3-(pyrazin-2-yl)phenylsulfonamide | H | Ac |
| (383) | H | 3-(pyrazin-2-yl)phenylsulfonamide | H | H |
| (384) | H | 3-(pyridin-2-yl)phenylsulfonamide | H | Ac |
| (385) | H | 3-(pyridin-2-yl)phenylsulfonamide | H | H |
| (386) | H | 3-(6-aminopyridin-2-yl)phenylsulfonamide | H | Ac |
| (387) | H | 3-(6-aminopyridin-2-yl)phenylsulfonamide | H | H |

TABLE 3-continued
| Compound | R20 | R1 | R2 | Rx |
|---|---|---|---|---|
| (388) | H | 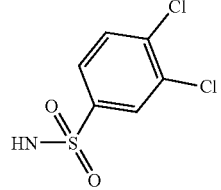 | H | Ac |
| (389) | H | 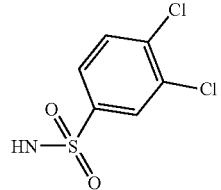 | H | H |
| (390) | H | 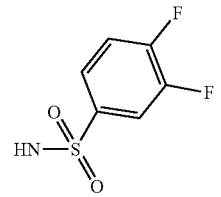 | H | Ac |
| (391) | H | 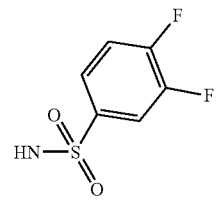 | H | H |
| (392) | H | 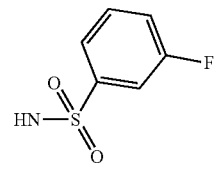 | H | Ac |
| (393) | H | 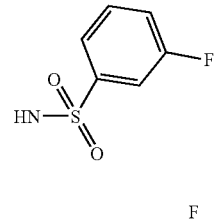 | H | H |
| (394) | H | 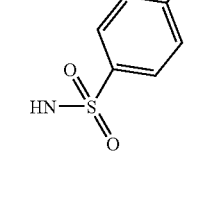 | H | Ac |
| (395) | H | 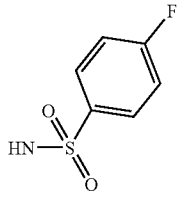 | H | H |
| (396) | H | 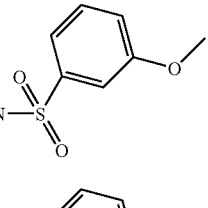 | H | Ac |
| (397) | H | 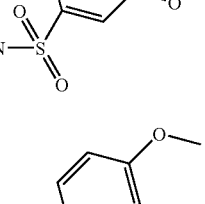 | H | H |
| (398) | H | 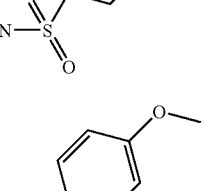 | H | Ac |
| (399) | H | 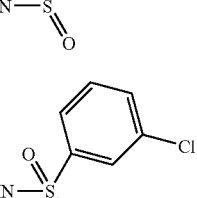 | H | H |
| (400) | H | 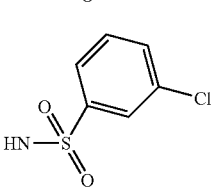 | H | Ac |
| (401) | H | 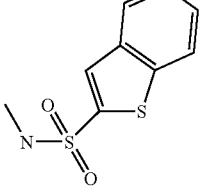 | H | H |
| (402) | H |  | H | H |

TABLE 3-continued

| Compound | R20 | R1 | R2 | Rx |
|---|---|---|---|---|
| (403) | H | (6-(1H-pyrazol-1-yl)pyridin-3-yl)methyl carbamate | H | Ac |
| (404) | H | (6-(1H-pyrazol-1-yl)pyridin-3-yl)methyl carbamate | H | H |
| (405) | H | (6-(1H-pyrazol-1-yl)pyridin-2-yl)methyl carbamate | H | Ac |
| (406) | H | (6-(1H-pyrazol-1-yl)pyridin-2-yl)methyl carbamate | H | H |
| (407) | H | quinolin-3-ylmethyl carbamate | H | Ac |
| (408) | H | quinolin-3-ylmethyl carbamate | H | H |

TABLE 3-continued

| Compound | R20 | R1 | R2 | Rx |
|---|---|---|---|---|
| (409) | H | quinolin-4-ylmethyl carbamate | H | Ac |
| (410) | H | quinolin-4-ylmethyl carbamate | H | H |
| (411) | H | isoquinoline-4-carboxamide | H | Ac |
| (412) | H | isoquinoline-4-carboxamide | H | H |
| (413) | H | quinoline-3-carboxamide | H | Ac |
| (414) | H | quinoline-3-carboxamide | H | H |
| (415) | H | 2-(quinolin-3-yl)acetamide | H | Ac |
| (416) | H | 2-(quinolin-3-yl)acetamide | H | H |

TABLE 3-continued

| Compound | R20 | R1 | R2 | Rx |
|---|---|---|---|---|
| (417) | H | [1-naphthyl-CH2-C(O)-NH-] | H | Ac |
| (418) | H | [1-naphthyl-CH2-C(O)-NH-] | H | H |
| (419) | H | [6-(pyrazol-1-yl)pyridin-3-yl-CH2-C(O)-NH-] | H | Ac |
| (420) | H | [6-(pyrazol-1-yl)pyridin-3-yl-CH2-C(O)-NH-] | H | H |
| (421) | H | [6-(pyrazol-1-yl)pyridin-2-yl-CH2-C(O)-NH-] | H | Ac |
| (422) | H | [6-(pyrazol-1-yl)pyridin-2-yl-CH2-C(O)-NH-] | H | H |
| (423) | H | [CH3-C(O)-NH-phenyl] | H | H |
| (424) | H | [CH3-C(O)-NH-1-naphthyl] | H | H |
| (425) | H | [CH3-C(O)-NH-2-naphthyl] | H | H |

16. A compound of claim 8, wherein $R_1$ and $R_2$ taken together with the carbon atom to which they are attached are $C=CH_2$, $R_3$ is H, and Rx is Ac.

17. A compound of claim 8, wherein $R_1$ and $R_2$ taken together with the carbon atom to which they are attached are $C=CH_2$, and $R_3$ is H.

18. A compound of claim 8, wherein $R_1$ and $R_2$ taken together with the carbon atom to which they are attached is $C=CH_2$, $R_3$ is phenylpropyl, and Rx is Ac.

19. A compound of claim 9, wherein $R_1$ and $R_2$ taken together with the carbon atom to which they are attached is $C=CH_2$, $R_3$ is H, and Rx is Ac.

20. A compound of claim 9, wherein $R_1$ and $R_2$ taken together with the carbon atom to which they are attached is $C=CH_2$, and $R_3$ is H.

21. A compound of claim 9, wherein $R_1$ and $R_2$ taken together with the carbon atom to which they are attached is $C=CH_2$, $R_3$ is (phenylpropyl) and Rx is Ac.

22. A compound claim 2, wherein $R_1$ and $R_2$ taken together with the carbon atom to which they are attached is $C(OH)CH_2OH$, W is H, and $R_6$ is Bz.

23. A compound of claim 2, wherein $R_1$ and $R_2$ taken together with the carbon atom to which they are attached is $C(OH)CH_2OH$, and W is H.

24. Compound of claim 5, wherein $R_1$ and $R_2$ taken together with the carbon atom to which they are attached are $C=NO[6'$-amino-$[2,2']$bipyridinyl-4-ylmethyl$]$, and Rx=Ac.

25. Compound of claim 5, wherein $R_1$ and $R_2$ taken together with the carbon atom to which they are attached are $C=NO[6'$-amino-$[2,2']$bipyridinyl-4-ylmethyl$]$, and Rx=H.

26. Compound of claim 10, wherein $R_1$ and $R_2$ taken together with the carbon atom to which they are attached are $C=CH_2$, X and Y taken together with the carbon atom to which they are attached are $C=NOH$, $R_{20}=H$, and Rx=Ac.

27. Compound of claim 10, wherein $R_1$ and $R_2$ taken together with the carbon atom to which they are attached are $C=CH_2$, X and Y taken together with the carbon atom to which they are attached are $C=NOH$, and $R_{20}=Rx=H$.

28. Compound of claim 10, wherein $R_1$ and $R_2$ taken together with the carbon atom to which they are attached are $C=CH_2$, X and Y taken together with the carbon atom to which they are attached are $C=NOCH_3$, $R_{20}=H$, and Rx=Ac.

29. Compound of claim 10, wherein $R_1$ and $R_2$ taken together with the carbon atom to which they are attached are $C=CH_2$, X and Y taken together with the carbon atom to which they are attached are $C=NOCH_3$, and $R_{20}=Rx=H$.

30. Compound of claim 10, wherein $R_1$ and $R_2$ taken together with the carbon atom to which they are attached are $C=CH_2$, X and Y taken together with the carbon atom to which they are attached are $C=NOCH_2CH_3$, $R_{20}=H$, and Rx=Ac.

31. Compound of claim 10, wherein $R_1$ and $R_2$ taken together with the carbon atom to which they are attached are C=CH$_2$, X and Y taken together with the carbon atom to which they are attached are C=NOCH$_2$CH$_3$, and R$_{20}$=Rx=H.

32. Compound of claim 10, wherein R$_1$ and R$_2$ taken together with the carbon atom to which they are attached are C=NO[quinoxalin-6-ylmethyl], X and Y taken together with the carbon atom to which they are attached are C=NOH, and R$_{20}$=Rx=H.

33. A compound of claim 1 having the Formula B, selected from the compounds 445 to 606 of Table 4:

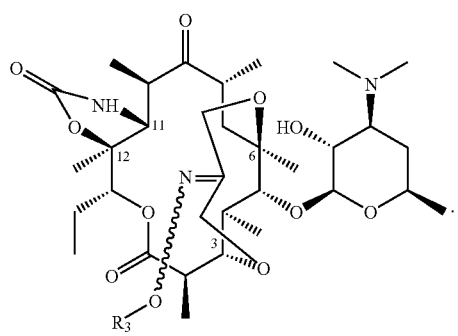

(B)

TABLE 4

| Compound | R$_3$ |
|---|---|
| (445) | 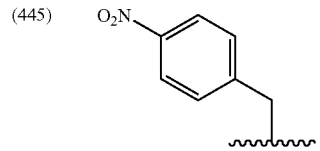 |
| (446) | 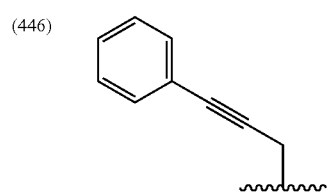 |
| (447) | 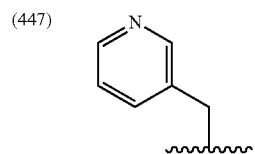 |
| (448) | 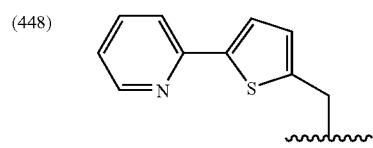 |
| (449) | 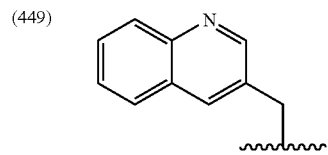 |

TABLE 4-continued

| Compound | R$_3$ |
|---|---|
| (450) | 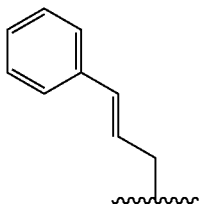 |
| (451) | 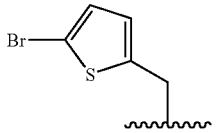 |
| (452) | 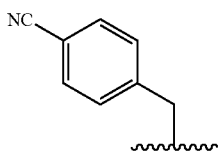 |
| (453) | 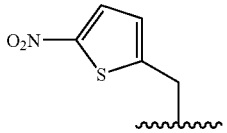 |
| (454) | 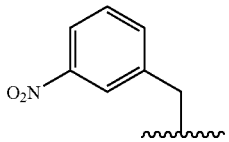 |
| (455) | 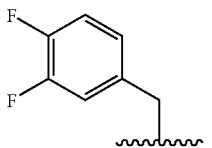 |
| (456) | 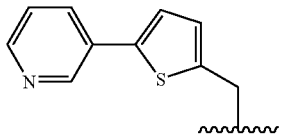 |
| (457) | 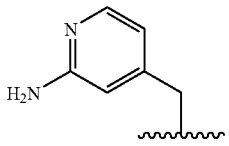 |
| (458) | 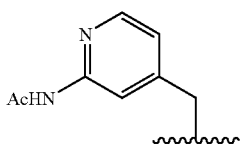 |

TABLE 4-continued

| Compound | R₃ |
|---|---|
| (459) | 3-pyridyl-isoxazol-5-yl-ethyl |
| (460) | 1-methyl-tetrazol-5-yl-thiophen-2-yl-methyl |
| (461) | 4-(pyrazol-1-yl)phenylmethyl |
| (462) | 4-(1,2,3-thiadiazol-4-yl)phenylmethyl |
| (463) | 4-(imidazol-1-yl)phenylmethyl |
| (464) | quinolin-8-ylmethyl |
| (465) | benzotriazol-1-yl-propyl |
| (466) | 4-(pyridin-2-yl)thiophen-2-ylmethyl |
| (467) | 3-aminophenylmethyl |
| (468) | 3-(thiophen-3-yl)phenylmethyl |
| (469) | 5-carbamoylthiophen-2-ylmethyl |
| (470) | 3-carbamoylphenylmethyl |
| (471) | 4-carbamoyl-2-methoxyphenylmethyl |
| (472) | 4-(N-hydroxycarbamoyl)phenylmethyl |

TABLE 4-continued

| Compound | R₃ |
|---|---|
| (473) | 4-vinylbenzyl |
| (474) | methyl 3-(methylene)benzoate |
| (475) | (6-methylpyridin-2-yl)thiophen-2-ylmethyl |
| (476) | (6-chloropyridin-3-yl)methyl |
| (477) | 4-carbamoylbenzyl |
| (478) | 4-aminobenzyl |
| (479) | 5-(pyridin-2-yl)-2,2'-bithiophen-5'-ylmethyl |
| (480) | 4-(5-(pyridin-2-yl)thiophen-2-yl)but-3-ynyl |
| (481) | 4-(quinolin-3-yl)but-3-ynyl |

TABLE 4-continued

| Compound | R₃ |
|---|---|
| (482) | 2,2'-bithiophen-5-ylmethyl |
| (483) | (Z)-4-(quinolin-3-yl)but-3-enyl |
| (484) | (2-aminopyridin-3-yl)methyl |
| (485) | 2-(5-phenyl-1,2,4-oxadiazol-3-yl)ethyl |
| (486) | 2-(3-phenyl-1,2,4-oxadiazol-5-yl)ethyl |
| (487) | 2-(5-(4-methoxyphenyl)-1,2,4-oxadiazol-3-yl)ethyl |

TABLE 4-continued
| Compound | R₃ |
|---|---|
| (488) | 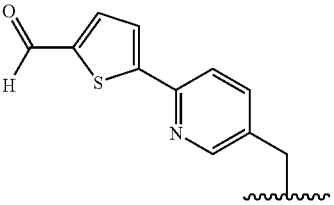 |
| (489) | 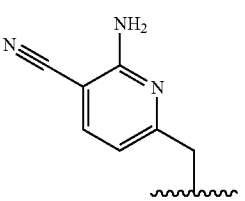 |
| (490) | 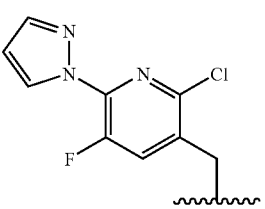 |
| (491) | 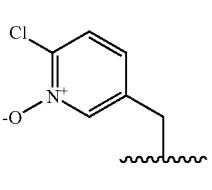 |
| (492) | 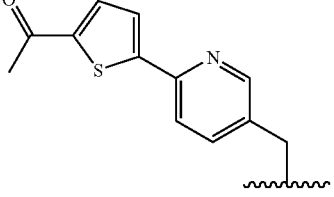 |
| (493) | 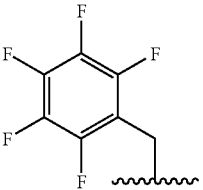 |
| (494) | 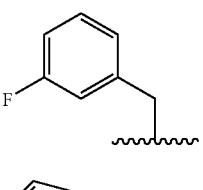 |
| (495) | 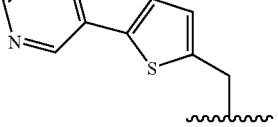 |
| (496) | 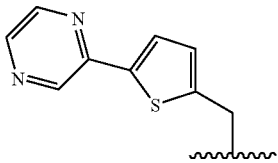 |
| (497) | 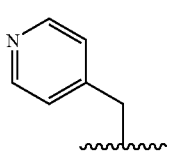 |
| (498) | 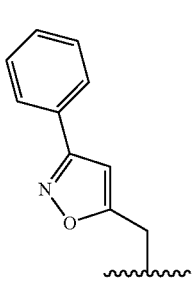 |
| (499) | 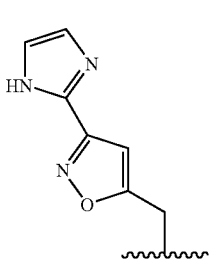 |
| (500) | 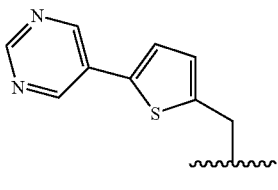 |
| (501) | 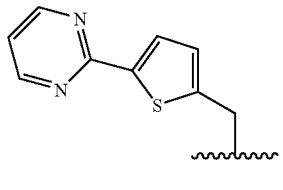 |
| (502) | 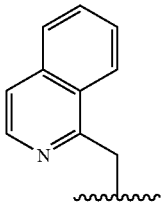 |

TABLE 4-continued
| Compound | R₃ |
|---|---|
| (503) | 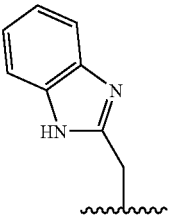 |
| (504) | 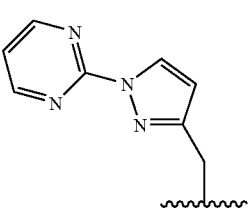 |
| (505) | 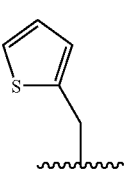 |
| (506) | 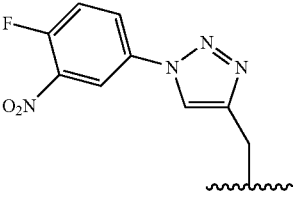 |
| (507) | 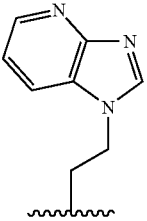 |
| (508) | 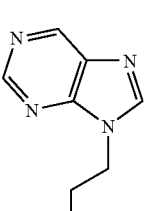 |
| (509) | 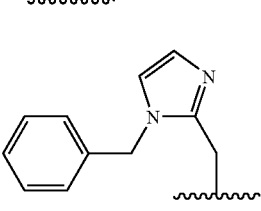 |
| (510) | 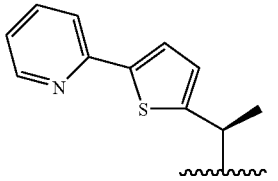 |
| (511) |  |
| (512) | 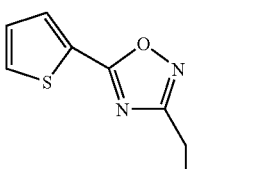 |
| (513) | 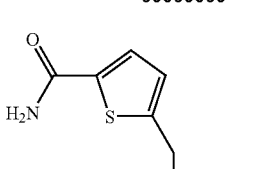 |
| (514) | 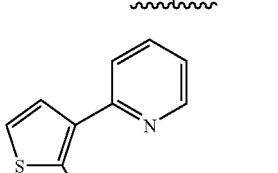 |
| (515) | 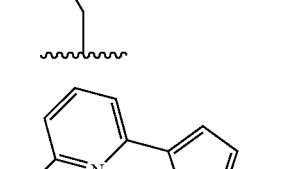 |
| (516) | 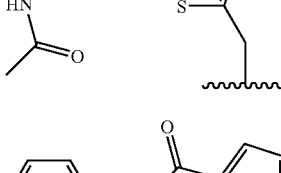 |
| (517) | 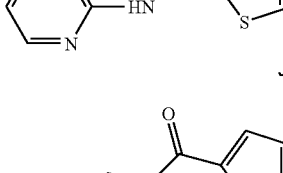 |

TABLE 4-continued
| Compound | R₃ |
|---|---|
| (518) | 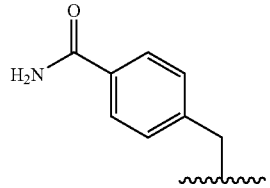 |
| (519) | 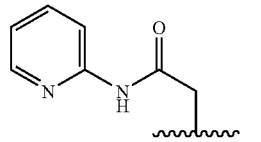 |
| (520) | 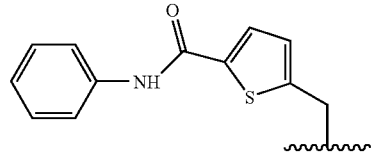 |
| (521) | 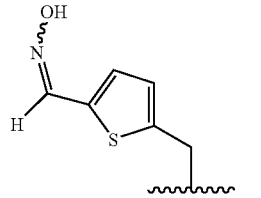 |
| (522) | 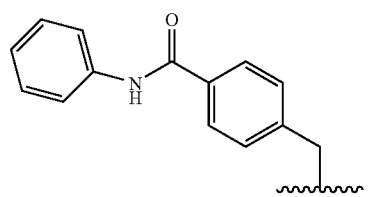 |
| (523) | 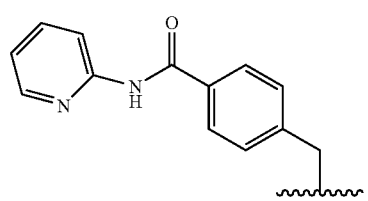 |
| (524) | 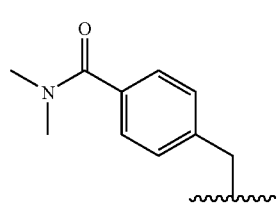 |
| (525) | 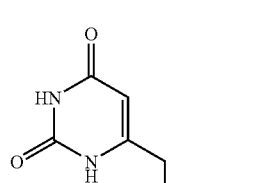 |
| (526) | 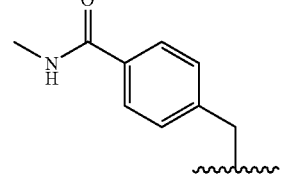 |
| (527) | 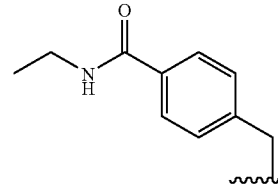 |
| (528) | 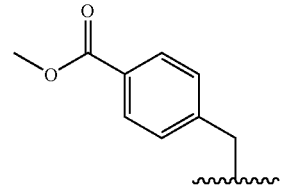 |
| (529) | 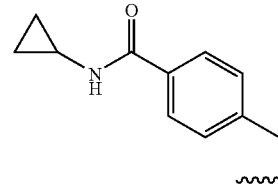 |
| (530) | 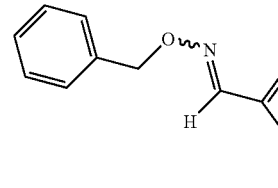 |
| (531) | 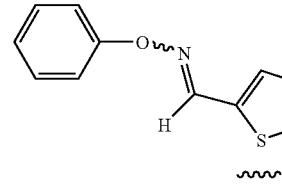 |
| (532) | 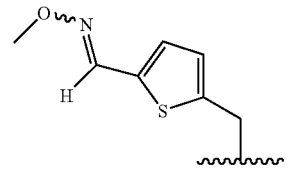 |
| (533) | 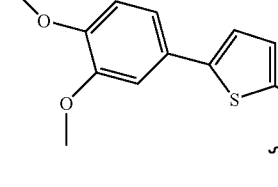 |

TABLE 4-continued
| Compound | R₃ |
|---|---|
| (534) | 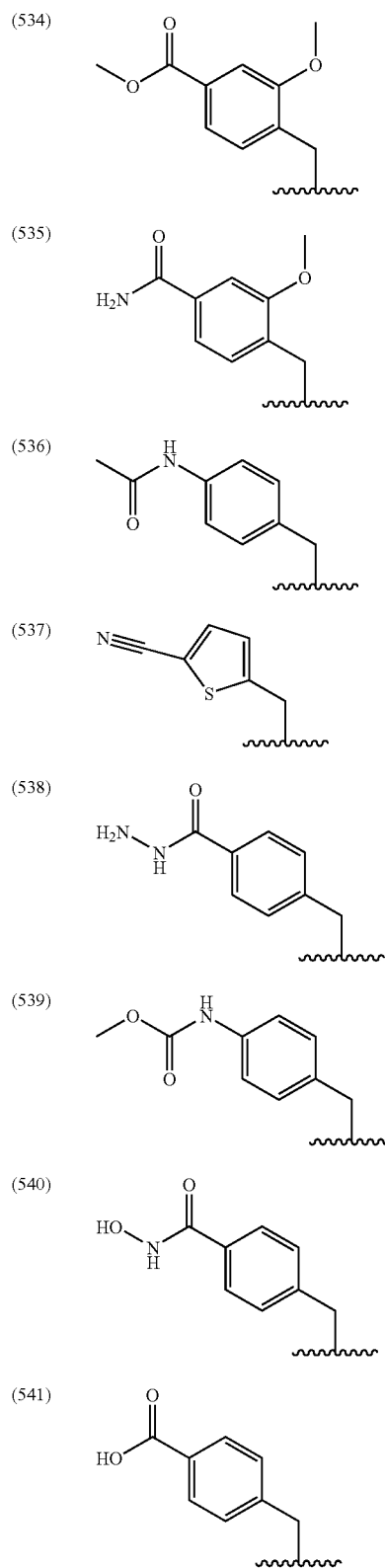 |
| (535) | |
| (536) | |
| (537) | |
| (538) | |
| (539) | |
| (540) | |
| (541) | |
TABLE 4-continued
| Compound | R₃ |
|---|---|
| (542) | 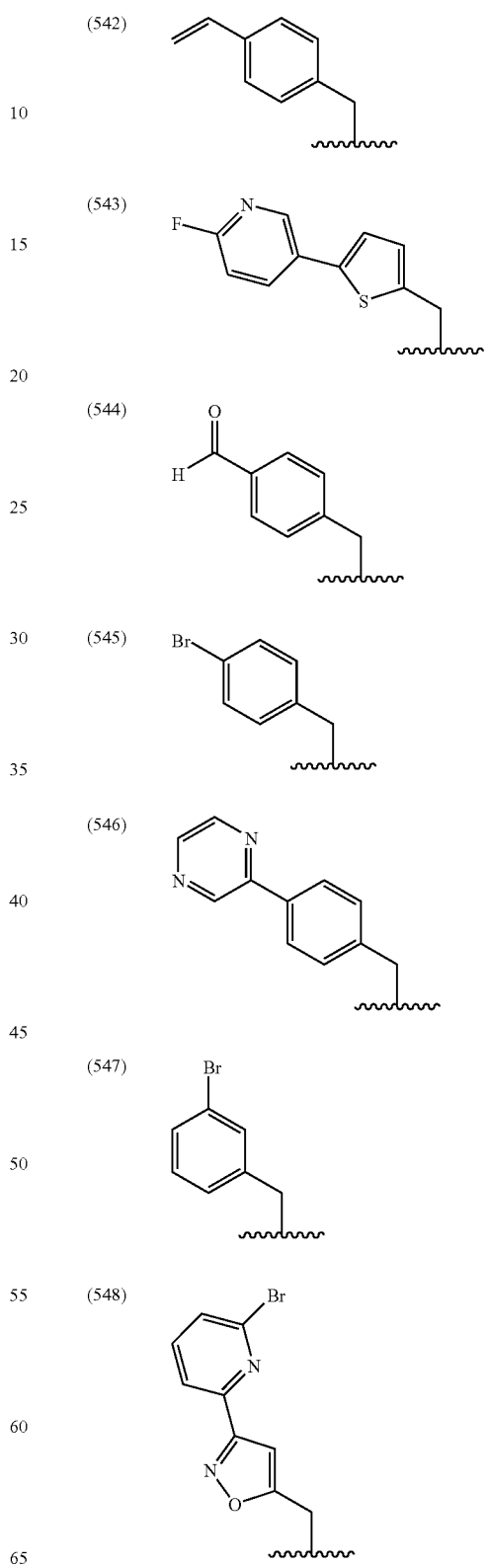 |
| (543) | |
| (544) | |
| (545) | |
| (546) | |
| (547) | |
| (548) | |

TABLE 4-continued
| Compound | R₃ |
|---|---|
| (549) | 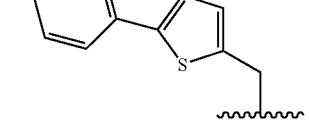 |
| (550) | 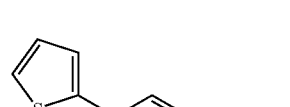 |
| (551) | 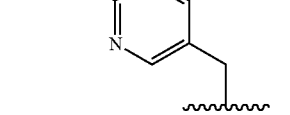 |
| (552) | 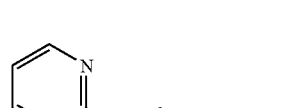 |
| (553) | 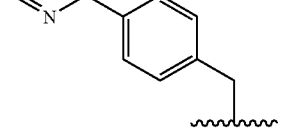 |
| (554) |  |
| (555) | |
| (556) | |
| (557) | |
| (558) | |
| (559) | |

TABLE 4-continued

| Compound | R₃ |
|---|---|
| (560) | [2,2'-bipyridin-5-yl]methyl group |
| (561) | [5-(thiophen-2-yl)pyridin-2-yl]methyl group |
| (562) | [6-(carbamoyl)pyridin-2-yl]-isoxazol-5-ylmethyl group |
| (563) | [6-aminopyridin-3-yl]methyl group |
| (564) | [6-cyanopyridin-3-yl]methyl group |
| (565) | [5-(thiazol-2-yl)thiophen-2-yl]methyl group |
| (566) | [3-bromo-2,3-dimethoxyphenyl]-isoxazol-5-ylmethyl group |
| (567) | [3-(2-nitrophenyl)isoxazol-5-yl]methyl group |
| (568) | [3-(5-bromothiophen-2-yl)isoxazol-5-yl]methyl group |
| (569) | [3-(5-cyanothiophen-2-yl)isoxazol-5-yl]methyl group |
| (570) | [3-(2,3-dimethoxyphenyl)isoxazol-5-yl]methyl group |
| (571) | [4-(1,2,3-thiadiazol-4-yl)phenyl]methyl group |
| (572) | [6-(thiophen-2-yl)pyridin-3-yl]methyl group |

TABLE 4-continued

| Compound | R₃ |
|---|---|
| (573) | [1,2,4-triazol-1-yl-pyridin-5-yl-methyl] |
| (574) | [imidazol-1-yl-pyridin-5-yl-methyl] |
| (575) | [6-ethynyl-pyridin-3-yl-methyl] |
| (576) | [2-(pyrimidin-2-yl)-imidazol-4-yl-methyl] |
| (577) | [5-amino-1,3,4-thiadiazol-2-yl-methyl] |
| (578) | [5-(5-amino-1,3,4-thiadiazol-2-yl)-pyridin-2-yl-methyl] |
| (579) | [6-(5-amino-1,3,4-thiadiazol-2-yl)-pyridin-3-yl-methyl] |
| (580) | [6-amino-pyridin-2-yl-ethynyl-methyl] |
| (581) | [5-bromo-6-amino-pyridin-2-yl-methyl] |
| (582) | [5-(thiophen-2-yl)-6-amino-pyridin-2-yl-methyl] |
| (583) | [5-vinyl-6-amino-pyridin-2-yl-methyl] |
| (584) | [6-amino-pyridin-2-yl-butenyl] |
| (585) | [7-azaindol-6-yl-methyl] |
| (586) | [4-methyl-pyrazol-1-yl-pyridin-5-yl-methyl] |
| (587) | [5-formyl-6-amino-pyridin-2-yl-methyl] |
| (588) | [1,2,3-triazol-1-yl-pyridin-5-yl-methyl] |

TABLE 4-continued
| Compound | R₃ |
|---|---|
| (589) | 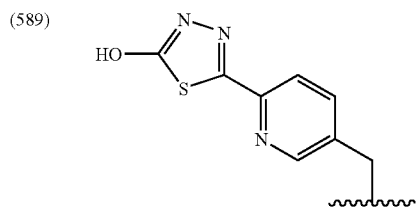 |
| (590) | 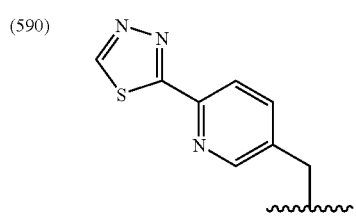 |
| (591) | 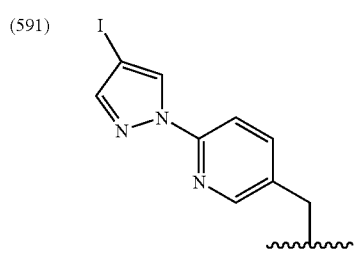 |
| (592) | 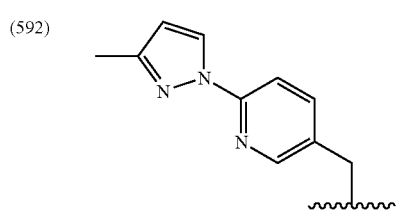 |
| (593) | 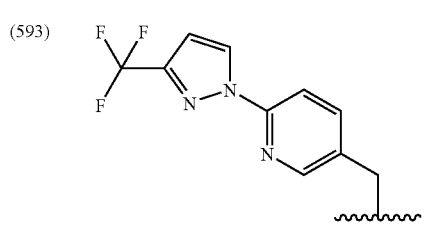 |
| (594) | 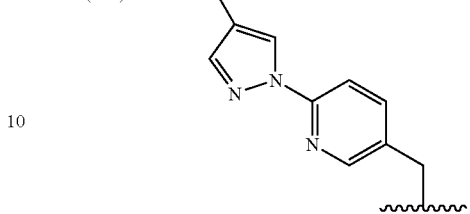 |
| (595) | 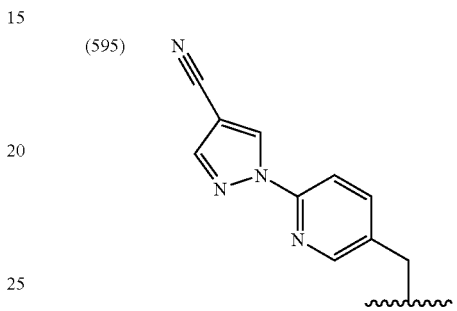 |
| (596) | 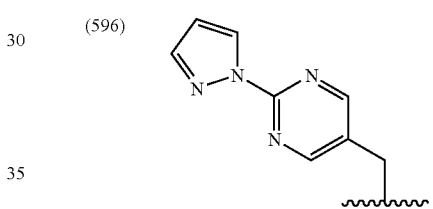 |
| (597) | 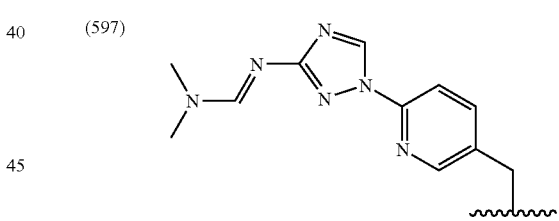 |
| (598) | 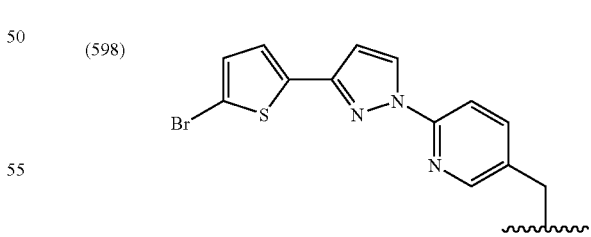 |
| (599) | 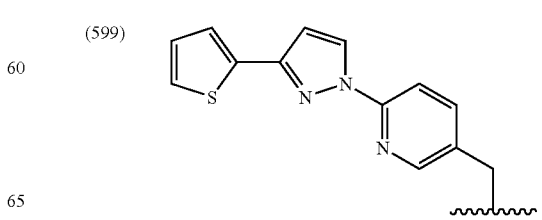 |

TABLE 4-continued

| Compound | $R_3$ |
|---|---|
| (600) | 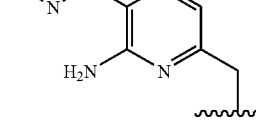 |
| (601) | 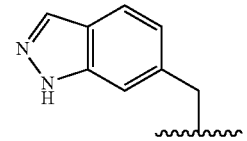 |
| (602) | 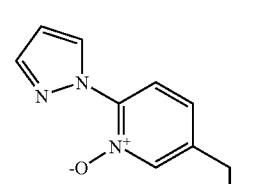 |
| (603) | 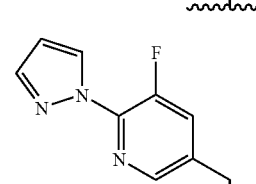 |
| (604) | 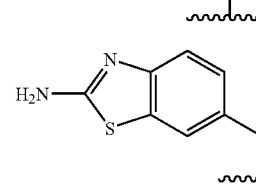 |
| (605) | 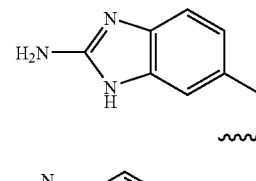 |
| (606) | 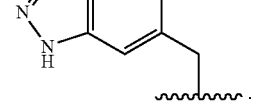 |

34. A method for treating a bacterial infection in a subject in need of such treatment, comprising administering to said subject a therapeutically effective amount of a compound according to claim 1.

35. A pharmaceutical composition comprising a therapeutically effective amount of a compound of claim 1 or a pharmaceutically acceptable salt, ester or prodrug thereof, in combination with a pharmaceutically acceptable carrier.

36. A method for treating a bacterial infection in a subject, comprising administering to said subject a therapeutically effective amount of a pharmaceutical composition according to claim 35.

37. A process for preparing a compound of claims 2 or 3 comprising the steps of:

(a) reacting a compound having a formula:

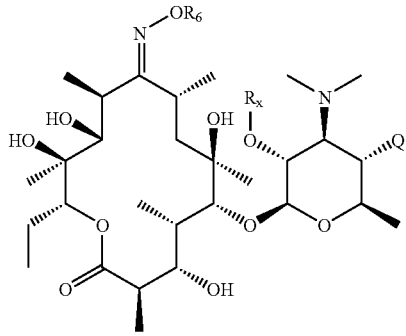

with

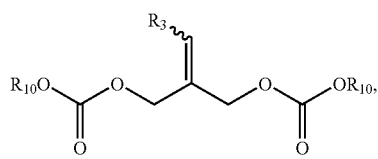

in the presence of a phosphine ligand and Pd(0) catalyst under room temperature to reflux conditions to prepare compounds of the formula:

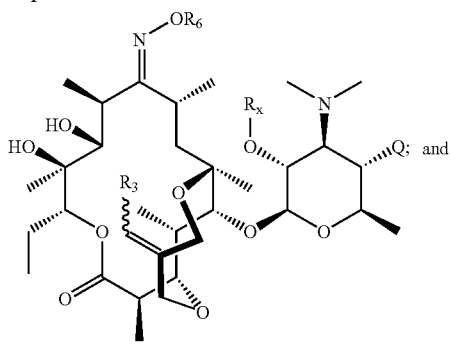

(b) deprotecting the 2' and the oxime groups of the compound obtained in step (a), followed by deoximating with an inorganic sulfur oxide salt or an inorganic nitrite salt in the presence to acid to form compound having a formula:

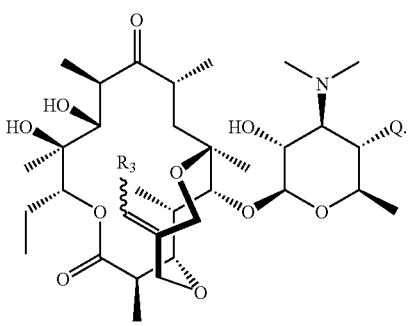

38. A process for preparing a compound of claims 2 or 3 via a stepwise process comprising, reacting a compound of the formula:

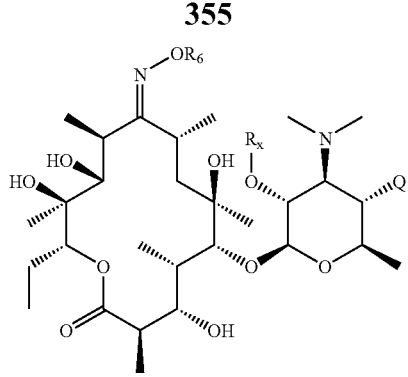

with

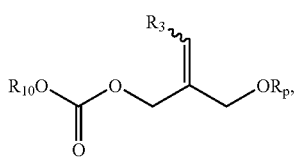

to obtain a compound of formula:

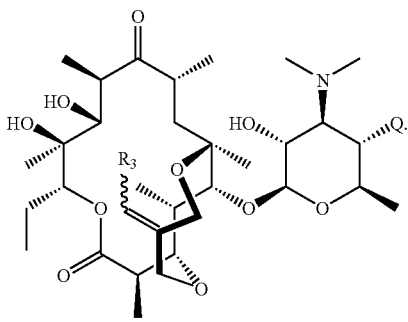

39. A process for preparing a compound of claim 4, comprising:
(a) reacting a compound having a formula:

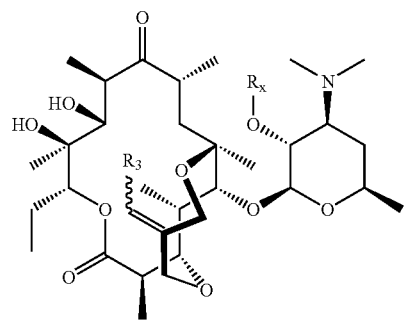

with formaldehyde in the presence of an acid or chloroiodomethane in the presence of a base to give a 11,12-methylenedioxy compound having formula:

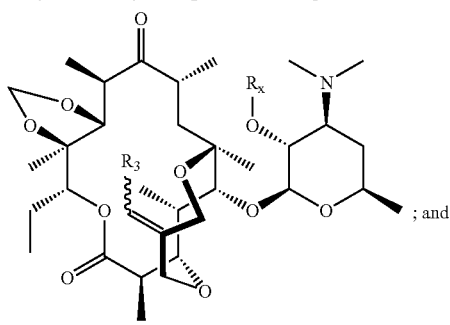

; and (b) deprotecting the 2' hydroxyl protecting group to the compound obtained in step (a).

40. A process for preparing a compound of claim 5, comprising:
(a) reacting a compound having a formula:

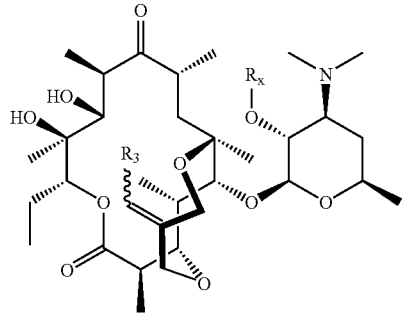

with a base;

(b) reacting the compound obtained in step (a) with a reagent selected from the group consisting of phosgene, diphosgene, triphosgene and substituted and unsubstituted benzyl chloroformate, to give compound having a formula:

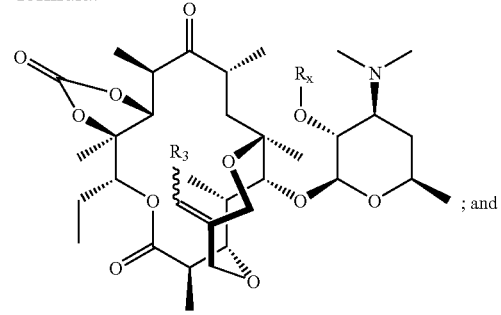

; and (c) deprotecting the 2' hydroxyl protecting group to the compound obtained in step (a).

41. A process for preparing a compound of claim 5, comprising the steps of:
(a) reacting a compound having a formula:

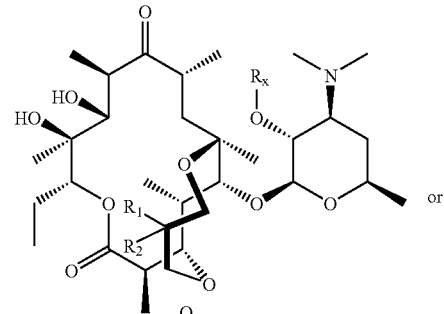

or

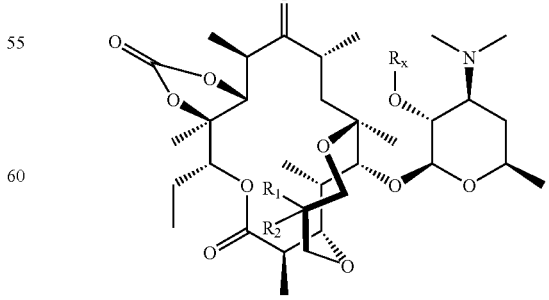

with a base and a reagent selected from the group consisting of CDI, phosgene equivatents, isocysanates, chloroformates and [1,3]dioxolan-2-one/Et₃N, to form a compound having a formula:

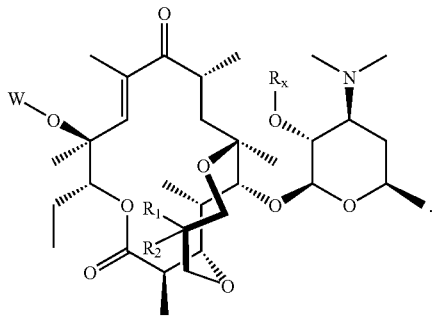

42. A process for preparing a compound of claim 7, comprising the steps of:

(a) reacting a compound having a formula:

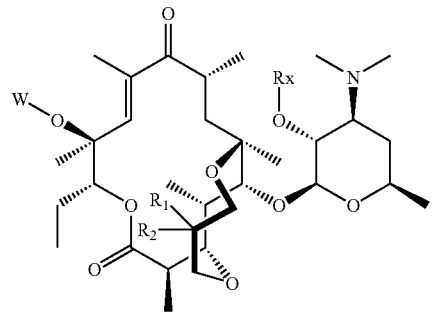

with a reagent selected from a group consisting of $R_{20}NH_2$, to form compound having a formula:

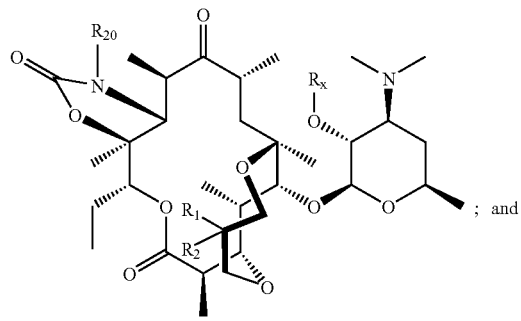

; and (b) deprotecting the 2' hydroxyl protecting group to the compound obtained in step (a).

43. A process for preparing a compound of claim 8 comprising the steps of:

(a) reacting a compound having a formula:

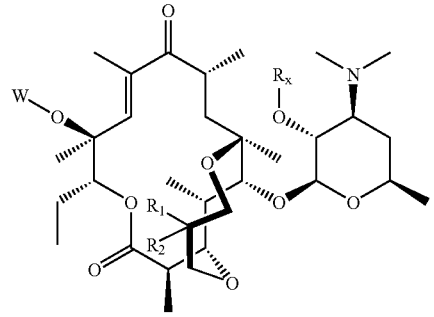

with a reagent selected from a group consisting of hydrazine, $R_{20}NHNH_2$ and $R_{20}CHO$, to form compound having a formula:

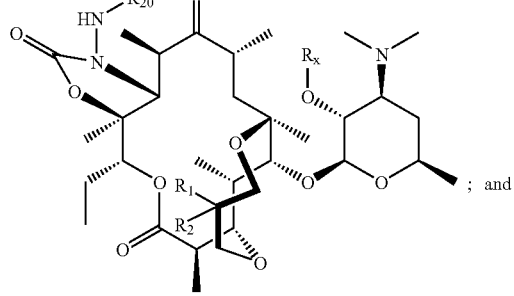

; and (b) deprotecting the 2' hydroxyl protecting group to the compound obtained in step (a).

44. A process for preparing a compound of claim 9 comprising:

(a) reacting a compound having a formula:

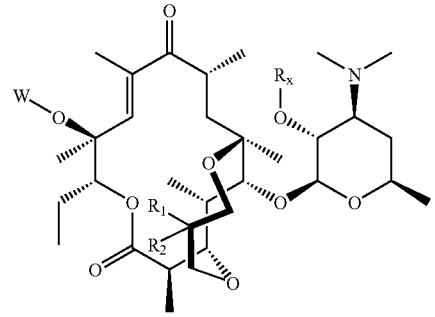

with a reagent selected from a group consisting of hydroxylamine and $R_{20}ONH_2$, to form compound having a formula:

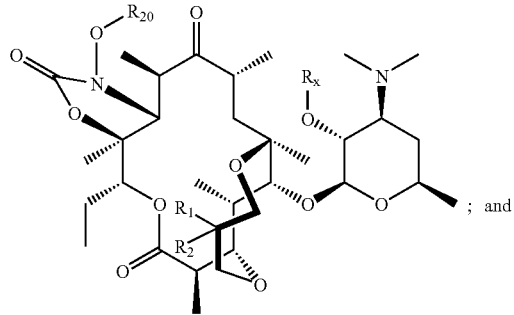

; and (b) deprotecting the 2' hydroxyl protecting group to the compound obtained in step (a).

45. A process for producing a compound of claim 1 having the formula:

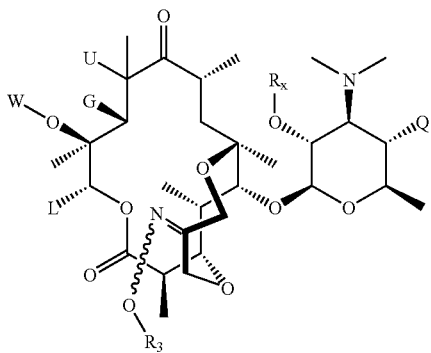

comprising the steps of:
(a) oxidative cleavage of the compounds with the following formula:

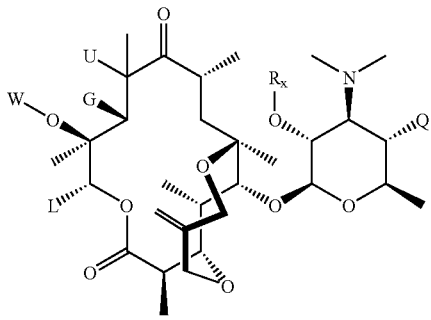

with an oxidizing reagent to give compounds of the following formula:

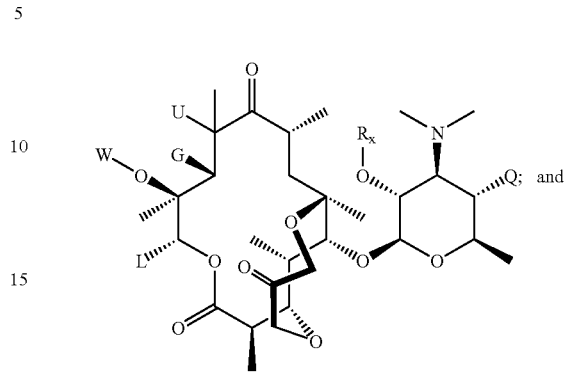

(b) reacting the compounds prepared in step (a) with $R_3ONH_2$, in a presence of a mild acid.

46. A method of treating cystic fibrosis in subject, comprising administering to said subject, a therapeutically effective amount of a pharmaceutical composition of claim 35.

47. A method of treating inflammation in a subject comprising administering to said subject, therapeutically effective amount of a pharmaceutical composition of claim 35.

* * * * *

UNITED STATES PATENT AND TRADEMARK OFFICE
CERTIFICATE OF CORRECTION

PATENT NO. : 7,419,962 B2
APPLICATION NO. : 11/295736
DATED : September 2, 2008
INVENTOR(S) : Yat Sun Or et al.

It is certified that error appears in the above-identified patent and that said Letters Patent is hereby corrected as shown below:

Column 250
Line 52, delete "–CH2OH" and replace with -- –CH$_2$OH --.

Column 251
Line 5, delete "I" and replace with -- f --;
Line 29, delete "L" and replace with -- E --; and
Line 62, delete "L" and replace with -- E --.

Column 252
Line 24, delete "form" and replace with -- from --; and
Line 27, delete "–C$_{1-C12}$" and replace with -- –C$_1$-C$_{12}$ --.

Column 356
Line 66, delete "chioroformates" and replace with -- chloroformates --.

Signed and Sealed this

Fourteenth Day of July, 2009

JOHN DOLL
*Acting Director of the United States Patent and Trademark Office*